United States Patent
Park et al.

(10) Patent No.: US 10,693,084 B2
(45) Date of Patent: Jun. 23, 2020

(54) COMPOUND FOR ORGANIC LIGHT-EMITTING DEVICE AND ORGANIC LIGHT-EMITTING DEVICE INCLUDING SAME

(71) Applicant: SFC CO., LTD., Cheongju-si (KR)

(72) Inventors: Seok-Bae Park, Geumsan-gun (KR); Hee-Dae Kim, Miryang-si (KR); Yoona Shin, Seoul (KR); Sang-woo Park, Seoul (KR); Soon-Wook Cha, Goyang-si (KR); Young-Hwan Park, Cheongju-si (KR); Seo-Yeon Yoon, Seongnam-si (KR); Sung-Wan Pyo, Daejeon (KR)

(73) Assignee: SFC CO., LTD., Cheongju-si (KR)

( * ) Notice: Subject to any disclaimer, the term of this patent is extended or adjusted under 35 U.S.C. 154(b) by 0 days.

(21) Appl. No.: 15/564,742

(22) PCT Filed: Apr. 15, 2016

(86) PCT No.: PCT/KR2016/003922
§ 371 (c)(1),
(2) Date: Oct. 6, 2017

(87) PCT Pub. No.: WO2016/171429
PCT Pub. Date: Oct. 27, 2016

(65) Prior Publication Data
US 2018/0123055 A1    May 3, 2018

(30) Foreign Application Priority Data
Apr. 23, 2015    (KR) .................. 10-2015-0057141

(51) Int. Cl.
*H01L 51/00* (2006.01)
*C07D 307/91* (2006.01)
*C09K 11/06* (2006.01)
*H01L 51/50* (2006.01)
*C07D 495/04* (2006.01)
*C07D 493/04* (2006.01)
*C07D 405/04* (2006.01)
*C07D 405/14* (2006.01)
*C07D 407/04* (2006.01)
*C07D 409/04* (2006.01)
(Continued)

(52) U.S. Cl.
CPC ........ *H01L 51/0073* (2013.01); *C07D 307/91* (2013.01); *C07D 307/93* (2013.01);
(Continued)

(58) Field of Classification Search
None
See application file for complete search history.

(56) References Cited

U.S. PATENT DOCUMENTS

2010/0045170 A1* 2/2010 Lee .................. C07C 13/547
313/504
2012/0056165 A1* 3/2012 Kawamura ............ C09K 11/06
257/40
(Continued)

FOREIGN PATENT DOCUMENTS

JP    2005314239 A    11/2005
JP    2010215759 A  *  9/2010  ............. C09K 11/06
(Continued)

OTHER PUBLICATIONS

Abstract for KR-1020140083107, 1 page, abstract generated Aug. 2018. (Year: 2018).*
(Continued)

*Primary Examiner* — Robert S Loewe
(74) *Attorney, Agent, or Firm* — STIP Law Group, LLC

(57) ABSTRACT

The present invention relates to an anthracene derivative selected from among compounds represented by Chemical
(Continued)

Formulas A-1, A-2, B-1, and B-2, and an organic light-emitting device including the same. Structures of individual moieties in the anthracene derivative are as defined in the specification.

20 Claims, 8 Drawing Sheets

(51) Int. Cl.
    *C07D 409/14*     (2006.01)
    *C07D 307/93*     (2006.01)
    *C09K 11/02*     (2006.01)
    *H01L 51/52*     (2006.01)

(52) U.S. Cl.
    CPC ......... *C07D 405/04* (2013.01); *C07D 405/14* (2013.01); *C07D 407/04* (2013.01); *C07D 409/04* (2013.01); *C07D 409/14* (2013.01); *C07D 493/04* (2013.01); *C07D 495/04* (2013.01); *C09K 11/025* (2013.01); *C09K 11/06* (2013.01); *H01L 51/50* (2013.01); *C09K 2211/1007* (2013.01); *C09K 2211/1011* (2013.01); *C09K 2211/1029* (2013.01); *C09K 2211/1088* (2013.01); *H01L 51/001* (2013.01); *H01L 51/0003* (2013.01); *H01L 51/5004* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5206* (2013.01); *H01L 51/5221* (2013.01)

(56) References Cited

U.S. PATENT DOCUMENTS

| | | | | |
|---|---|---|---|---|
| 2014/0061622 | A1* | 3/2014 | Ikeda | H01L 51/0073 |
| | | | | 257/40 |
| 2014/0246657 | A1* | 9/2014 | Kim | H01L 51/0058 |
| | | | | 257/40 |

FOREIGN PATENT DOCUMENTS

| | | | |
|---|---|---|---|
| JP | 5608978 | B2 | 4/2011 |
| JP | 2014224047 | A * | 12/2014 |
| JP | 2015018883 | A | 1/2015 |
| KR | 1020060022676 | A | 3/2006 |
| KR | 1020080018218 | A | 2/2008 |
| KR | 100910150 | B1 | 8/2009 |
| KR | 1020100093064 | A | 8/2010 |
| KR | 1020100123735 | A | 11/2010 |
| KR | 1020120092555 | B1 | 8/2012 |
| KR | 1020120135501 | A | 12/2012 |
| KR | 1020130067312 | A | 6/2013 |
| KR | 1020140083107 | A | 7/2014 |
| KR | 1020150141271 | A | 12/2015 |
| WO | WO2015033559 | A1 | 3/2017 |

OTHER PUBLICATIONS

English language translation of JP-2010215759, translation generated Oct. 2019, 59 pages. (Year: 2019).*
International Search Report of PCT/KR2016/003922, dated Oct. 10, 2015, English Translation.
Office Action from Korean Intellectual Property office of 10-2016-0046184, dated Nov. 20, 2018.
Office Action from Korean Intellectual Property Office of 10-2019-0031936, dated Jun. 20, 2019.

* cited by examiner

COMPOUND FOR ORGANIC LIGHT-EMITTING DEVICE AND ORGANIC LIGHT-EMITTING DEVICE INCLUDING SAME

CROSS-REFERENCE TO RELATED APPLICATIONS

This application is the U.S. National Phase under 35 U.S.C. § 371 of International Application No. PCT/KR2016/003922 filed on Apr. 15, 2016, which in turn claims the benefit of Korean Application No. 10-2015-0057141, filed on Apr. 23, 2015, the disclosures of which are incorporated by reference into the present application.

TECHNICAL FIELD

The present invention relates to a compound for an organic light-emitting device, and an organic light-emitting device including the same. More particularly, the present invention relates to a compound that can be used in a light-emitting layer or in a layer arranged between a light-emitting layer and an electron injection layer so as to increase the efficiency of an organic light-emitting device, and an organic light-emitting device including the same.

BACKGROUND ART

Organic light-emitting diodes, based on self-luminescence, exhibit the advantages of having a wide viewing angle, excellent contrast, fast response time, high brightness, excellent driving voltage and response rate characteristics, and of allowing for a polychromic display.

A typical organic light-emitting diode includes a positive electrode (anode) and a negative electrode (cathode), facing each other, with an organic emissive layer disposed therebetween.

As to the general structure of the organic light-emitting diode, a hole transport layer, a light-emitting layer, an electron transport layer, and a cathode are formed in that order on an anode. Here, all of the hole transport layer, the light-emitting layer, and the electron transport layer are organic films comprising organic compounds.

An organic light-emitting diode having such a structure operates as follows: when a voltage is applied between the anode and the cathode, the anode injects holes which are then transferred to the light-emitting layer via the hole transport layer while electrons injected from the cathode move to the light-emitting layer via the electron transport layer. In the luminescent zone, the carriers such as holes and electrons recombine to produce an exciton. When the exciton returns to the ground state from the excited state, the molecule of the light-emitting layer emits light.

Materials used as the organic layers in organic light-emitting diodes may be divided according to functions into luminescent materials and charge carrier materials, for example, a hole injection material, a hole transport material, an electron injection material, and an electron transport material. The light-emitting mechanism forms the basis of classification of luminescent materials as fluorescent and phosphorescent materials, which use excitons in singlet and triplet states, respectively.

Meanwhile, when a single material is employed as the luminescent material, intermolecular actions cause the maximum luminescence wavelength to shift toward a longer wavelength, resulting in a reduction in color purity and light emission efficiency due to light attenuation. In this regard, a host-dopant system may be used as a luminescent material so as to increase the color purity and the light emission efficiency through energy transfer. This is based on the principle whereby, when a dopant which is smaller in energy band gap than a host forming a light-emitting layer is added in a small amount to the light-emitting layer, excitons are generated from the light-emitting layer and transported to the dopant, emitting light at high efficiency. Here, light with desired wavelengths can be obtained depending on the kind of the dopant because the wavelength of the host moves to the wavelength range of the dopant.

In relation to the efficiency of an organic light-emitting device, Korean Patent Publication No. 10-2012-0092555 A (Aug. 21, 2012) proposes the effective occurrence of a triplet-triplet fusion (TTF) phenomenon accounting for the generation of singlet excitons through the collision and fusion of two triplet excitons. For this, this reference discloses an electroluminescence device in which a blocking layer is interposed between a light-emitting layer and an electron injection layer, with an affinity difference between the electron injection layer and the blocking layer. In this regard, the blocking layer is set to have a triplet energy larger than that of the host of the light-emitting layer so as to confine triplet excitons within the light-emitting layer, whereby the effective occurrence of the TTF phenomenon is induced. In addition, the electroluminescence device employs a material in which respective affinities of both the electron injection layer and the blocking layer satisfy a specific condition. As described above, the reference document is designed to control the amount of electrons or to cause the effective occurrence of a TTF phenomenon in order to provide high emission efficiency for an organic electroluminescence device. To this end, the blocking layer should include a material that is higher in triplet energy than the host to prevent the annihilation of the triplet excitations generated in the host, and an aromatic heterocyclic compound of a specific fused ring should be employed in the blocking layer.

Another technique for improving luminance efficiency can be found in Korean Patent Publication No. 10-2006-0022676 A (Mar. 10, 2006), which describes an organic electroluminescence device having a blocking layer, disposed between a light-emitting layer and an electron transport layer, for controlling electron density. In the device, an electron injection blocking layer material lower in electron mobility than an electron injection layer material is employed, with limitations imparted to the kinds thereof which have specific structures, such as metal chelate compounds or imidazole derivatives, i.e., heterocyclic compounds in which a 6-membered and a 5-membered ring are fused each other.

Although various efforts have been made to fabricate organic light-emitting devices having more effective luminescence characteristics, the development of organic light-emitting devices having a higher effective luminance efficiency still continues to be needed.

With regard to related arts pertaining to host compounds in the light-emitting layer, reference may be made to Korean Patent No. 10-0910150 (Aug. 3, 2009), which discloses an organic light-emitting diode comprising a luminescent medium layer containing a compound in which an anthracene structure has a heterocyclic ring as a substituent at a terminal position thereof, and Japanese Patent No. 5608978 (Oct. 22, 2014), which describes an organic light-emitting diode comprising a luminescent medium layer containing an anthracene derivative in which an anthracene moiety has a dibenzofuran moiety as a substituent at a terminal position thereof.

Despite a variety of kinds of compounds prepared for use in luminescent media layers including the related art, there is still a continued need to develop organic layer materials that are capable of driving OLEDs at a lower voltage and have improved low dynamic range properties.

DETAILED DESCRIPTION OF THE INVENTION

Technical Problem

Accordingly, a purpose of the present invention is to provide an anthracene derivative for use in an electron density control layer additionally arranged between a light-emitting layer and an electron transport layer.

Another purpose of the present invention is to provide an organic light-emitting device including the anthracene derivative in an electron density control layer thereof.

A further purpose of the present invention is to provide a compound for use as a host in a light-emitting layer of an organic light-emitting device operable at a low voltage, and an organic light-emitting device including the same.

Technical Solution

The present invention provides an anthracene derivative selected from among compounds represented by the following Chemical Formulas A-1, A-2, B-1, and B-2:

[Chemical Formula A-1]

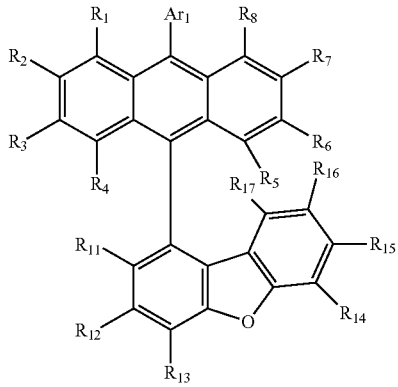

[Chemical Formula A-2]

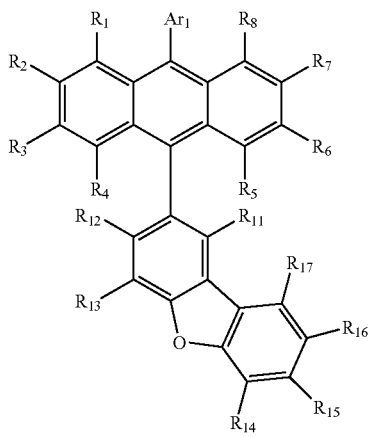

[Chemical Formula B-1]

Q:

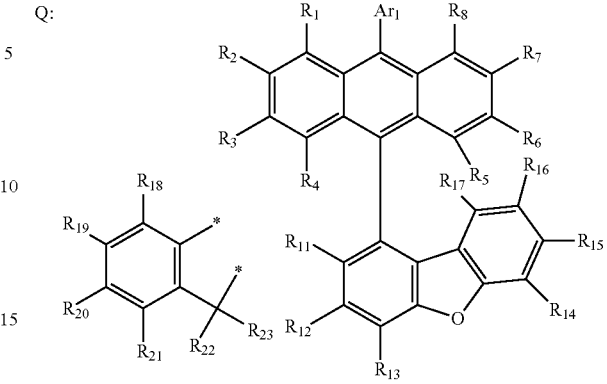

[Chemical Formula B-2]

Q:

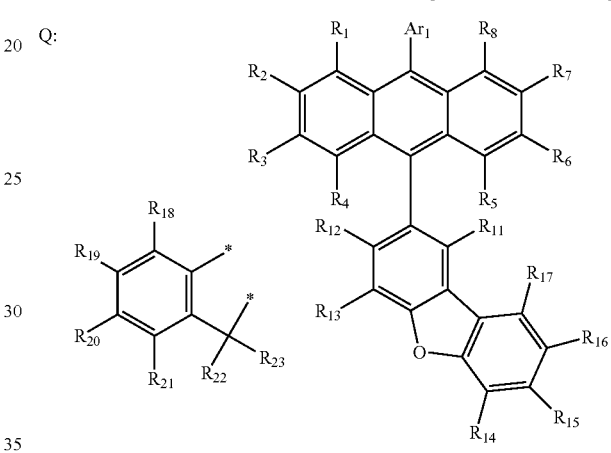

wherein,

R1 to R8, and R11 to R23, which may be the same or different, are each independently any one selected from among a hydrogen, a deuterium, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted aryl of 6 to 50 carbon atoms, heteroaryl of 2 to 50 carbon atoms bearing O, N, or S as a heteroatom, a cyano, a nitro, a halogen, a substituted or unsubstituted silyl of 1 to 30 carbon atoms, a substituted or unsubstituted germanium of 1 to 30 carbon atoms, a substituted or unsubstituted boron of 1 to 30 carbon atoms, a substituted or unsubstituted aluminum of 1 to 30 carbon atoms, a carbonyl, a phosphoryl, an amino, a thiol, a hydroxy, a selenium, a tellurium, an amide, an ether, and an ester;

the substituent Ar1 is a substituted or unsubstituted aryl of 6 to 50 carbon atoms or a substituted or unsubstituted heteroaryl of 2 to 50 carbon atoms;

two adjacent substituents of R11 to R13 in Chemical Formulas B-1 and B-2 are respective single bonds involved in forming a 5-membered ring as a fused ring with the carbon atom to which the substituents R22 and R23 in Structural Formula Q are both bonded; and R22 and R23 may be connected to each other to form a ring.

In addition, the present invention provides an organic light-emitting device, including: a first electrode; a second electrode facing the first electrode; and an organic layer interposed between the first electrode and the second electrode, wherein the organic layer includes at least one anthracene derivative selected from among compounds represented by Chemical Formulas A-1, A-2, B-1, and B-2.

Further, the present invention provides an organic light-emitting device, including an anode, a hole transport layer, a light-emitting layer sequentially including a host and a dopant, an electron density control layer including at least one of the anthracene derivatives represented by Chemical Formulas A-1, A-2, B-1, and B-2, an electron transport layer, and a cathode.

Advantageous Effects

Arranged between a light-emitting layer and an electron transport layer to lower the barrier electron injection from the electron transport layer to the light-emitting layer, the anthracene derivative according to the present invention allows for the effective injection of electrons into the light-emitting layer so that it can increase the electron density of the light-emitting layer and the density of excitons generated in the light-emitting layer, resulting in an improvement in external quantum efficiency (EQE).

In addition, when used as a host in the light-emitting layer, the anthracene derivative according to the present invention allows the organic light-emitting device to operate at lower voltages and to have a high luminance decrease rate in a low dynamic range level.

BEST MODE FOR INVENTION

Mode for Carrying Out the Invention

Figure 1:
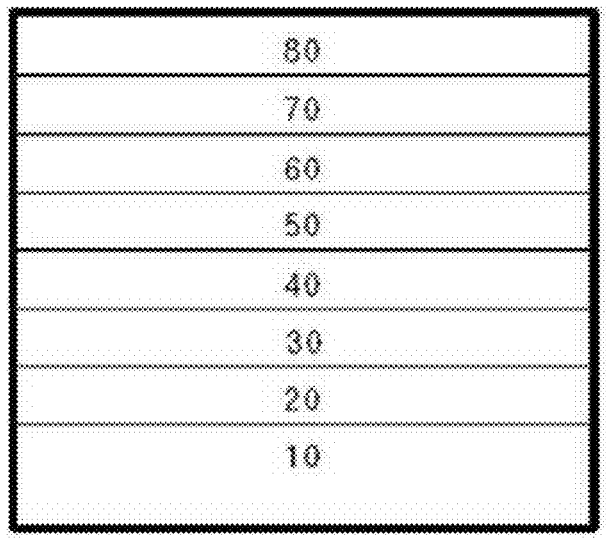
FIG. 1 is a schematic diagram of the structure of an organic light-emitting device according to an embodiment of the present invention.

Hereinafter, some embodiments which can be easily embodied by those skilled in the art will be described with reference to the accompanying drawings. In the drawings of the invention, sizes and dimensions of structures are illustrated by enlarging or reducing as compared with the actual sizes and dimensions to clarify the invention, the known configurations are not illustrated to exhibit characteristic configurations, and the invention is not limited to the drawings.

In addition, the size and thickness of each configuration illustrated in the drawings are arbitrarily illustrated for the sake of convenience of explanation, and thus the present invention may not be necessarily limited to the illustration. Further, in the drawings, the thickness of layers and regions are illustrated in enlargement for clarity. For the sake of explanation, thicknesses of certain layers and regions are exaggerated.

Throughout the specification, when a portion may "include" a certain constituent element, unless explicitly described to the contrary, it may not be construed to exclude another constituent element but may be construed to further include other constituent elements. Further, throughout the specification, the word "on" means positioning on or below the object portion, but does not essentially mean positioning on the lower side of the object portion based on a gravity direction.

In accordance with an aspect thereof, the present invention provides a compound for use as a host in a light-emitting layer of an organic light-emitting device or for use in an electron density control layer arranged between a light-emitting layer and an electron injection layer in an organic light-emitting device.

In the present invention, the organic light-emitting for use in a light-emitting layer or an electron density control layer of an organic light-emitting device may be any one selected from among the compounds represented by the following Chemical Formulas A-1, A-2, B-1, and B-2:

[Chemical Formula A-1]

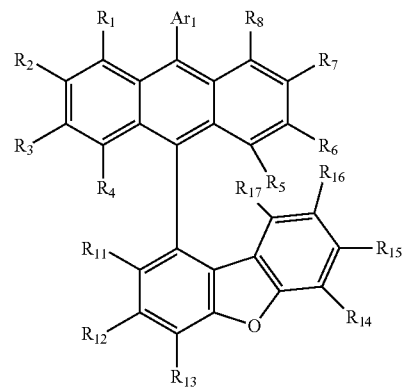

-continued

[Chemical Formula A-2]

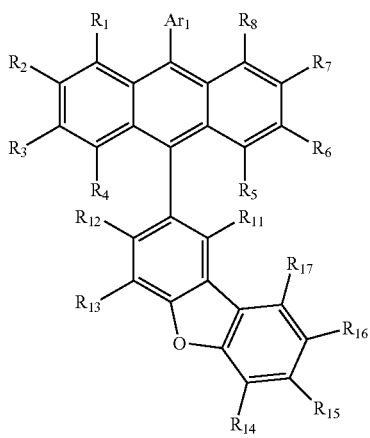

[Chemical Formula B-1]

Q:

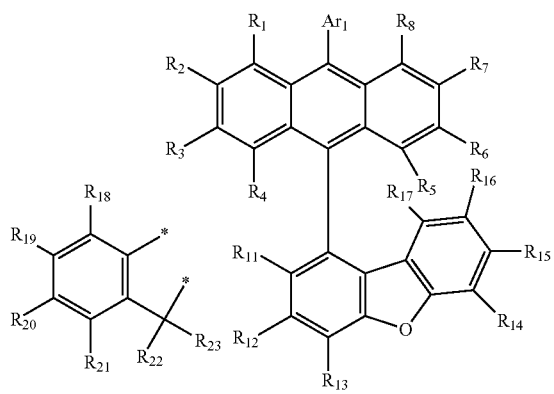

[Chemical Formula B-2]

Q:

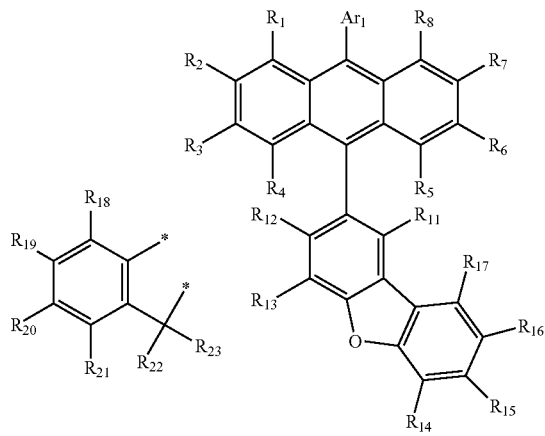

wherein,

R1 to R8, and R11 to R23, which may be the same or different, are each independently any one selected from among a hydrogen, a deuterium, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted aryl thioxy of 6 to 30 carbon atoms, a substituted or unsubstituted alkyl amine of 1 to 30 carbon atoms, a substituted or unsubstituted aryl amine of 6 to 30 carbon atoms, a substituted or unsubstituted aryl of 6 to 50 carbon atoms, heteroaryl of 2 to 50 carbon atoms bearing 0, N or S as a heteroatom, a cyano, a nitro, a halogen, a substituted or unsubstituted silyl of 1 to 30 carbon atoms, a substituted or unsubstituted germanium of 1 to 30 carbon atoms, a substituted or unsubstituted boron of 1 to 30 carbon atoms, a substituted or unsubstituted aluminum of 1 to 30 carbon atoms, a carbonyl, a phosphoryl, an amino, a thiol, a hydroxy, a selenium, a tellurium, an amide, an ether, and an ester, the substituent Ar1 is a substituted or unsubstituted aryl of 6 to 50 carbon atoms, or a substituted or unsubstituted heteroaryl of 2 to 50 carbon atoms;

two adjacent substituents of R11 to R13 in Chemical Formulas B-1 and B-2 are respective single bonds involved in forming a 5-membered ring as a fused ring with the carbon atom to which the substituents R22 and R23 in Structural Formula Q are both bonded;

R22 and R23 may be connected to each other to form a ring, wherein the term 'substituted in the expression "substituted or unsubstituted" means having at least one substituent selected from the group consisting of a duetrium, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

Meanwhile, the expression indicating the number of carbon atoms such as in "a substituted or unsubstituted alkyl of 1 to 30 carbon atoms", "a substituted or unsubstituted aryl of 5 to 50 carbon atoms", etc. means the total number of carbon atoms of, for example, the alkyl or aryl radical or moiety alone, exclusive of the number of carbon atoms of the substituent. For instance, a phenyl group with a butyl at the para position falls within the scope of an aryl of 6 carbon atoms although it is substituted with a butyl radical of 4 carbon atoms.

As used herein, the term "aryl" refers to an organic radical derived from an aromatic hydrocarbon by removing one hydrogen atom and encompasses a 5- to 7-membered and preferably a 5- or 6-membered monocyclic ring or fused ring system. In addition, the aromatic system may further include a fused ring that is formed by adjacent substituents, if present, on the aryl radical.

Examples of the aryl include phenyl, naphthyl, biphenyl, terphenyl, anthryl, indenyl, fluorenyl, phenanthryl, triphenylenyl, pyrenyl, perylenyl, chrysenyl, naphthacenyl, and fluoranthenyl, but are not limited thereto.

At least one hydrogen atom on the aryl radical may be substituted by a deuterium atom, a halogen atom, a hydroxy, a nitro, a cyano, a silyl, an amino (—NH2, —NH(R), —N(R')(R")) wherein R' and R" are each independently an alkyl of 1 to 10 carbon atoms, in this case called "alkylamino"), an amidino, a hydrazine, a hydrazone, a carboxyl, a sulfonic acid, a phosphoric acid, an alkyl of 1 to 24 carbon atoms, a halogenated alkyl of 1 to 24 carbon atoms, an alkenyl of 1 to 24 carbon atoms, an alkynyl of 1 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms or a heteroarylalkyl of 2 to 24 carbon atoms.

The substituent heteroaryl used in the compound of the present invention refers to a cyclic aromatic system of 2 to 24 carbon atoms bearing one to three heteroatoms selected from among N, O, P, Se, Te, Si, Ge, and S. In the aromatic system, two or more rings may be fused.

One or more hydrogen atoms on the heteroaryl may be substituted by the same substituents as on the aryl.

Examples of the substituent alkyl useful in the present invention include methyl, ethyl, propyl, isobutyl, sec-butyl, tert-butyl, pentyl, iso-amyl, and hexyl. At least one hydrogen atom of the alkyl may be substituted by the same substituent as in the aryl.

Examples of the substituent alkoxy used in the compounds of the present invention include methoxy, ethoxy, propoxy, isobutyloxy, sec-butyloxy, pentyloxy, iso-amyloxy, and hexyloxy. At least one hydrogen atom of the alkoxy may be substituted by the same substituent as in the aryl.

Representative of the silyl useful in the present invention are trimethylsilyl, triethylsilyl, triphenylsilyl, trimethoxysilyl, dimethoxyphenylsilyl, diphenylmethylsilyl, silyl, diphenylvinylsilyl, methylcyclobutylsilyl, and dimethylfurylsilyl. At least one hydrogen atom in the silyl may be substituted by the same substituent as in the aryl.

In the compounds represented by Chemical Formulas A-1, A-2, B-1, and B-2 according to the present invention, the anthracene ring moiety may have various substituents, such as a hydrogen, a deuterium, a substituted or unsubstituted alkyl of 1 to 30 carbon atoms, a substituted or unsubstituted cycloalkyl of 3 to 30 carbon atoms, a substituted or unsubstituted arylene of 6 to 50 carbon atoms, a substituted or unsubstituted heteroarylene of 2 to 50 carbon atoms, etc., bonded at position 10 thereof and is directly connected with a dibenzofuran ring between position 9 of the anthracene ring moiety and position 1 or 2 of the dibenzofuran ring, as shown in Diagram 1, below.

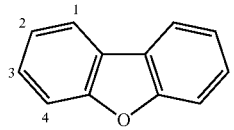

[Diagram 1]

Hereinafter, a description will be given with regard only to the case where the anthracene derivative of the present invention is used in an additional layer between a light-emitting layer and an electron transport layer in an organic light-emitting device.

The anthracene derivative represented by Chemical Formula A-1, A-2, B-1, or B-2 can enhance the efficiency of an organic light-emitting device when used in an additional layer disposed between a light-emitting layer and an electron transport layer in the organic light-emitting device.

Meanwhile, as shown in Chemical Formula B-1 or B-2, two adjacent substituents of R11 to R13 on the anthracene-connected ring moiety of the dibenzofuran ring correspond respectively to a single bond involved in forming a 5-membered ring as a fused ring with the carbon atom to which the substituents R22 and R23 on Structural Formula Q are both bonded in such a way that the dibenzofuran ring is bonded at two adjacent positions of positions 2 to 4 (Chemical Formula B-1) or at positions 3 and 4 (Chemical Formula B-2) with the radical represented by Structural Formula Q.

In one embodiment of the present invention, the substituents R22 and R23 in Structural Formula Q may be the same or different and may each be independently a substituted or unsubstituted aryl of 6 to 24 carbon atoms.

Further, the substituent Ar1 may be a substituted or unsubstituted aryl of 6 to 50 carbon atoms and preferably a substituted or unsubstituted aryl of 6 to 18 carbon atoms.

In another embodiment, the substituent Ar1 may be a substituted or unsubstituted heteroaryl of 3 to 50 carbon atoms and preferably a substituted or unsubstituted heteroaryl of 3 to 18 carbon atoms.

In addition, the substituents R22 and R23 may be connected to each other to form a ring. By way of example, when the substituent R22 and R23 are connected to each other, the compound represented by Chemical Formula B-1 may include a substituted or unsubstituted spirobisfluorene ring as illustrated in Diagram 2, below. This is true of the anthracene derivative represented by Chemical Formula B-2.

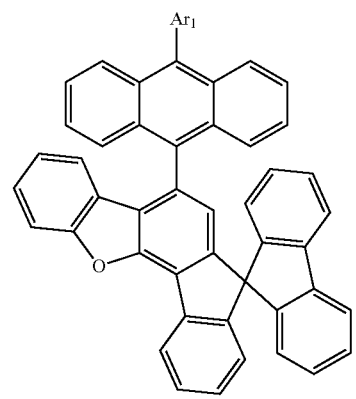

[Diagram 2]

In the anthracene derivative represented by Chemical Formulas A-1, A-2, B-1, and B-2 according to the present invention, the substituent Ar1 may be represented by the following Structural Formula C:

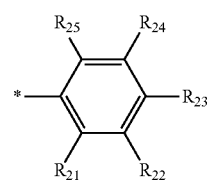

[Structural Formula C]

wherein the substituents R21 to R25, which may be the same or different, are each independently any one selected from among a hydrogen, a deuterium, a halogen, a cyano, a substituted or unsubstituted alkyl of 1 to 30 carbon atoms, a substituted or unsubstituted cycloalkyl of 3 to 30 carbon atoms, a substituted or unsubstituted alkoxy of 1 to 30 carbon atoms, a substituted or unsubstituted aryloxy of 6 to 30 carbon atoms, a substituted or unsubstituted aryl of 6 to 50 carbon atoms, and a substituted or unsubstituted silyl of 1 to 30 carbon atoms, and '*' refers to a bonding site to the anthracene moiety.

In some embodiments of the present invention, when the substituent Ar1 is represented by Structural Formula C, the substituents R21 to R25 thereon may each contain or be a hydrogen atom or a deuterium atom. For instance, all the substituents R21 to R25 may be hydrogen atoms or deuterium atoms.

Meanwhile, the anthracene derivatives represented by Chemical Formulas A-1, A-2, B-1, and B-2 may each be used as a host in a light-emitting layer.

In the anthracene derivatives, the anthracene ring moiety is bonded to position 1 or 2 of one phenyl ring of the substituted or unsubstituted dibenzofuran moiety while the other phenyl ring has a substituent represented by '-(L)m-(B)n' at at least one of positions 1' to 3', as shown in Diagram 3, below.

[Diagram 3]

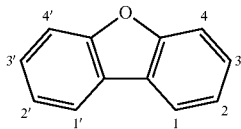

That is, the anthracene derive has the structure of -(L)m-(B)n for at least one of R15 to R17 when represented by Chemical Formula A-1 or B-1, and for at least one of R11 and R15 to R17 when represented by Chemical Formula A-2 or B-2.

Here, L denotes a linker and is a single bond or a substituted or unsubstituted arylene of 6 to 60 carbon atoms, B is a deuterium, a substituted or unsubstituted alkyl of 1 to 30 carbon atoms, or a substituted or unsubstituted aryl of 6 to 60 carbon atoms, m is an integer of 0 to 2, with a proviso that when m is 2, the corresponding L's may be the same or different, and, n is an integer of 0 to 5, with a proviso that when n is 2 or greater, the corresponding B's may be the same or different.

For use in a light-emitting layer, the anthracene derivative has the structure of -(L)m-(B)n as only one of the substituents R15 to R17 in Chemical Formula A-1 or B-1 and as only one of the substituents R11 and R15 to R17 in Chemical Formula A-2 or B-2 in accordance with particular embodiments.

For greater detailed explanation, the anthracene moiety (X) in the anthracene derivative represented by Chemical Formula A-1, A-2, B-1, or B-2 is bonded to position 1 or 2 of the dibenzofuran moiety, as illustrated in Diagrams 4 and 5, respectively.

[Diagram 4]

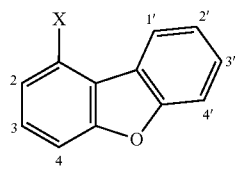

[Diagram 5]

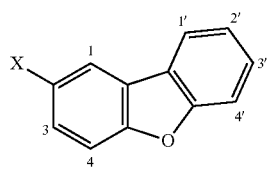

The compound of the present invention can improve the organic light-emitting device in low dynamic range characteristic when the dibenzofuran moiety has an alkyl, a substituted alkyl, an aryl or a substituted aryl as a substituent at position 1', 2' or 3', or at position 1', 2', 3', or 1 in case of Diagram 5. In contrast, the organic light-emitting device degrades in low dynamic range characteristic when a substituent such as a phenyl or a biphenyl is introduced to position 4 of the dibenzofuran moiety in Diagrams 4 and 5. This finding is a basis on which an organic light-emitting device improved in low dynamic range characteristic can be fabricated.

That is, an organic light-emitting device can operate at a low voltage and exhibit a high luminance decrease rate when its light emitting layer includes the anthracene derivative of the present invention.

In one embodiment of the organic light-emitting device employing the anthracene derivative of the present invention as a host in a light-emitting layer, the substituents R1 to R8, and R11 to R13 are each a hydrogen or a deuterium, and B is a substituted or unsubstituted aryl of 6 to 60 carbon atoms. In this case, B may be any one selected from among a phenyl, a biphenyl, a naphthyl, and a phenanthrene.

In another embodiment of the organic light-emitting device employing the anthracene derivative of the present invention as a host in a light-emitting layer, the linker L may be a single bond or any one selected from among the following Structural Formulas 1 to 3.

[Structural Formula 1] [Structural Formula 2] [Structural Formula 3]

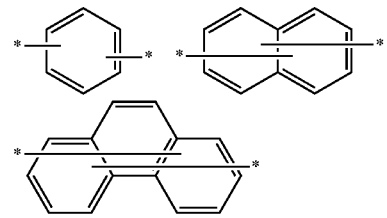

In the linker L, each of the unsubstituted carbon atoms of the aromatic ring moiety is bound with a hydrogen atom or a deuterium atom.

Concrete examples of the anthracene derivatives represented by Chemical Formulas A-1, A-2, B-1 and B-2 according to the present invention include, but are not limited to, the compounds represented by the following Compounds 1 to 156:

<Compound 1>

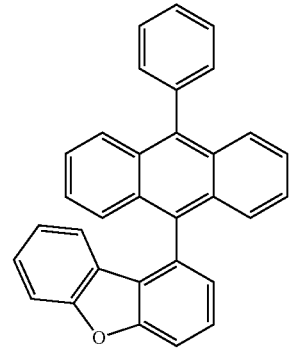

<Compound 2>
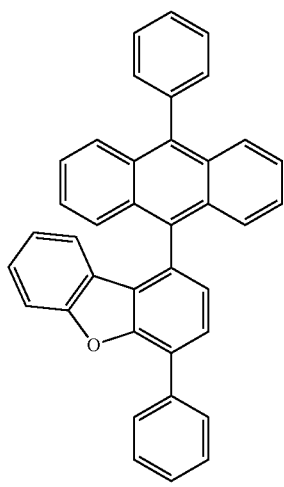
<Compound 3>
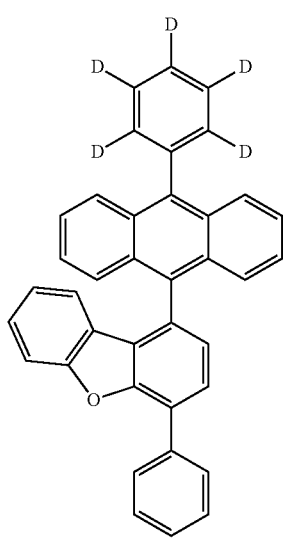
<Compound 4>
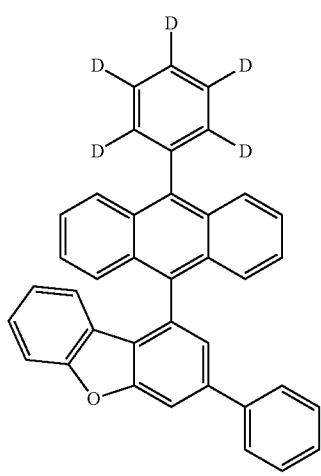
<Compound 5>
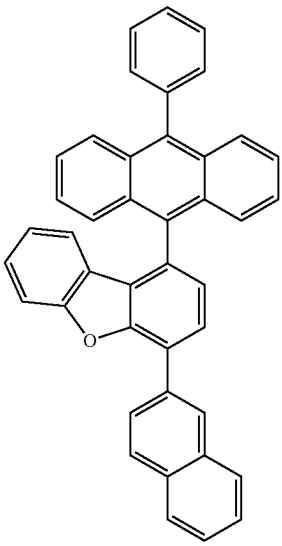
<Compound 6>
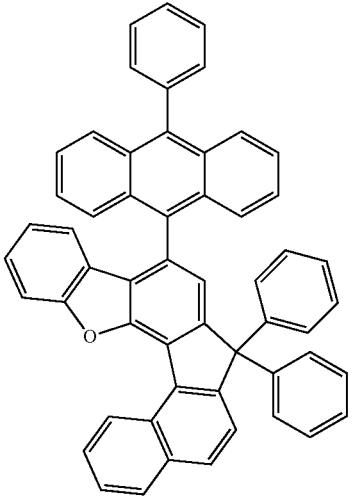
<Compound 7>
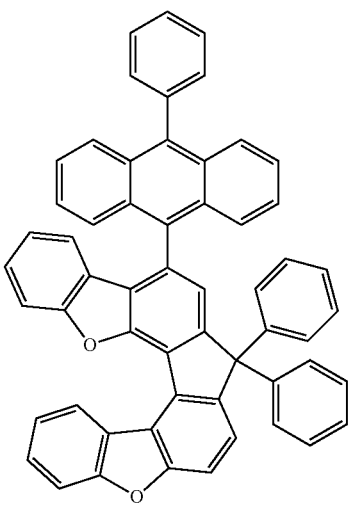

<Compound 8>
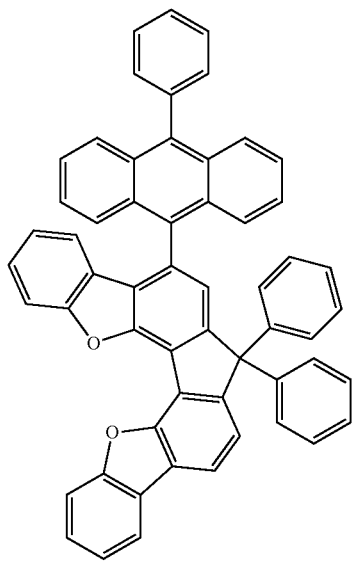
<Compound 9>
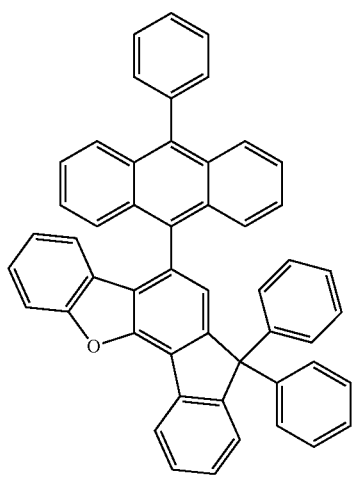
<Compound 10>
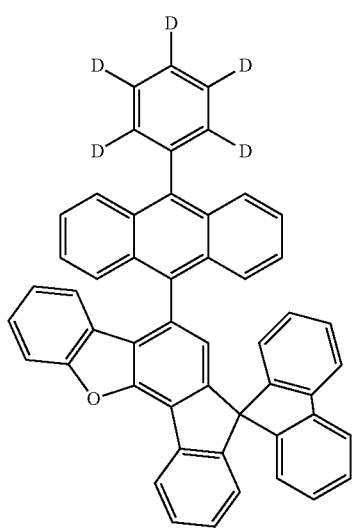
<Compound 11>
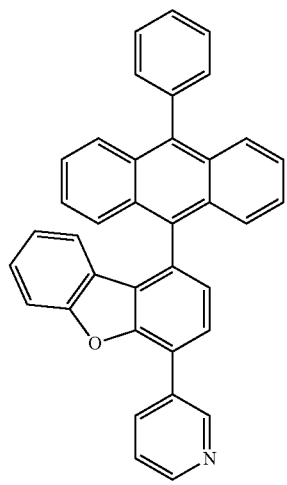
<Compound 12>
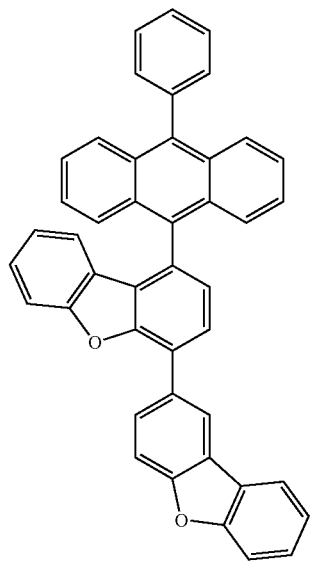
<Compound 13>
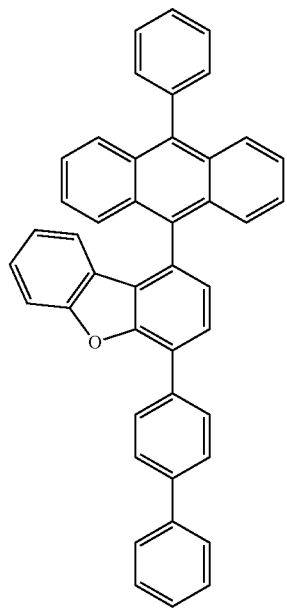

<Compound 14>
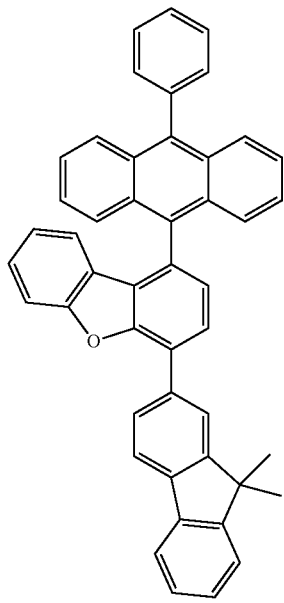
<Compound 16>
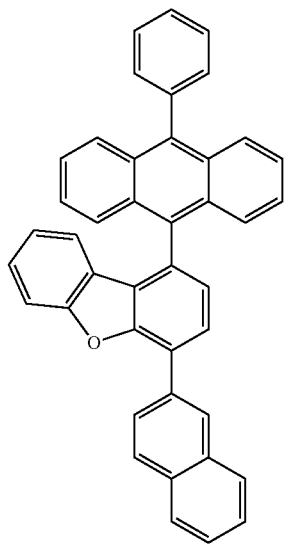
<Compound 17>
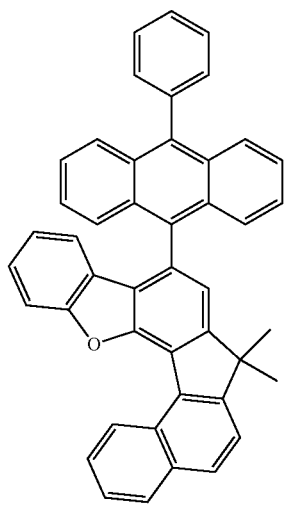
<Compound 15>
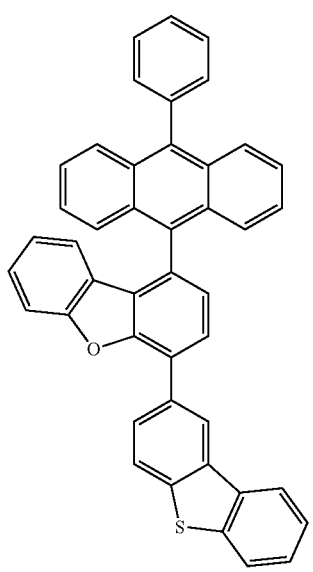
<Compound 18>
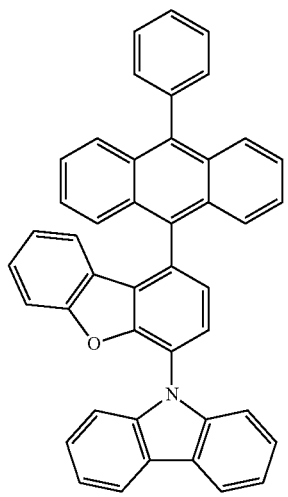

<Compound 19>
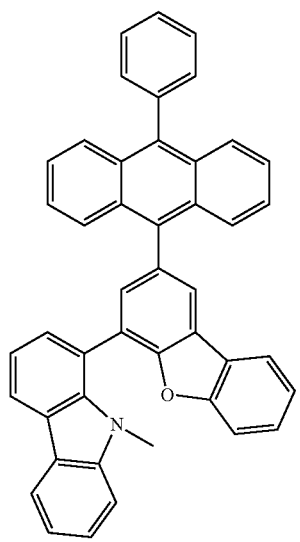
<Compound 20>
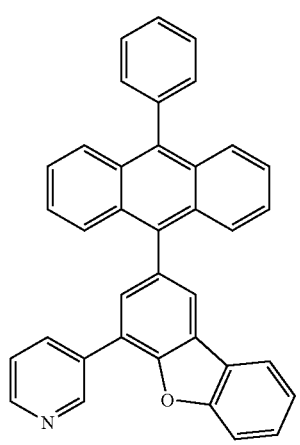
<Compound 21>
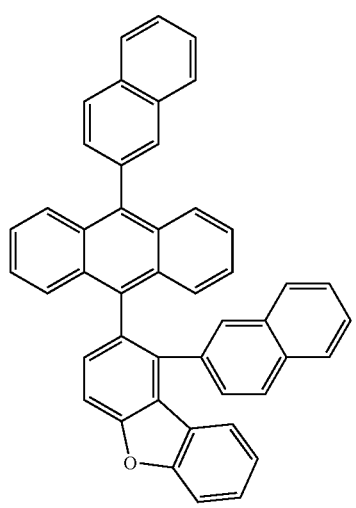
<Compound 22>
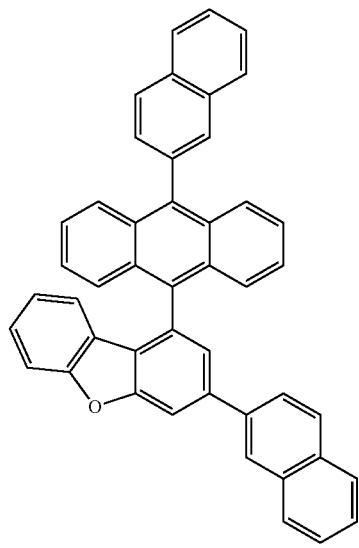
<Compound 23>
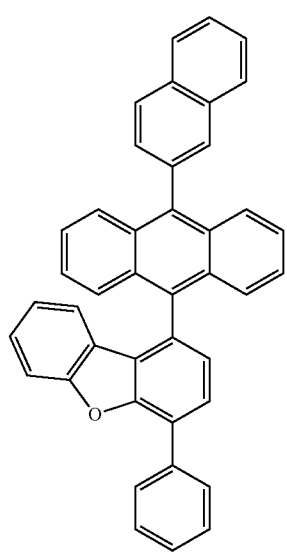
<Compound 24>
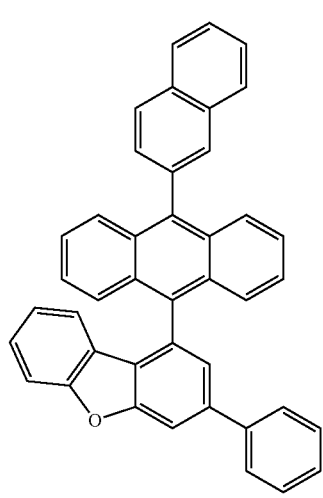

<Compound 25>
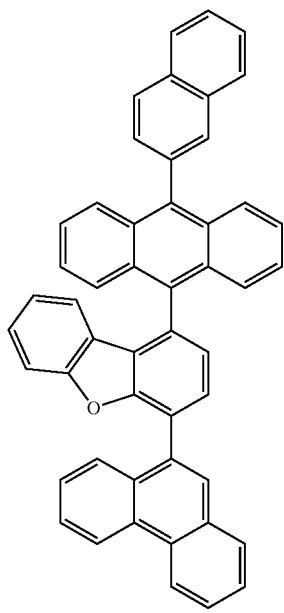
<Compound 26>
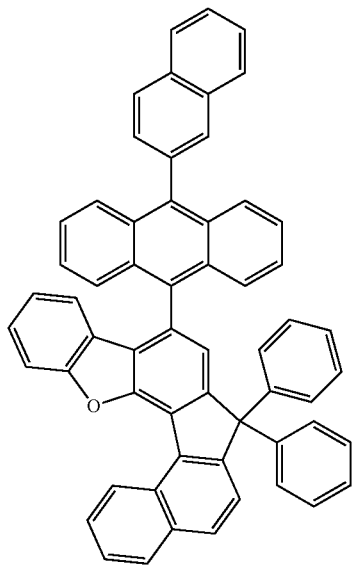
<Compound 27>
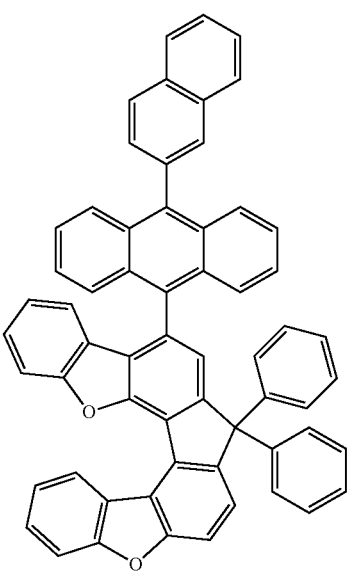
<Compound 28>
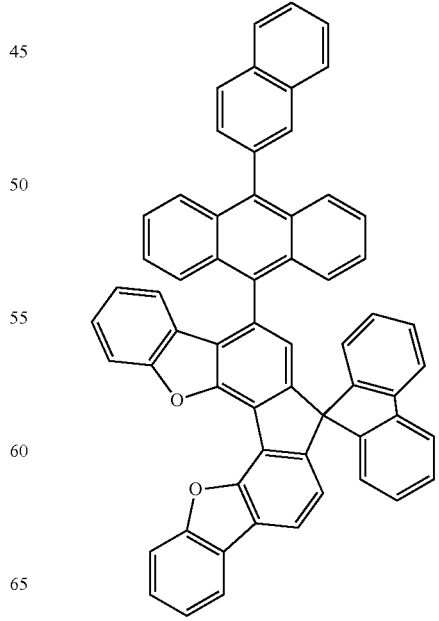

<Compound 29>
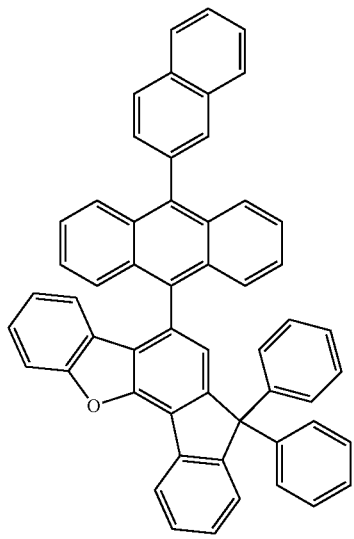
<Compound 30>
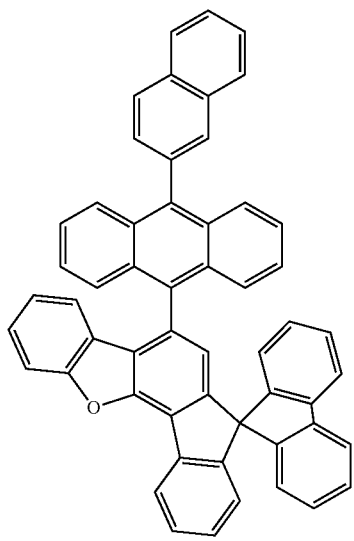
<Compound 31>
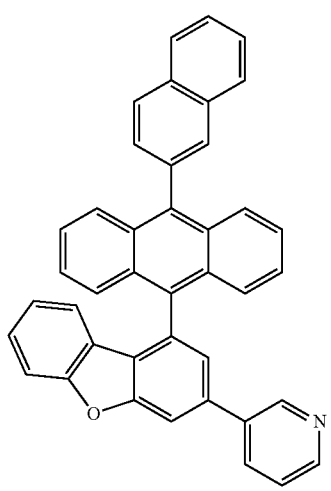
<Compound 32>
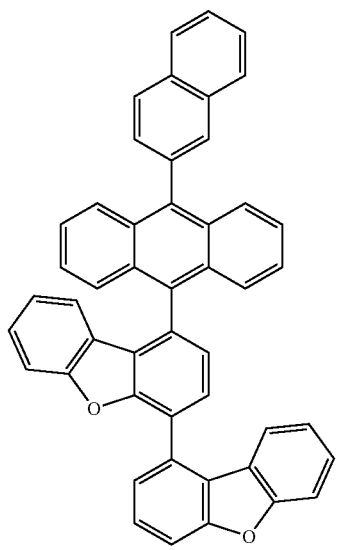
<Compound 33>
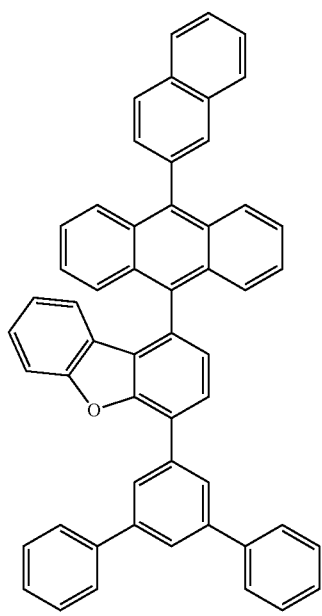

<Compound 34>
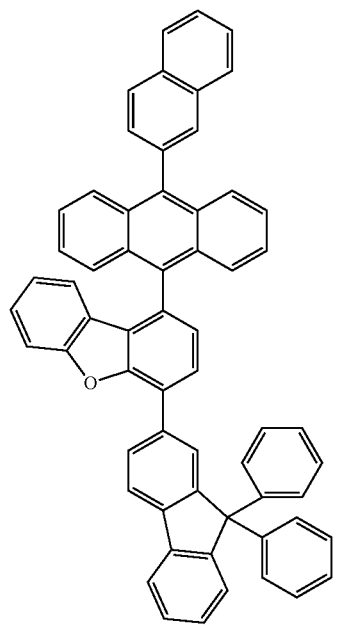
<Compound 36>
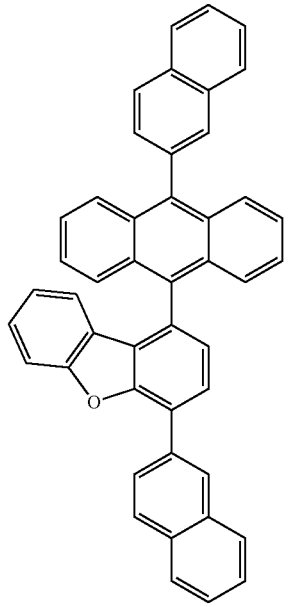
<Compound 35>
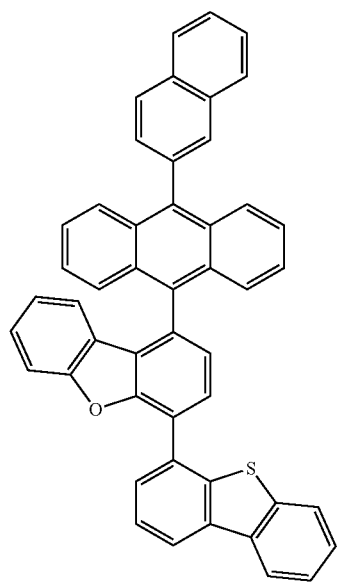
<Compound 37>
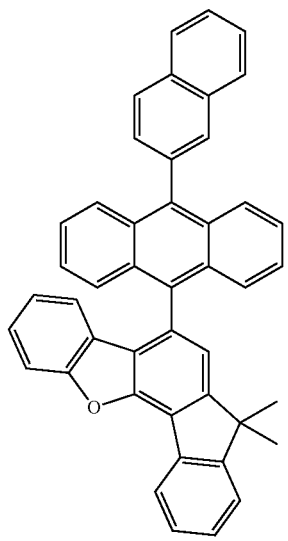

<Compound 38>
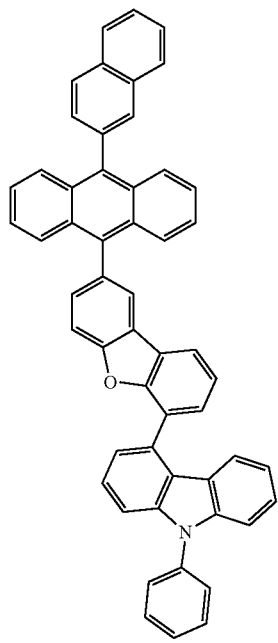
<Compound 39>
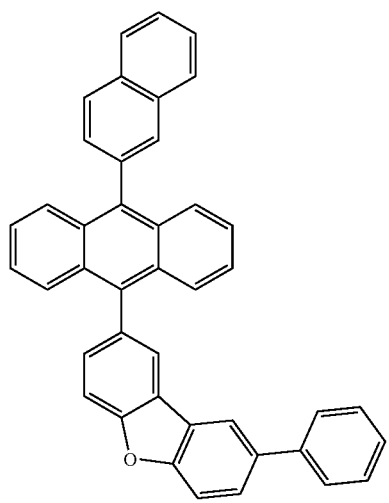
<Compound 40>
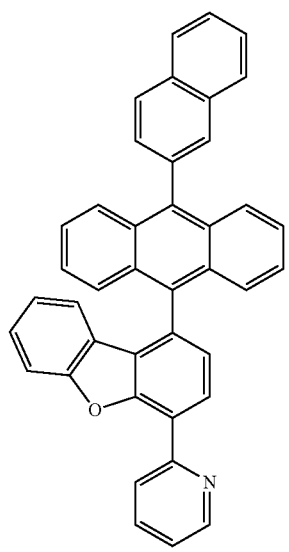
<Compound 41>
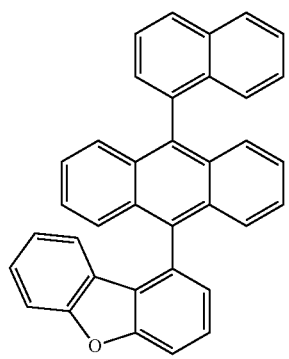
<Compound 42>
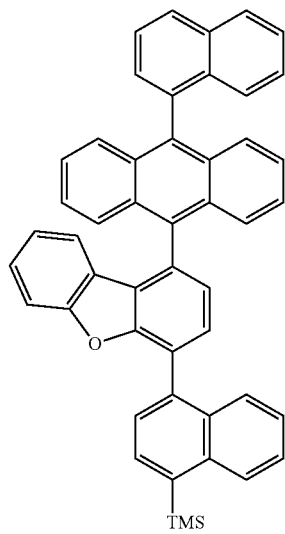

<Compound 43>
<Compound 44>
<Compound 45>
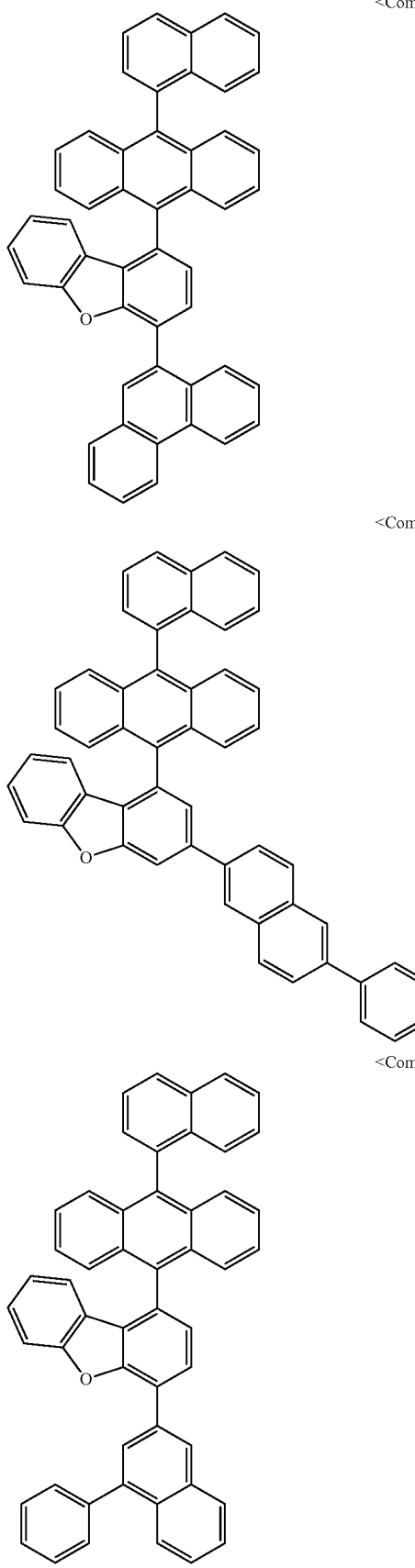
<Compound 46>
<Compound 47>
<Compound 48>
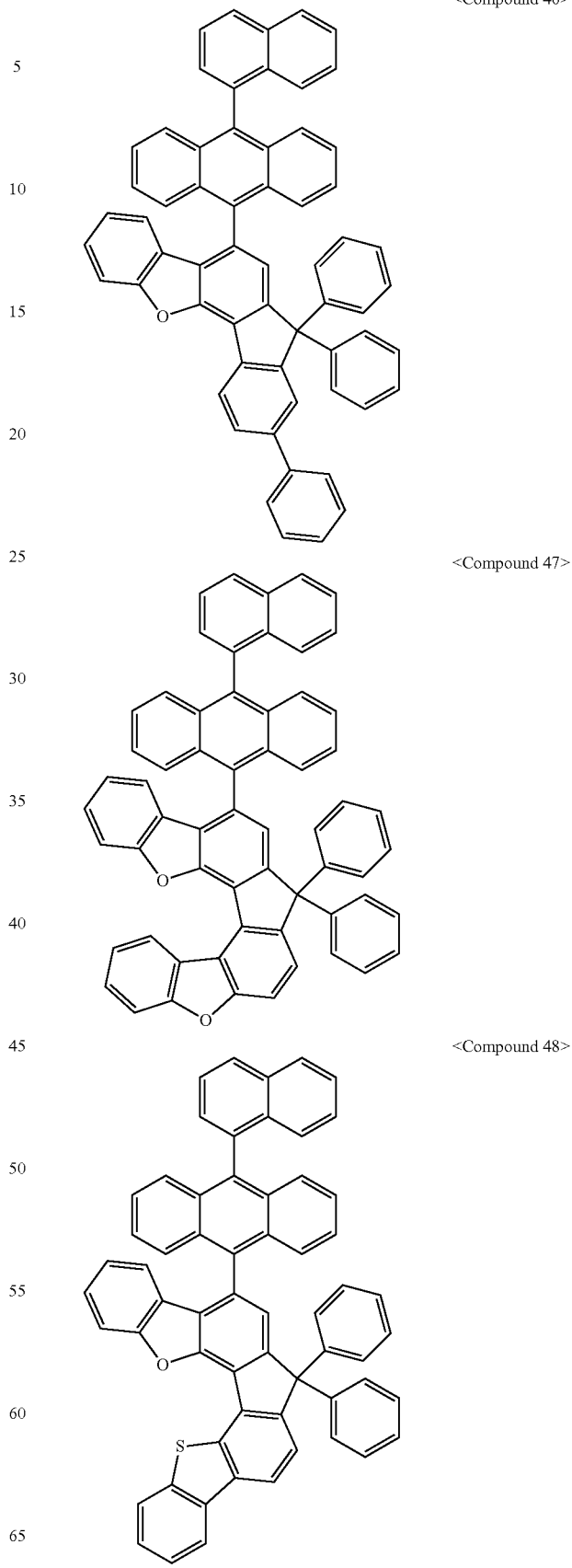

<Compound 49>
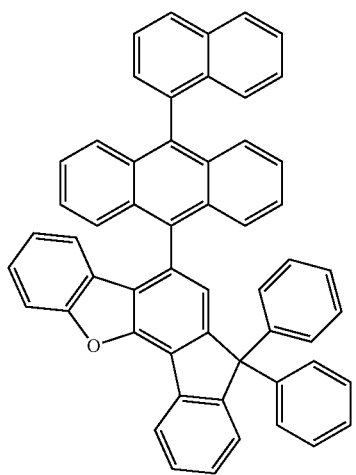
<Compound 50>
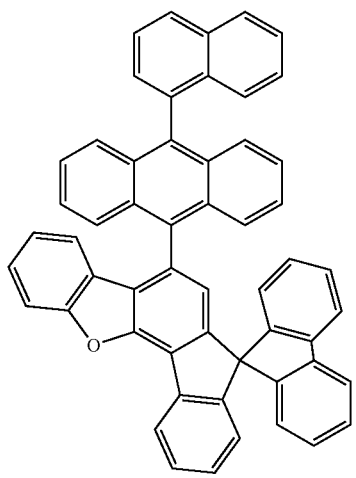
<Compound 51>
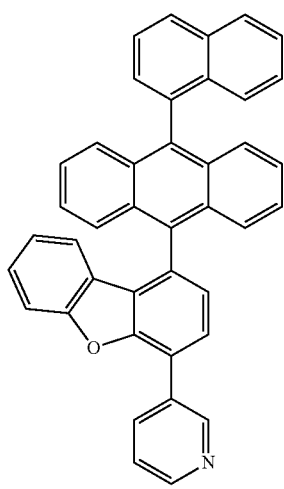
<Compound 52>
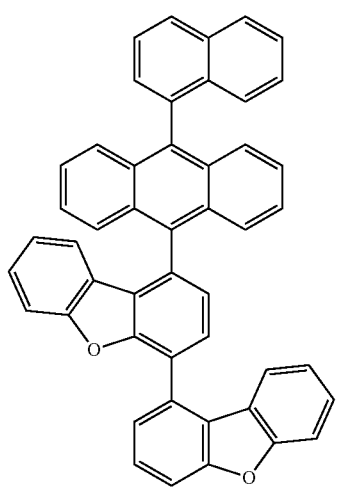
<Compound 53>
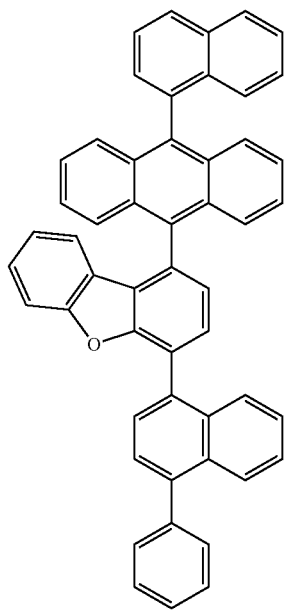

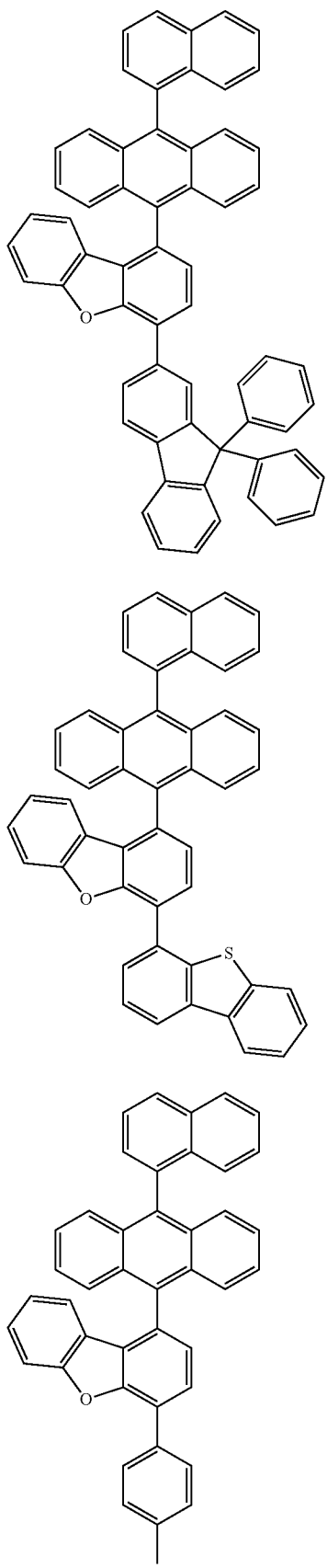
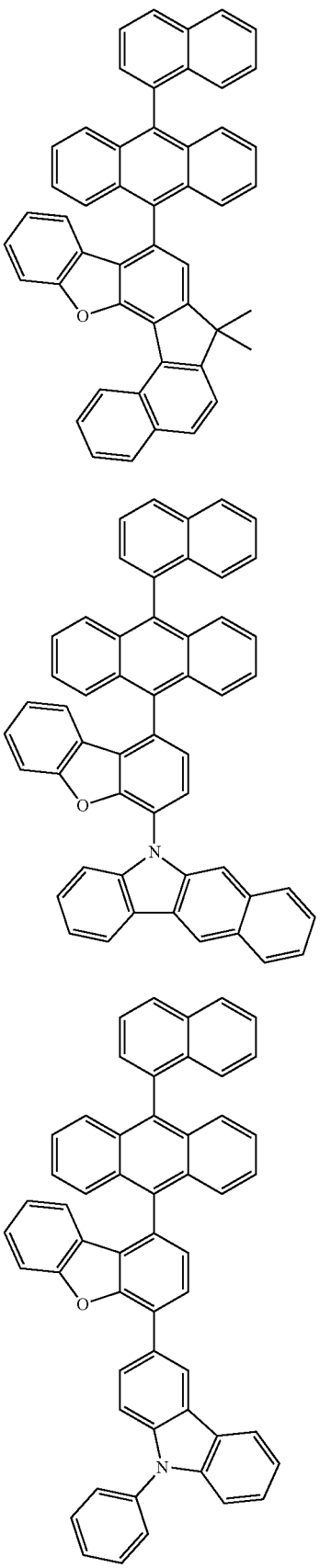

<Compound 60>
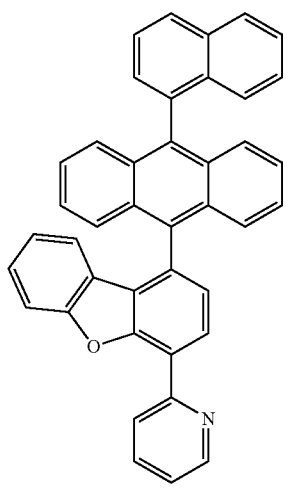
<Compound 61>
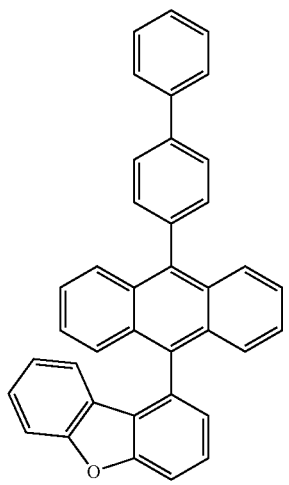
<Compound 62>
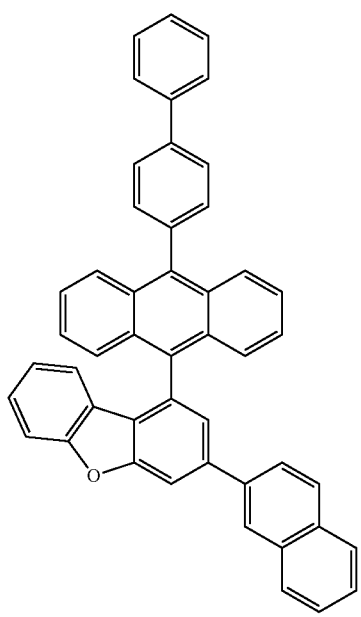
<Compound 63>
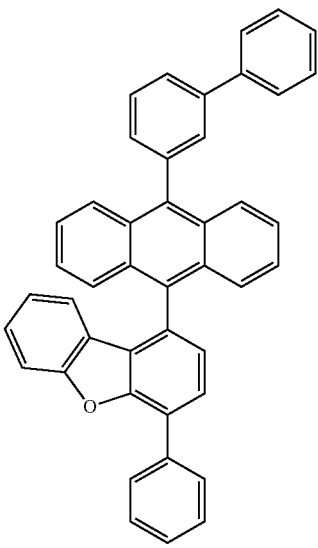
<Compound 64>
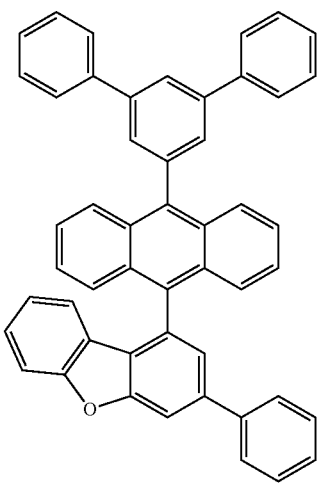
<Compound 65>
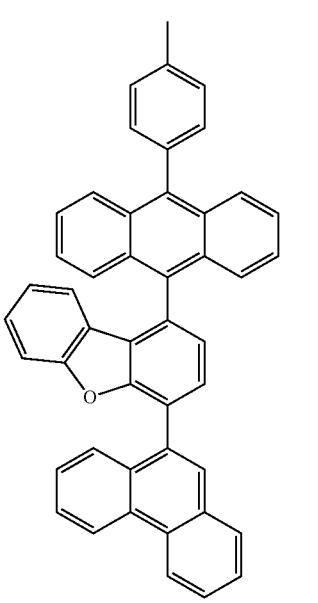

<Compound 66>
<Compound 67>
<Compound 68>
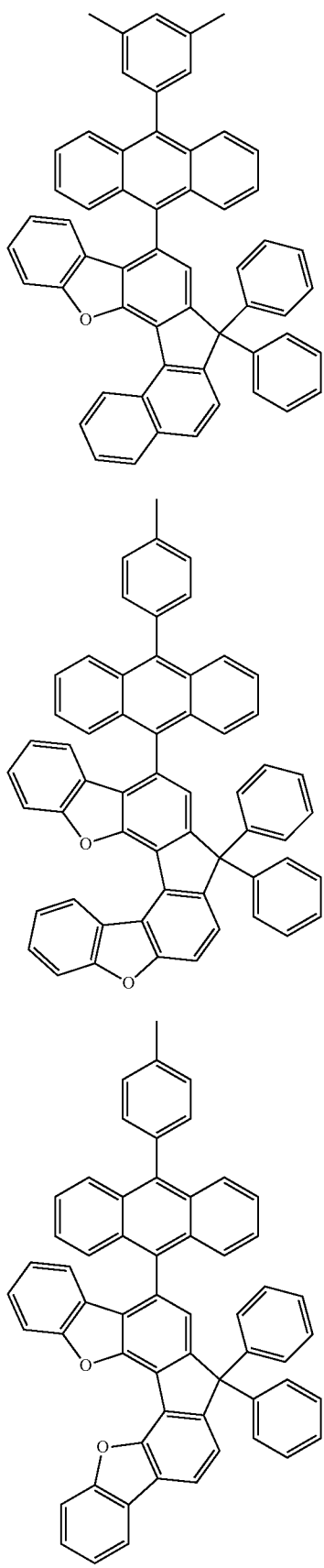
<Compound 69>
<Compound 70>
<Compound 71>
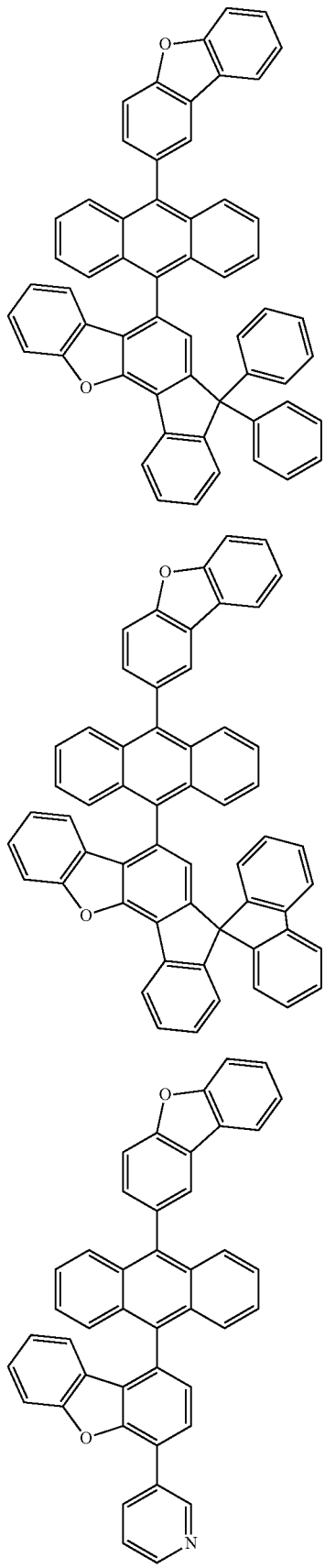

<Compound 72>
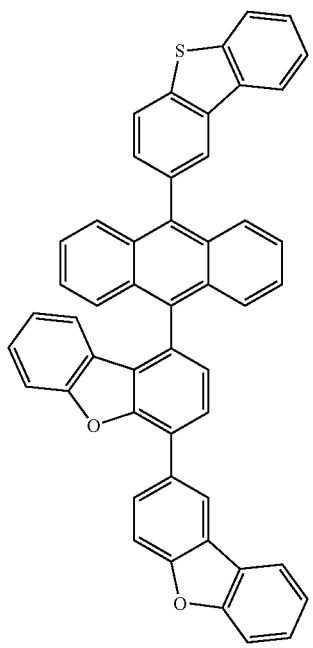
<Compound 73>
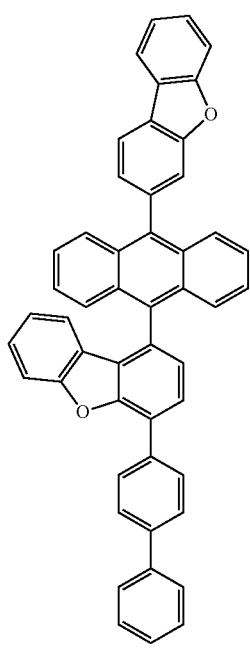
<Compound 74>
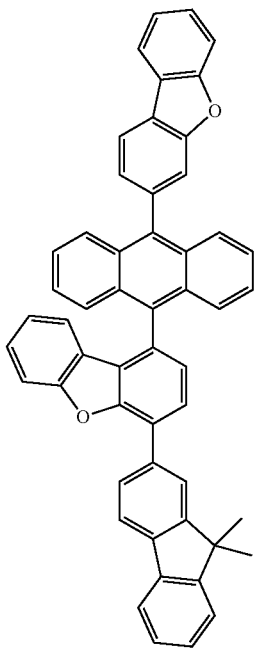
<Compound 75>
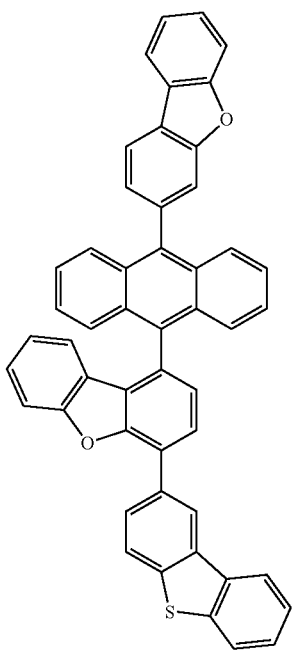

<Compound 76>
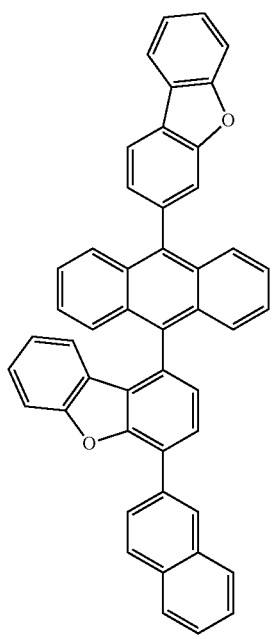
<Compound 77>
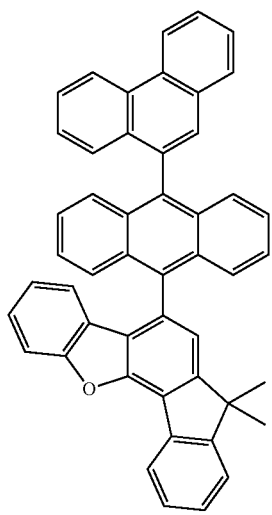
<Compound 78>
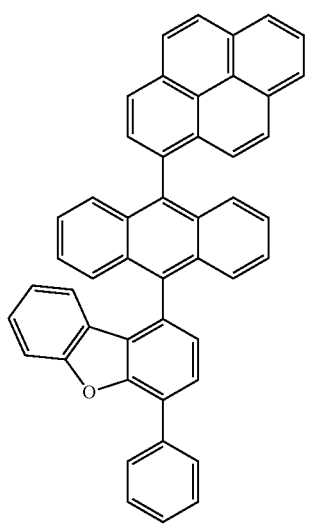
<Compound 79>
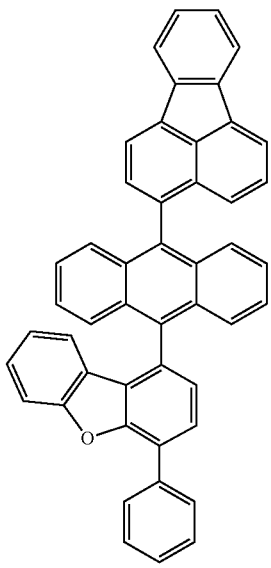
<Compound 80>
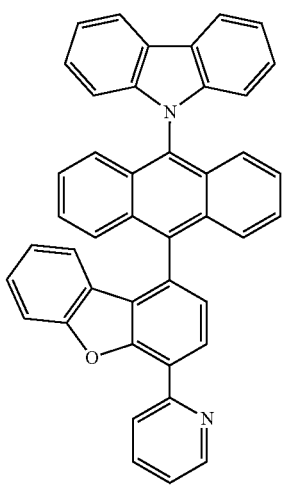
<Compound 81>
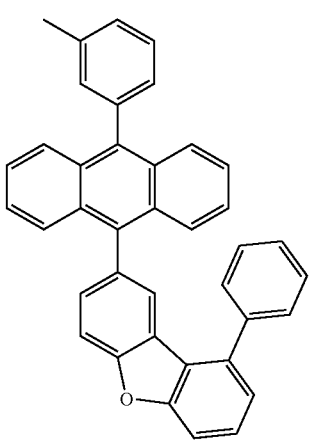

<Compound 82>
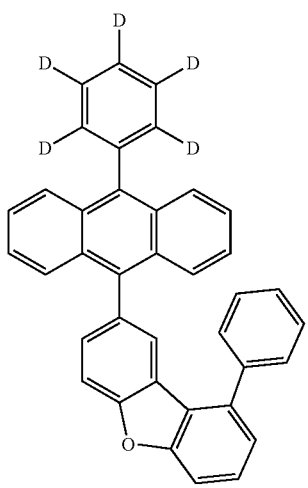
<Compound 83>
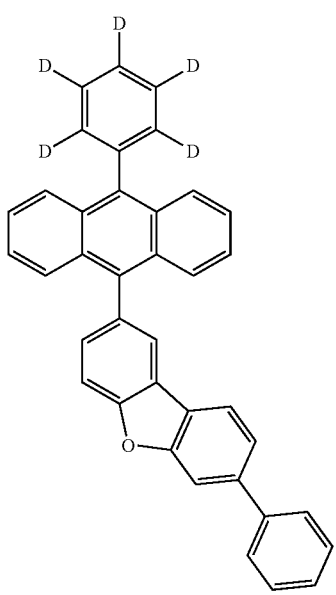
<Compound 84>
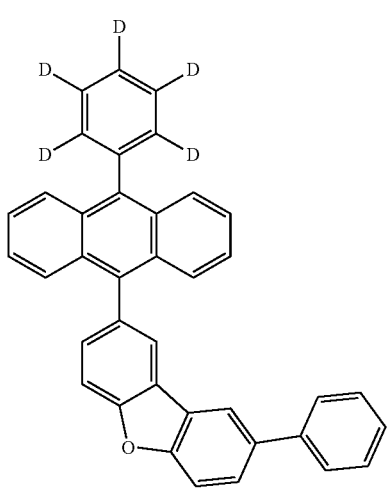
<Compound 85>
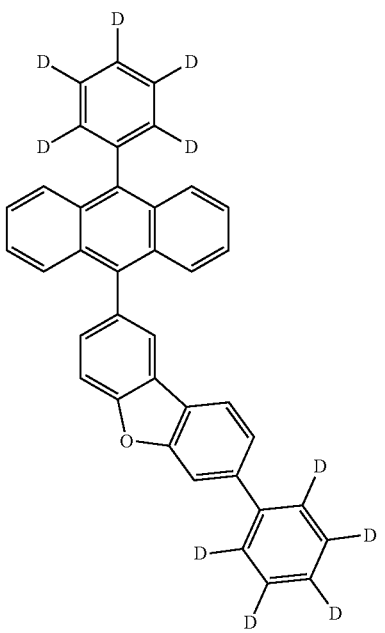
<Compound 86>
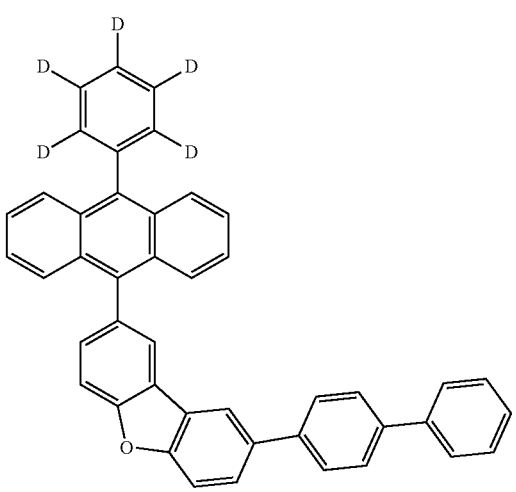

<Compound 87>
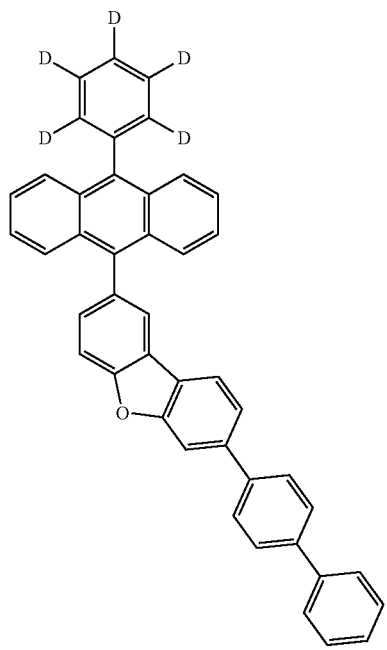
<Compound 88>
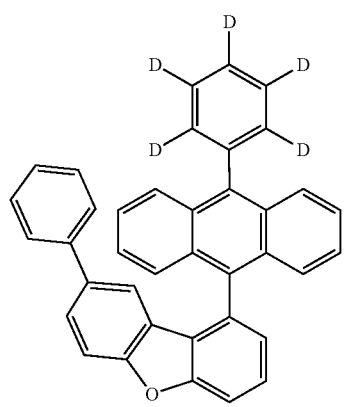
<Compound 89>
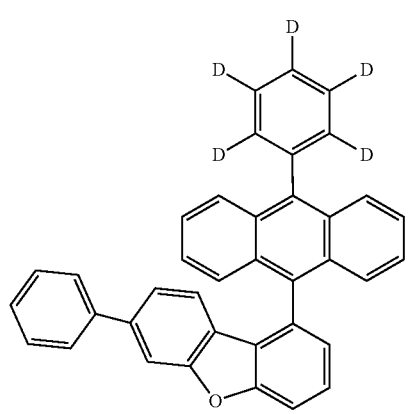
<Compound 90>
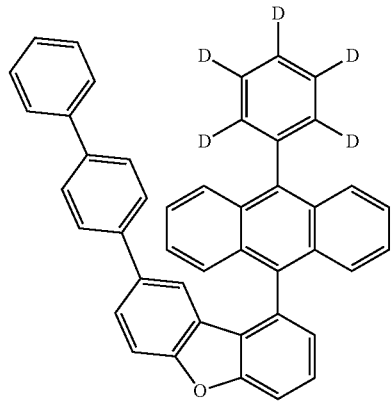
<Compound 91>
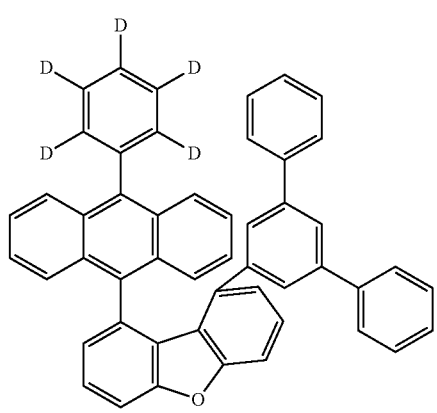
<Compound 92>
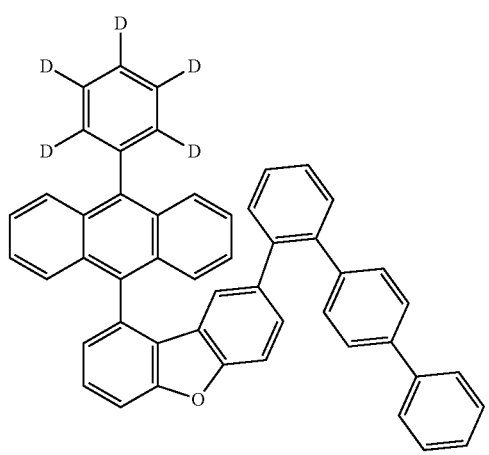

-continued
<Compound 93>
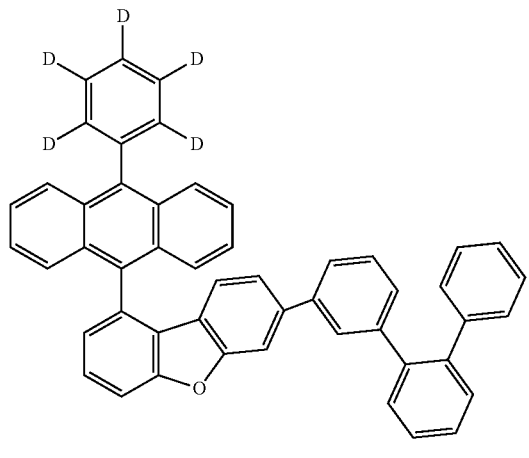
<Compound 94>
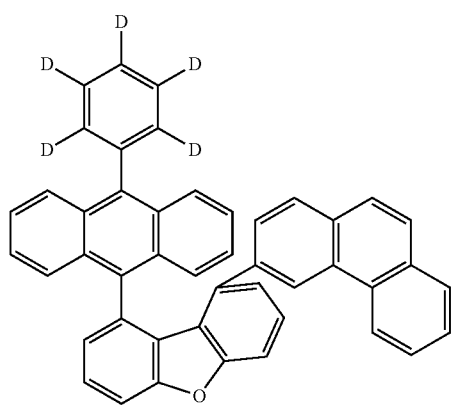
<Compound 95>
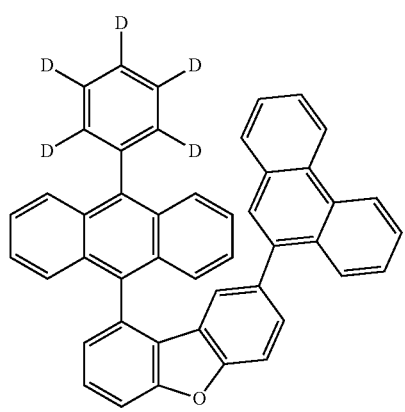
-continued
<Compound 96>
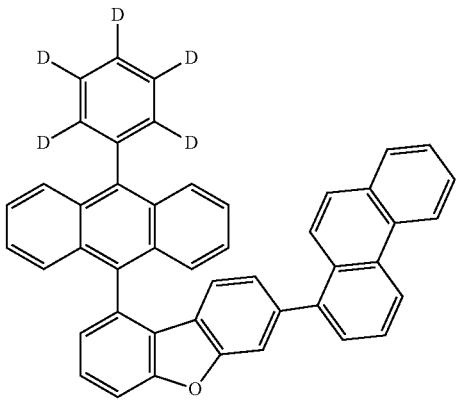
<Compound 97>
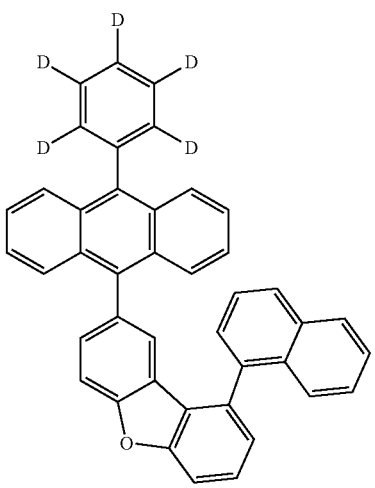
<Compound 98>
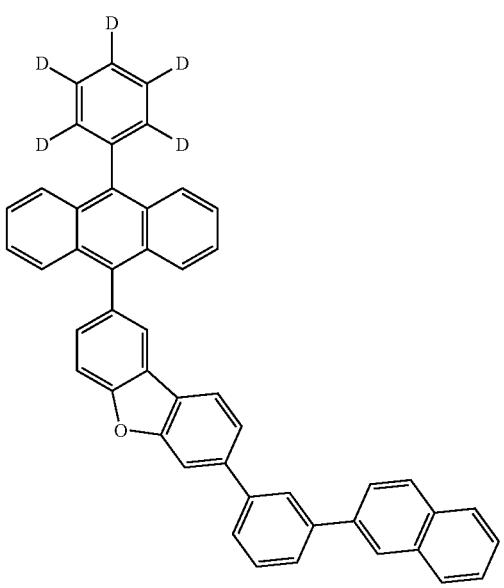

<Compound 99>
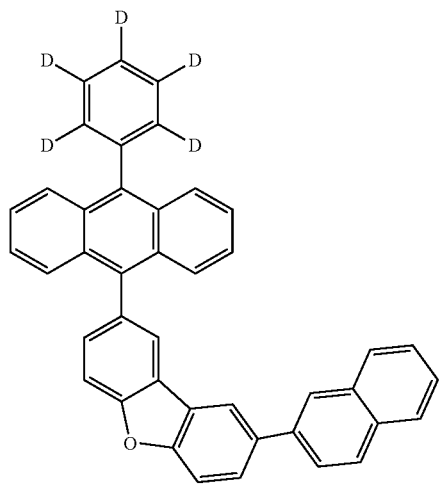
<Compound 102>
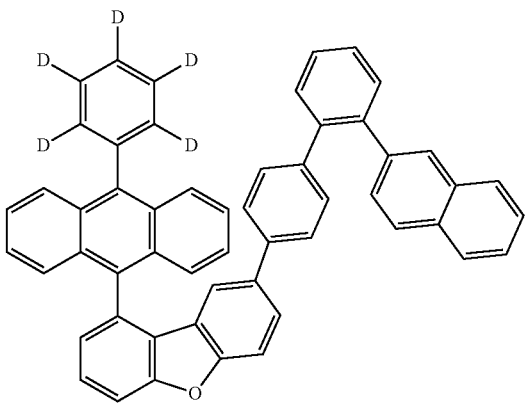
<Compound 100>
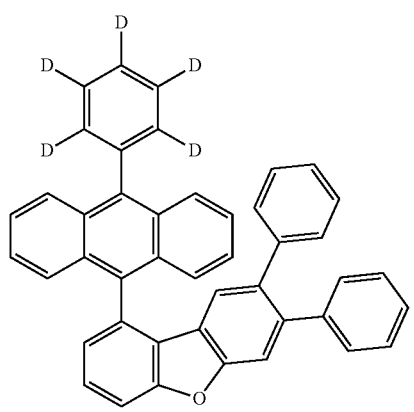
<Compound 103>
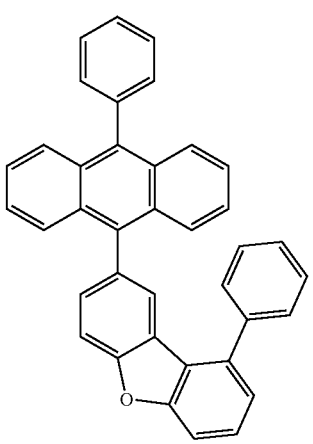
<Compound 101>
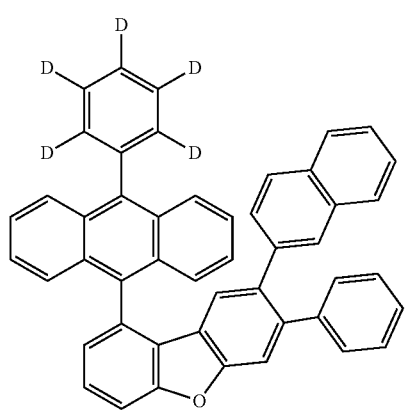
<Compound 104>
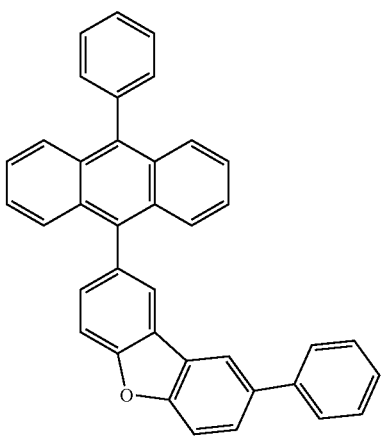

<Compound 105>
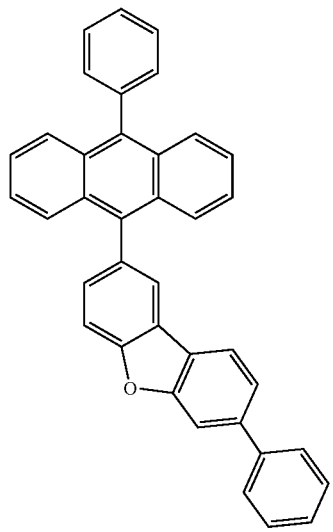
<Compound 106>
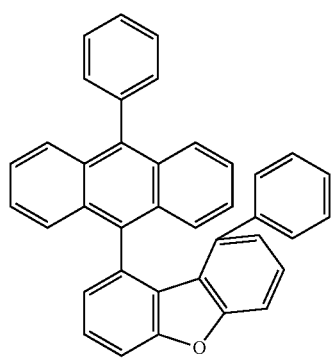
<Compound 107>
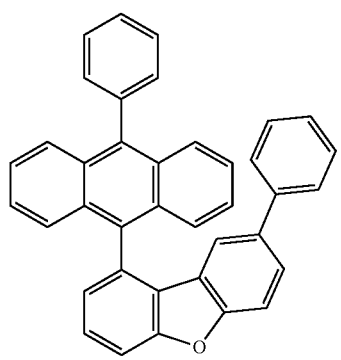
<Compound 108>
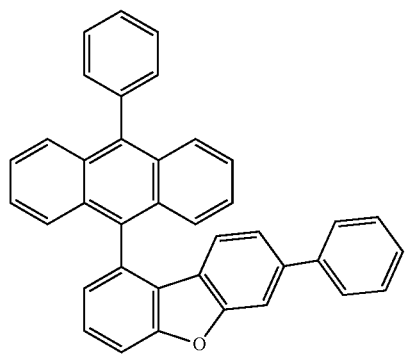
<Compound 109>
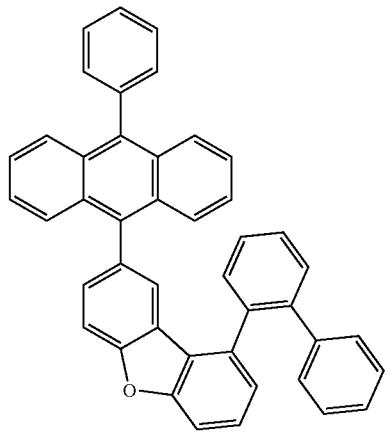
<Compound 110>
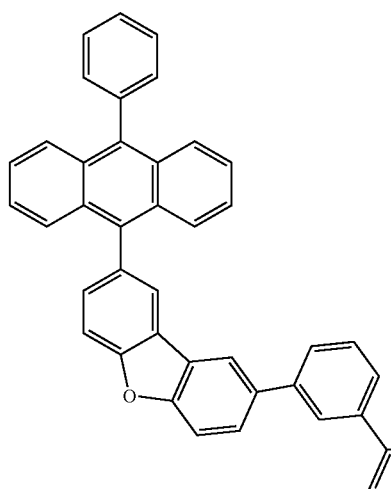
<Compound 111>
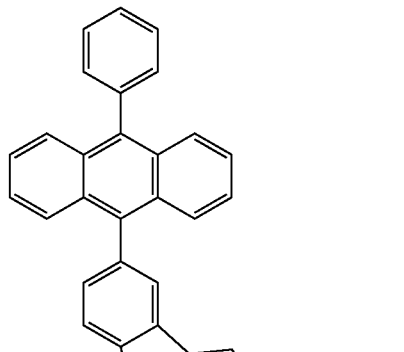

<Compound 112>
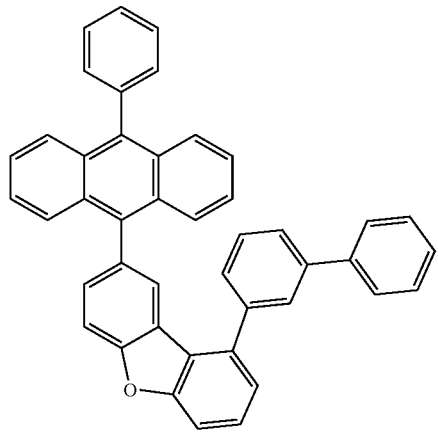
<Compound 113>
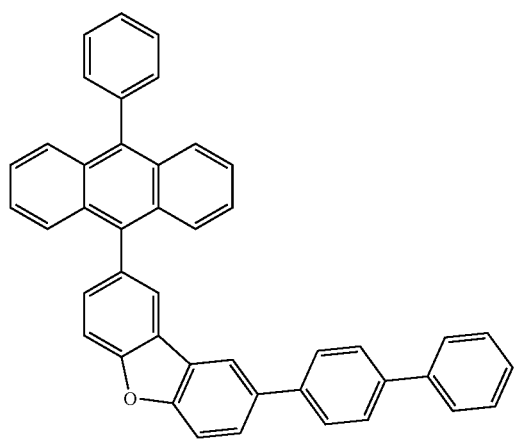
<Compound 114>
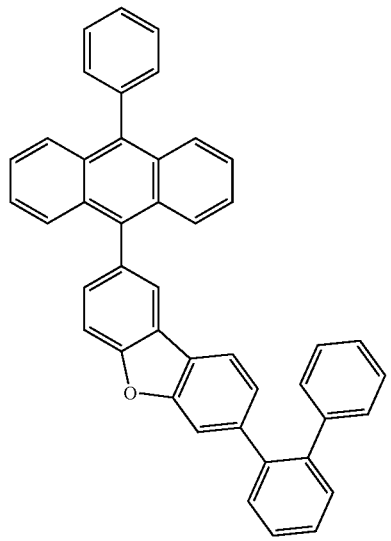
<Compound 115>
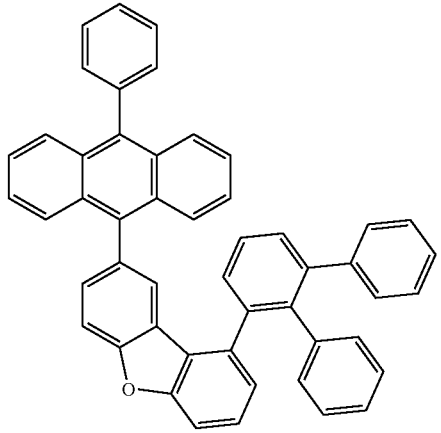
<Compound 116>
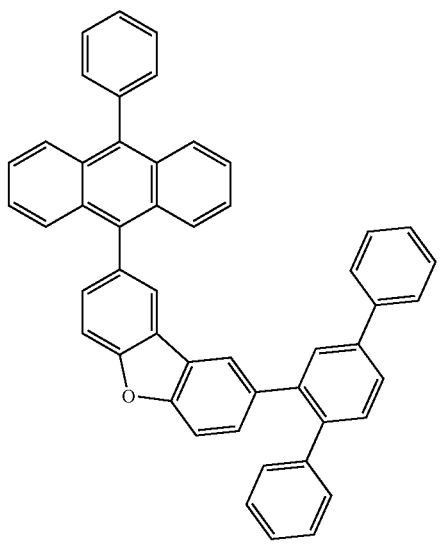
<Compound 117>
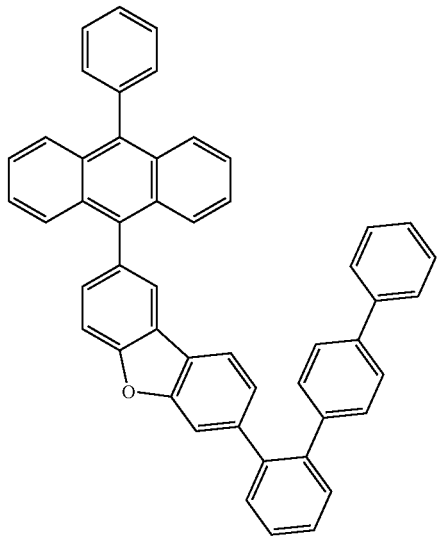

<Compound 118>
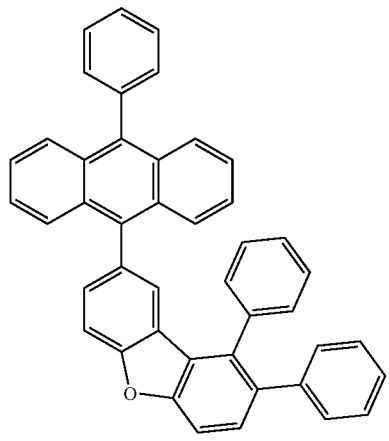
<Compound 119>
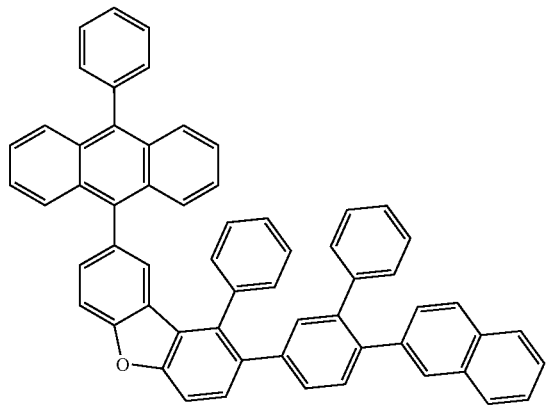
<Compound 120>
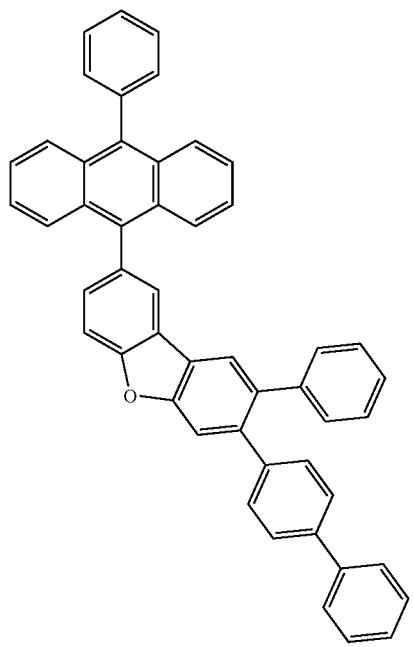
<Compound 121>
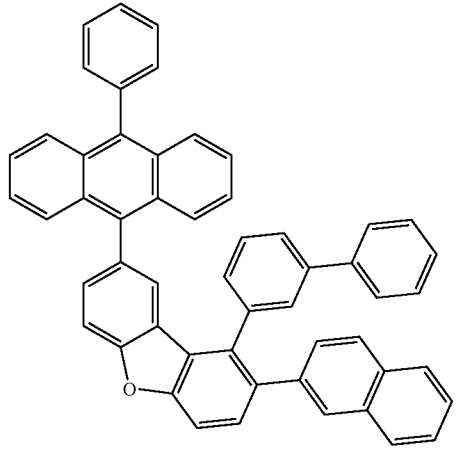
<Compound 122>
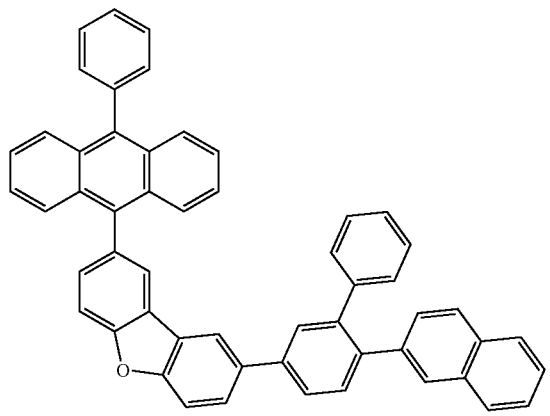
<Compound 123>
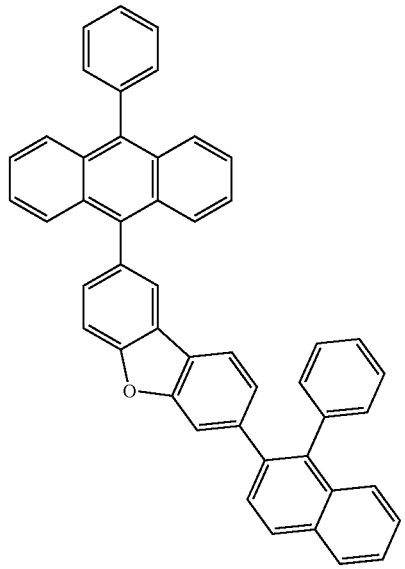

<Compound 124>
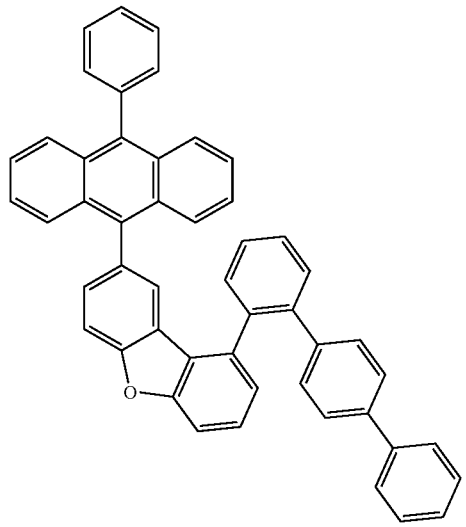
<Compound 125>
<Compound 126>
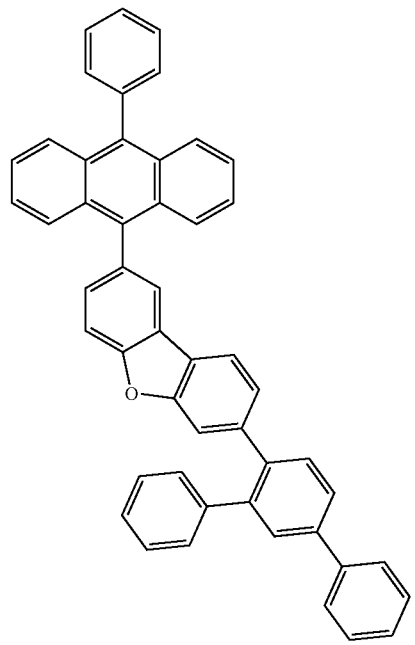
<Compound 127>
<Compound 128>
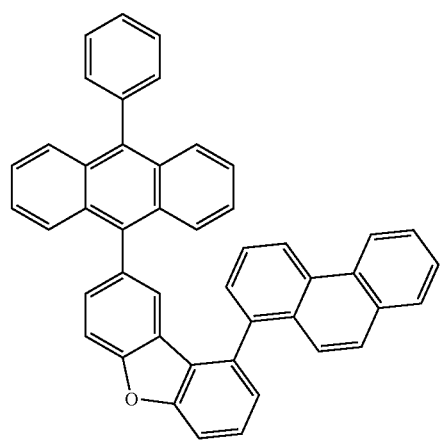

<Compound 129>
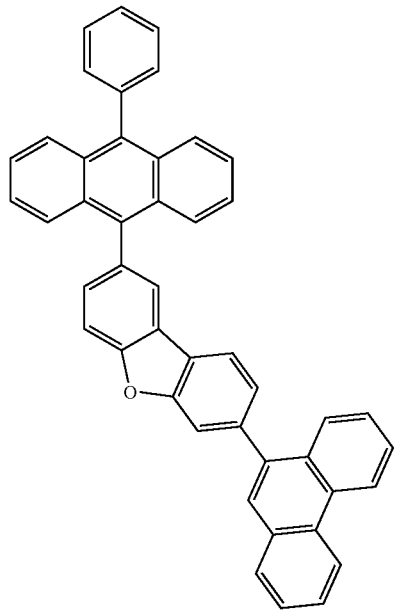
<Compound 130>
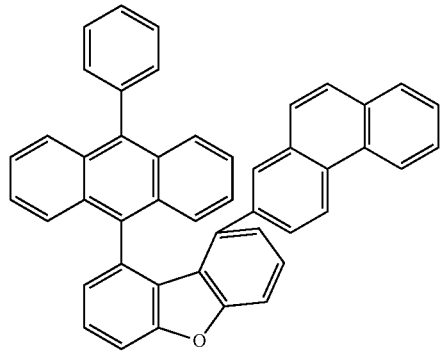
<Compound 131>
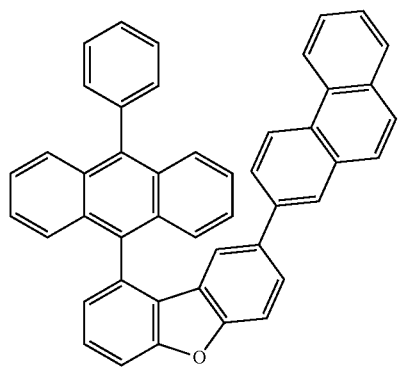
<Compound 132>
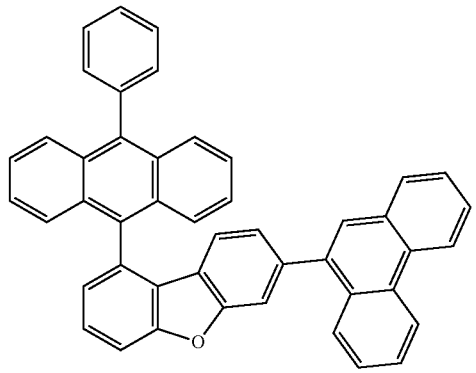
<Compound 133>
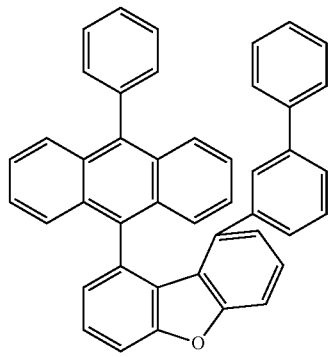
<Compound 134>
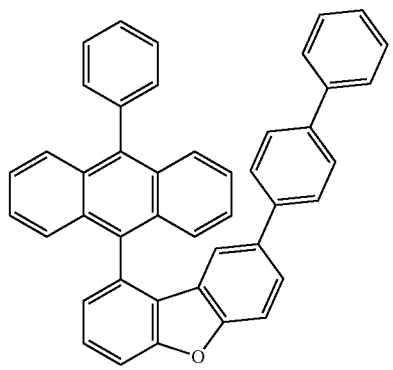
<Compound 135>

<Compound 136>
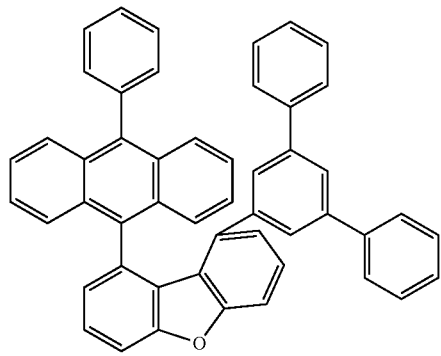
<Compound 139>
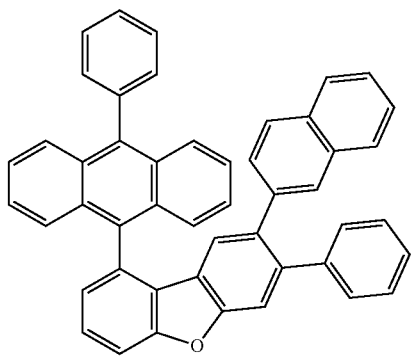
<Compound 137>
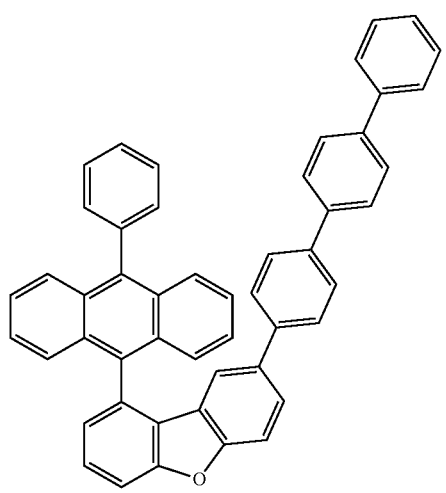
<Compound 140>
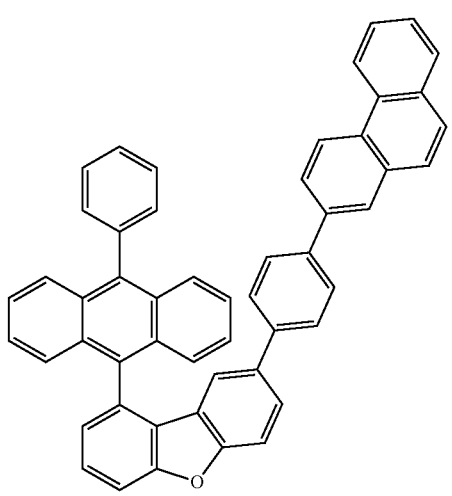
<Compound 138>
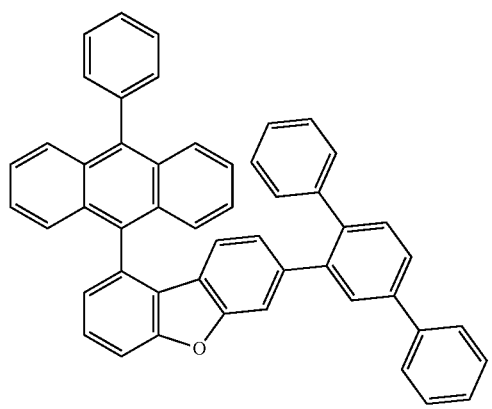
<Compound 141>
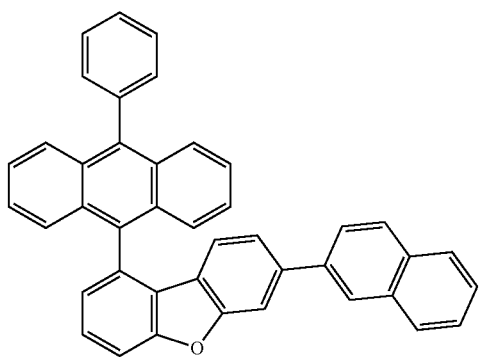

<Compound 142>
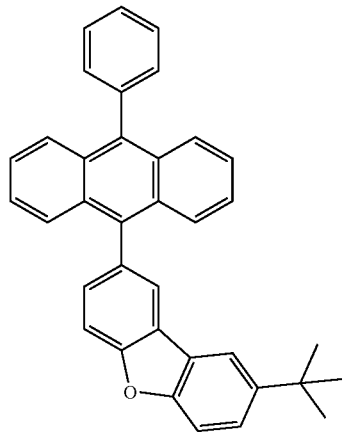
<Compound 143>
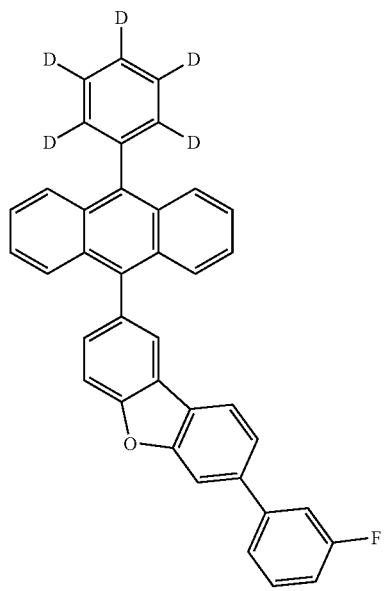
<Compound 144>
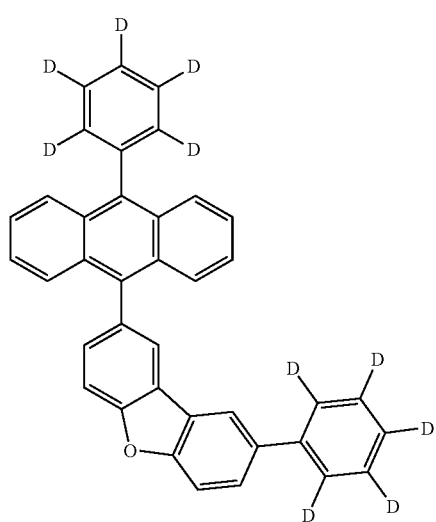
<Compound 145>
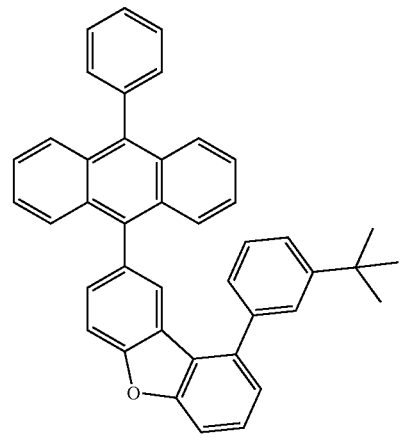
<Compound 146>
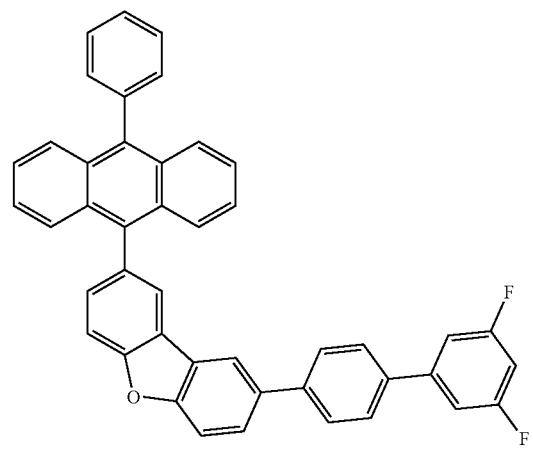
<Compound 147>
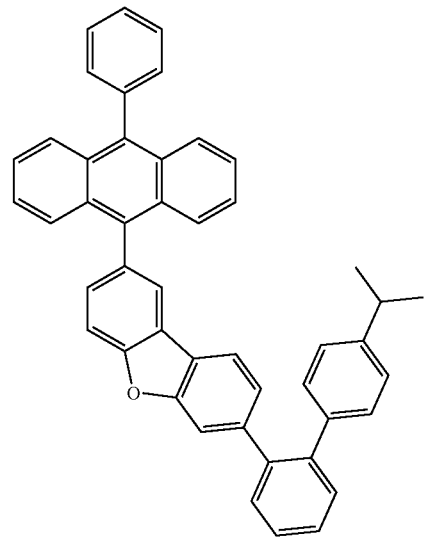

<Compound 148>
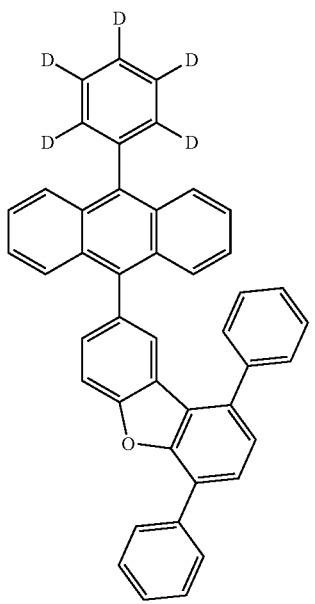
<Compound 149>
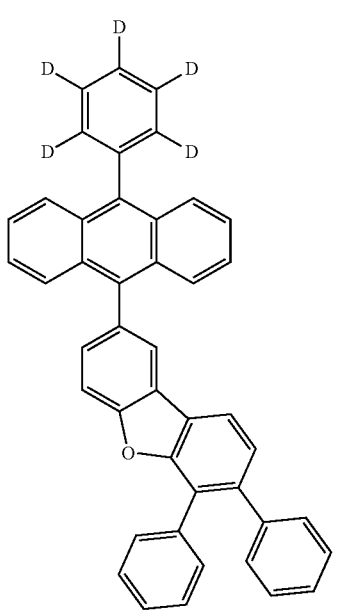
<Compound 150>
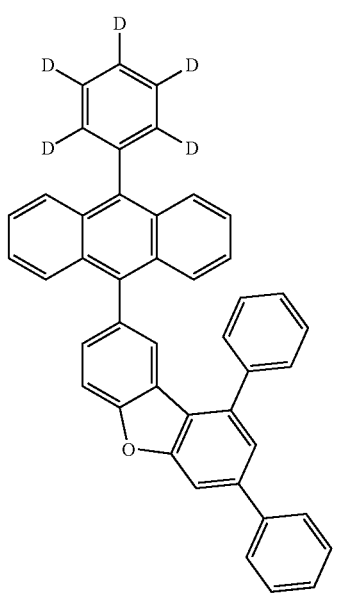
<Compound 151>
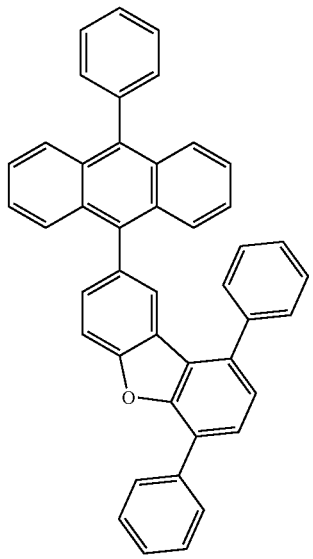

<Compound 152>
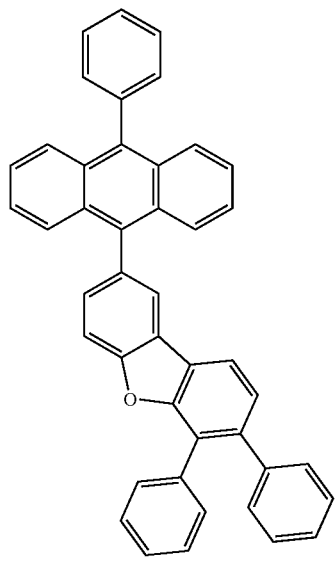
<Compound 154>
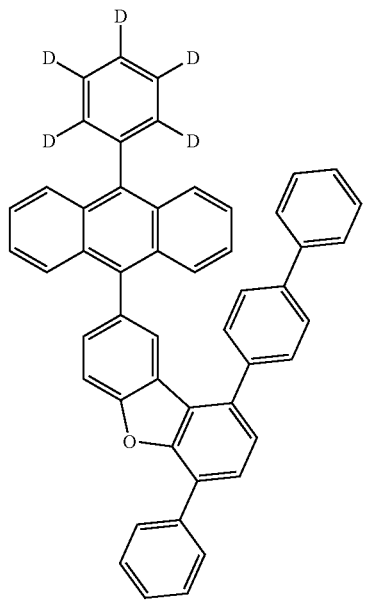
<Compound 153>
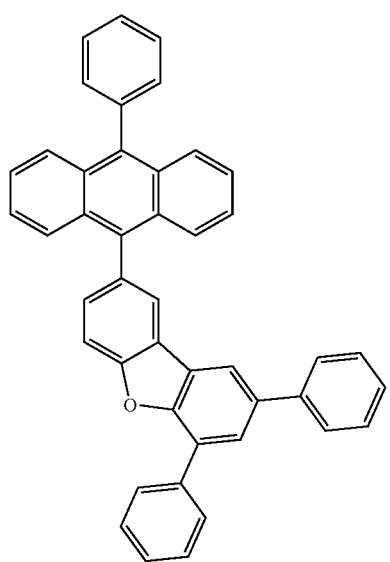
<Compound 155>
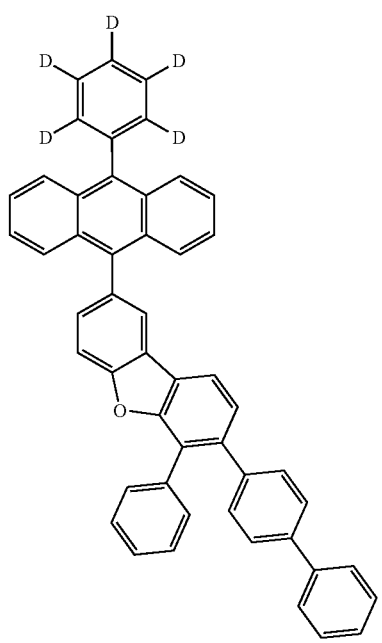

-continued

<Compound 156>

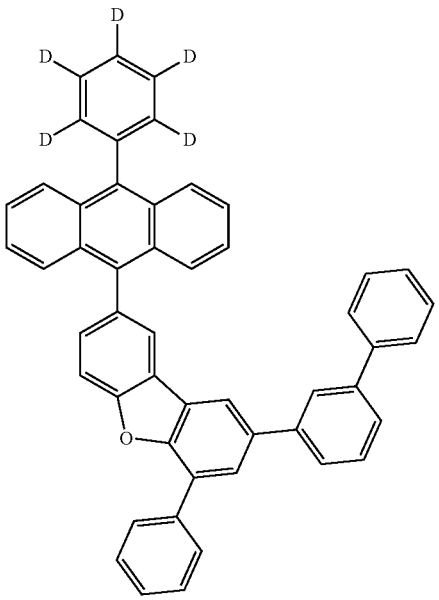

In addition, another aspect of the present invention provides an organic light-emitting device, including a first electrode; a second electrode facing the first electrode; and an organic layer interposed between the first electrode and the second electrode, wherein the organic layer includes at least one selected from anthracene derivatives represented by Chemical Formulas A-1, A-2, B-1, and B-2.

As used herein, the expression "(the organic layer) includes at least one organic compound" is construed to mean that (the organic layer) may include one organic compound falling within the scope of the present invention or two or more different compounds falling within the scope of the present invention.

In some particular embodiments, the organic layer including the compound of the present invention may include at least one of a hole injection layer, a hole transport layer, a functional layer capable of both hole injection and hole transport, an electron transport layer, and an electron injection layer.

In addition, the organic layer interposed between the first electrode and the second electrode may be a light-emitting layer. In this regard, the light-emitting layer may be composed of a host and a dopant wherein the anthracene derivative compound may be used as the host.

Concrete examples of the dopant material used in the light-emitting layer include pyrene compounds, deuterium-substituted pyrene compounds, aryl amines, deuterium-substituted aryl amines, perylene compounds, deuterium-substituted perylene compounds, pyrrole compounds, deuterium-substituted pyrrole compounds, hydrazone compounds, deuterium-substituted hydrazone compounds, carbazole compounds, deuterium-substituted carbazole compounds, stilbene compounds, deuterium-substituted stilbene compounds, starburst-type compounds, deuterium-substituted starburst-type compounds, oxadiazole compounds, deuterium-substituted oxadiazole compounds, coumarin, and deuterium-substituted coumarin, but are not limited thereto.

When the light-emitting layer includes a host and a dopant, the content of the dopant in the light-emitting layer may range from about 0.01 to 20 parts by weight based on 100 parts by weight of the host, but is not limited thereto.

Further, one or more layers selected from among a hole injection layer, a hole transport layer, a functional layer capable of both hole injection and hole transport, a light-emitting layer, an electron transport layer, and an electron injection layer may be deposited using a single-molecule deposition process or a solution process. Here, the deposition process is a process by which a material is vaporized in a vacuum or at a low pressure and deposited to form a layer, and the solution process is a method in which a material is dissolved in a solvent and applied for the formation of a thin film by means of inkjet printing, roll-to-roll coating, screen printing, spray coating, dip coating, spin coating, etc.

Also, the organic light-emitting diode of the present invention may be applied to a device selected from among flat display devices, flexible display devices, monochrome or yellow to white flat illumination devices, and monochrome or yellow to white flexible illumination devices.

In one embodiment of the present invention, a hole transport layer (HTL) may be further deposited between the anode and the organic light-emitting layer while an electron transport layer (ETL) may be further deposited between the cathode and the organic light-emitting layer.

As a material for the hole transport layer, an electron donating molecule with low ionization potential is used. Predominantly, diamine, triamine or tetraamine derivatives having a triphenylamine skeleton are employed, as exemplified by N,N'-bis(3-methylphenyl)-N,N'-diphenyl-[1,1-biphenyl]-4,4'-diamine (TPD) and N,N'-di(naphthalen-1-yl)-N,N'-diphenylbenzidine (a-NPD).

A hole injection layer (HIL) may be further deposited beneath the hole transport layer. No particular limitations are imparted to the hole injection layer material, as long as it is one that is typically used in the art. Examples include CuPc (copper phthalocyanine), and the starburst amines TCTA (4,4',4"-tri(N-carbazolyl)triphenyl-amine), and m-MTDATA (4,4',4"-tris-(3-methylphenylphenyl amino)triphenylamine).

Further, other examples of the hole injection layer material include the oxadiazole derivatives PBD, BMD, BND, and Alq3.

An electron injection layer that functions to facilitate electron injection from the cathode, thus improving the power efficiency of the diode, may be further deposited on the electron transport layer. So long as it is conventionally used in the art, any material can be available for the electron injecting layer without particular limitations. Examples include LiF, NaCl, CsF, $Li_2O$, and BaO.

Below, an organic light-emitting device including the compound of the present invention in a light-emitting layer thereof is explained with reference to FIG. 1.

FIG. 1 is a schematic cross-sectional view of the structure of an organic light-emitting device according to some embodiments of the present invention. The organic light-emitting device includes an anode 20, a hole transport layer 40, an organic light-emitting layer 50, an electron transport layer 60, and a cathode 80, and optionally a hole injection layer 30 or an electron injection layer 70. In addition, one or two intermediate layers may be further formed in the organic light-emitting diode.

Reference is made to FIG. 1 with regard to the organic light-emitting device of the present invention and the fabrication thereof. First, a substrate 10 is coated with an anode electrode material to form an anode 20. So long as it is used in a typical organic EL device, any substrate may be used as the substrate 10. Preferable is an organic substrate or transparent plastic substrate that exhibits excellent transparency, surface smoothness, ease of handling, and waterproofness. As the anode electrode material, indium tin oxide (ITO), indium zinc oxide (IZO), tin oxide (SnO2), or zinc oxide (ZnO), which are transparent and superior in terms of conductivity, may be used.

A hole injection layer material is applied on the anode electrode 20 by thermal deposition in a vacuum or by spin coating to form a hole injecting layer 30. Subsequently, thermal deposition in a vacuum or by spin coating may also be conducted to form a hole transport layer 40 with a hole transport layer material on the hole injecting layer 30.

No particular limitations are imparted to a hole injection layer material that is typically used in the art. For example, mention may be made of 2-TNATA [4,4',4"-tris(2-naphth-ylphenyl-phenylamino)-triphenylamine], NPD [N,N'-di(1-naphthyl)-N,N'-diphenylbenzidine)], TPD [N,N'-diphenyl-N,N'-bis(3-methylphenyl)-1,1'-biphenyl-4,4'-diamine], or DNTPD [N,N'-diphenyl-N,N'-bis-[4-(phenyl-m-tolyl-amino)-phenyl]-biphenyl-4,4'-diamine].

So long as it is typically used in the art, any material for the hole transport layer may be selected without particular limitations. Examples include, but are not limited to, N,N'-bis(3-methylphenyl)-N,N'-diphenyl-[1,1-biphenyl]-4,4'-diamine (TPD) or N,N'-di(naphthalen-1-yl)-N,N'-diphenyl-benzidine (a-NPD).

Then, an organic light-emitting layer 50 is deposited on the hole transport layer 40, optionally followed by the formation of a hole barrier layer (not shown) on the organic light-emitting layer 50 by deposition in a vacuum or by spin coating. When holes traverse the organic light-emitting layer and are introduced into the cathode, the device becomes poor in efficiency and lifespan. Formed of a material with a low HOMO (Highest Occupied Molecular Orbital) level, the hole barrier layer serves to prevent the introduction of holes into the cathode. Any material that has a higher ionization potential than the light emitting compound, as well as being able to carry electrons may be used for the hole barrier layer without limitations. Representative among the hole barrier materials are BAlq, BCP, and TPBI.

Using a vacuum deposition method or a spin coating method, an electron transport layer 60 may be deposited on the hole barrier layer, and then overlaid with an electron injection layer 70. A cathode metal is deposited on the electron injection layer 70 by thermal deposition in a vacuum to form a cathode 80, thus obtaining an organic EL device. Here, the cathode may be made of lithium (Li), magnesium (Mg), aluminum (Al), aluminum-lithium (Al—Li), calcium (Ca), magnesium-indium (Mg—In), or magnesium-silver (Mg—Ag). For a top-emitting OLED, a transparent cathode made of ITO or IZO may be employed.

In some embodiments of the present invention, the light-emitting layer particularly ranges in thickness from 50 to 2,000 Å. Further, the light-emitting layer may be composed of a host and a dopant, with the anthracene derivative of the present invention serving as the host.

Meanwhile, the dopant may be a compound represented by any one of the following Chemical Formulas 1 to 4. In this regard, the light-emitting layer may further contain various dopant materials.

[Chemical Formula 1]

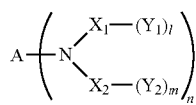

[Chemical Formula 2]

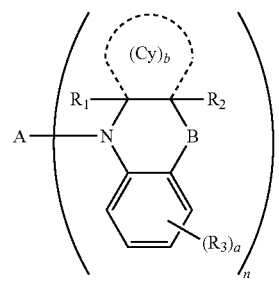

wherein,

A may be any one selected from among a substituted or unsubstituted aryl of 5 to 50 carbon atoms, a substituted or unsubstituted heteroaryl of 3 to 50 carbon atoms bearing O, N, or S as a heteroatom, a substituted or unsubstituted arylene of 6 to 60 carbon atoms, and a substituted or unsubstituted heteroarylene of 3 to 50 carbon atoms bearing O, N, or S as a heteroatom.

In greater detail, A may be a substituted or unsubstituted arylene of 6 to 60 carbon atoms, or a single bond, and particularly any one selected from among anthracene, pyrene, phenanthrene, indenophenanthrene, chrysene, naphthacene, pycene, triphenylene, perylene, and pentacene, and more particularly a substituent represented by the following Chemical Formulas A1 to A10:

[Chemical Formula A1]

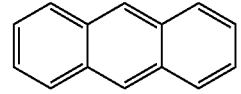

[Chemical Formula A2]

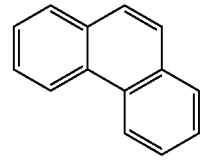

[Chemical Formula A3]

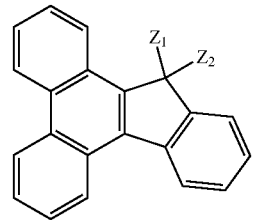

[Chemical Formula A4]

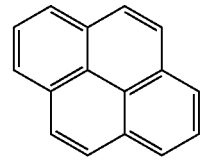

[Chemical Formula A5]

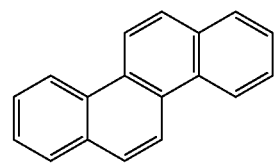

-continued

[Chemical Formula A6]
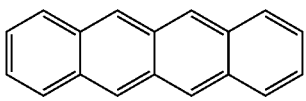

[Chemical Formula A7]
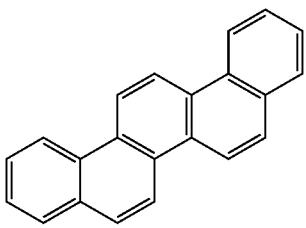

[Chemical Formula A8]
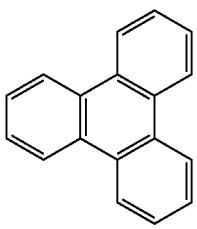

[Chemical Formula A9]
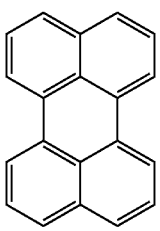

[Chemical Formula A10]
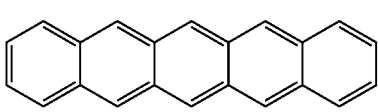

In Chemical Formula A3, Z1 and Z2, which may be the same or different, are each independently selected from the group consisting of a hydrogen atom, a deuterium atom, a substituted or unsubstituted alkyl of 1 to 60 carbon atoms, a substituted or unsubstituted alkenyl of 2 to 60 carbon atoms, a substituted or unsubstituted alkynyl of 2 to 60 carbon atoms, a substituted or unsubstituted alkoxy of 1 to 60 carbon atoms, a substituted or unsubstituted alkylthio of 1 to 60 carbon atoms, a substituted or unsubstituted cycloalkyl of 3 to 60 carbon atoms, a substituted or unsubstituted aryl of 6 to 60 carbon atoms, a substituted or unsubstituted aryloxy of 5 to 60 carbon atoms, a substituted or unsubstituted arylthio of 5 to 60 carbon atoms, a substituted or unsubstituted heteroaryl of 2 to 60 carbon atoms, a substituted or unsubstituted (alkyl)amino of 1 to 60 carbon atoms, a di(substituted or unsubstituted alkyl)amino of 1 to 60 carbon atoms or a (substituted or unsubstituted aryl)amino of 6 to 60 carbon atoms, and a di(substituted or unsubstituted aryl) amino of 6 to 60 carbon atoms and may each form a fused ring with an adjacent radical.

In Chemical Formula 1,

X1 and X2 may each be independently a substituted or unsubstituted arylene of 6 to 30 carbon atoms or a single bond, with a proviso that X1 and X2 may bond to each other, Y1 and Y2, which may the same or different, are each independently selected from the group consisting of a substituted or unsubstituted aryl of 6 to 24 carbon atoms, a substituted or unsubstituted heteroaryl of 2 to 24 carbon atoms, a substituted or unsubstituted alkyl of 1 to 24 carbon atoms, a substituted or unsubstituted heteroalkyl of 1 to 24 carbon atoms, a substituted or unsubstituted cycloalkyl of 3 to 24 carbon atoms, a substituted or unsubstituted alkoxy of 1 to 24 carbon atoms, a cyano, a halogen, a substituted or unsubstituted aryloxy of 6 to 24 carbon atoms, a substituted or unsubstituted alkylsilyl of 1 to 40 carbon atoms, a substituted or unsubstituted arylsilyl of 6 to 30 carbon atoms, a germanium, a phosphorus, a boron, a deuterium, and a hydrogen, with a proviso that Y1 and Y2 may each form with an aliphatic, aromatic, heteroaliphatic, or heteroaromatic fused ring with an adjacent radical, l and m are each an integer of 1 to 20, and n is an integer of 1 to 4.

In Chemical Formula 2,

Cy is a substituted or unsubstituted cycloalkyl of 3 to 8 carbon atoms and b is an integer of 1 to 4, with a proviso that when b is an integer of 2 or greater, the corresponding cycloalkanes may be the same or different and may each be in a fused form having a deuterium or an alkyl as a substituent;

B is a single bond or —[C(R5)(R6)]p- wherein p is an integer of 1 to 3, with a proviso that when p is 2 or greater, the corresponding two or more R5's are the same or different and the corresponding two or more R6's are the same or different;

R1, R2, R3, R5, and R6 may each be independently selected from among a hydrogen atom, a deuterium atom, a halogen atom, a hydroxyl, a cyano, a nitro, an amino, an amidino, a hydrazine, a hydrazone, a carboxyl or a salt thereof, a sulfonic acid or a salt thereof, a phosphoric acid or a salt thereof, a substituted or unsubstituted alkyl of 1 to 60 carbon atoms, a substituted or unsubstituted alkenyl of 2 to 60 carbon atoms, a substituted or unsubstituted alkynyl of 2 to 60 carbon atoms, a substituted or unsubstituted alkoxy of 1 to 60 carbon atoms, a substituted or unsubstituted alkylthio of 1 to 60 carbon atoms, a substituted or unsubstituted cycloalkyl of 3 to 60 carbon atoms, a substituted or unsubstituted aryl of 6 to 60 carbon atoms, a substituted or unsubstituted aryloxy of 5 to 60 carbon atoms, a substituted or unsubstituted arylthio of 5 to 60 carbon atoms, a substituted or unsubstituted heteroaryl of 2 to 60 carbon atoms, a substituted or unsubstituted (alkyl)amino of 1 to 60 carbon atoms, a di(substituted or unsubstituted alkyl)amino of 1 to 60 carbon atoms or a (substituted or unsubstituted aryl) amino of 6 to 60 carbon atoms, a di(substituted or unsubstituted aryl)amino of 6 to 60 carbon atoms, a substituted or unsubstituted alkylsilyl of 1 to 40 carbon atoms, a substituted or unsubstituted arylsilyl of 6 to 30 carbon atoms, a germanium, a phosphorus, and a boron, a is an integer of 1 to 4, with a proviso that when a is 2 or greater, the corresponding plural R3's may be the same or different and may each be in a fused form; and n is an integer of 1 to 4.

[Chemical Formula 3]
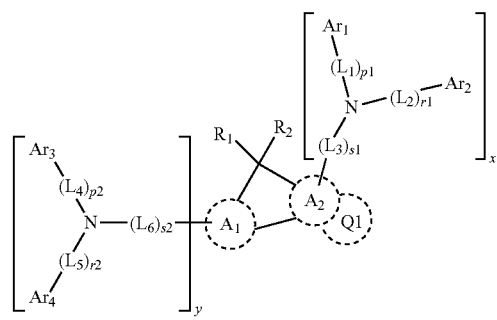

-continued

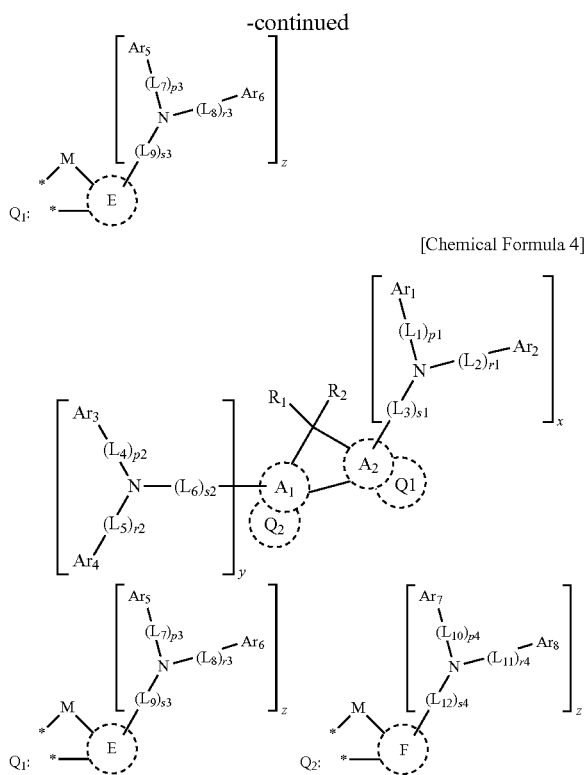

[Chemical Formula 4]

wherein,

A1, A2, E, and F, which may be the same or different, are each independently a substituted or unsubstituted aromatic hydrocarbon ring of 6 to 50 carbon atoms, or a substituted or unsubstituted heteroaromatic ring of 2 to 40 carbon atoms wherein two adjacent carbon atoms of the aromatic ring A1 and two adjacent carbon atoms of the aromatic ring A2 form a 5-membered fused ring together with a carbon atom to which substituents R1 and R2 are bonded;

linkers L1 to L12 may be the same or different and are each independently selected from among a direct bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

M is any one selected from among N—R3, CR4R5, SiR6R7, GeR8R9, O, S, and Se;

R1 to R9, and Ar1 to Ar8 may be the same or different and are each independently any one selected from among a hydrogen, a deuterium, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkyl-thioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkylgermanium of 1 to 30 carbon atoms, a substituted or unsubstituted arylgermanium of 6 to 30 carbon atoms, a cyano, a nitro, and a halogen, with a proviso that R1 and R2 together may form a mono- or polycyclic aliphatic or aromatic ring that may be a heterocyclic ring containing a heteroatom selected from among N, O, P, Si, S, Ge, Se, and Te as a ring member;

p1 to p4, r1 to r4, and s1 to s4 are each independently an integer of 1 to 3, with a proviso that when any of them is 2 or greater, the corresponding linkers may be the same or different, x is an integer of 1 or 2, and y and z may be the same or different and are each independently an integer of 0 to 3;

respective rings may be formed between Ar1 and Ar2, between Ar3 and Ar4, between Ar5 and Ar6, and between Ar7 and Ar8;

two adjacent carbon atoms of the A2 ring moiety of Chemical Formula 3 may occupy respective positions * of Structural Formula Q1 to form a fused ring; and two adjacent carbon atoms of the A1 ring moiety of Chemical Formula 4 may occupy respective positions * of structural Formula Q2 to form a fused ring.

The amine radical of Chemical Formulas 1 to 4 may be represented by any one selected from among, but not limited to, the following Substituents 1 to 52:

[Substituent 1]

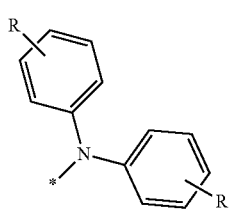

[Substituent 2]

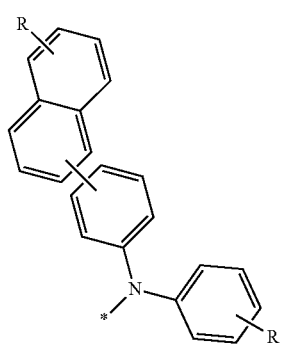

[Substituent 3]

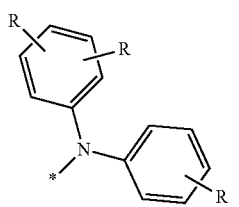

[Substituent 4]
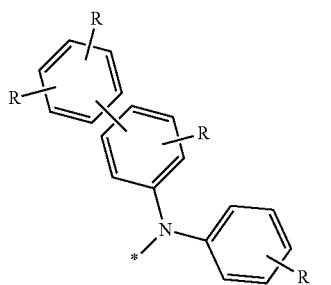
[Substituent 5]
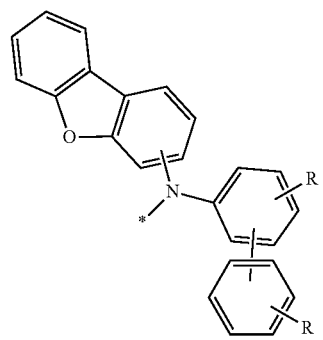
[Substituent 6]
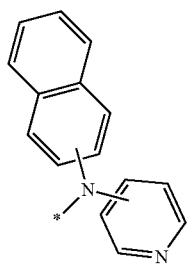
[Substituent 7]
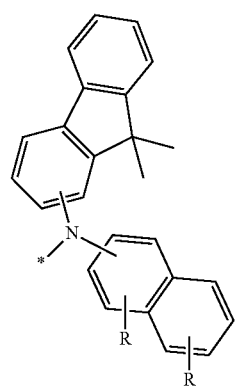
[Substituent 8]
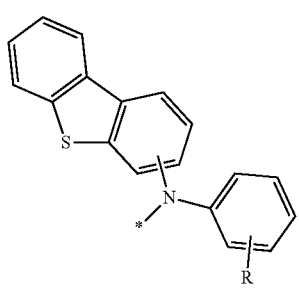
[Substituent 9]
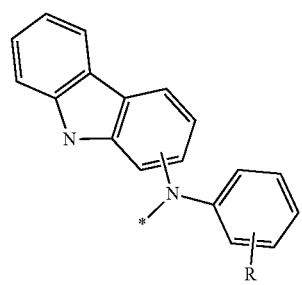
[Substituent 10]
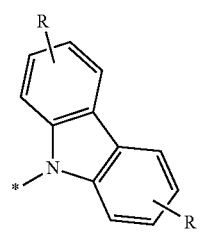
[Substituent 11]
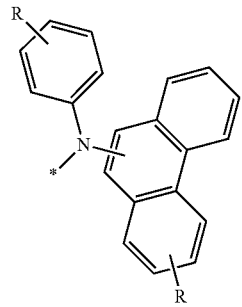
[Substituent 12]
[Substituent 13]

[Substituent 14]
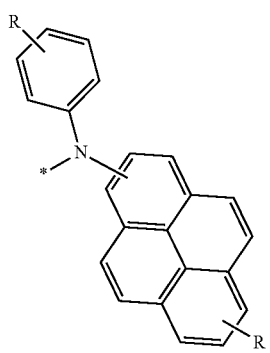
[Substituent 15]
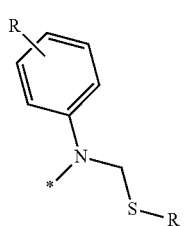
[Substituent 16]
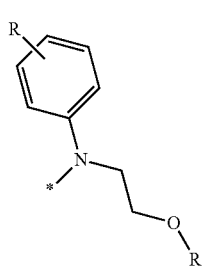
[Substituent 17]
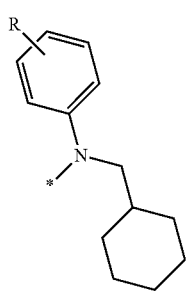
[Substituent 18]
[Substituent 19]
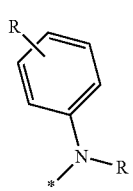
[Substituent 20]
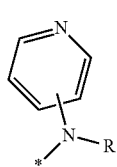
[Substituent 21]
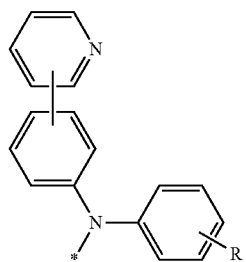
[Substituent 22]
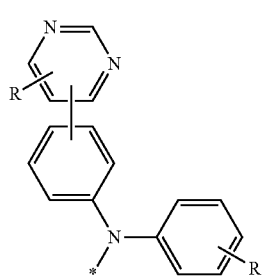
[Substituent 23]
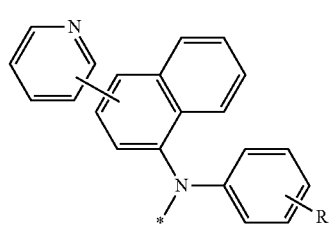
[Substituent 24]
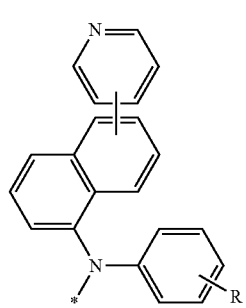
[Substituent 25]
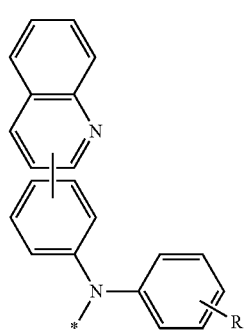

[Substituent 26]
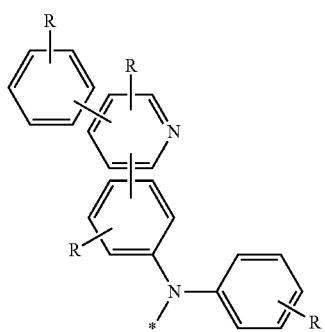
[Substituent 27]
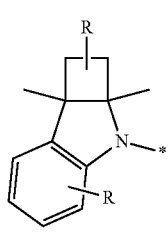
[Substituent 28]
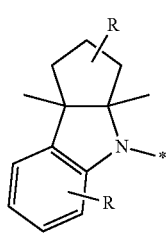
[Substituent 29]
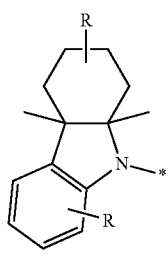
[Substituent 30]
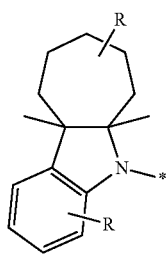
[Substituent 31]
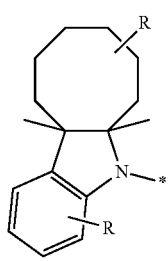
[Substituent 32]
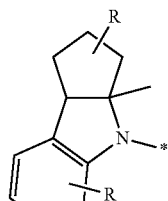
[Substituent 33]
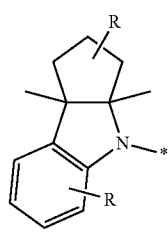
[Substituent 34]
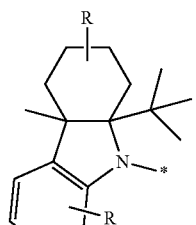
[Substituent 35]
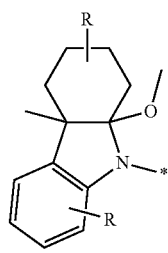
[Substituent 36]
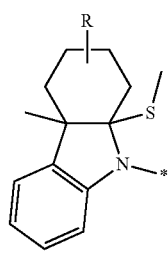
[Substituent 37]
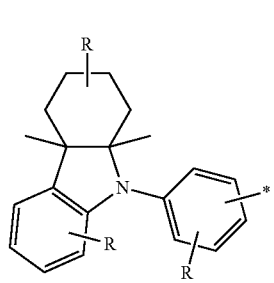

[Substituent 38]
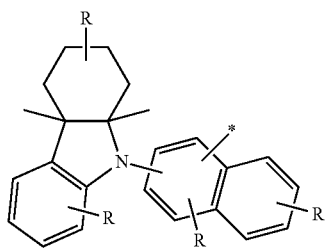
[Substituent 39]
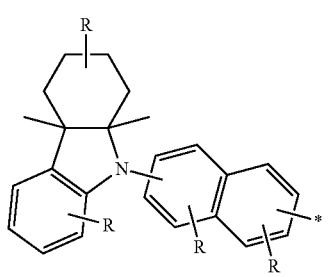
[Substituent 40]
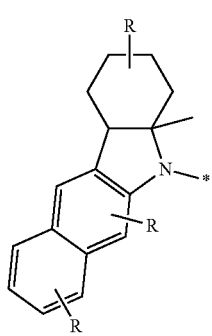
[Substituent 41]
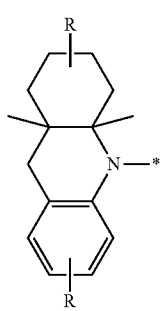
[Substituent 42]
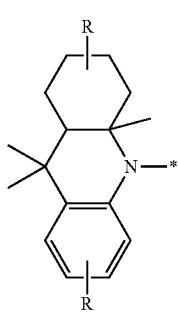
[Substituent 43]
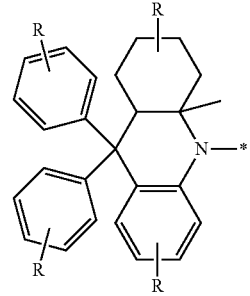
[Substituent 44]
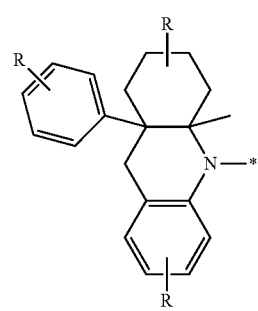
[Substituent 45]
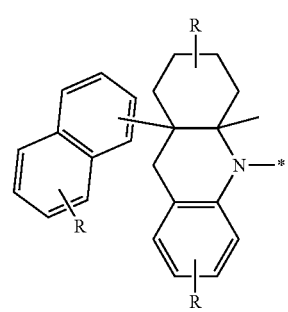
[Substituent 46]
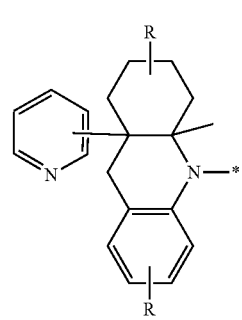
[Substituent 47]
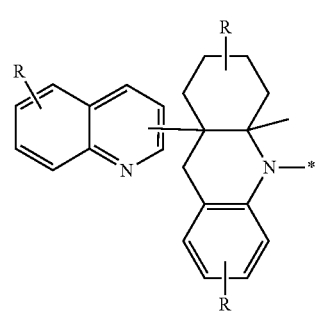

[Substituent 48]

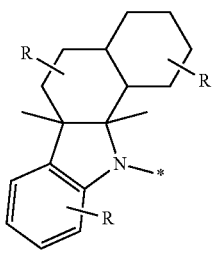

[Substituent 49]

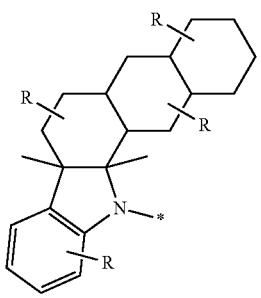

[Substituent 50]

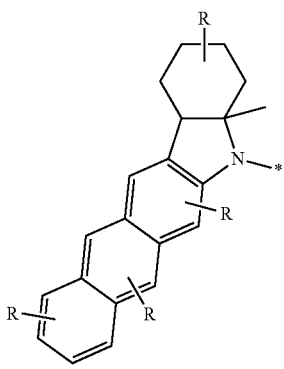

[Substituent 51]

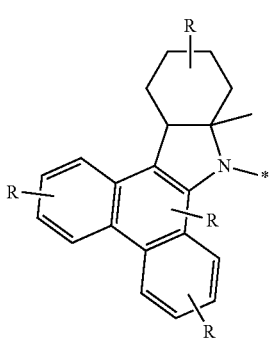

[Substituent 52]

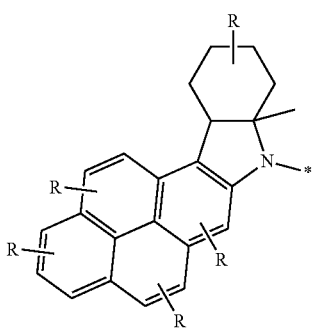

wherein R's, which may be the same or different, are each independently selected from among a hydrogen atom, a deuterium atom, a halogen atom, a hydroxyl, a cyano, a nitro, an amino, an amidino, a hydrazine, a hydrazone, a carboxyl or a salt thereof, a sulfonic acid or a salt thereof, a phosphoric acid or a salt thereof, a substituted or unsubstituted alkyl of 1 to 60 carbon atoms, a substituted or unsubstituted alkenyl of 2 to 60 carbon atoms, a substituted or unsubstituted alkynyl of 2 to 60 carbon atoms, a substituted or unsubstituted alkoxy of 1 to 60 carbon atoms, a substituted or unsubstituted alkylthio of 1 to 60 carbon atoms, a substituted or unsubstituted cycloalkyl of 3 to 60 carbon atoms, a substituted or unsubstituted aryl of 6 to 60 carbon atoms, a substituted or unsubstituted aryloxy of 5 to 60 carbon atoms, a substituted or unsubstituted arylthio of 5 to 60 carbon atoms, a substituted or unsubstituted heteroaryl of 2 to 60 carbon atoms, a substituted or unsubstituted (alkyl)amino of 1 to 60 carbon atoms, a di(substituted or unsubstituted alkyl)amino of 1 to 60 carbon atoms or a (substituted or unsubstituted aryl)amino of 6 to 60 carbon atoms, a di(substituted or unsubstituted aryl)amino of 6 to 60 carbon atoms, a substituted or unsubstituted alkylsilyl of 1 to 40 carbon atoms, a substituted or unsubstituted arylsilyl of 6 to 30 carbon atoms, may each have 1 to 12 substituents, and may each form a fused ring with an adjacent radical.

Meanwhile, between the light-emitting layer and the electron transport layer in the organic light-emitting device, a layer may be further arranged (hereinafter referred to as "electron density control layer") and the anthracene compound of the present invention may be used in the electron density control layer.

In detail, the light-emitting device according to some embodiments of the present invention may include an anode, a hole transport layer, a light-emitting layer including both a host and a dopant, an electron density control layer containing at least one of the anthracene derivatives represented by Chemical Formulas A-1, A-2, B-1, and B-2, an electron transport layer, and a cathode in that order.

In this regard, the organic light-emitting device may further include a hole injection layer between the anode and the hole transport layer, and an electron injection layer between the electron transport layer and the cathode.

Figure 2:
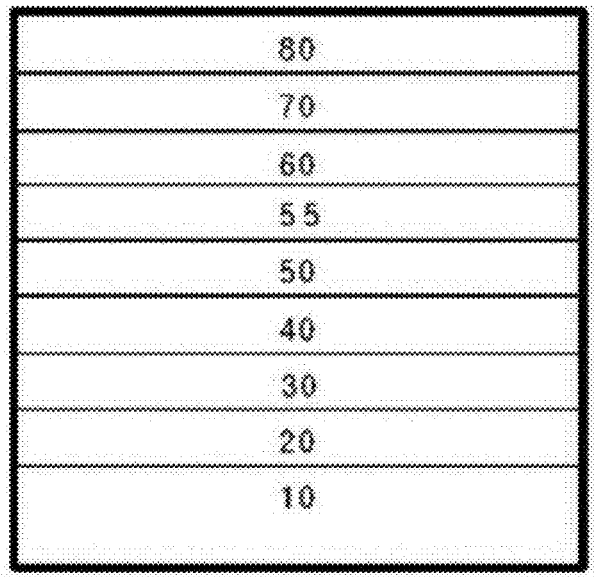
FIG. 2 is a schematic diagram of the structure of an organic light-emitting device including an electron density control layer according to another embodiment of the present invention.

FIG. 2 is a schematic view of the structure of the organic light-emitting device including a hole injection layer and an electron injection layer according to some embodiments of the present invention.

As can be seen, the organic light-emitting device according to some embodiments of the present invention comprises an anode 20, a hole transport layer 40, a light-emitting layer 50, an electron density control layer 55, an electron transport layer 60, and a cathode 80, and optionally a hole injection layer 30 and an electron injection layer 70. In addition, one or two intermediate layers may further be formed in the organic light-emitting diode.

Here, the electron density control layer may contain at least one of the anthracene derivatives represented by Chemical Formulas A-1, A-2, B-1, and B-2.

FIG. 2 is a structure obtained by forming an electron density control layer 55 between the light-emitting layer 50 and the electron transport layer 60 in the structure of FIG. 1. Except the electron density layer and the light-emitting layer, the layers of FIG. 2 may be formed to have the same configuration as is described in FIG. 1.

That is, using a vacuum deposition method or a spin coating method, a light-emitting layer 50 may be deposited on the same hole transport layer 40 as is formed in FIG. 1, and subsequently overlaid with an electron density control layer 55 according to the present invention.

Here, the host in the light-emitting layer may be an anthracene derivative selected from among compounds represented by Chemical Formulas A-1, A-2, B-1, and B-2 or may be a compound different from the anthracene derivative.

As a host useful in the light-emitting layer according to the present invention, at least one of the compounds represented by the following Chemical Formula 1A may be used:

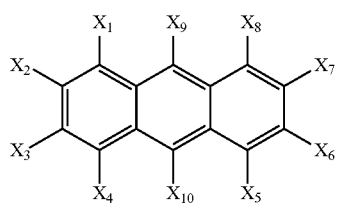

[Chemical Formula A1]

wherein,

X1 to X10 may be the same or different and are each independently selected from the group consisting of a hydrogen atom, a deuterium atom, a substituted or unsubstituted alkyl of 1 to 30 carbon atoms, a substituted or unsubstituted alkenyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted aryl thioxy of 5 to 30 carbon atoms, a substituted or unsubstituted alkyl amine of 1 to 30 carbon atoms, a substituted or unsubstituted arylamine of 6 to 30 carbon atoms, a substituted or unsubstituted aryl of 6 to 50 carbon atoms, a substituted or unsubstituted heteroaryl of 3 to 50 carbon atoms bearing at least one heteroatom selected from among O, N, and S, a substituted or unsubstituted silicone, a substituted or unsubstituted boron, a substituted or unsubstituted silane, a carbonyl, a phosphoryl, an amino, a nitrile, a hydroxy, a nitro, a halogen, an amide, and an ester wherein adjacent moieties of X1 to X10 may form a fused, aliphatic, aromatic, heteroaliphatic or heteroaromatic ring.

Concrete examples of the host may include, but are not limited to, compounds represented by the following Chemical Formula 101 to 296:

[Chemical Formula 101]

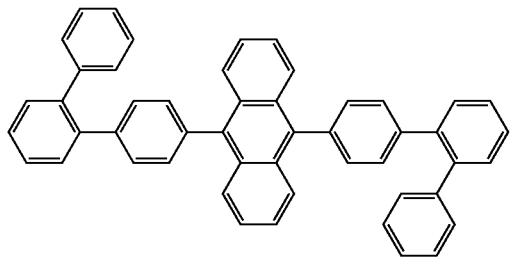

[Chemical Formula 102]

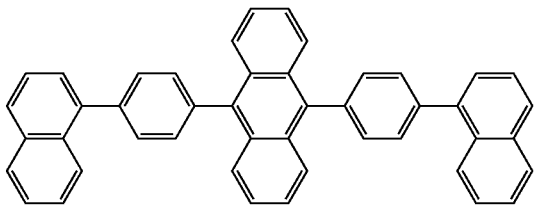

[Chemical Formula 103]

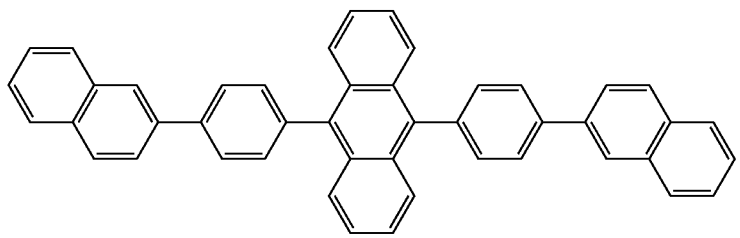

[Chemical Formula 104]

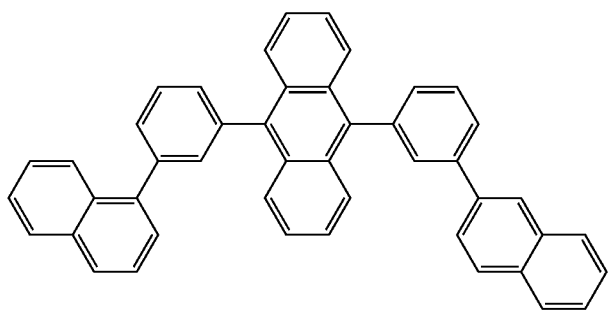

-continued
[Chemical Formula 105]
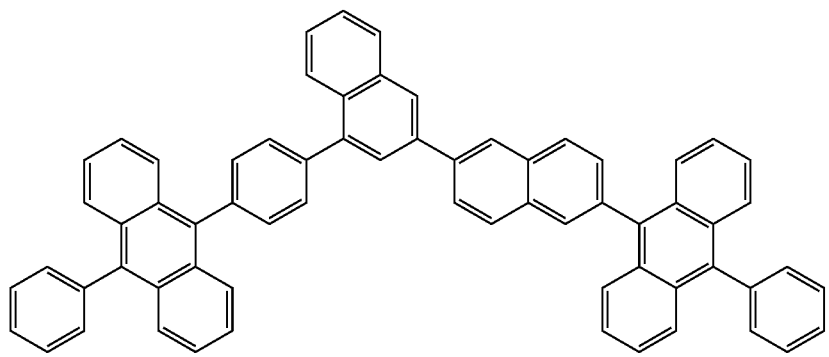
[Chemical Formula 106]
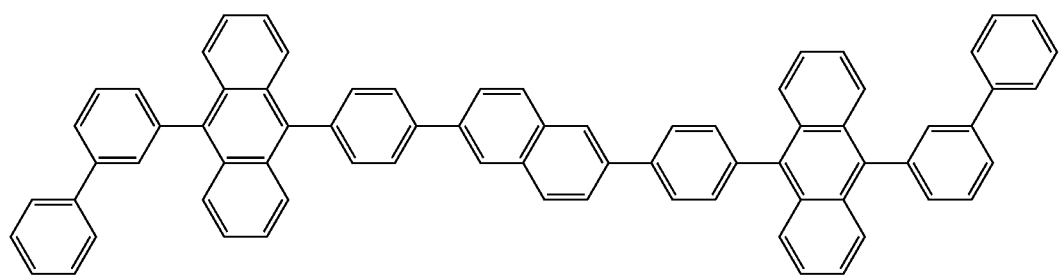
[Chemical Formula 107]
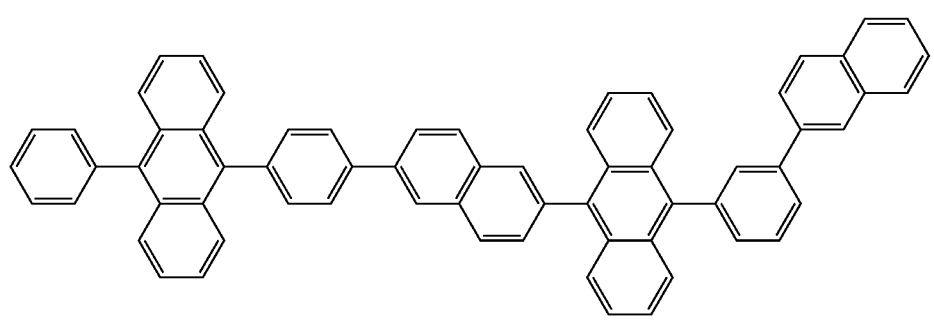
[Chemical Formula 108]
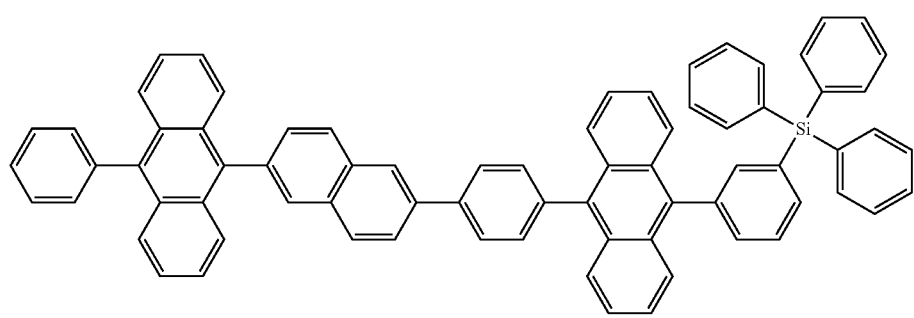
[Chemical Formula 109]
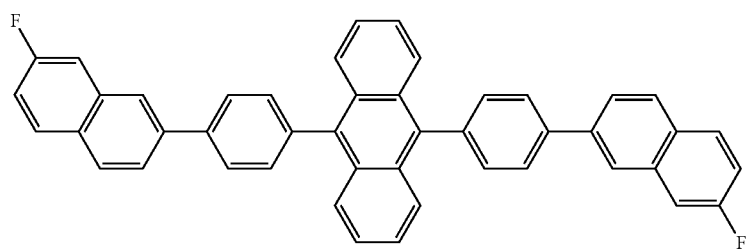

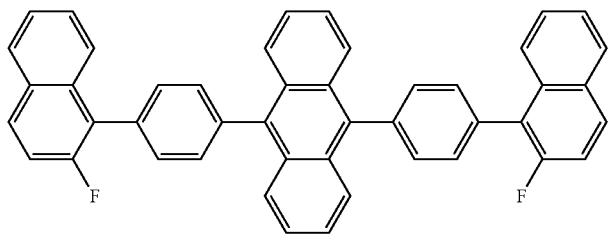
[Chemical Formula 110]
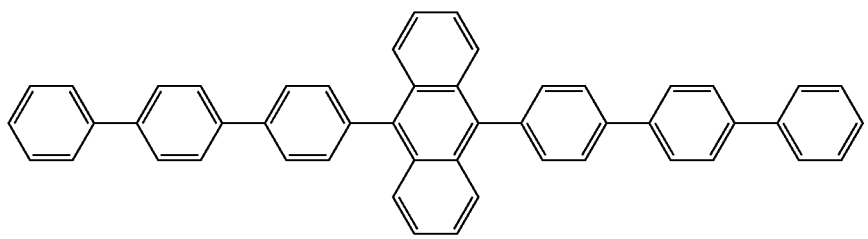
[Chemical Formula 111]
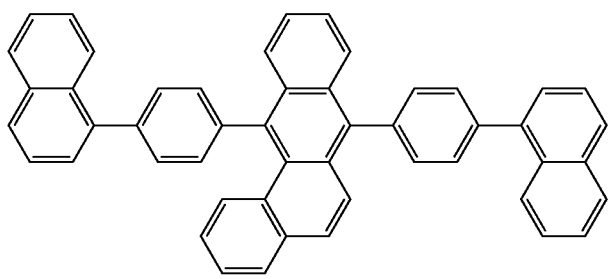
[Chemical Formula 112]
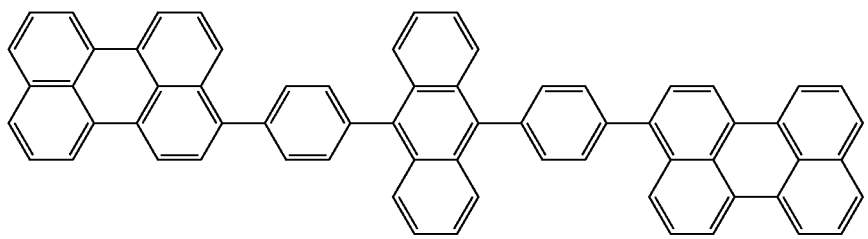
[Chemical Formula 113]
[Chemical Formula 114]
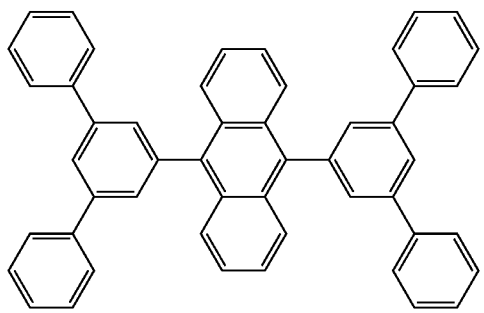
[Chemical Formula 115]
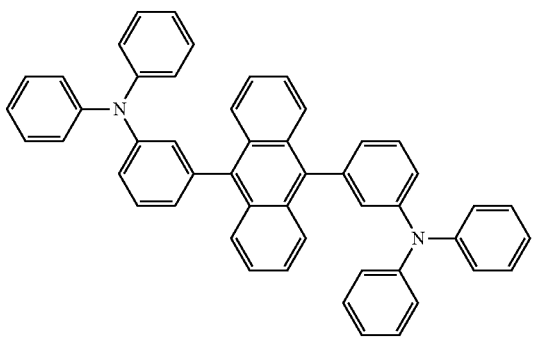
[Chemical Formula 116]
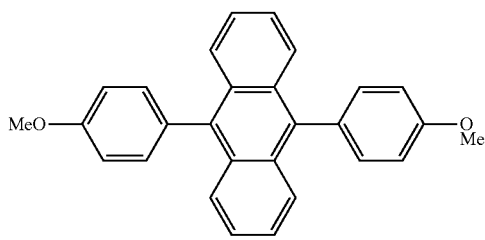
[Chemical Formula 117]
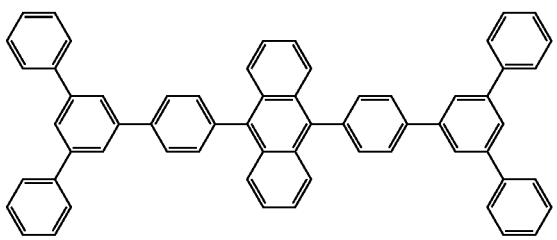

[Chemical Formula 118]
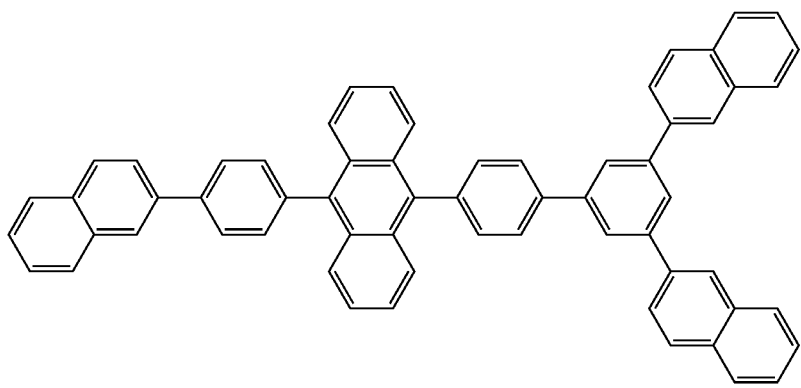
[Chemical Formula 119]
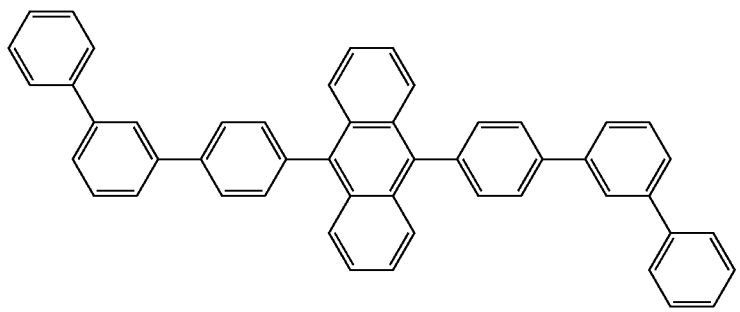
[Chemical Formula 120]
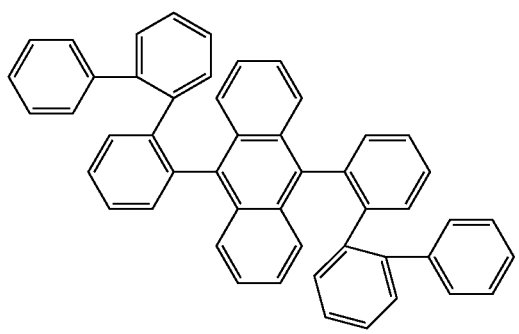
[Chemical Formula 121]
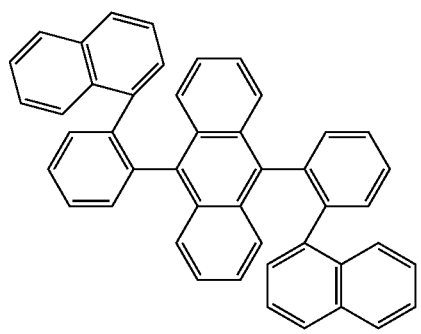
[Chemical Formula 122]
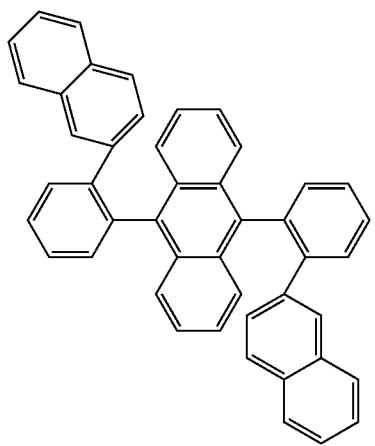
[Chemical Formula 123]
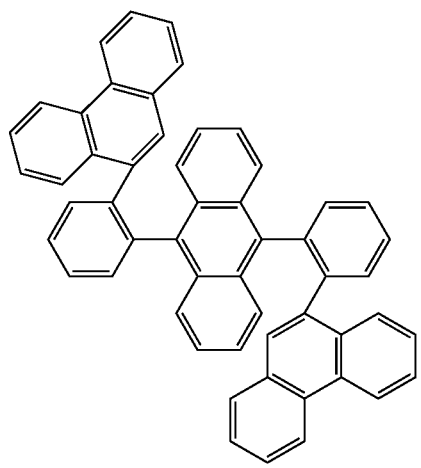

-continued
[Chemical Formula 124]
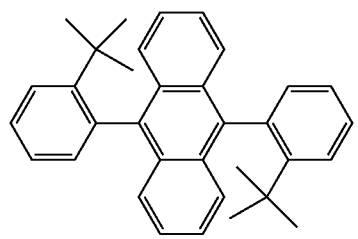
[Chemical Formula 125]
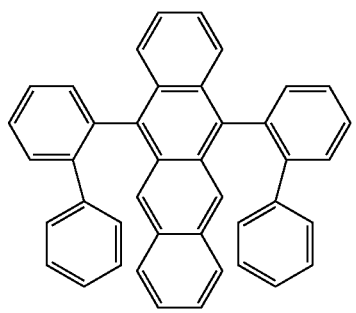
[Chemical Formula 126]
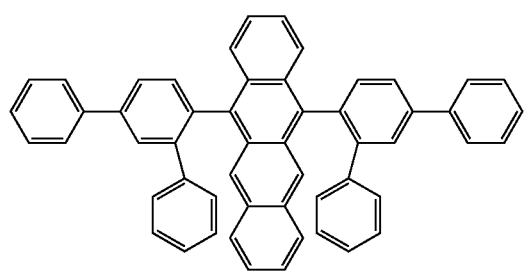
[Chemical Formula 127]
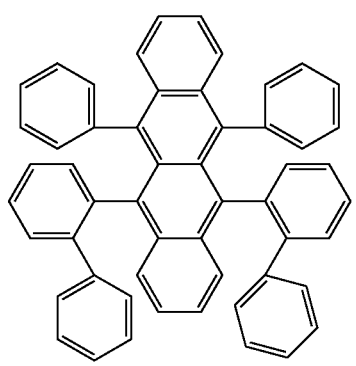
[Chemical Formula 128]
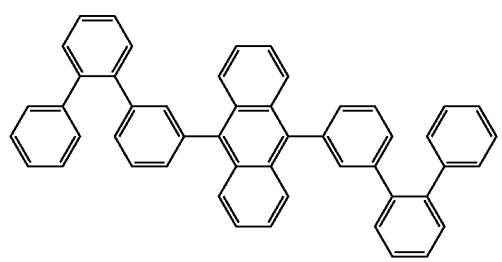
[Chemical Formula 129]
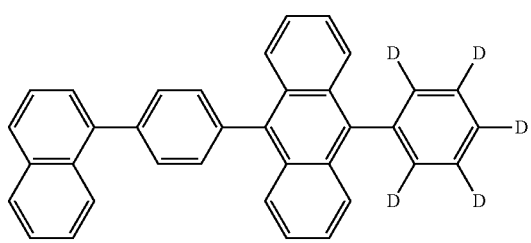
[Chemical Formula 130]
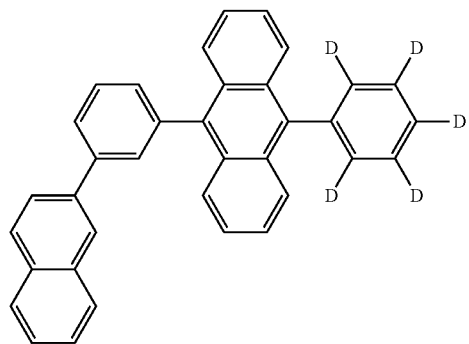
[Chemical Formula 131]
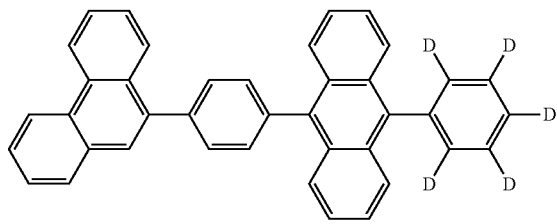

[Chemical Formula 132]
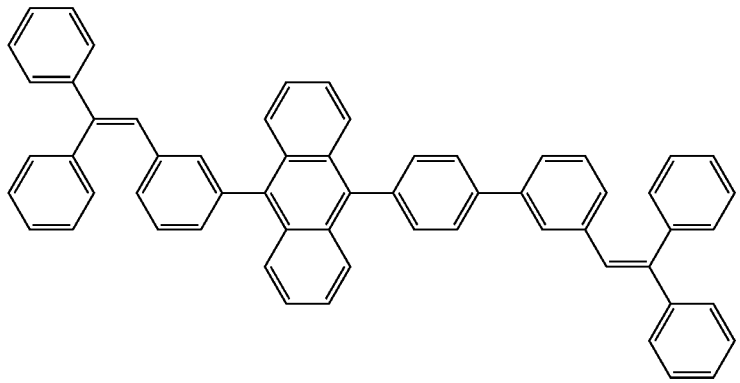
[Chemical Formula 133]
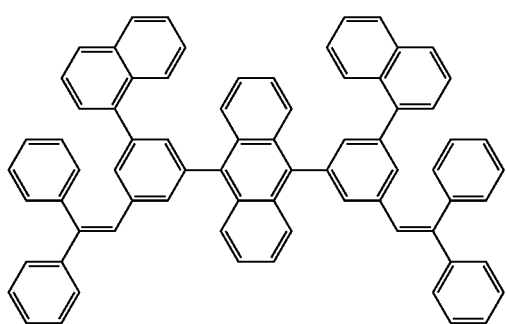
[Chemical Formula 134]
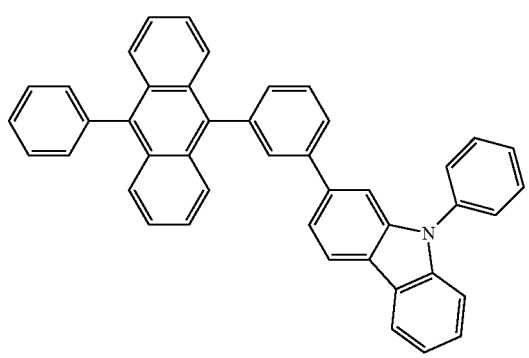
[Chemical Formula 135]
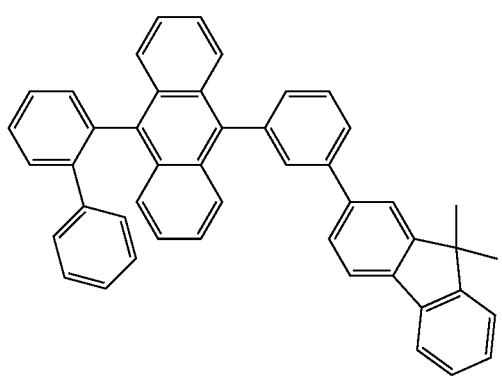
[Chemical Formula 136]
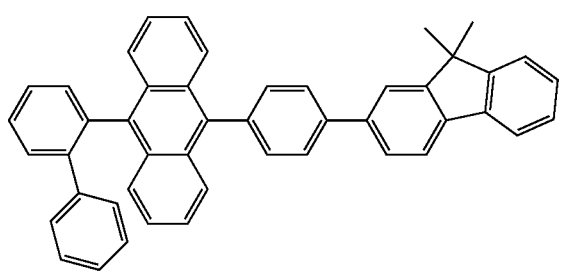
[Chemical Formula 137]
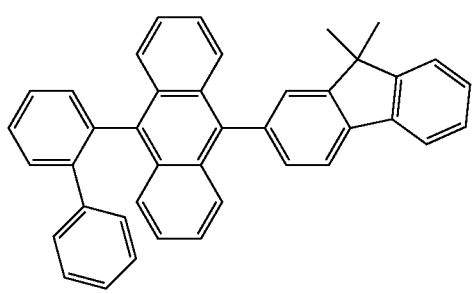
[Chemical Formula 138]
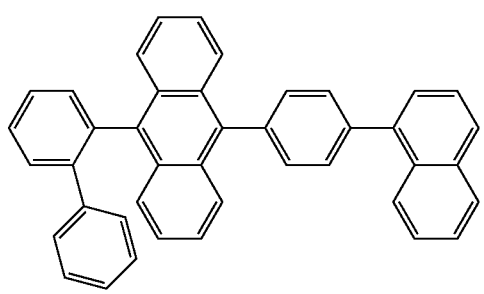

-continued
[Chemical Formula 139]
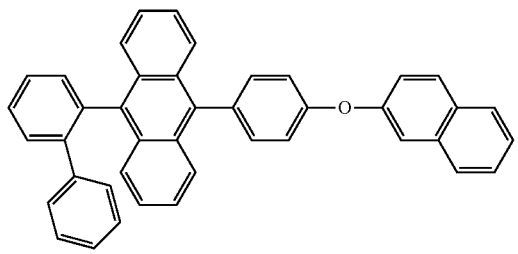
[Chemical Formula 140]
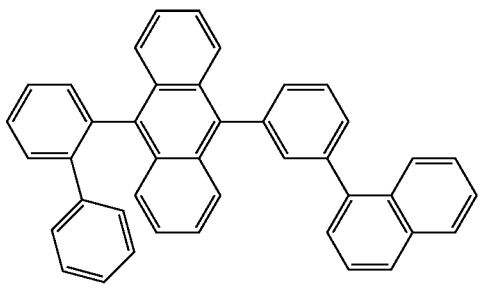
[Chemical Formula 141]
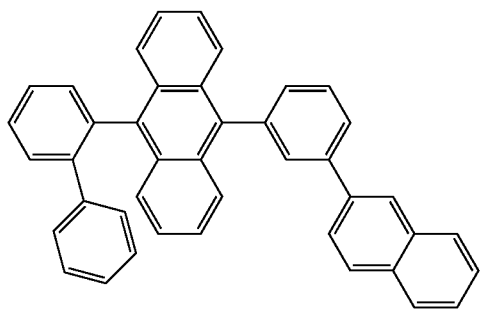
[Chemical Formula 142]
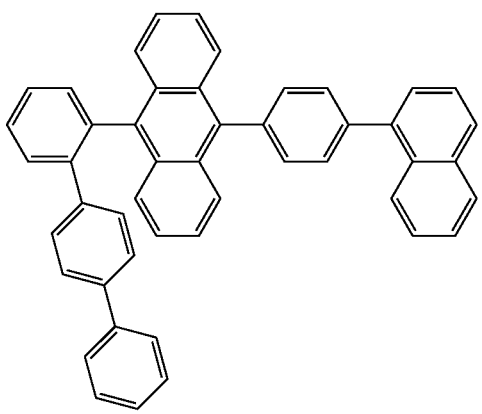
[Chemical Formula 143]
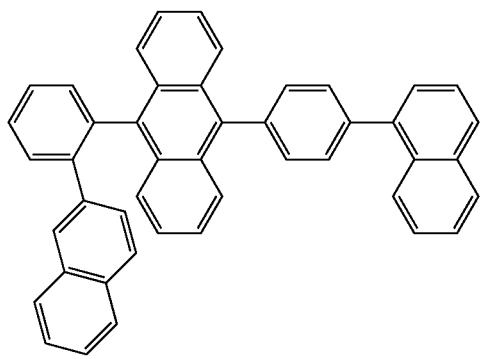
[Chemical Formula 144]
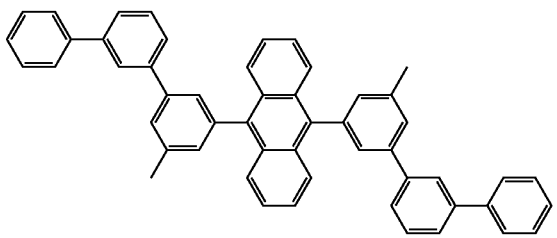
[Chemical Formula 145]
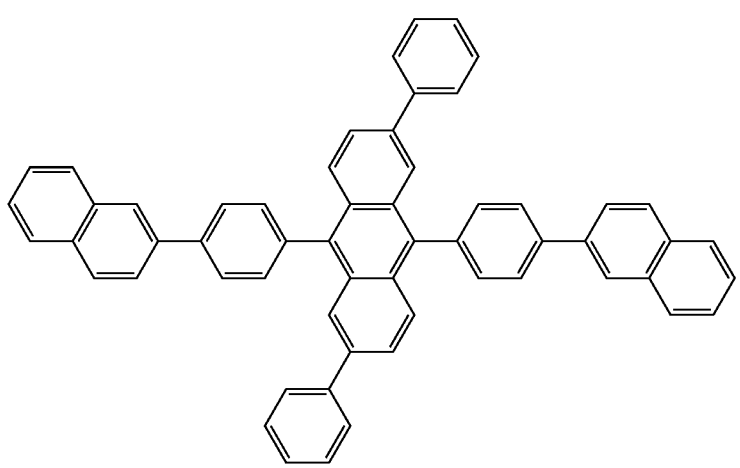

-continued
[Chemical Formula 146]
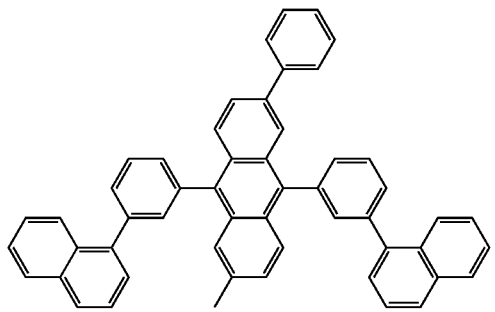
[Chemical Formula 147]
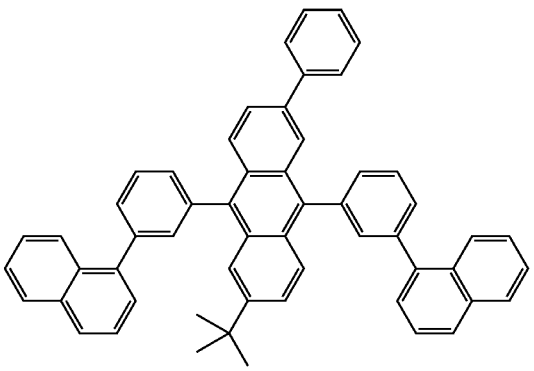
[Chemical Formula 148]
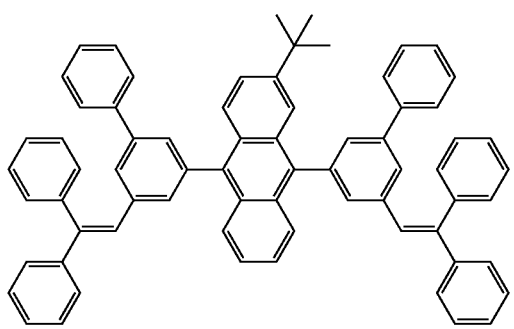
[Chemical Formula 149]
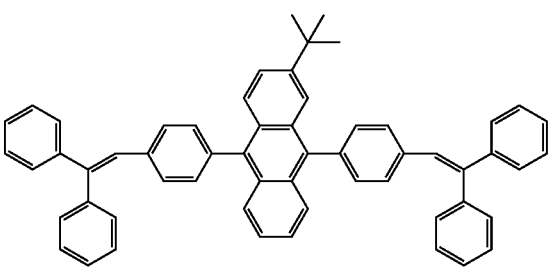
[Chemical Formula 150]
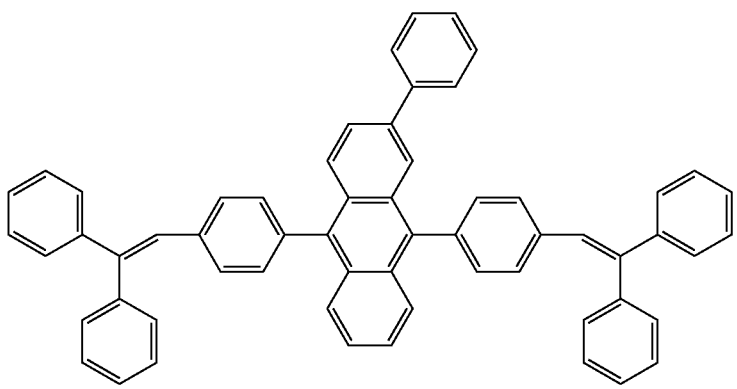
[Chemical Formula 151]
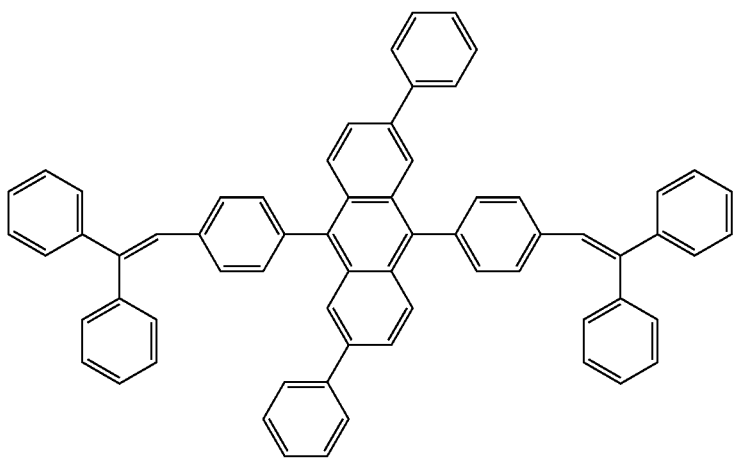

[Chemical Formula 152]
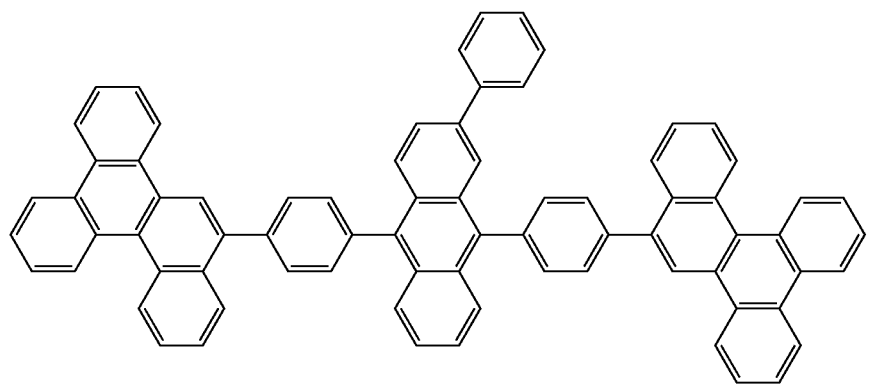
[Chemical Formula 153]
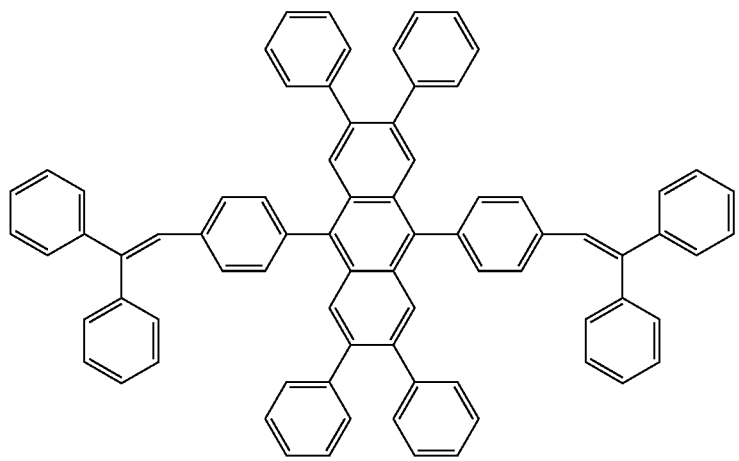
[Chemical Formula 154]
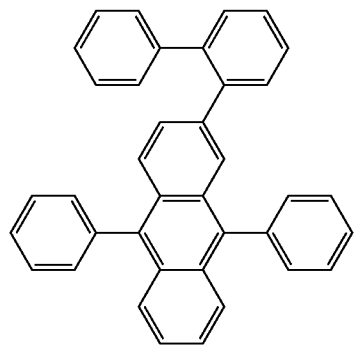
[Chemical Formula 155]
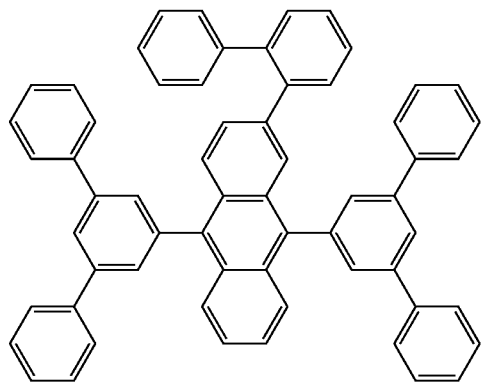
[Chemical Formula 156]
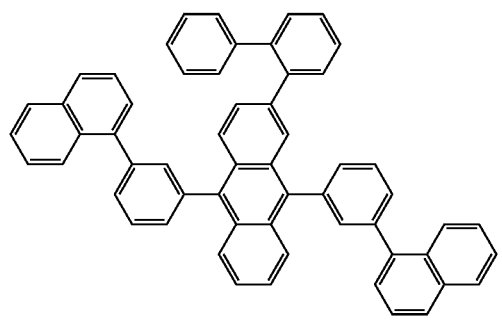
[Chemical Formula 157]
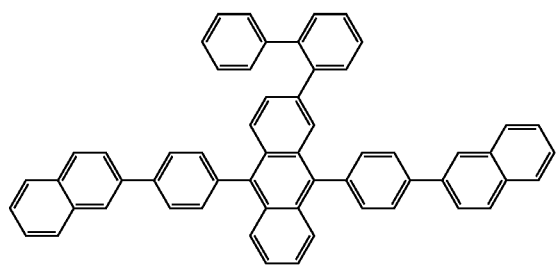

[Chemical Formula 158]
[Chemical Formula 159]
[Chemical Formula 160]
[Chemical Formula 161]
[Chemical Formula 162]
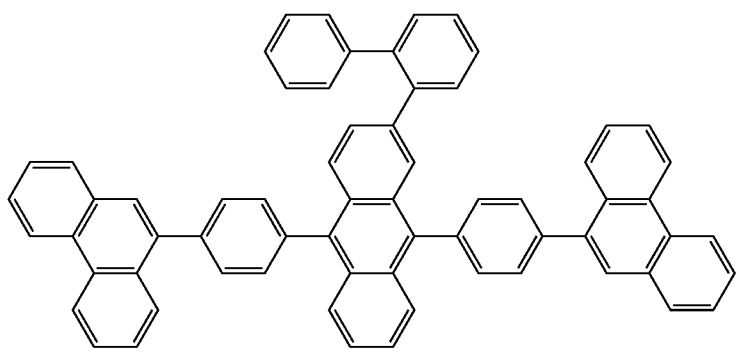

[Chemical Formula 163]
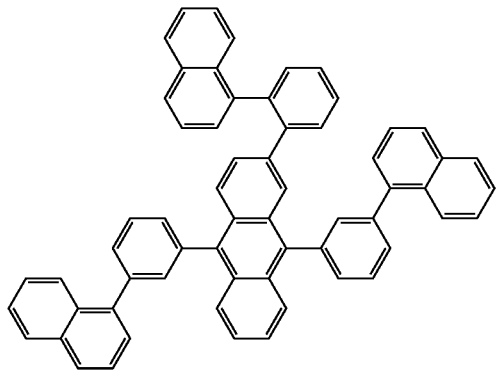
[Chemical Formula 164]
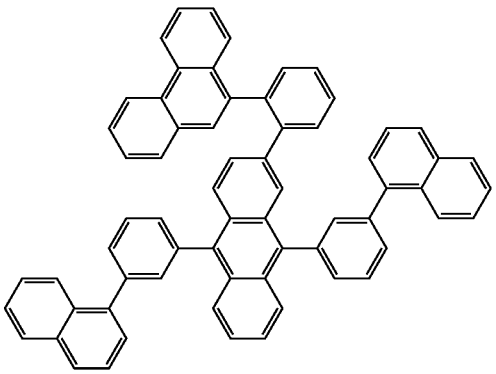
[Chemical Formula 165]
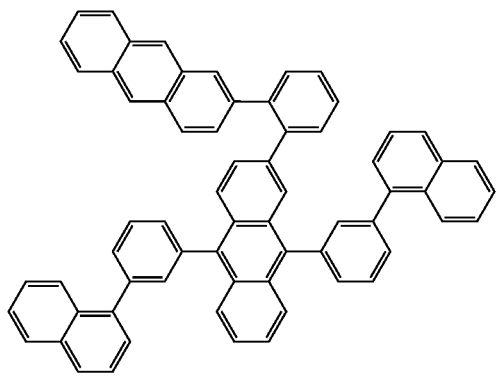
[Chemical Formula 166]
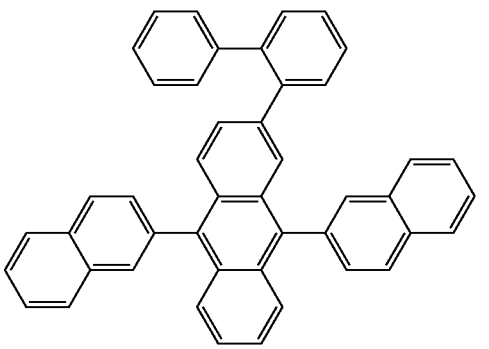
[Chemical Formula 167]
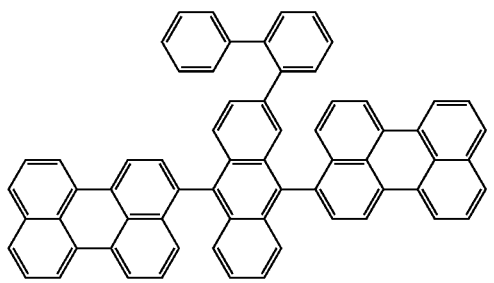
[Chemical Formula 168]
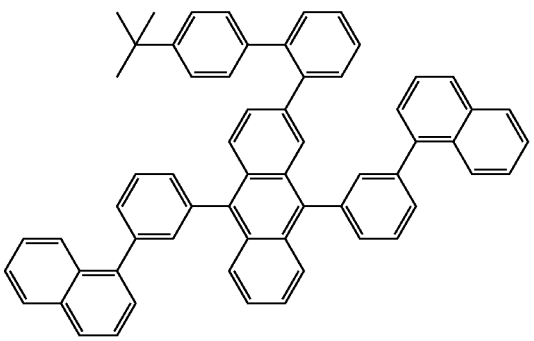
[Chemical Formula 169]
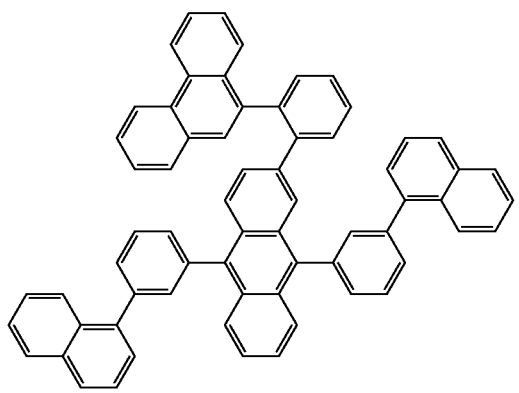
[Chemical Formula 170]
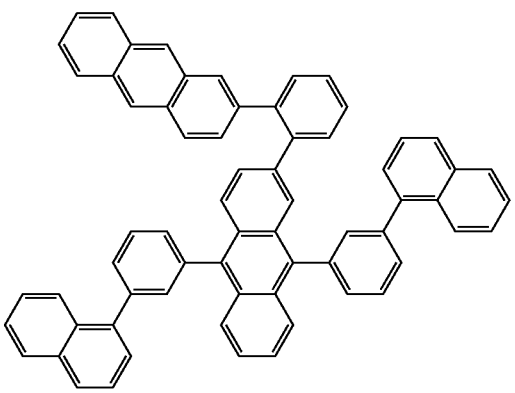

-continued
[Chemical Formula 171]
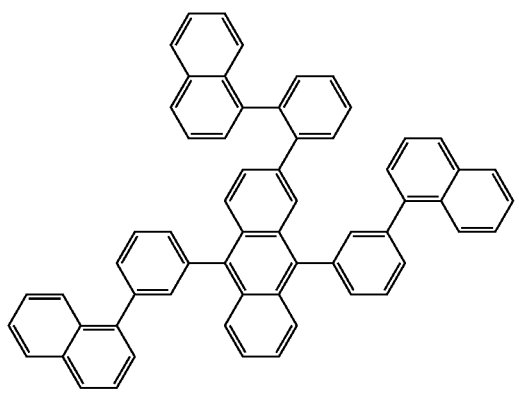
[Chemical Formula 172]
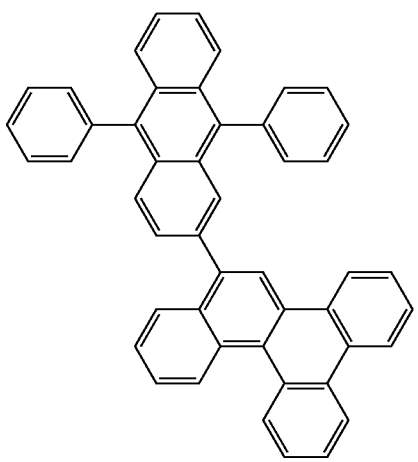
[Chemical Formula 173]
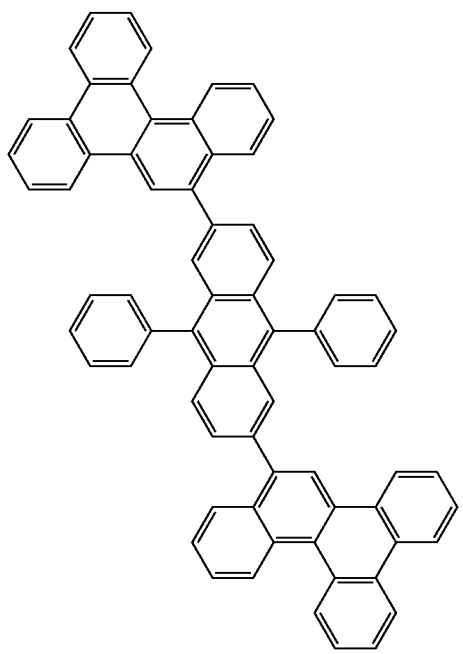
[Chemical Formula 174]
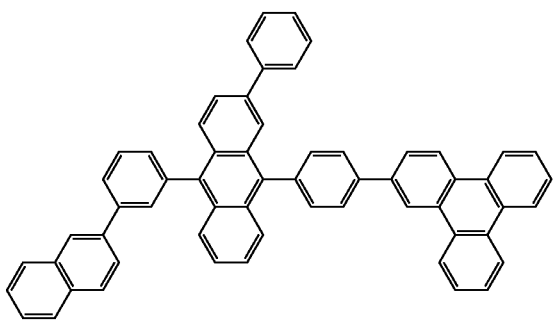
[Chemical Formula 175]
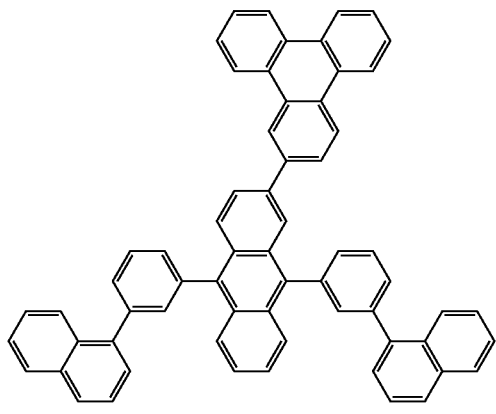
[Chemical Formula 176]
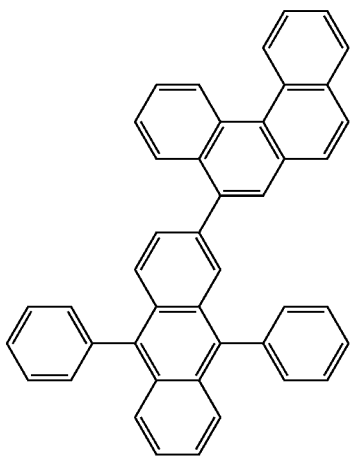

[Chemical Formula 177]
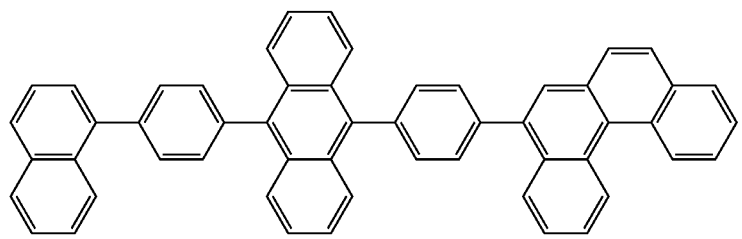
[Chemical Formula 178]
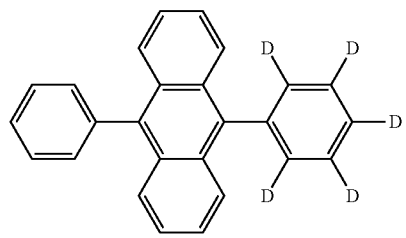
[Chemical Formula 179]
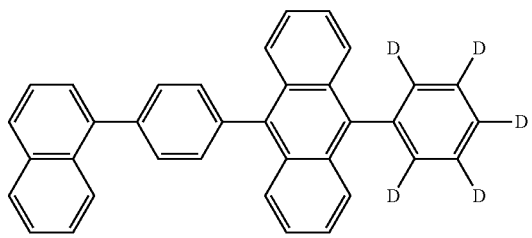
[Chemical Formula 180]
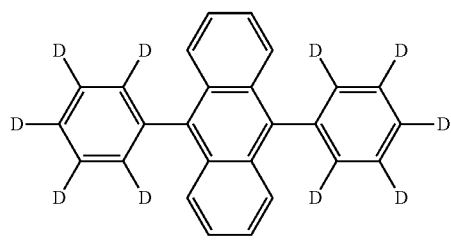
[Chemical Formula 181]
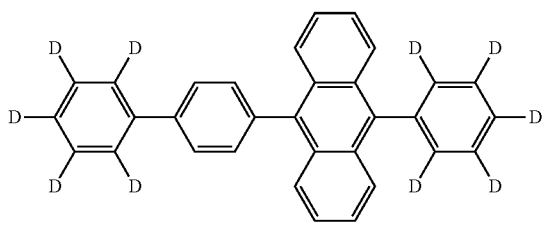
[Chemical Formula 182]
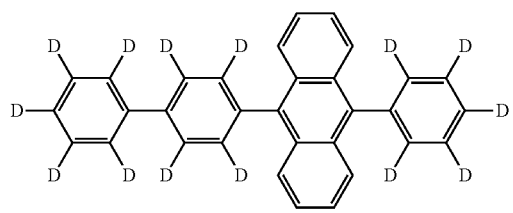
[Chemical Formula 183]
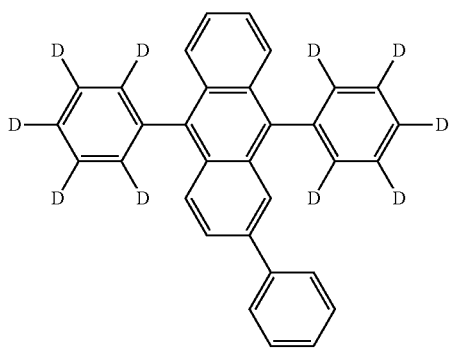
[Chemical Formula 184]
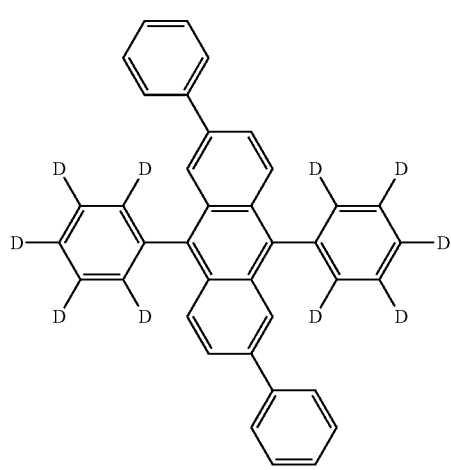
[Chemical Formula 185]
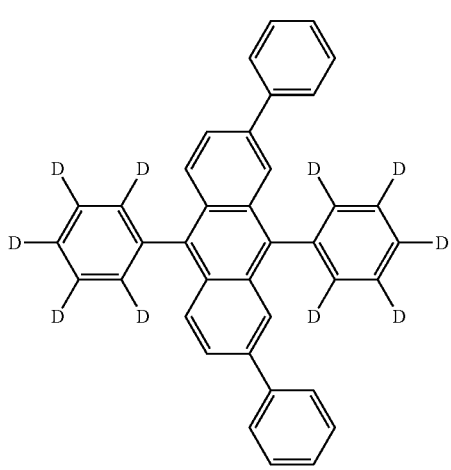

-continued
[Chemical Formula 186]
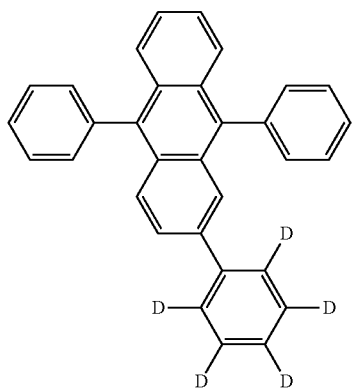
[Chemical Formula 187]
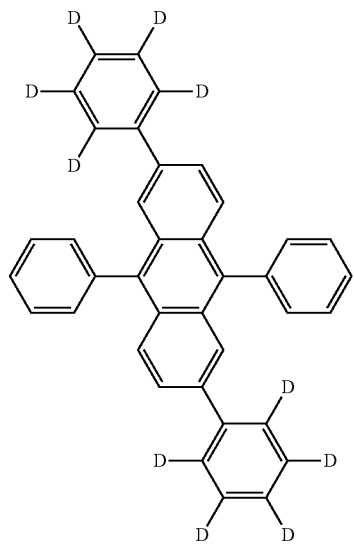
[Chemical Formula 188]
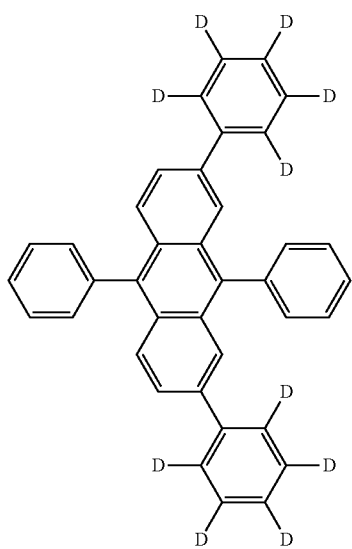
[Chemical Formula 189]
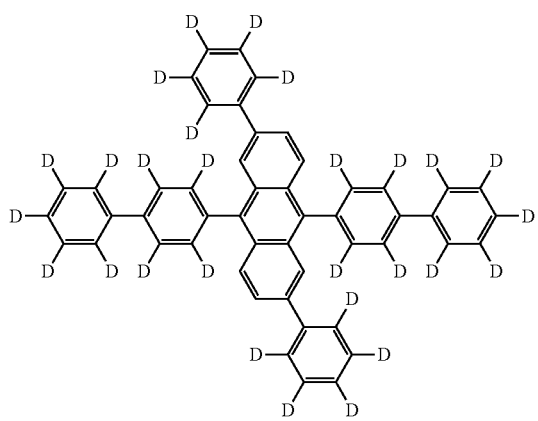
[Chemical Formula 190]
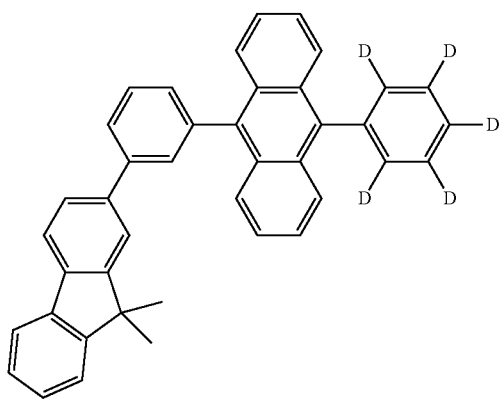
[Chemical Formula 191]
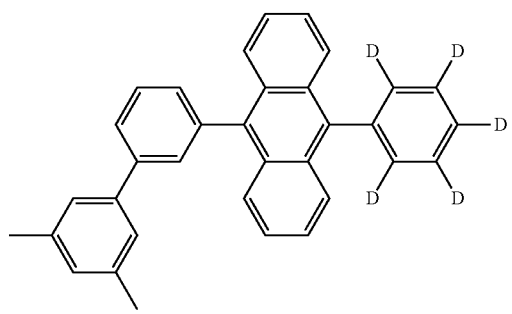

[Chemical Formula 192]
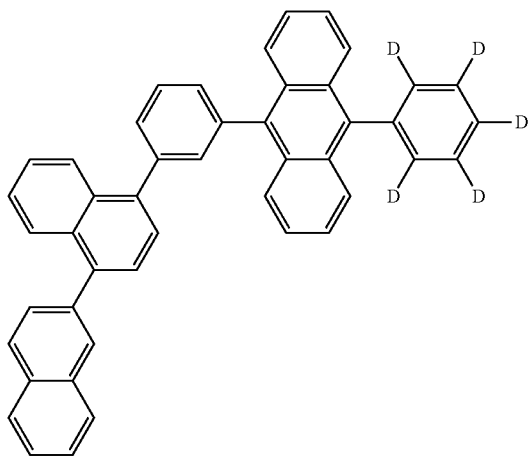
[Chemical Formula 193]
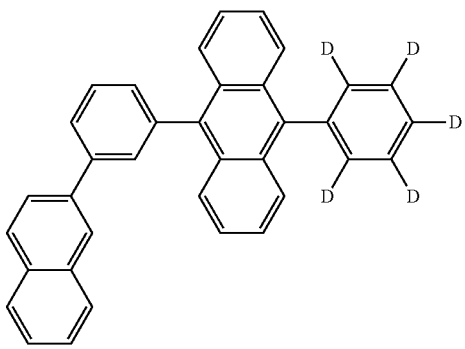
[Chemical Formula 194]
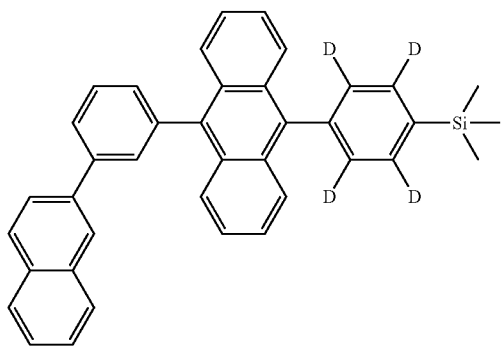
[Chemical Formula 195]
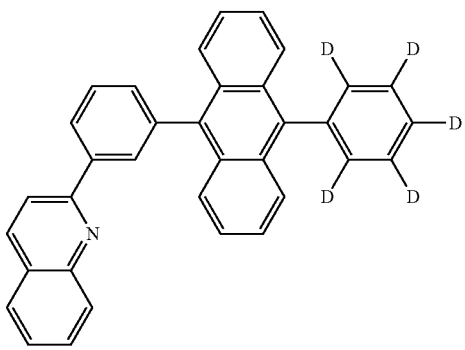
[Chemical Formula 196]
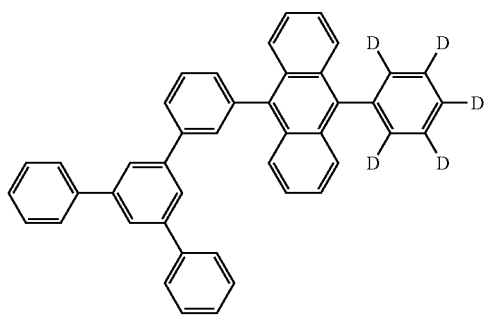
[Chemical Formula 197]
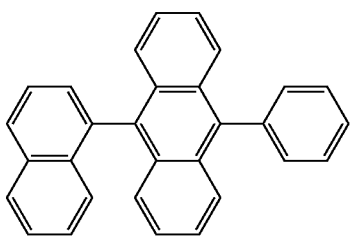
[Chemical Formula 198]
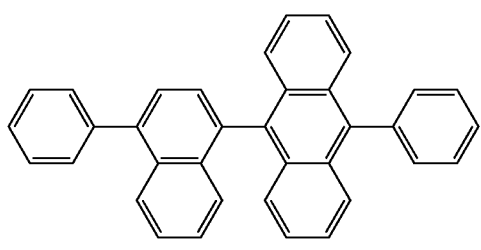
[Chemical Formula 199]
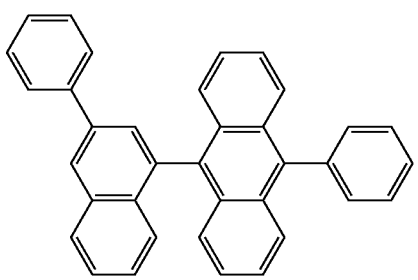

[Chemical Formula 200]
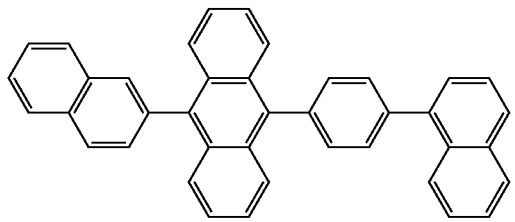
[Chemical Formula 201]
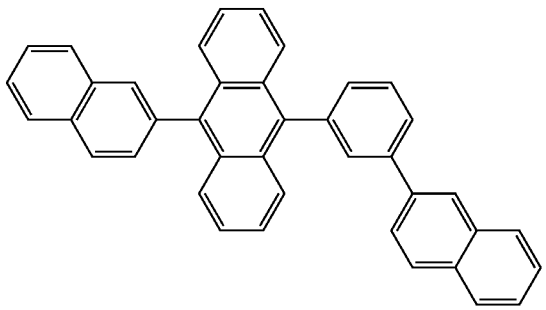
[Chemical Formula 202]
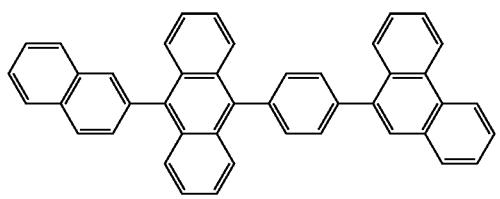
[Chemical Formula 203]
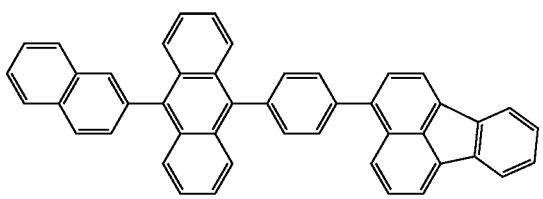
[Chemical Formula 204]
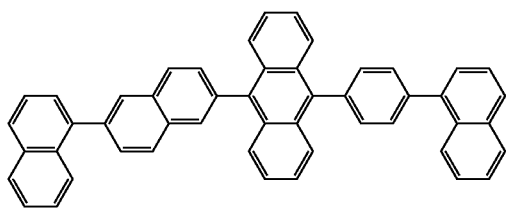
[Chemical Formula 205]
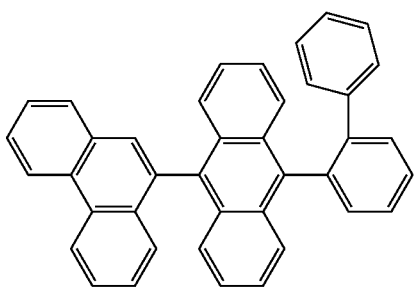
[Chemical Formula 206]
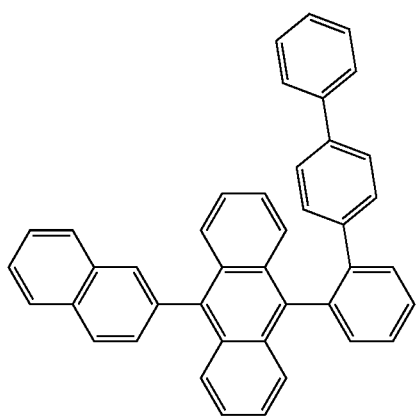
[Chemical Formula 207]
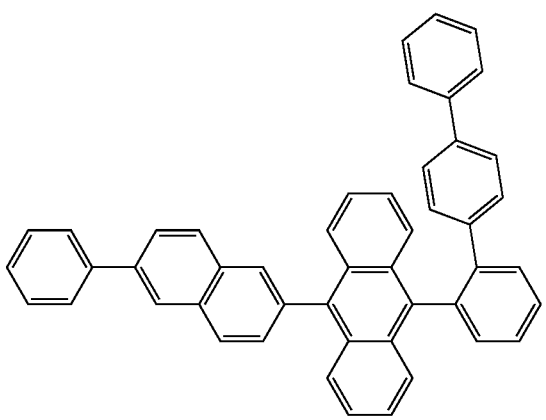

[Chemical Formula 208]
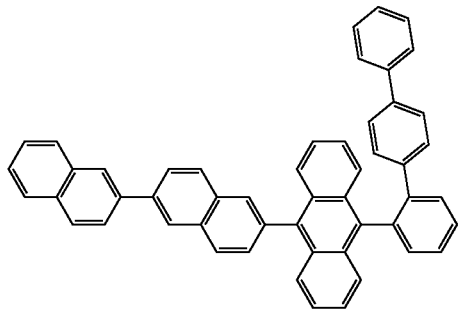
[Chemical Formula 209]
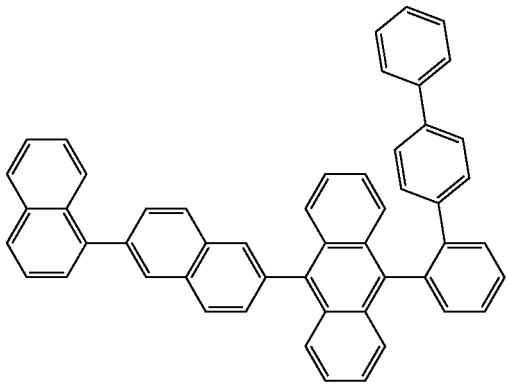
[Chemical Formula 210]
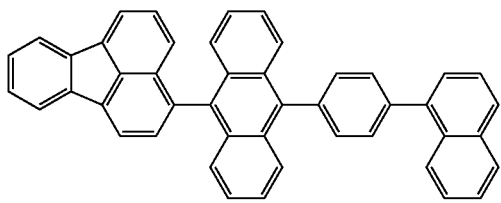
[Chemical Formula 211]
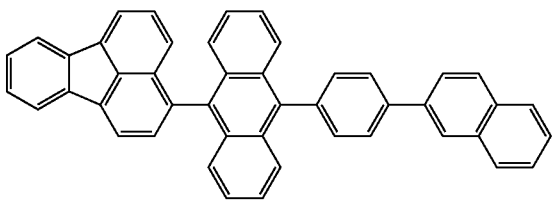
[Chemical Formula 212]
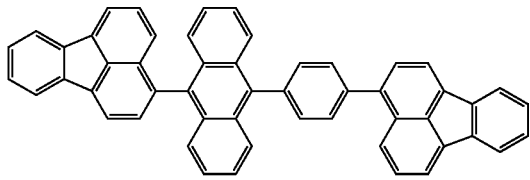
[Chemical Formula 213]
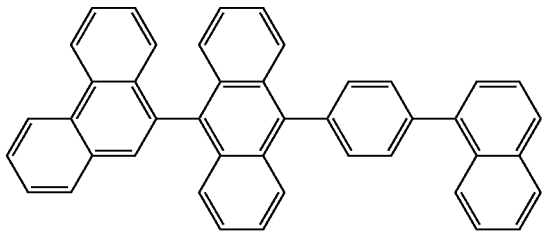
[Chemical Formula 214]
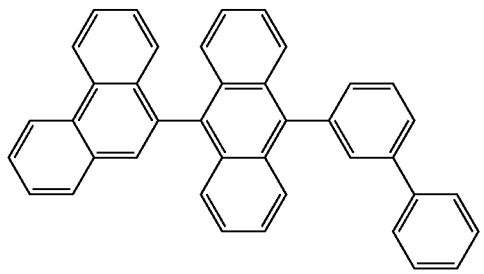
[Chemical Formula 215]
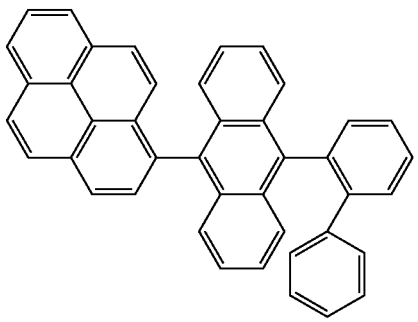
[Chemical Formula 216]
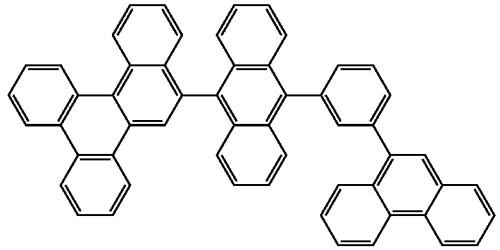
[Chemical Formula 217]
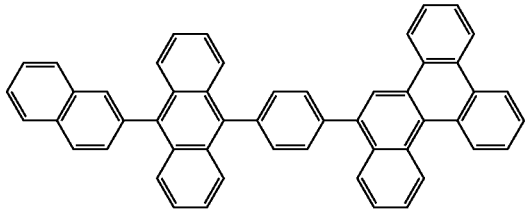

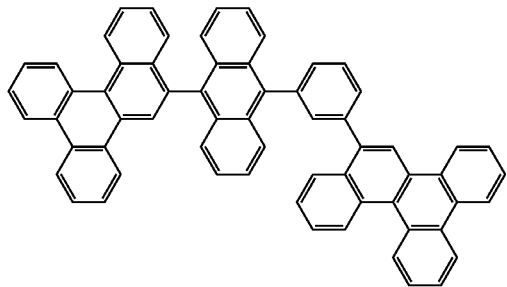

[Chemical Formula 226]
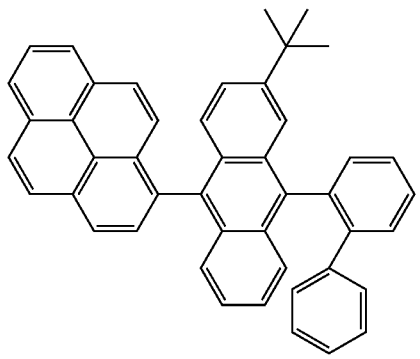
[Chemical Formula 227]
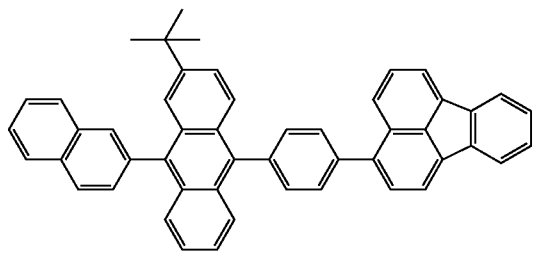
[Chemical Formula 228]
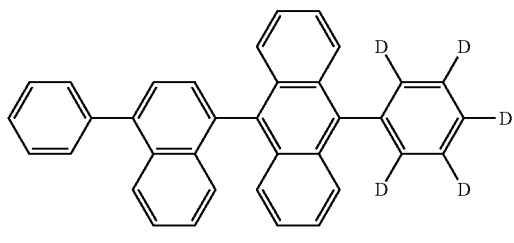
[Chemical Formula 229]
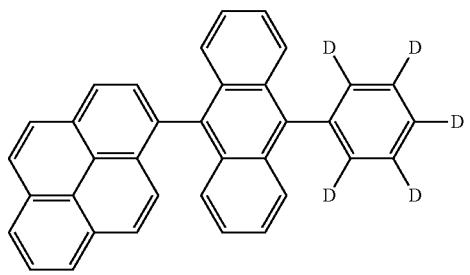
[Chemical Formula 230]
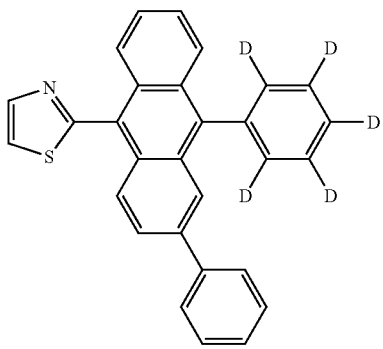
[Chemical Formula 231]
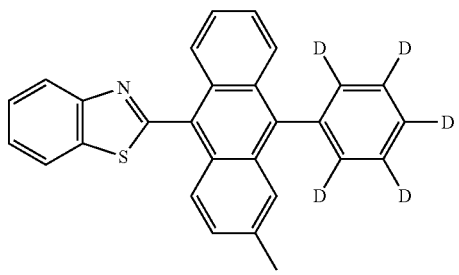
[Chemical Formula 232]
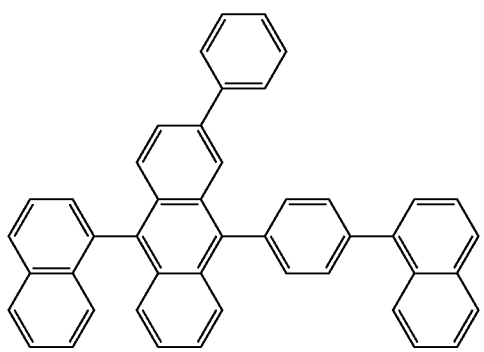
[Chemical Formula 233]
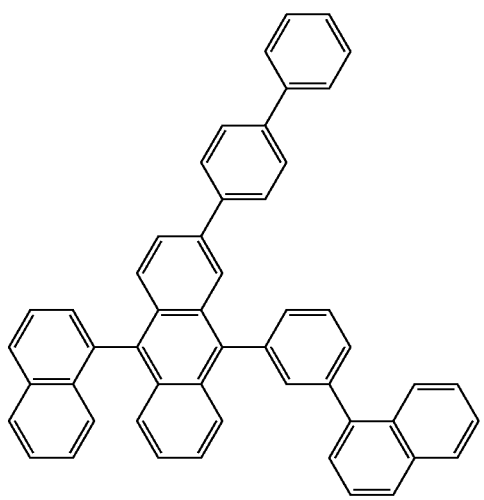

[Chemical Formula 234]

[Chemical Formula 235]

[Chemical Formula 236]

[Chemical Formula 237]

[Chemical Formula 238]

[Chemical Formula 239]

-continued
[Chemical Formula 240]
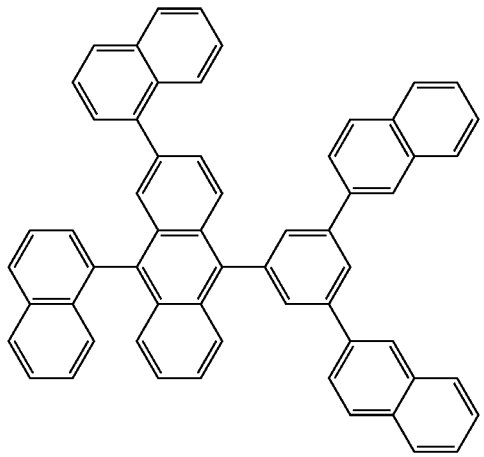
[Chemical Formula 241]
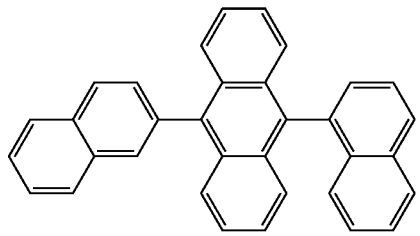
[Chemical Formula 242]
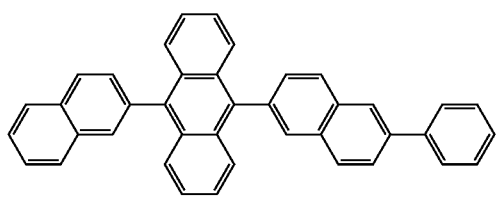
[Chemical Formula 243]
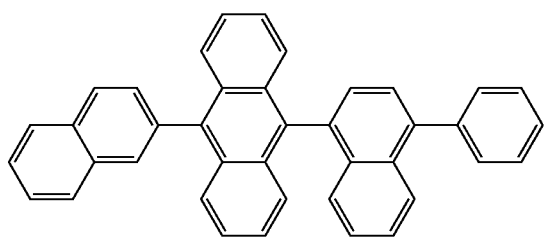
[Chemical Formula 244]
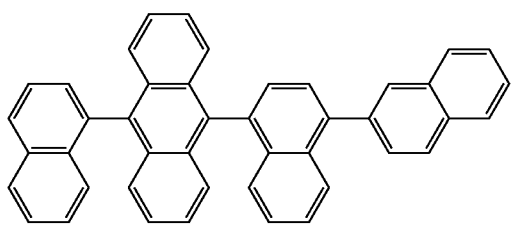
[Chemical Formula 245]
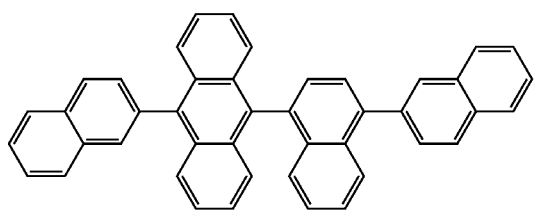
[Chemical Formula 246]
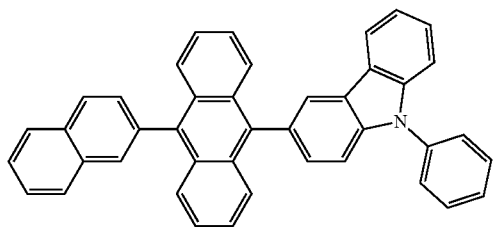
[Chemical Formula 247]
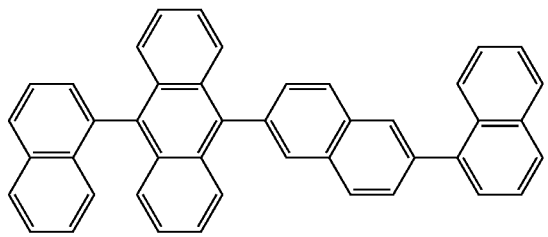
[Chemical Formula 248]
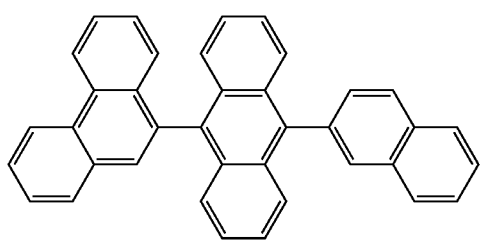
[Chemical Formula 249]
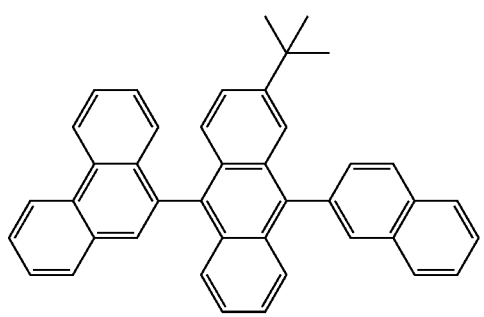

-continued
[Chemical Formula 250]
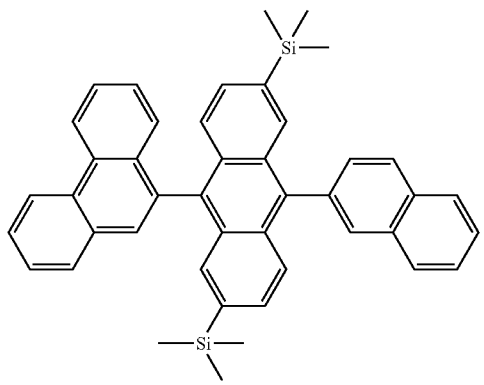
[Chemical Formula 251]
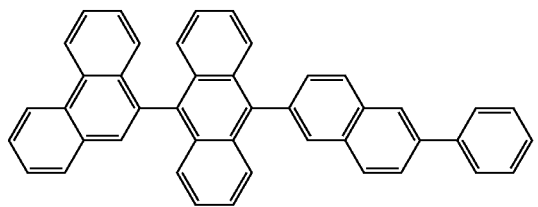
[Chemical Formula 252]
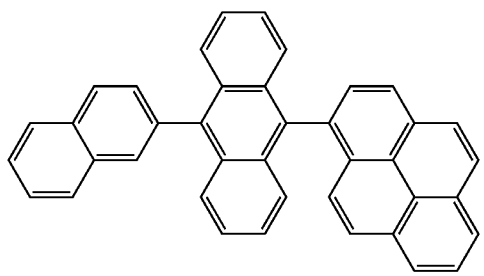
[Chemical Formula 253]
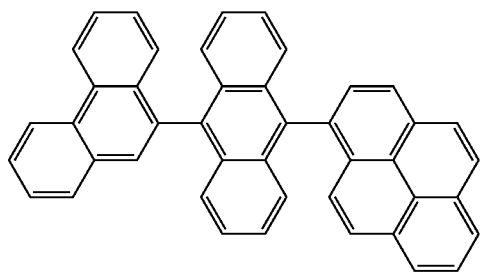
[Chemical Formula 254]
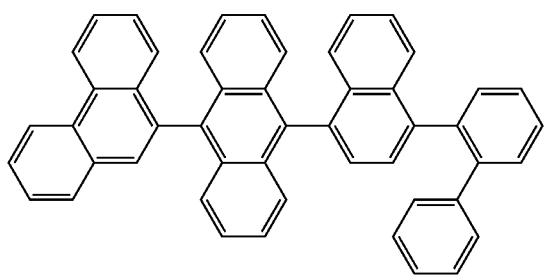
[Chemical Formula 255]
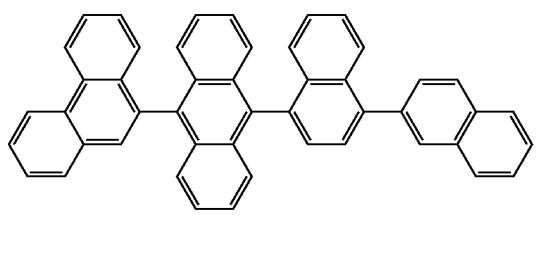
[Chemical Formula 256]
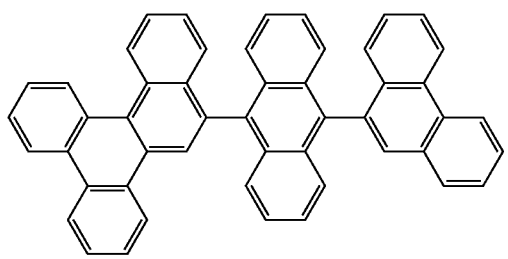
[Chemical Formula 257]
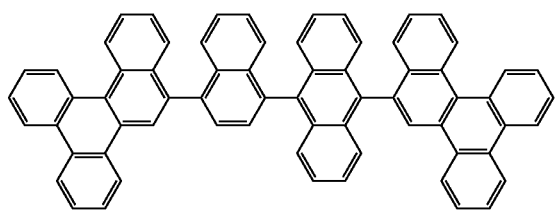

[Chemical Formula 258]
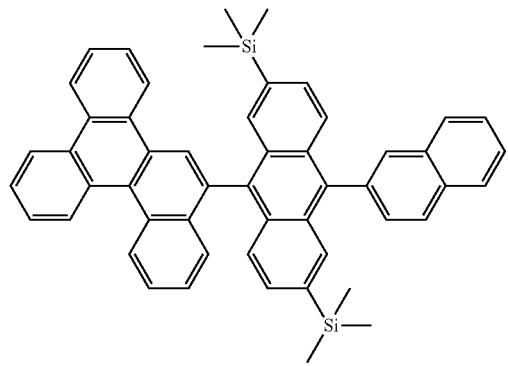
[Chemical Formula 259]
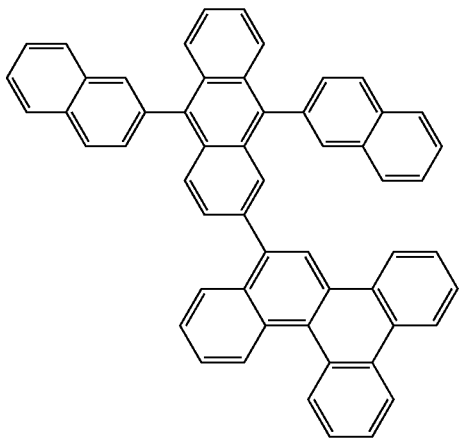
[Chemical Formula 260]
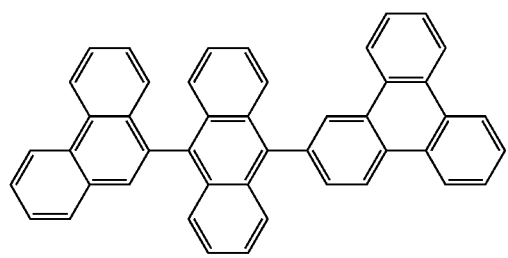
[Chemical Formula 261]
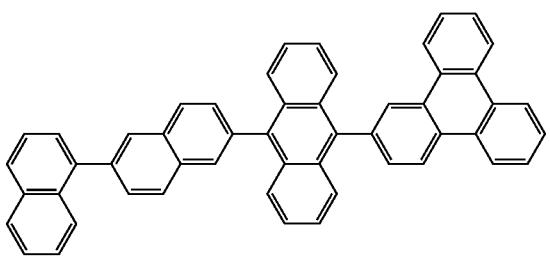
[Chemical Formula 262]
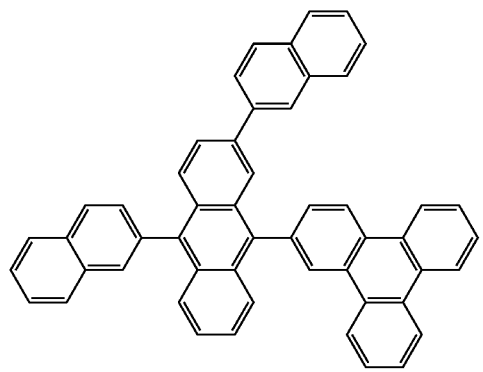
[Chemical Formula 263]
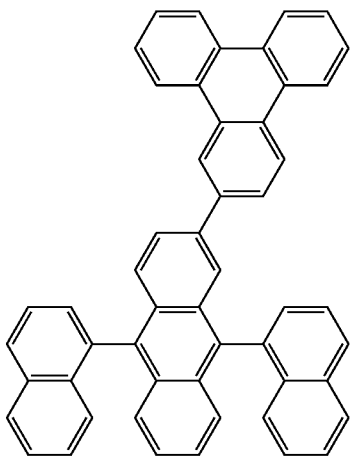
[Chemical Formula 264]
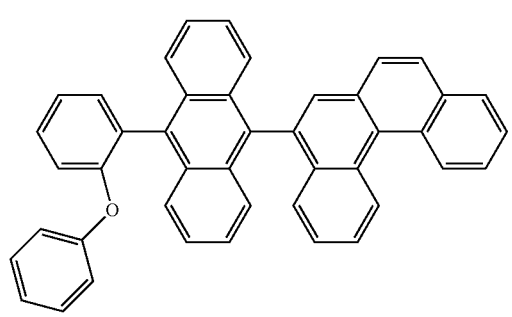

-continued
[Chemical Formula 265]
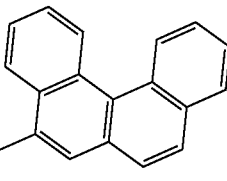
[Chemical Formula 266]
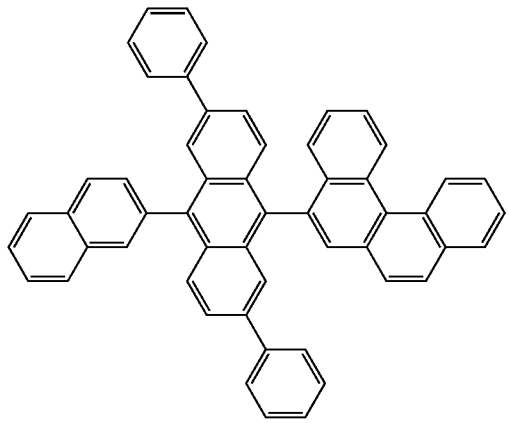
[Chemical Formula 267]
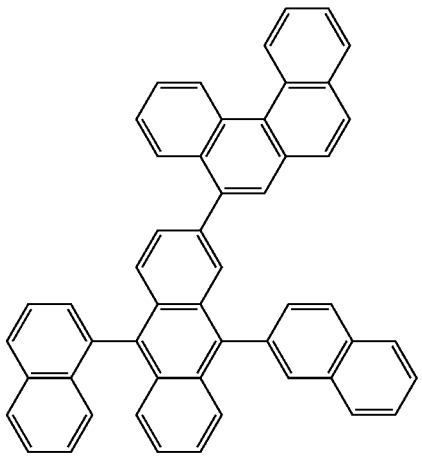
[Chemical Formula 268]
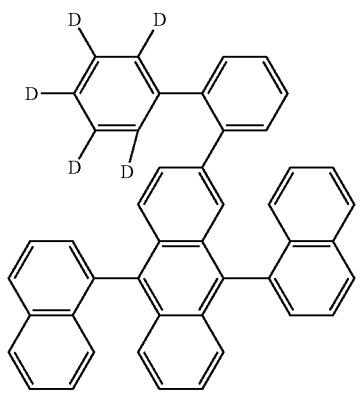
[Chemical Formula 269]
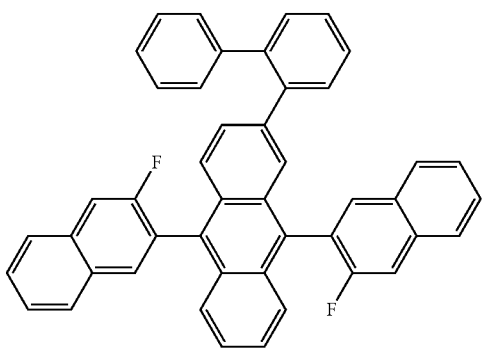
[Chemical Formula 270]
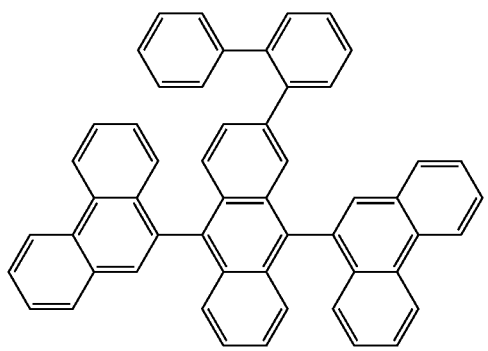
[Chemical Formula 271]
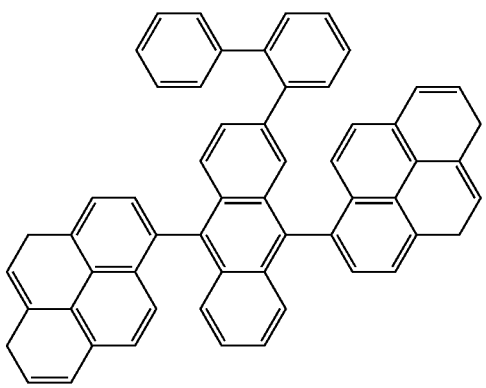

-continued
[Chemical Formula 272]
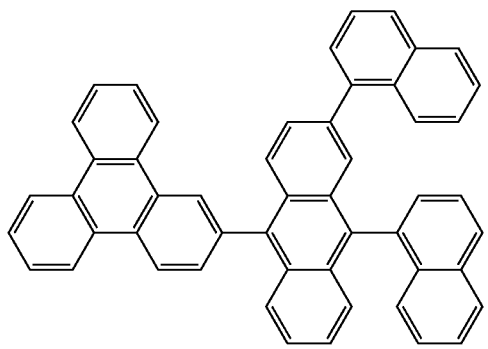
[Chemical Formula 273]
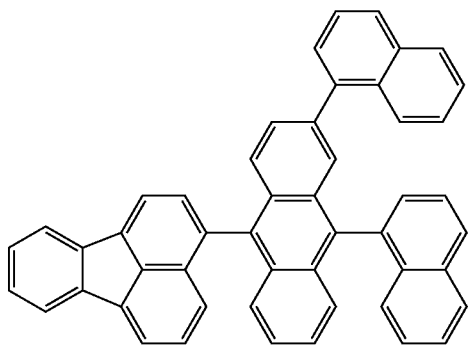
[Chemical Formula 274]
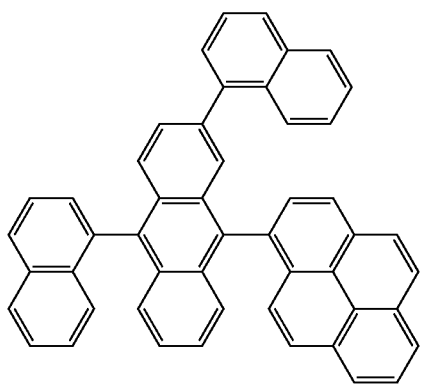
[Chemical Formula 275]
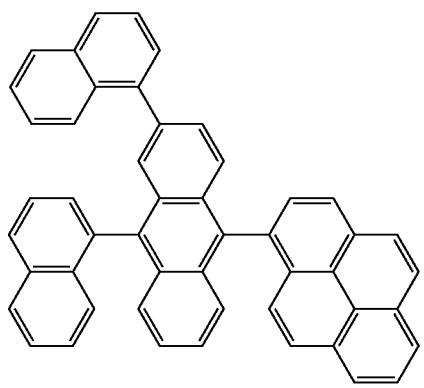
[Chemical Formula 276]
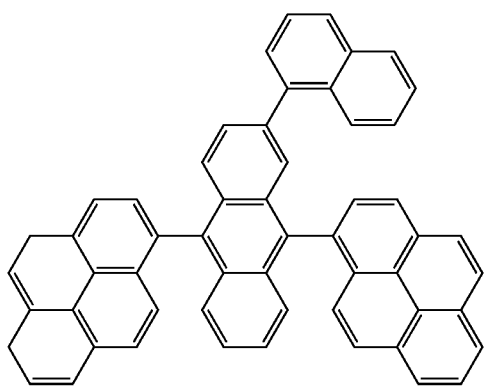
[Chemical Formula 277]
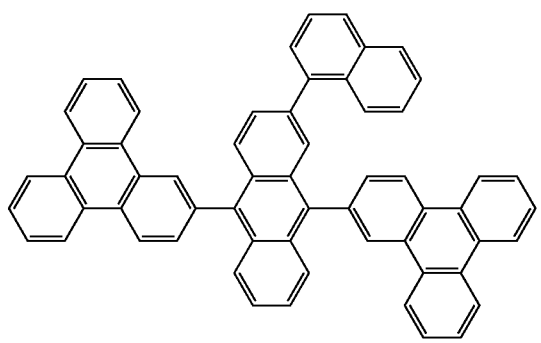
[Chemical Formula 278]
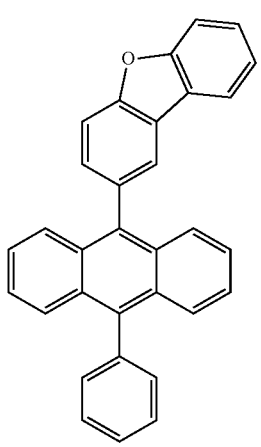
[Chemical Formula 279]
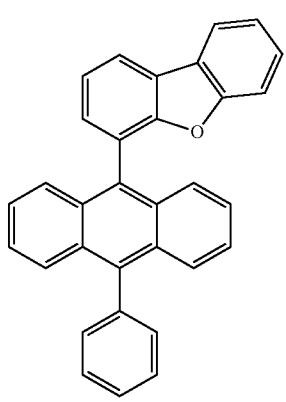

-continued
[Chemical Formula 280]
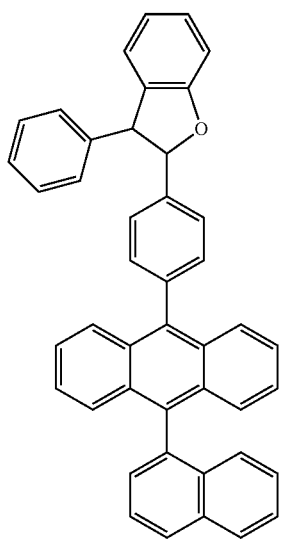
[Chemical Formula 281]
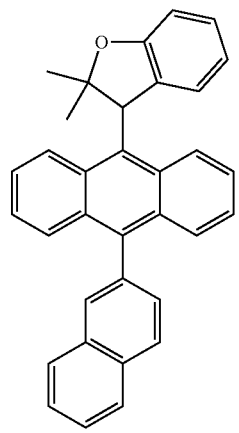
[Chemical Formula 282]
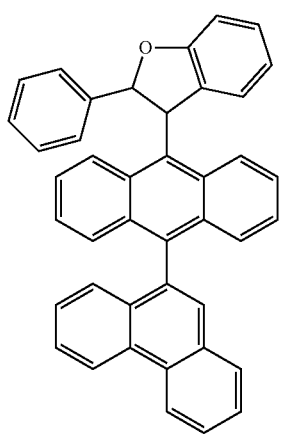
[Chemical Formula 283]
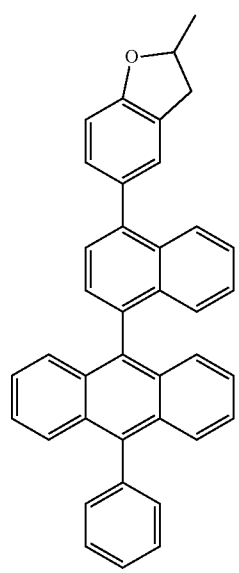
[Chemical Formula 284]
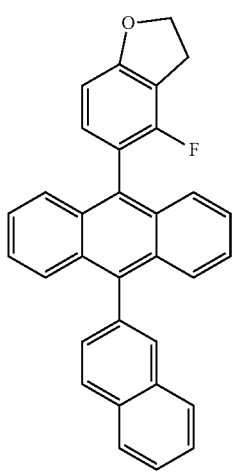
[Chemical Formula 285]
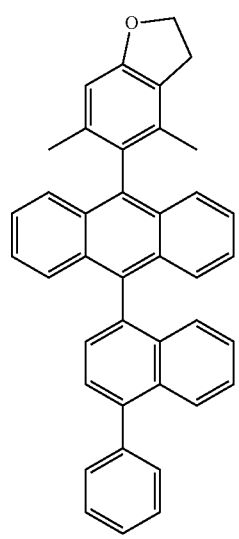

[Chemical Formula 286]
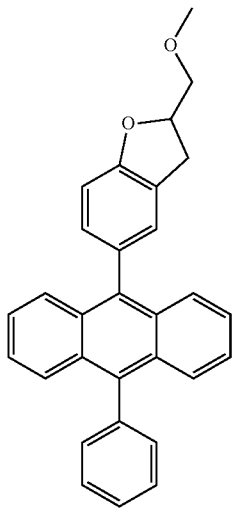
[Chemical Formula 287]
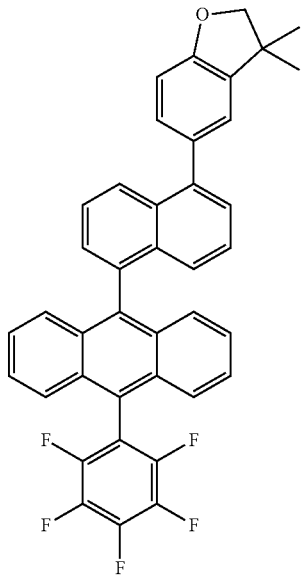
[Chemical Formula 288]
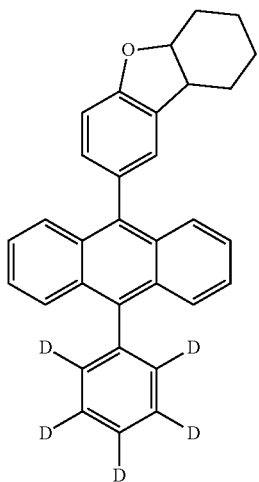
[Chemical Formula 289]
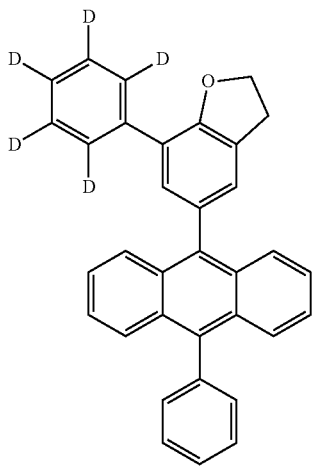
[Chemical Formula 290]
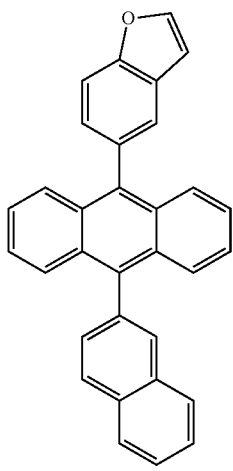
[Chemical Formula 291]
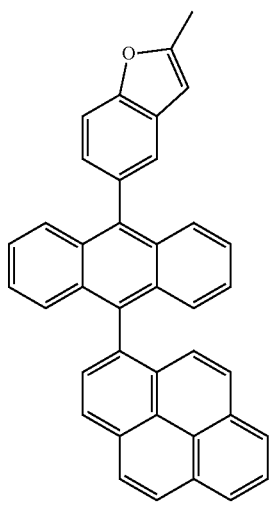

-continued
[Chemical Formula 292]
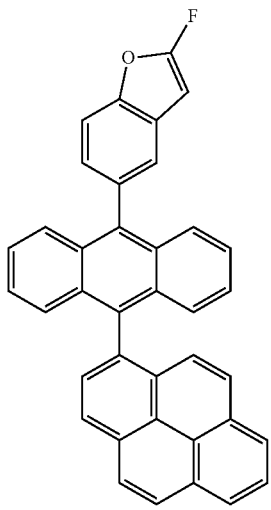
[Chemical Formula 293]
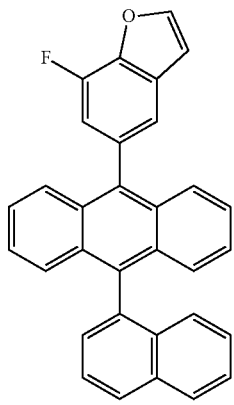
[Chemical Formula 294]
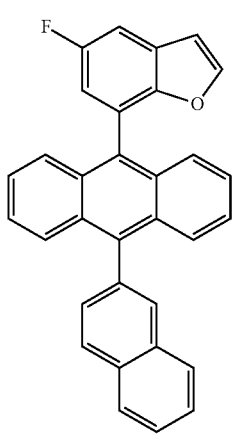
[Chemical Formula 295]
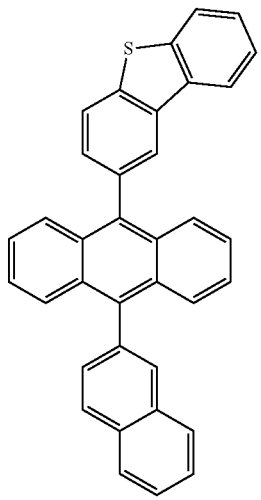
[Chemical Formula 296]
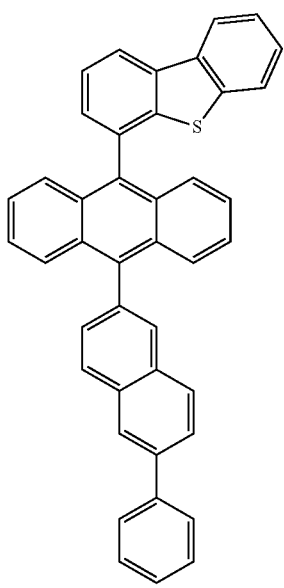
Meanwhile, after being formed on the light-emitting layer, an electron-density-controlling layer 55 of FIG. 2 is covered with an electron transport layer 60 by vacuum deposition or spin coating and then with an electron injection layer 70. A cathode metal is deposited on the electron injection layer 70 by thermal vacuum deposition to form a cathode 80, thus obtaining an organic EL device.

In accordance with some embodiments of the present invention, the affinity Aed (eV) of the electron-density-controlling layer may fall between the affinity Ah (eV) of the host in the light-emitting layer and the affinity Ae (eV) of the electron transport layer (Ah≥Aed≥Ae).

Figure 3:
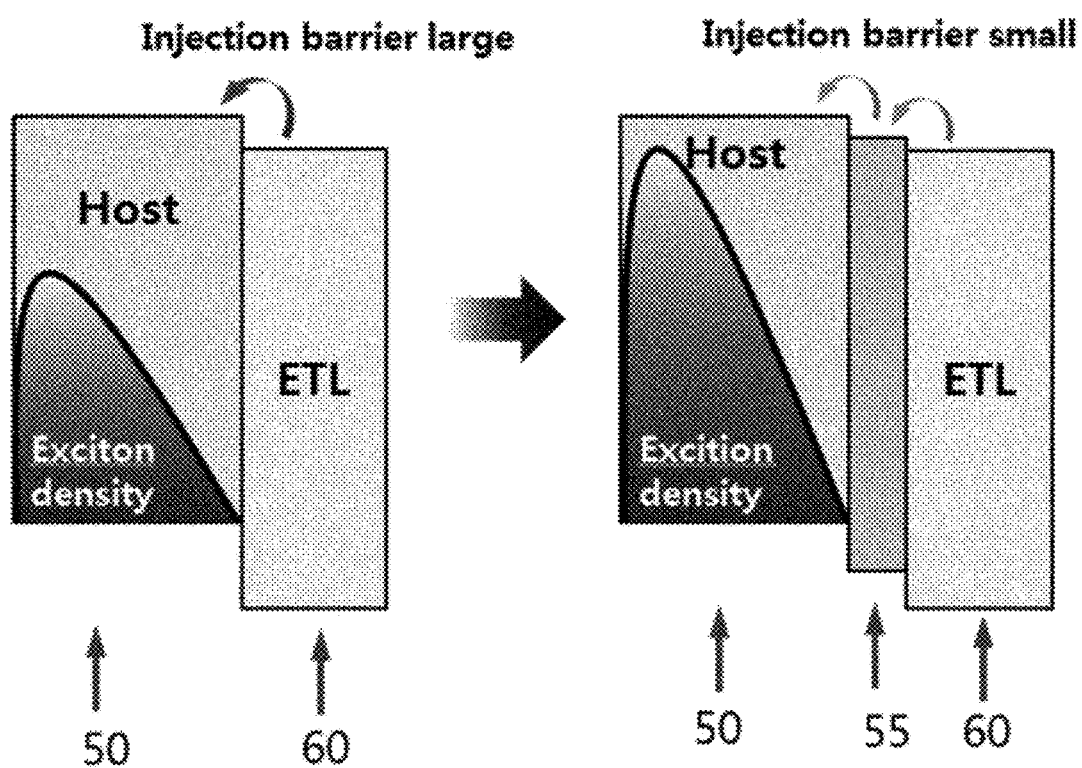
FIG. 3 shows the structures of light-emitting diodes in which an electron density control layer is absent or present in accordance with some embodiments of the present invention.

This can be elucidated in greater detail with reference to FIG. 3. FIG. 3 shows the structure of a light-emitting diode in which an electron-density-controlling layer is absent (left panel) or present (right panel).

As shown in the left panel of FIG. 3, when the electron transport layer 60 is in direct contact with the light-emitting layer 50, the electrons injected from the cathode are less prone to move through the electron transport layer 60 to the host 50 in the light-emitting layer because there is a large electron injection barrier between the cathode and the host 50, resulting in low exciton density in the host of the light-emitting layer. In contrast, as in the present invention, when an affinity Aed (eV) of the electron density control layer is set to be between an affinity Ah (eV) of the host in the light-emitting layer and an affinity Ae (eV) of the electron transport layer (Ah≥Aed≥Ae), smaller interlayer electron injection barriers exist, resulting in greater exciton density in the host of the light-emitting layer.

Figure 4:
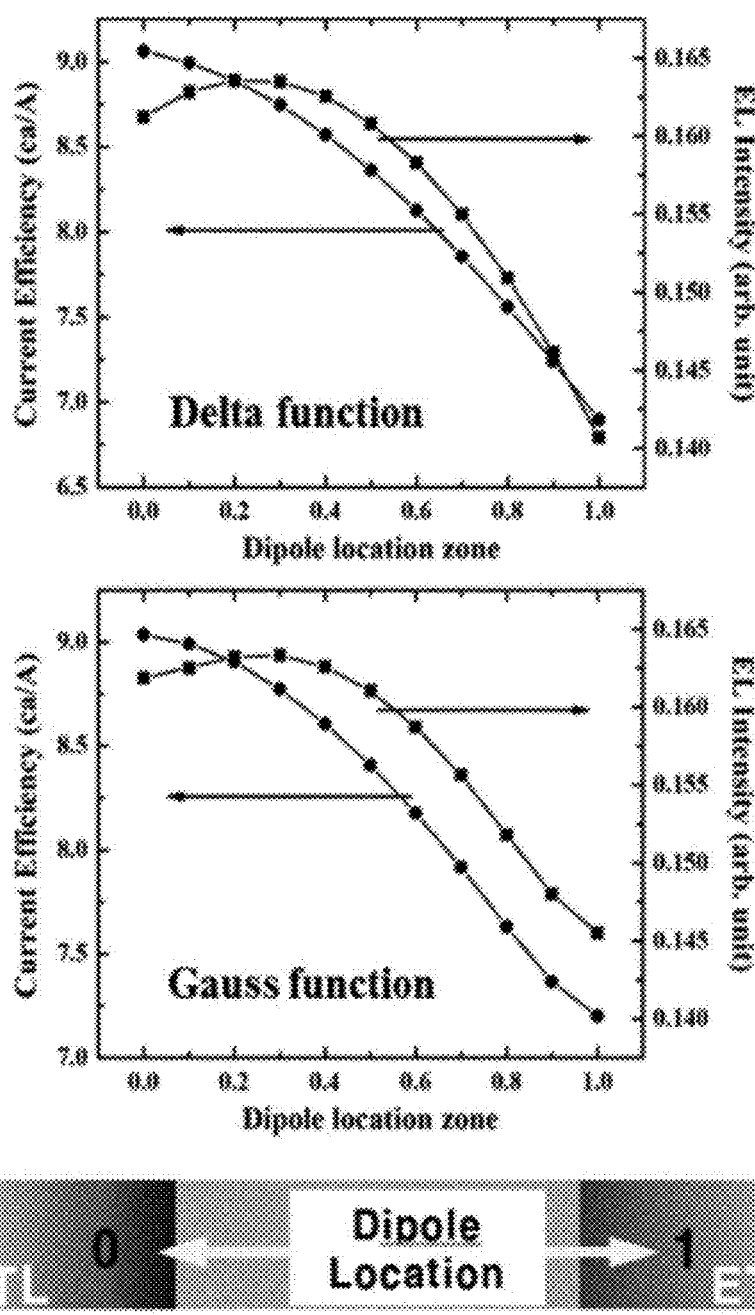
FIG. 4 shows the results of simulation of changes in current efficiency (left) and EL intensity (right) against dipole location zones of excitons in the light-emitting layer of the organic light-emitting diode according to the present invention.

A further explanation may be made in FIG. 4. FIG. 4 shows the simulation results of changes in current efficiency (left) and EL intensity (right) against dipole location zones of excitons in the light-emitting layer of the organic lighting emitting diode according to the present invention.

In FIG. 4, the X-axis for the dipole location zone within the light-emitting layer in which excitons recombine is divided from 0 (zero) for the side of the hole transport layer to 1 for the side of the electron transport layer. As can be seen, higher current efficiency and EL intensities are detected at positions of excitons nearer to the hole transport layer.

Similar patterns are drawn whether the current efficiency and the EL intensity follow a delta function or a Gaussian function, as can be seen in FIG. 4.

That is, given the condition that the affinity Aed (eV) of the electron-density-controlling layer is between the affinity Ah (eV) of the host of the light-emitting layer and the affinity Ae (eV) of the electron transport layer (Ah≥Aed≥Ae), the organic light-emitting diode of the present disclosure can increase the electron density in the light-emitting layer, which shifts the dipole location zone toward the hole transport layer, with the consequent improvement of current efficiency and EL intensity.

According to one embodiment of the present disclosure, the electron mobility of the anthracene derivative in the electron density control layer may be the same as or greater than that of the material in the electron transport layer.

Since the material of the electron density control layer is not smaller in electron mobility than that of the electron transport layer, the electrons supplied from the electron transport layer can move quickly toward the light-emitting layer without delay in the electron density control layer, thereby facilitating the elevation of exciton density in the light-emitting layer.

Figure 5:
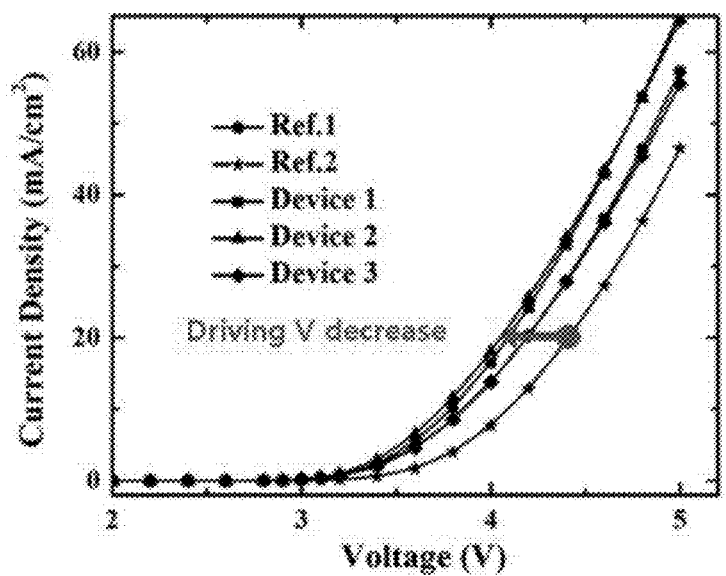
FIG. 5 is a diagram of current density plotted against driving voltage according to the Examples and the Comparative Examples.

With regard to details of current density, reference may made to FIG. 5.

FIG. 5 shows changes in current efficiency with voltage in the presence or absence of electron-density-controlling layer according to Examples and Comparative Example. In order to obtain the effect of the electron density control layer on electron mobility, an electron-only device (EOD), fabricated as shown in the lower panel of FIG. 5, was measured for current density while applying direct voltages thereto.

As can be understood from the upper diagram of FIG. 5, an electron-density controlling layer helps increase the current density at the same voltage.

Even from this measurement result, it can be discovered that the introduction of an electron density control layer enhances the electron injection properties of the device.

For more accurate arithmetic comparison, the electron mobility (p) in each device may be measured. In this regard, whether or not an electron density control layer is introduced thereinto, all the devices to be tested were fabricated to have the same overall thickness so as to exclude an error factor in calculating electron mobility.

To calculate the electron mobility from the data measured in EOD devices, the following relationship between mobility and electric conductivity was used (G. Paasch et al. Synthetic Metals Vol. 132, pp. 97-104 (2002)).

First, the device was measured for resistance from the current-voltage data, and for electric conductivity from the overall thickness (d) and pixel area (A) using the following Formula 1. Based on the electric conductivity, electron mobility was obtained according to the following Formula 2. The data thus obtained are summarized in Table 2, below.

Figure 6:
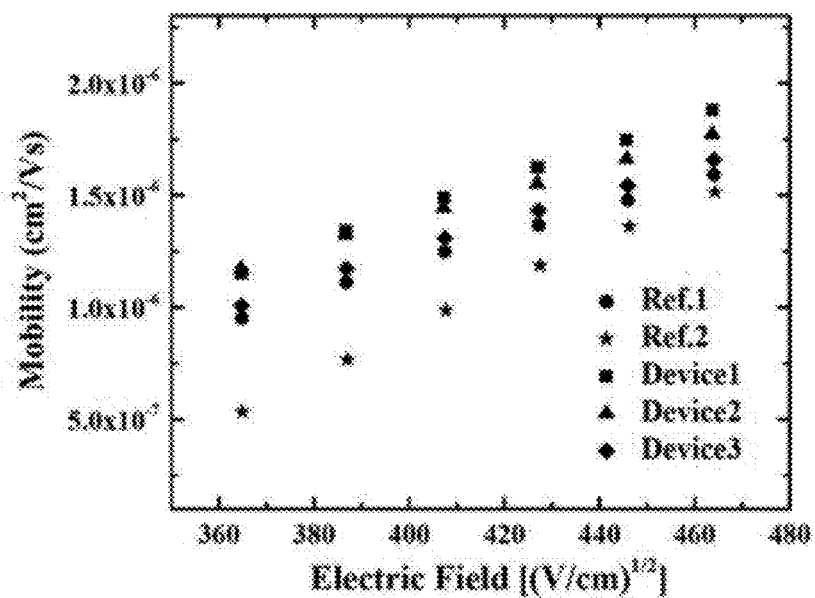
FIG. 6 is a diagram of electron mobility plotted against electric field according to the Examples and the Comparative Examples.

FIG. 6 is a diagram of mobility plotted against electric field.

$$\sigma = \frac{1}{R} \times \frac{d}{A}, \quad R = \frac{V}{I} \qquad \text{Formula (1)}$$

$$\mu(\text{cm}^2/Vs) = \sigma^{0.76}(\text{S/cm}) \qquad \text{Formula (2)}$$

It is therefore understood that when the electron-density-controlling layer is not lower in electron mobility than the electron transport layer, the electrons supplied from the electron transport layer can move quickly toward the light-emitting layer without a delay in the electron-density-controlling layer, thereby facilitating the increase of exciton density in the light-emitting layer.

According to exemplary embodiments of the present disclosure, the electron density control layer and the electron transport layer may have electron mobility of at least $10^{-6}$ cm2/Vs at an electronic field strength of 0.04 MV/cm to 0.5 MV/cm.

So long as it functions to stably transport the electrons from the cathode, any known material may be used for the electron transport layer. Examples of the known electron transport material include quinoline derivatives, particularly tris(8-quinolinolate)aluminum (Alq3), Liq, TAZ, Balq, beryllium bis(benzoquinolin-10-oate: Bebq2), ADN, compound 201, compound 202, BCP, and the oxadiazole derivatives PBD, BMD, and BND, but are not limited thereto.

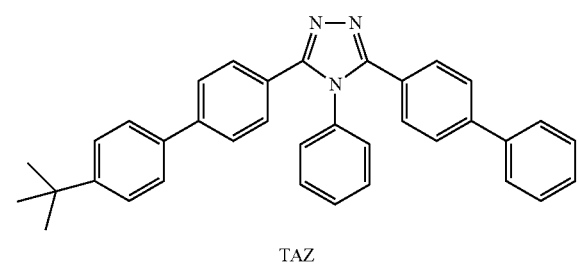

TAZ

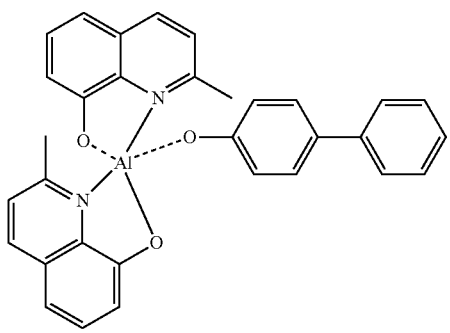

BAlq

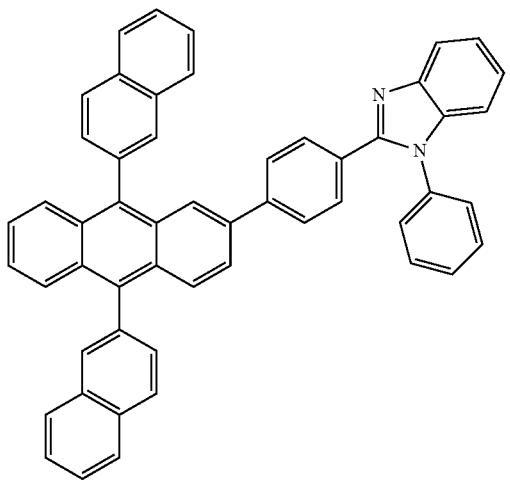

<Compound 201>

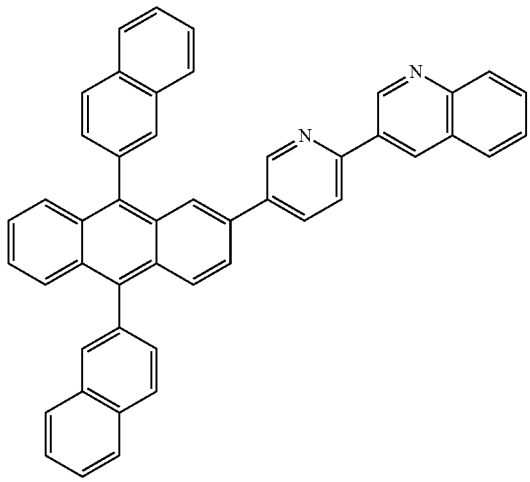

<Compound 202>

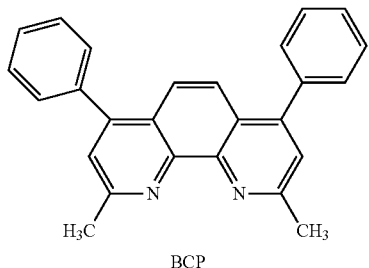

BCP

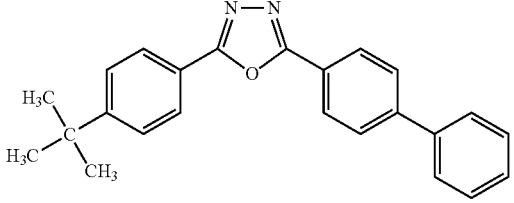

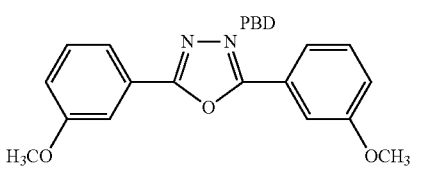

PBD

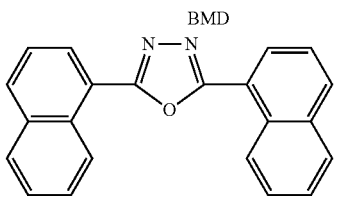

BMD

BND

In addition, the electron transport layer may be made of the organic metal compound represented by Chemical Formula F, either alone or in combination with the aforementioned material.

$$Y_m\text{-}M\text{-}(OA)_n \qquad \text{[Chemical Formula F]}$$

wherein,

Y is a ligand that contains two moieties respectively responsible for forming a single bond with M through a direct bond M and for forming a coordinate bond with M, each moiety being selected from among C, N, O and S, and which is chelated by the single bond and the coordinate bond;

M is an alkali metal, an alkaline earth metal, aluminum (Al), or a boron (B) atom, with a proviso that:

when M is an alkali metal, m=1, n=0 when M is an alkaline earth metal, m=1 and n=1, or m=2 and n=0, or when M is aluminum or a boron, m is an integer of 1 to 3 and n is an integer of 0 to 2, satisfying the relationship m+n=3;

OA is a monodentate ligand capable of forming a single bond or a coordinate bond with M, wherein O is oxygen, and A is selected from among a substituted or unsubstituted alkyl of 1 to 30 carbon atoms, a substituted or unsubstituted aryl of 5 to 50 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, and a substituted or unsubstituted heteroaryl of 2 to 50 carbon atoms bearing as a heteroatom at least one selected from among O, N, S and Si.

The term 'substituted' in the expression 'substituted or unsubstituted' means having at least one substituent selected from the group consisting of a deuterium atom, a cyano, a halogen, a hydroxy, a nitro, an alkyl, an alkoxy, an alkylamino, an arylamino, a hetero arylamino, an alkylsilyl, an arylsilyl, an aryloxy, an aryl, a heteroaryl, germanium, phosphorus, and boron.

In the present disclosure, the Y's may be the same or different and are each independently selected from among the following Structural Formulas C1 to C39, but are not limited thereto:

[Structural Formula C1]

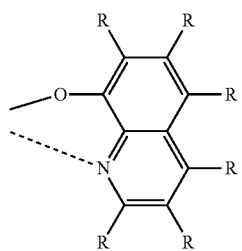

[Structural Formula C2]

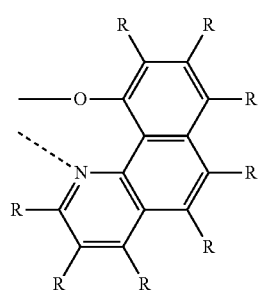

[Structural Formula C3]

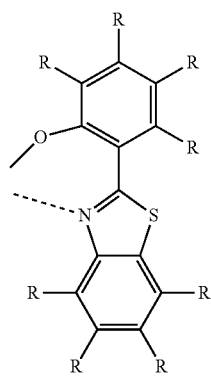

[Structural Formula C4]

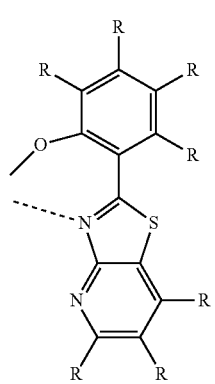

-continued

[Structural Formula C5]

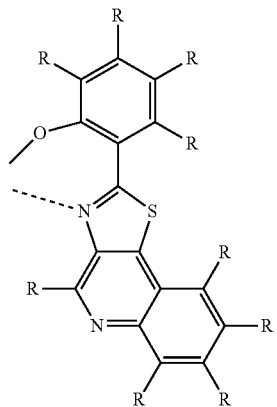

[Structural Formula C6]

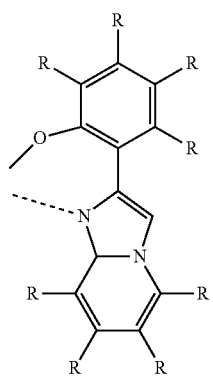

[Structural Formula C7]

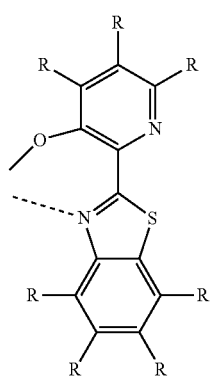

[Structural Formula C8]

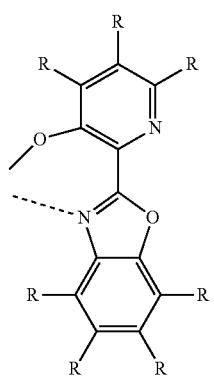

[Structural Formula C9]
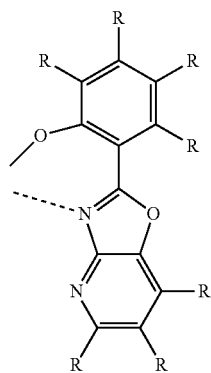
[Structural Formula C10]
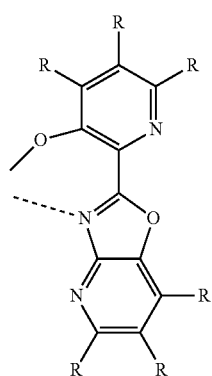
[Structural Formula C11]
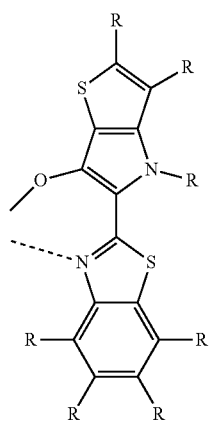
[Structural Formula C12]
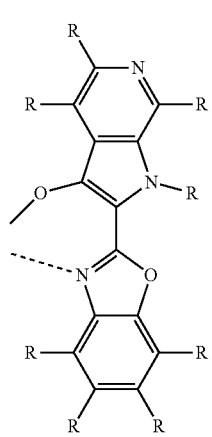
[Structural Formula C13]
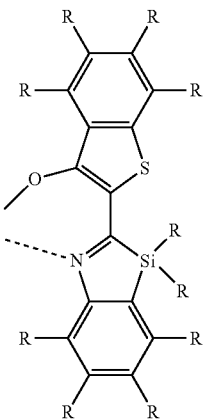
[Structural Formula C14]
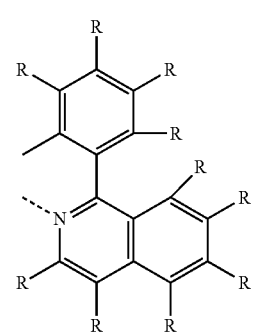
[Structural Formula C15]
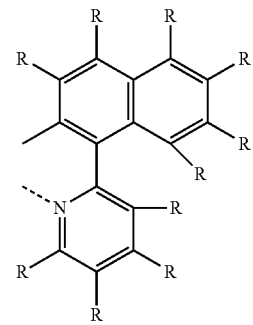
[Structural Formula C16]
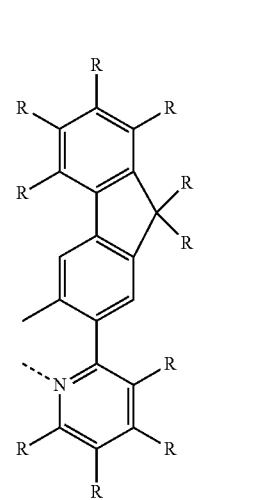

-continued
[Structural Formula C17]
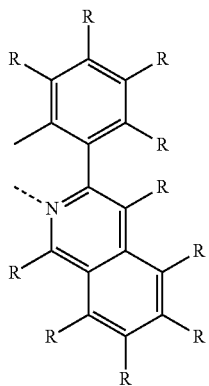
[Structural Formula C18]
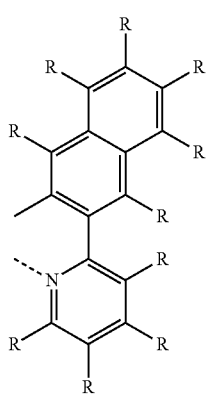
[Structural Formula C19]
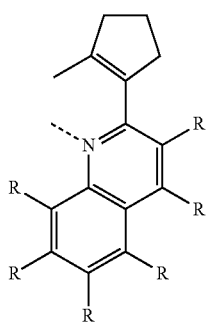
[Structural Formula C20]
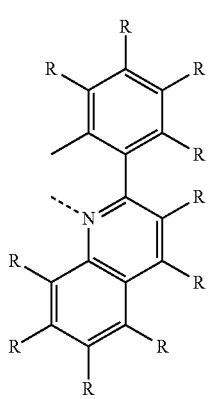
-continued
[Structural Formula C21]
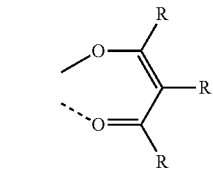
[Structural Formula C22]
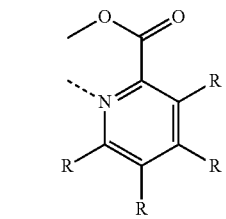
[Structural Formula C23]
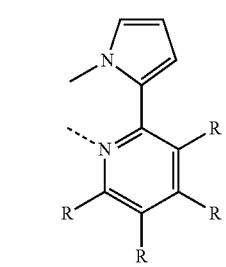
[Structural Formula C24]
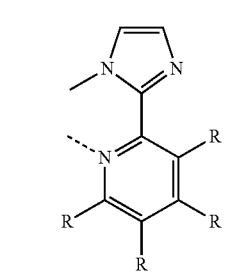
[Structural Formula C25]
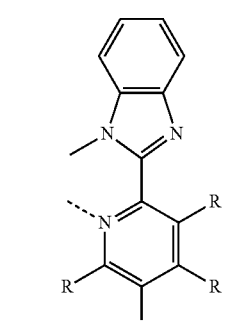
[Structural Formula C26]
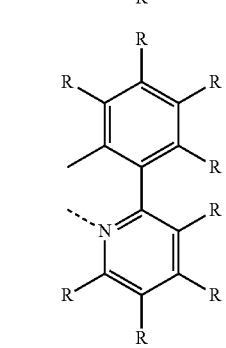

[Structural Formula C27]
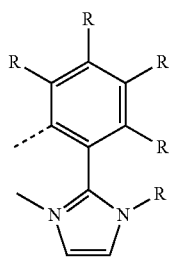
[Structural Formula C28]
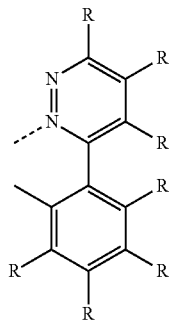
[Structural Formula C29]
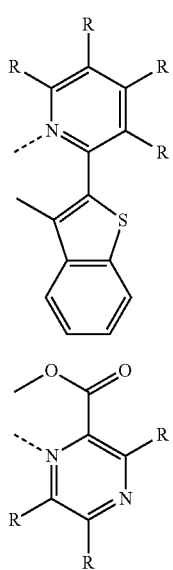
[Structural Formula C30]
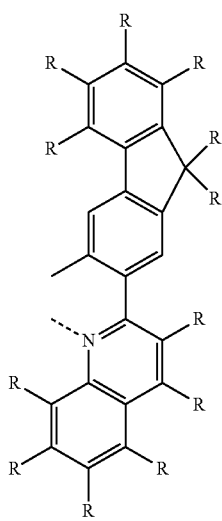
[Structural Formula C31]
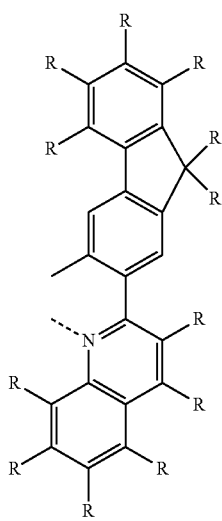
[Structural Formula C32]
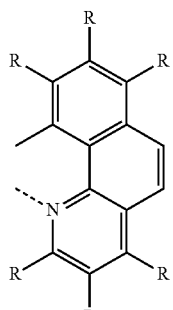
[Structural Formula C33]
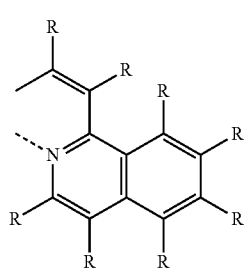
[Structural Formula C34]
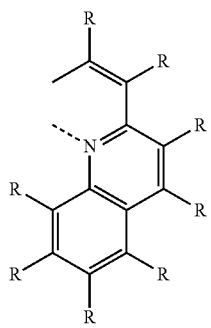
[Structural Formula C35]
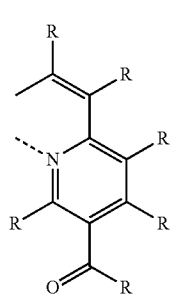
[Structural Formula C36]
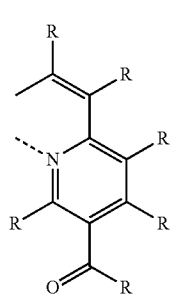

-continued

[Structural Formula C37]

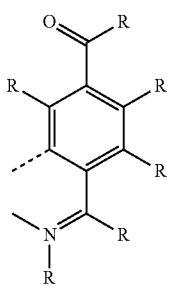

[Structural Formula C38]

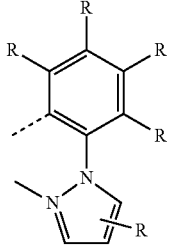

[Structural Formula C39]

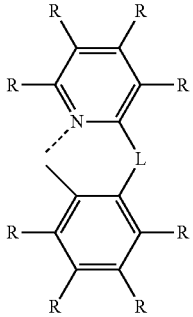

wherein,

R's, which may be the same or different, are each independently selected from among a hydrogen, a deuterium, a halogen, a cyano, a substituted or unsubstituted alkyl of 1 to 30 carbon atoms, a substituted or unsubstituted aryl of 6 to 60 carbon atoms, a substituted or unsubstituted heteroaryl of 3 to 30 carbon atoms, a substituted or unsubstituted alkoxy of 1 to 30 carbon atoms, a substituted or unsubstituted cycloalkyl of 3 to 30 carbon atoms, a substituted or unsubstituted alkenyl of 2 to 30 carbon atoms, a substituted or unsubstituted alkylamino of 1 to 30 carbon atoms, a substituted or unsubstituted alkylsilyl of 1 to 30 carbon atoms, a substituted or unsubstituted arylamino of 6 to 60 carbon atoms, and a substituted or unsubstituted arylsilyl of 6 to 60 carbon atoms, and may form a spiro or fused ring with an adjacent substituent via an alkylene or alkenylene linker.

As described above, an electron injection layer (EIL) is positioned on the electron transport layer in the organic light-emitting diode of the present invention. So long as it functions to facilitate the injection of electrons from the cathode, any known material may be available for forming the electron injection layer, without particular limitations.

By way of example, a material for the electron injection layer may be CsF, NaF, LiF, NaCl, $Li_2O$, or BaO. The condition for depositing the electron injection layer is dependent on the compound that is employed, but may fall within the range of conditions for the formation of the hole injection layer.

The electron injection layer may range in thickness from about 1 Å to about 100 Å, and particularly from about 3 Å to about 90 Å. Given this thickness range, the electron injection layer can exhibit satisfactory electron injection properties without an actual increase in driving voltage.

The cathode may be made of a metal or metal alloy such as lithium (Li), magnesium (Mg), aluminum (Al), aluminum-lithium (Al—Li), calcium (Ca), magnesium-indium (Mg—In), and magnesium-silver (Mg—Ag). Alternatively, ITO or IZO may be employed to form a transparent cathode for a top-emitting organic light-emitting diode.

In another embodiment, the light-emitting device of the present disclosure may further comprise a light-emitting layer, made of a blue light-emitting material, a green light-emitting material, or a red light-emitting material, which can emit light in a wavelength range of 380 nm to 800 nm. That is, the light-emitting layer in the organic light-emitting device of the present disclosure may have a multilayer structure in which the additional blue, green, and/or red light-emitting layer may be made of a fluorescent or phosphorescent material.

A better understanding of the light-emitting diode according to the present disclosure may be obtained through the following examples which are set forth to illustrate, but are not to be construed as limiting the present disclosure.

EXAMPLES

1) Preparation of Electron Density Control Layer Compound

Synthesis Example 1: Synthesis of Compound 3

Synthesis Example 1-(1): Synthesis of Intermediate 1-a

Intermediate 1-a was synthesized as illustrated in the following Reaction Scheme 1.

<Reaction Scheme 1>

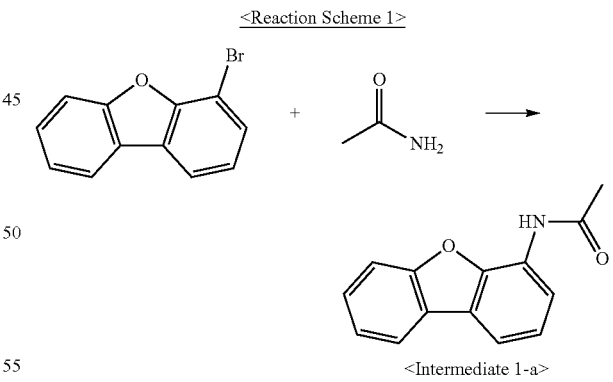

<Intermediate 1-a>

In a 2-L round-bottom flask reactor, 4-bromodibenzofuran (150.0 g, 0.607 mol), acetamide (53.8 g, 0.911 mol), copper iodide (57.8 g, 0.30 mol), (±)trans-1,2-diaminocyclihexane (63.9 g, 0.60 mol), potassium carbonate (167.8 g, 1.21 mol), and toluene (1500 ml) were together stirred under reflux. After completion of the reaction, the reaction mixture was filtered through a silica gel pad and then washed many times with hot toluene. The filtrate was concentrated in a vacuum, and the concentrate was crystallized in acetonitrile and filtered to afford Intermediate 1-a as a solid. (70.0 g, 51%)

Synthesis Example 1-(2): Synthesis of Intermediate 1-b

Intermediate 1-b was synthesized as illustrated in the following Reaction Scheme 2:

<Reaction Scheme 2>

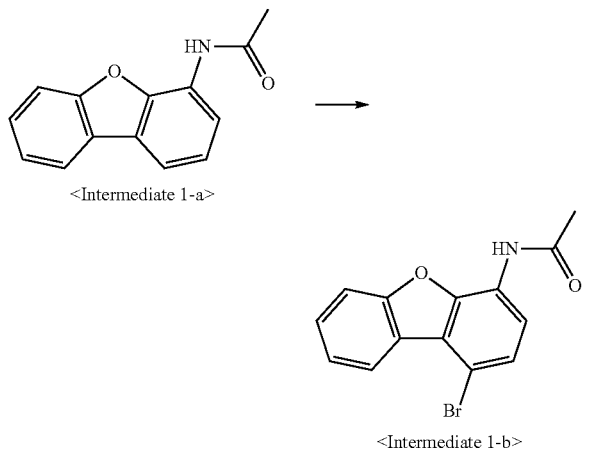

<Intermediate 1-b>

In a 2-L round-bottom flask reactor, Intermediate 1-a (70.0 g, 0.311 mol) was dissolved in acetic acid (630 ml). A mixture of bromine (49.7 g, 0.311 mol) and acetic acid (280 ml) was dropwise added to the reactor, followed by stirring at room temperature for 2 hours. After completion of the reaction, water (100 ml) was added to the reaction mixture which was then stirred. The gray solid thus formed was placed in ethanol (500 ml), stirred, and filtered. The solid was slurried in ethanol, filtered and dried to afford Intermediate 1-b. (86.0 g, 91%)

Synthesis Example 1-(3): Synthesis of Intermediate 1-c

Intermediate 1-c was synthesized as illustrated in the following Reaction Scheme 3:

<Reaction Scheme 3>

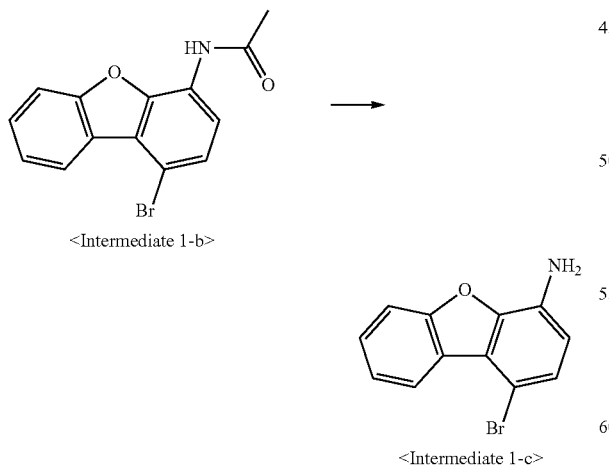

In a 2-L round-bottom flask reactor, Intermediate 1-b (86.0 g, 0.283 mol) was dissolved in ethanol (600 ml) and tetrahydrofuran (430 ml) and stirred. A solution of potassium hydroxide (47.6 g, 0.848 mol) in water (260 ml) was slowly added to the reactor and stirred overnight under reflux. After completion of the reaction, the reaction mixture was cooled to room temperature. Extraction with ethyl acetate and water was conducted, followed by the isolation and vacuum concentration of the organic layer. The solid thus obtained was added with an excess of ethanol, stirred, and then filtered. Recrystallization in methylene chloride and heptane afforded Intermediate 1-c. (73.0 g, 98%)

Synthesis Example 1-(4): Synthesis of Intermediate 1-d

Intermediate 1-d was synthesized as illustrated in the following Reaction Scheme 4:

<Reaction Scheme 4>

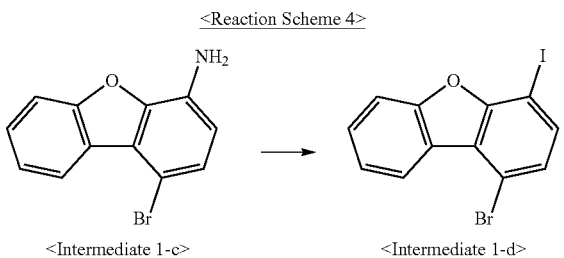 [SMILES: Nc1ccc(Br)c2c1oc1ccccc12 ; Brc1ccc(I)c2oc3ccccc3c12]

In a 2-L round-bottom flask reactor, Intermediate 1-c (73.0 g, 0.279 mol), HCl (90 ml), and water (440 ml) were cooled to 0° C. and stirred together. A solution of sodium nitrite (25.0 g, 0.362 mol) in water (90 ml) was dropwise added to the reactor and stirred at the same temperature for 1 hour. Again, a solution of potassium iodide (92.5 g, 0.557 mol) in water (90 ml) was dropwise added to the reactor and stirred at room temperature. After completion of the reaction, the reaction mixture was extracted with ethyl acetate and water. The organic layer was washed with an aqueous sodium thiosulfate pentahydrate solution, isolated, and concentrated in a vacuum. Purification by column chromatography afforded Intermediate 1-d. (52.3 g, 50.3%)

Synthesis Example 1-(5): Synthesis of Intermediate 1-e

Intermediate 1-e was synthesized as illustrated in the following Reaction Scheme 5:

<Reaction Scheme 5>

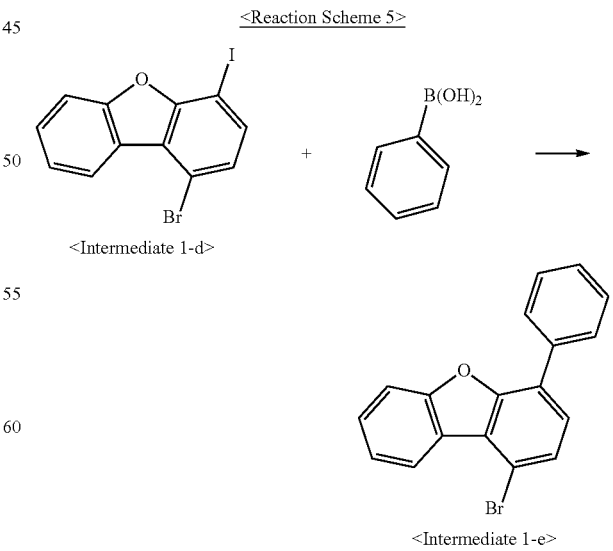

In a 2-L round-bottom flask reactor were placed Intermediate 1-d (15.0 g, 40 mmol), phenylboronic acid (5.4 g, 44 mmol), tetrakis(triphenylphosphine)palladium (0.9 g, 1 mmol), and potassium carbonate (11.1 g, 80 mmol), followed by toluene (100 mL), methanol (45 mL), and water (30 mL). The mixture was stirred overnight under reflux. After completion of the reaction, the reaction mixture was cooled to room temperature and extracted with ethyl acetate. The organic layer thus formed was concentrated in a vacuum and isolated by column chromatography. Recrystallization in heptane afforded Intermediate 1-e as a solid. (7.0 g, 53.9%)

Synthesis Example 1-(6): Synthesis of Compound 3

Compound 3 was synthesized as illustrated in the following Reaction Scheme 6:

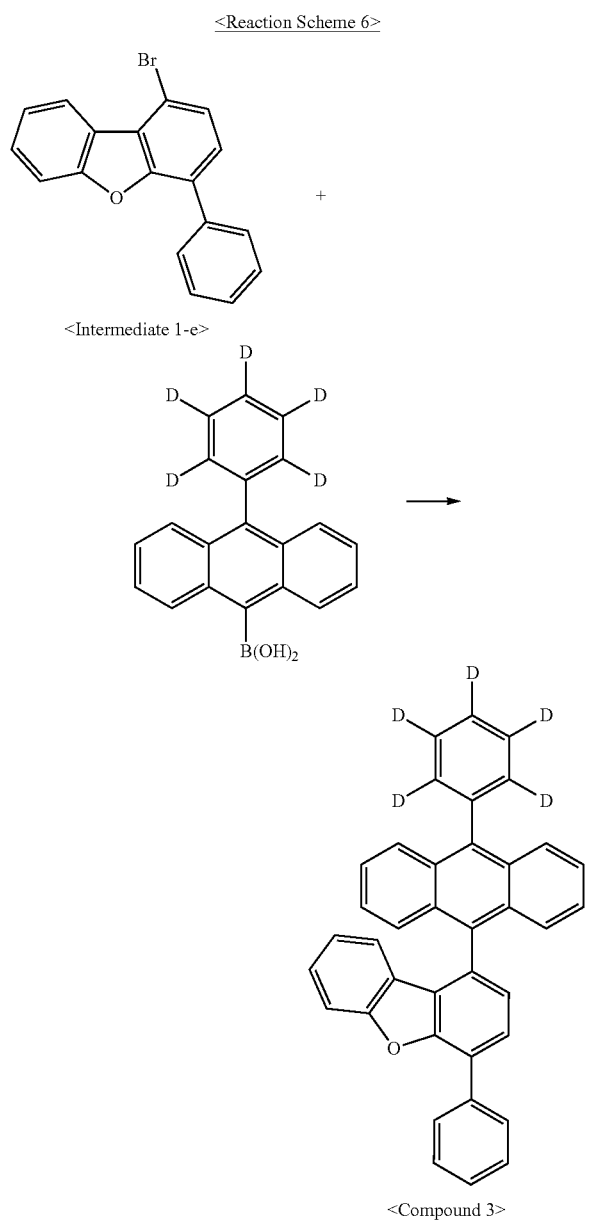

In a 250-mL round-bottom flask reactor were placed Intermediate 1-e (7.0 g, 22 mmol), (10-phenyl(d5)-anthracene-9-boronic acid (7.9 g, 26 mmol), tetrakis(triphenylphosphine)palladium (0.5 g, 1 mmol), and potassium carbonate (6.0 g, 43 mmol), followed by toluene (50 mL), ethanol (21 mL), and water (14 mL). The reactor was heated to 90° C. before stirring overnight. After completion of the reaction, the reaction mixture was cooled to room temperature and then stirred together with methanol (50 ml) at room temperature. The solid thus formed was washed with methanol. Recrystallization in toluene and acetone afforded Compound 3 as a solid.

MS (MALDI-TOF): m/z 501.21 [M+]

Synthesis Example 2: Synthesis of Compound 9

Synthesis Example 2-(1): Synthesis of Intermediate 2-a

Intermediate 2-a was synthesized as illustrated in the following Reaction Scheme 7:

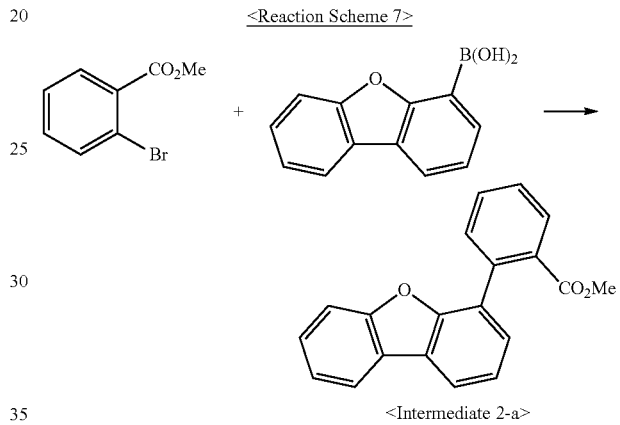

In a 500-mL round-bottom flask reactor were placed methyl 2-bromobenzoate (30.0 g, 0.140 mol), 4-dibenzoboronic acid (32.5 g, 0.153 mol), tetrakis(triphenylphosphine)palladium (3.2 g, 3 mmol), and potassium carbonate (38.6 g, 0.279 mol), followed by toluene (210 mL), methanol (90 mL), and water (60 mL). The mixture was stirred overnight under reflux. After completion of the reaction, the reaction mixture was cooled to room temperature and extracted with ethylacetate. After being isolated, the organic layer was concentrated in a vacuum. Purification by column chromatography afforded Intermediate 2-a. (25.0 g, 59.1%)

Synthesis Example 2-(2): Synthesis of <Intermediate 2-b>

Intermediate 2-b was synthesized as illustrated in the following Reaction Scheme 8:

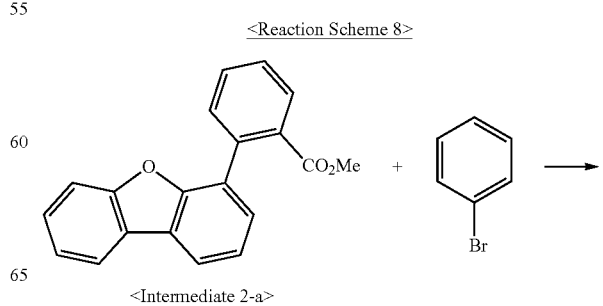

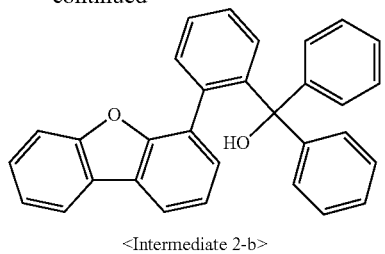

<Intermediate 2-b>

In a 500-ml round-bottom flask reactor, a mixture of bromobenzene (28.6 g, 182 mmol) and tetrahydrofuran (220 ml) was chilled to −78° C. under a nitrogen atmosphere. To the chilled reaction solution, n-butyl lithium (104.6 ml, 167 mmol) was dropwise added at the same temperature, followed by stirring 2 hours. Intermediate 2-a (22.0 g, 73 mmol) was added little by little to the reaction solution while stirring at room temperature. After the reaction was stopped with H2O (50 ml), extraction was conducted with ethyl acetate and water. The organic layer was separated and concentrated in a vacuum afford Intermediate 2-b. (28.0 g, 90%)

Synthesis Example 2-(3): Synthesis of Intermediate 2-c

Intermediate 2-c was synthesized as illustrated in the following Reaction Scheme 9:

<Reaction Scheme 9>

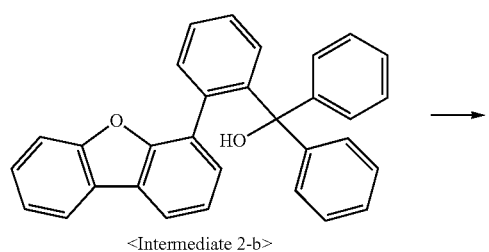

<Intermediate 2-b>

<Intermediate 2-c>

In a 500-ml round-bottom flask reactor, a mixture of Intermediate 2-b (28.0 g, 66 mmol), acetic acid (310 ml) and HCl (2 ml) was stirred for 1 hour under reflux. When a precipitate was formed, the completion of the reaction was confirmed using thin-layer chromatography. Thereafter, the reaction mixture was then cooled to room temperature and filtered. The filtrate was washed with H2O and methanol and dried to afford Intermediate 2-c. (22.3 g, 83.2%)

Synthesis Example 2-(4): Synthesis of Intermediate 2-d

Intermediate 2-d was synthesized as illustrated in the following Reaction Scheme 10:

<Reaction Scheme 10>

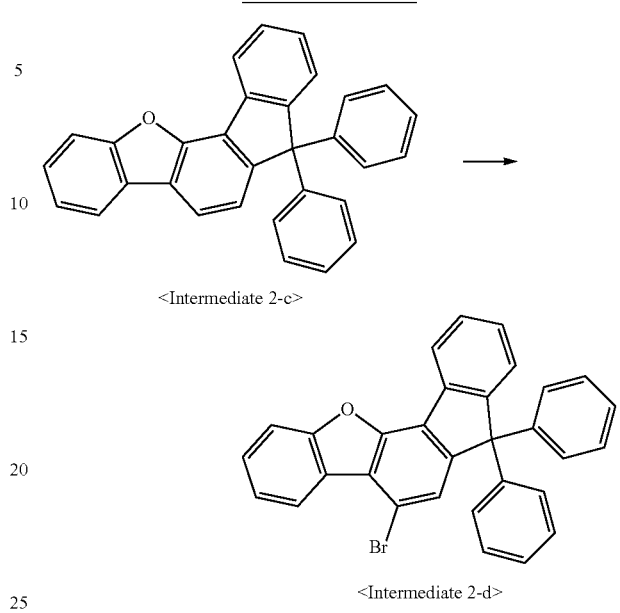

<Intermediate 2-c>

<Intermediate 2-d>

In a 2-L round-bottom flask reactor, Intermediate 2-c (22.3 g, 55 mmol) dissolved in methylene chloride (500 ml). Drops of a solution of bromine (8.72 g, 55 mmol) in methylene chloride (250 ml) were slowly added to the reactor, and then stirred at room temperature for 3 hours. After completion of the reaction, the reaction mixture was washed with an aqueous sodium hydrogen carbonate solution. The precipitate thus formed was filtered and recrystallized in toluene and acetone to afford Intermediate 2-d. (25.0 g, 94%)

Synthesis Example 2-(5): Synthesis of Compound 9

Compound 9 was synthesized as illustrated in the following Reaction Scheme 11:

<Reaction Scheme 11>

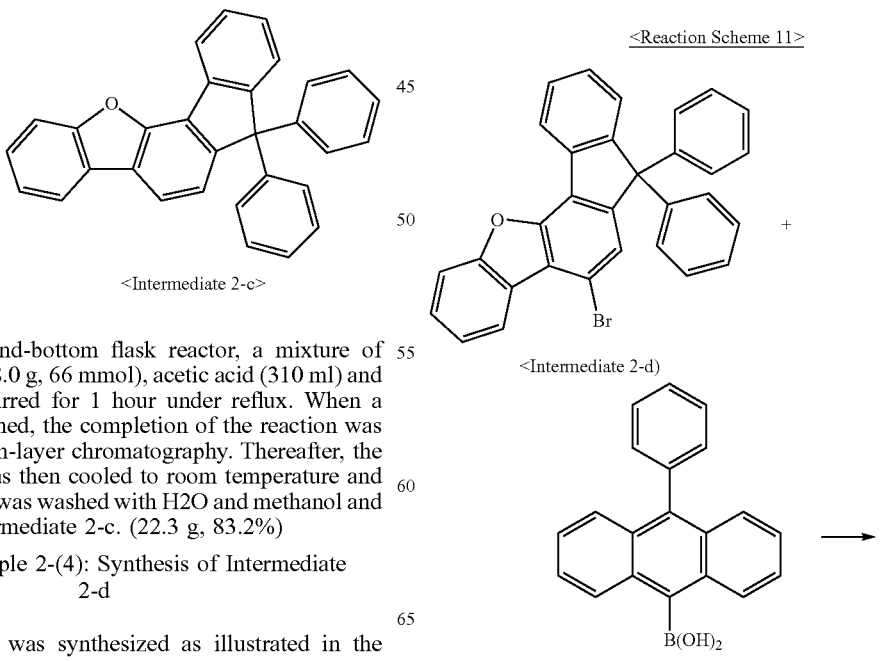

<Intermediate 2-d>

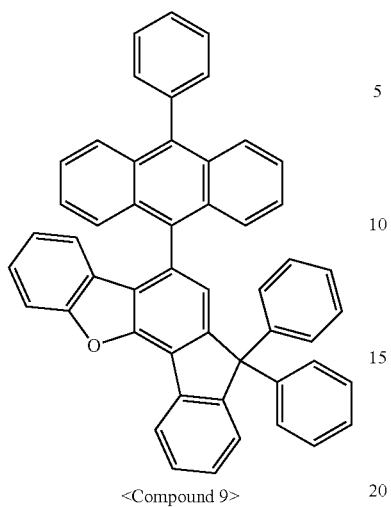
<Compound 9>

In a 250-mL round-bottom flask reactor were placed Intermediate 2-d (7.0 g, 14 mmol), (10-phenyl-anthracene-9-boronic acid (5.1 g, 17 mmol), tetrakis(triphenylphosphine)palladium (0.3 g, 3 mmol), and potassium carbonate (4.0 g, 29 mmol), followed by toluene (49 mL), ethanol (21 mL), and water (14 mL). The mixture was heated to 90° C. and stirred overnight. After completion of the reaction, the reaction mixture was cooled to room temperature, and extracted with ethyl acetate. The organic layer thus formed was separated and concentrated in a vacuum. Following purification by column chromatography, recrystallization in methylene chloride and acetone afforded Compound 9 as a crystal.

MS (MALDI-TOF): m/z 660.25 [M+]

Synthesis Example 3: Synthesis of Compound 13

Synthesis Example 3-(1): Synthesis of Intermediate 3-a

Intermediate 3-a was synthesized as illustrated in the following Reaction Scheme 12:

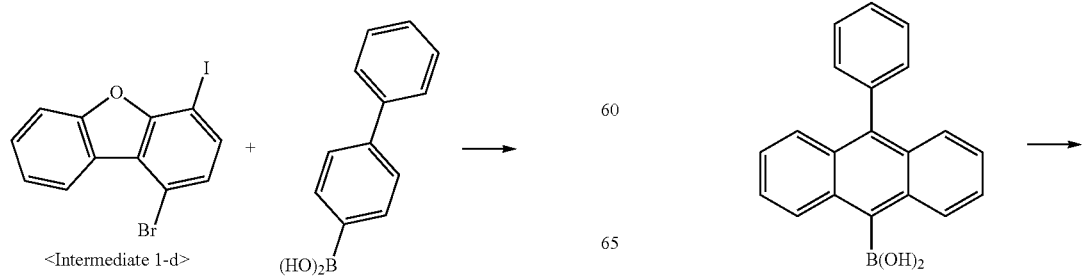

<Intermediate 1-d>   (HO)₂B

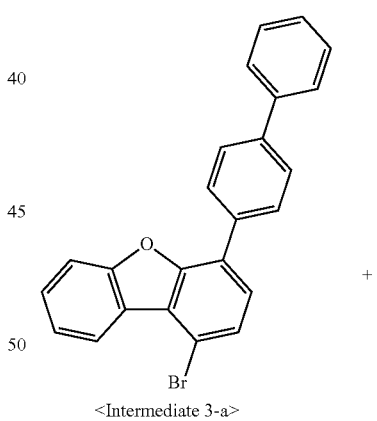
<Intermediate 3-a>

The same procedure as in Synthesis Example 1-(5) was performed, with the exception of using 4-biphenyl boronic acid instead of phenyl boronic acid, to afford Intermediate 3-a (8.5 g, 55.9%).

Synthesis Example 3-(2): Synthesis of Compound 13

Compound 13 was synthesized as illustrated in the following Reaction Scheme 13:

<Reaction Scheme 13>

-continued

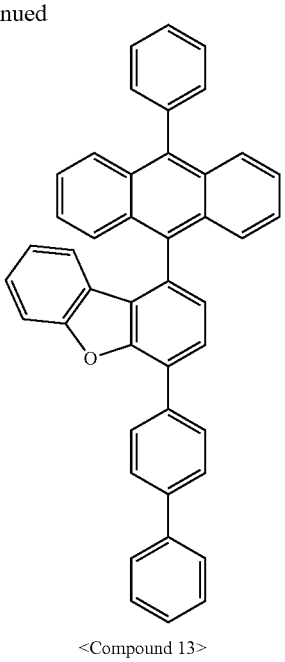

<Compound 13>

The same procedure as in Synthesis Example 2-(5) was performed, with the exception of using Intermediate 3-a instead of Intermediate 2-d, to afford Compound 13 (6.3 g, 51%).

MS (MALDI-TOF): m/z 572.21 [M+]

2) Dopant Preparation: Synthesis of BD Compound

Synthesis Example 4: BD

Synthesis Example 4-(1): Synthesis of Intermediate 4-a

<Reaction Scheme 14>

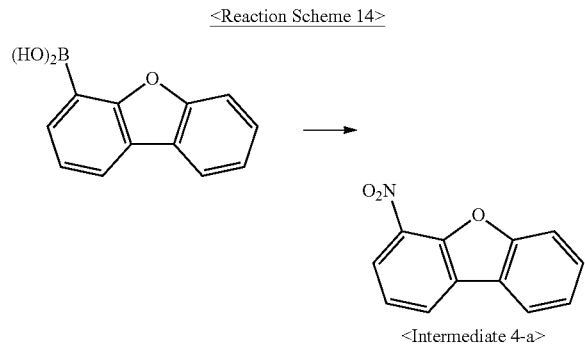

<Intermediate 4-a>

In a 1-L round-bottom flask reactor, 4-dibenzoboronic acid (85.0 g, 0.401 mol), bismuth(III) nitrate pentahydrate (99.2 g, 0.200 mol) and toluene (400 ml) were stirred together at 70° C. for 3 hrs under a nitrogen atmosphere. After completion of the reaction, the reaction mixture was cooled to room temperature, and the precipitates thus formed were filtered and washed with toluene to afford Intermediate 4-a (61.5 g, 72%).

Synthesis Example 4-(2): Synthesis of Intermediate 4-b

<Reaction Scheme 15>

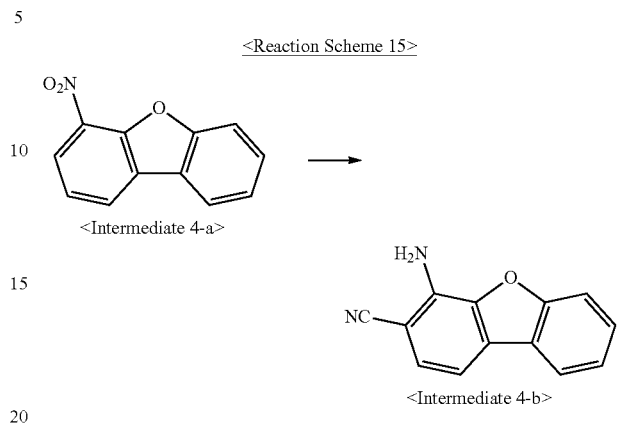

<Intermediate 4-b>

In a 2-L round-bottom flask reactor, ethyl cyanoacetate (202.9 g, 1.794 mol) and dimethyl formamide (500 ml) were placed. Potassium hydroxide (67.10 g, 1.196 mol) and potassium cyanide (38.95 g, 0.598 mol) were added thereto, followed by dimethyl formamide (200 ml). The reaction solution was stirred at room temperature. Intermediate 4-a (127.5 g, 0.737 mol) was incrementally added to the reaction solution, followed by stirring at 50° C. for 72 hrs. After completion of the reaction, an aqueous sodium hydroxide solution (25%, 200 ml) was added to the reaction solution, which was then stirred for 3 hours under reflux and cooled to room temperature. Extraction was performed using ethyl acetate and water. The organic layer was isolated and concentrated in a vacuum. Purification through column chromatography afforded Intermediate 4-b (20.0 g, 16%).

Synthesis Example 4-(3): Synthesis of Intermediate 4-c

<Reaction Scheme 16>

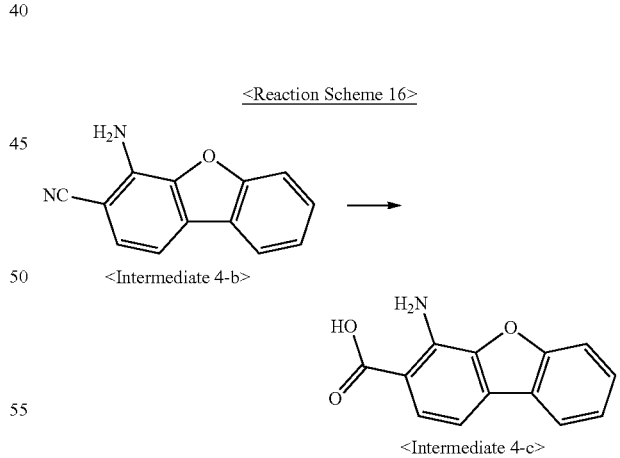

<Intermediate 4-c>

In a 2-L round-bottom flask reactor, Intermediate 4-b (20.0 g, 0.096 mol), ethanol (600 ml), and an aqueous potassium hydroxide solution (142.26 g, 2.53 mol, 170 ml) were stirred together for 12 hours under reflux. After completion of the reaction, the reaction mixture was cooled to room temperature and acidified with 6-N HCl (400 ml). The solid thus formed was stirred for 20 min and filtered. The filtrate was washed with ethanol to afford Intermediate 4-c (17.0 g, 88.5%).

Synthesis Example 4-(4): Synthesis of Intermediate 4-d

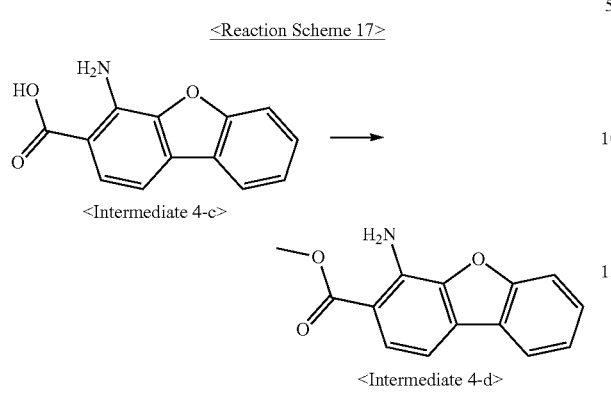

In a 2-L round-bottom flask reactor, Intermediate 4-c (17.0 g, 0.075 mol) and sulfuric acid (15 ml) were stirred together for 72 hours under reflux. After completion of the reaction, the reaction mixture was cooled to room temperature and then extracted with ethyl acetate and water. The organic layer was isolated and washed with an aqueous sodium hydrogen carbonate, followed by concentration in a vacuum. The concentrate was crystallized in an excess of methanol and filtered to afford Intermediate 4-d (14.0 g, 77.6%).

Synthesis Example 4-(5): Synthesis of Intermediate 4-e

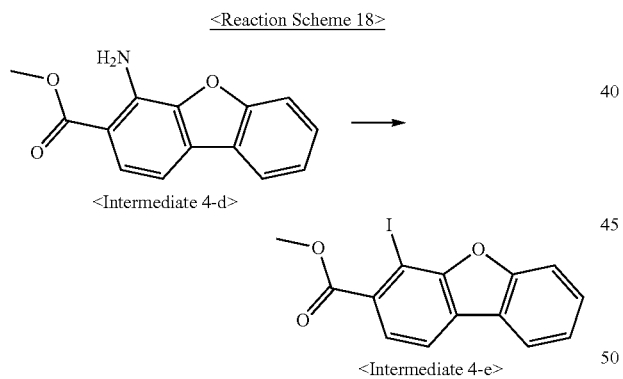

In a 500-mL round-bottom flask reactor, a mixture of Intermediate 4-d (14.0 g, 0.058 mol), HCl (20 ml), and water (100 ml) was cooled to 0° C. and stirred for 1 hour. At the same temperature, a solution of sodium nitrite (7.4 g, 0.116 mol) in water (50 ml) was dropwise added and then stirred for 1 hour. A solution of potassium iodide (30.0 g, 0.180 mol) in water (100 ml) was dropwise added, taking care not to increase the temperature of the reaction solution above 5° C. Stirring was continued for 5 hours at room temperature, and after completion of the reaction, the reaction mixture was washed with an aqueous sodium thiosulfate solution and extracted with ethyl acetate and water. The organic layer was separated and concentrated in a vacuum. Purification by column chromatography afforded Intermediate 4-e (9.1 g, 48%).

Synthesis Example 4-(6): Synthesis of Intermediate 4-f

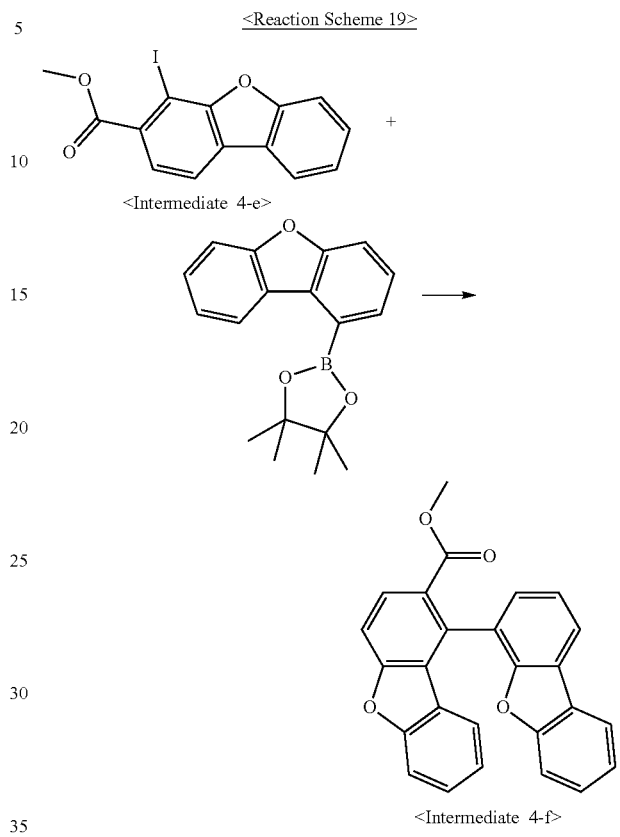

In a 250-mL round-bottom flask reactor were placed methyl 5-bromo-2-iodobenzoate (9.3 g, 25 mmol), 4-dibenzoboronic acid (8.3 g, 28 mmol), and tetrakis(triphenylphosphine)palladium (0.6 g, 0.05 mmol), and potassium carbonate (6.7 g, 50 mmol), followed by toluene (50 mL), tetrahydrofuran (50 mL), and water (20 mL). The mixture was heated to 80° C. and stirred for 10 hours. After completion of the reaction, the reaction mixture was cooled to room temperature and extracted with ethyl acetate. The organic layer thus formed was isolated and concentrated in a vacuum. Purification by column chromatography afforded Intermediate 4-f (5.3 g, 52.3%).

Synthesis Example 4-(7): Synthesis of Intermediate 4-g

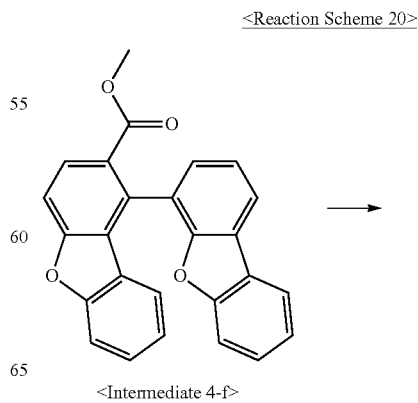

-continued

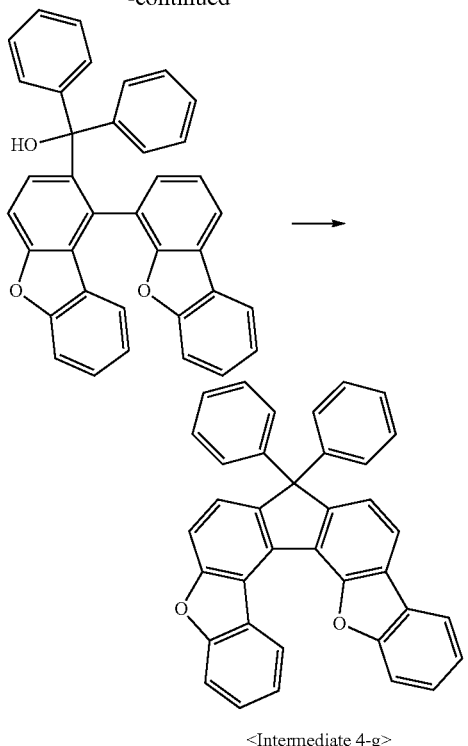

<Intermediate 4-g>

In a 500-ml round-bottom flask reactor, a mixture of bromobenzene (25.5 g, 0.163 mol) and tetrahydrofuran (170 ml) was cooled to −78° C. under a nitrogen atmosphere. n-Butyl lithium (1.6 M, 95.6 ml, 0.153 mol) was dropwise added to the cold mixture, after which stirring was conducted at the same time. Intermediate 4-f (20.0 g, 0.051 mol) was added to the mixture and then stirred at room temperature for 3 hours. After completion of the reaction, the reaction mixture was added with water (50 ml) and stirred for 30 min. Extraction with ethyl acetate and water gave an organic layer which was then isolated and concentrated in a vacuum. The concentrate was mixed with acetic acid (200 ml) and HCl (1 ml) and stirred at 80° C. After the reaction was completed, the reaction mixture was cooled to room temperature and the precipitate thus formed was filtered and washed with methanol to afford Intermediate 4-g (20.0 g, 78%).

Synthesis Example 4-(8): Synthesis of Intermediate 4-h

<Reaction Scheme 21>

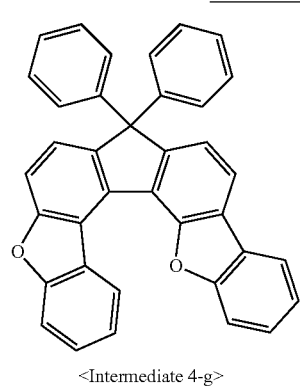

<Intermediate 4-g>

-continued

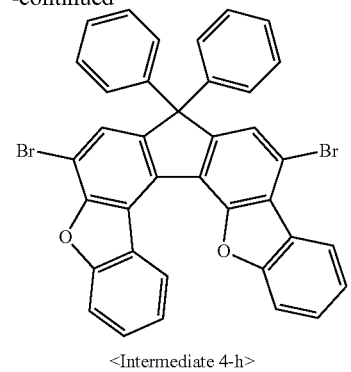

<Intermediate 4-h>

In a 100-mL round-bottom flask reactor, a mixture of Intermediate 4-g (20 g, 58 mmol) and dichloromethane (40 ml) was stirred at room temperature. A dilution of bromine (5.8 ml, 116 mmol) in dichloromethane (10 ml) was dropwise added to the reactor and stirred for 8 hours at room temperature. After completion of the reaction, acetone (20 ml) was added to the reactor and stirred. The solid thus formed was filtered and washed with acetone. Recrystallization in monochlorobenzene afforded Intermediate 4-h as a solid (15.8 g, 55%).

Synthesis Example 4-(9): Synthesis of BD

<Reaction Scheme 22>

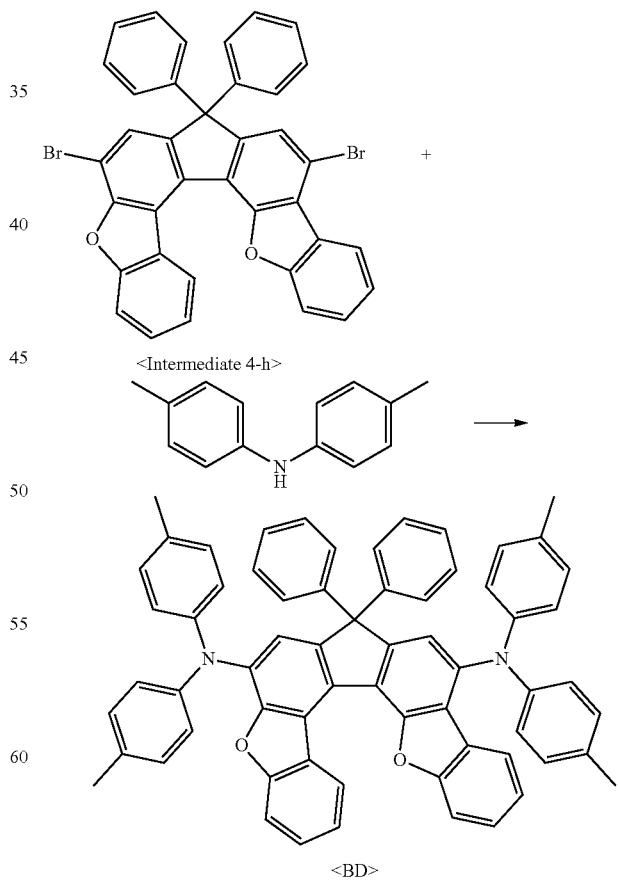

<BD>

In a 100-ml round-bottom flask reactor, a mixture of <Intermediate 4-h> (4.0 g, 0.006 mol), di-p-tolyl amine (3.2 g, 0.016 mol), palladium(II) acetate (0.08 g, 0.4 mmol), sodium tert-butoxide (3.2 g, 0.032 mol), tri-tert-butyl phosphine (0.08 g, 0.4 mmol), and toluene (50 ml) was stirred for 2 hours under reflux. After completion of the reaction, the reaction mixture was cooled to room temperature and then extracted with dichloromethane and water. The organic layer thus formed was separated, dried over magnesium sulfate, and concentrated in a vacuum. The concentrate was purified by column chromatography and recrystallized in dichloromethane and acetone to afford BD (2.1 g, 41%).

MS (MALDI-TOF): m/z 890.0 [M+]

3) Host Preparation

Synthesis Example 5: Synthesis of Compound 83

Synthesis Example 5-(1): Synthesis of Intermediate 5-a

Intermediate 5-a was synthesized as illustrated in Reaction Scheme 23:

<Reaction Scheme 23>

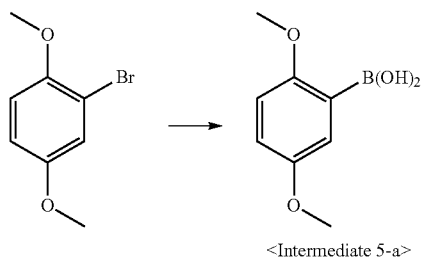

<Intermediate 5-a>

In a 1-L round-bottom flask, 2-bromo-1,4-dimethoxy benzene (50 g, 230 mmol) was dissolved in tetrahydrofuran (400 ml) under a nitrogen atmosphere. The solution was cooled to −78° C. and added with drops of n-butyl lithium (167 ml, 280 mmol). Thereafter, the solution was stirred for 2 hours at the same temperature and then overnight together with trimethyl borate (36 ml, 320 mmol) at room temperature. After completion of the reaction, drops of 2 N HCl was slowly added for acidification. Extraction was made with water and ethyl acetate, and the organic layer thus formed was isolated and dried over magnesium sulfate, followed by concentration in a vacuum and recrystallization in heptane and toluene to afford Intermediate 15-a (20.8 g, 50%).

Synthesis Example 5-(2): Synthesis of Intermediate 5-b

Intermediate 5-b was synthesized as illustrated in the following Reaction Scheme 24:

<Reaction Scheme 24>

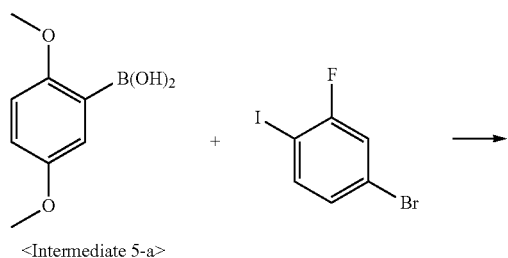

<Intermediate 5-a>

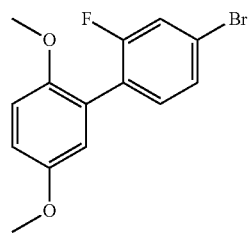

<Intermediate 5-b>

The same procedure as in Synthesis Example 1-(5) was performed, with the exception of using 1-bromo 3-fluoro 4-iodo benzene and Intermediate 5-a instead of Intermediate 1-d and phenyl boronic acid, respectively, to afford Intermediate 5-b. (22.3 g, 63%)

Synthesis Example 5-(3): Synthesis of Intermediate 5-c

Intermediate 5-c was synthesized as illustrated in the following Reaction Scheme 25:

<Reaction Scheme 25>

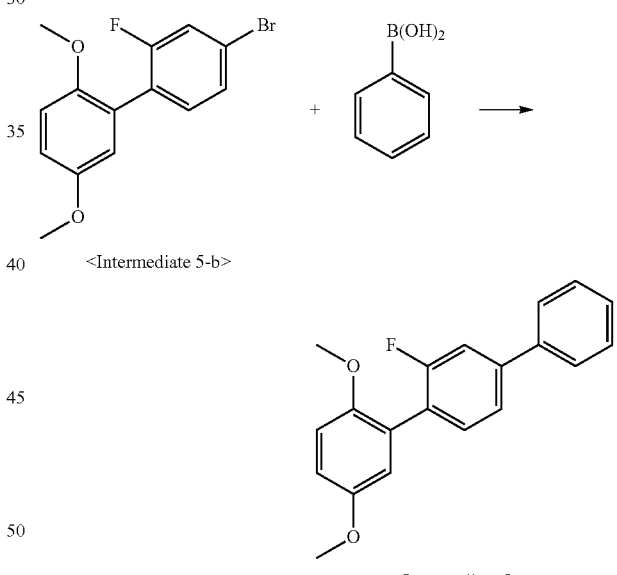

<Intermediate 5-c>

The same procedure as in Synthesis Example 1-(6) was performed, with the exception of using Intermediate 5-b and phenylboronic acid instead of Intermediate 1-e and 10-phenyl(d5)-anthracene-9-boronic acid, respectively, to afford Intermediate 5-c. (16.3 g, 74%)

Synthesis Example 5-(4): Synthesis of Intermediate 5-d

Intermediate 5-d was synthesized as illustrated in the following Reaction Scheme 26:

<Reaction Scheme 26>

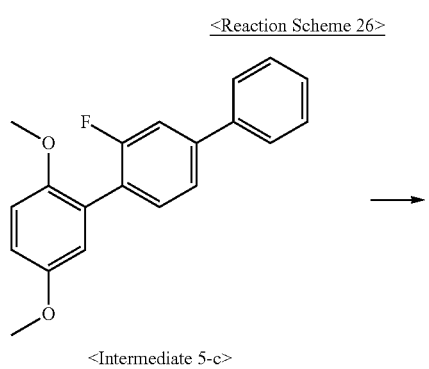

<Intermediate 5-c>

In a 500-ml round bottom flask reactor, Intermediate 5-c (16.3 g, 53 mmol), hydrobromic acid (48 ml, 260 mmol), and acetic acid (100 ml) were stirred together for 12 hours. After completion of the reaction, the reaction mixture was cooled to room temperature and then stirred together with water. Extraction was made with water and ethyl acetate. The organic layer thus formed was isolated, concentrated in a vacuum, recrystallized in heptane, filtered and dried to afford Intermediate 5-d. (14 g, 95%)

Synthesis Example 5-(5): Synthesis of Intermediate 5-e

Intermediate 5-e was synthesized as illustrated in the following Reaction Scheme 27:

<Reaction Scheme 27>

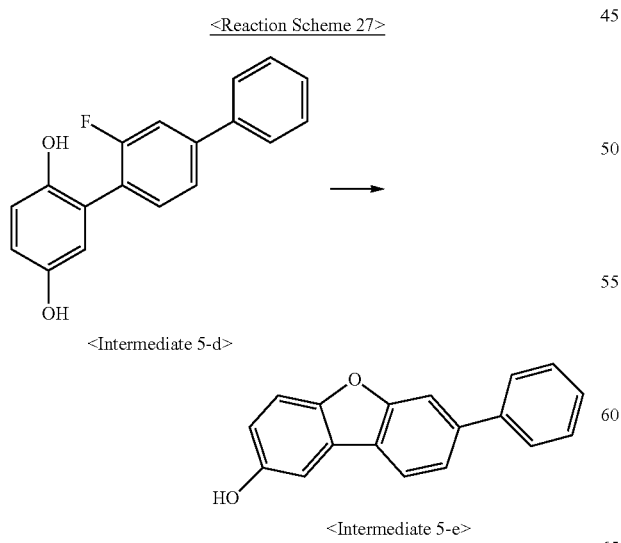

In a 500-ml round-bottom flask reactor, Intermediate 5-d (14 g, 50 mmol), potassium carbonate (20.7 g, 150 mmol), and N-methyl-2-pyrrolidone (112 ml) was stirred together for 12 hours. After completion of the reaction, the reaction mixture was cooled to room temperature and extracted with water and ethyl acetate. The organic layer was isolated and concentrated in a vacuum, followed by recrystallization in heptane to afford Intermediate 5-e. (10.5 g, 81%)

Synthesis Example 5-(6): Synthesis of Intermediate 5-f

Intermediate 5-f was synthesized as illustrated in the following Reaction Scheme 28:

<Reaction Scheme 28>

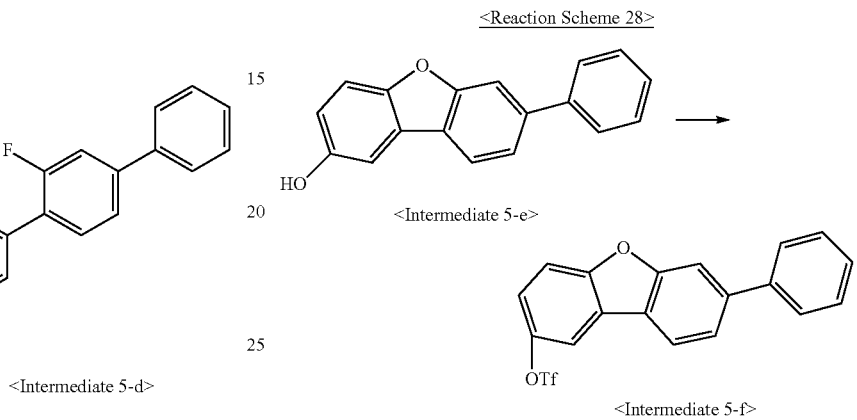

In a 500-ml round bottom flask reactor, Intermediate 5-e (10.5 g, 40 mmol) was dissolved in dichloromethane (136 ml) under a nitrogen atmosphere. The solution was cooled to 0° C. and added with pyridine (10 ml, 110 mmol) and then with drops of trifluoromethanesulfonyl anhydride (12.7 g, 68 mmol) at the same temperature. The reaction mixture was stirred at room temperature for 12 hours and then together with water (20 ml). Extraction was made with water and dichloromethane. The organic layer thus formed was isolated and concentrated in a vacuum, followed by recrystallization in heptane to afford Intermediate 5-f. (7.5 g, 37%)

Synthesis Example 5-(7): Synthesis of Compound 83

Compound 83 was synthesized as illustrated in the following Reaction Scheme 29:

<Reaction Scheme 29>

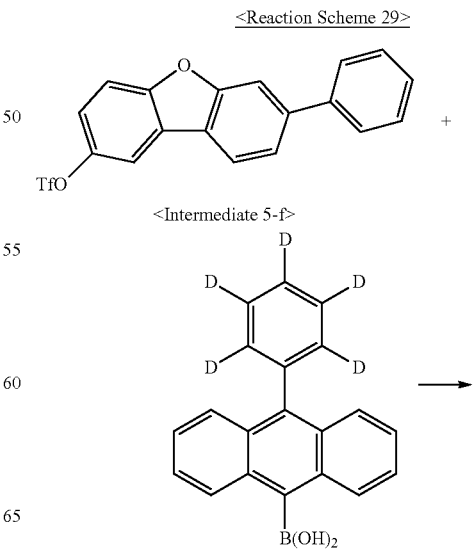

-continued

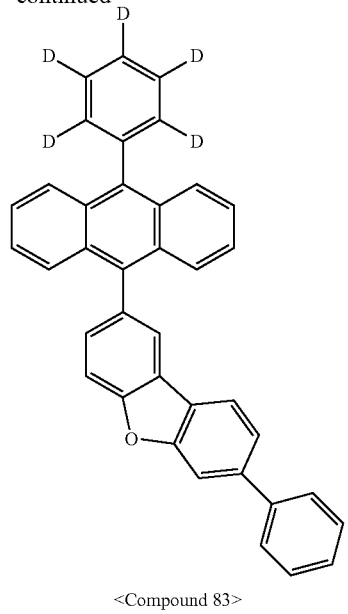
<Compound 83>

In a 250-ml round bottom flask reactor, Intermediate 5-f (7.5 g, 19 mmol), 10-phenyl(d5)-anthracene-9-boronic acid (7 g, 23 mmol), tetrakis(triphenylphosphine) palladium (0.66 g, 0.6 mmol), and potassium carbonate (7.9 g, 57 mmol) were stirred together with toluene (53 ml), ethanol (23 ml) and water (23 ml) for 12 hours. After completion of the reaction, the reaction mixture was cooled to room temperature and added with methanol. The organic layer was isolated, concentrated in a vacuum, and recrystallized in toluene and acetone to afford Compound 83. (6 g, 63%) MS: m/z 501.21 [M+]

Synthesis Example 6: Synthesis of Compound 84

Synthesis Example 6-(1): Synthesis of Intermediate 6-a

Intermediate 6-a was synthesized as illustrated in the following Reaction Scheme 30:

<Reaction Scheme 30>

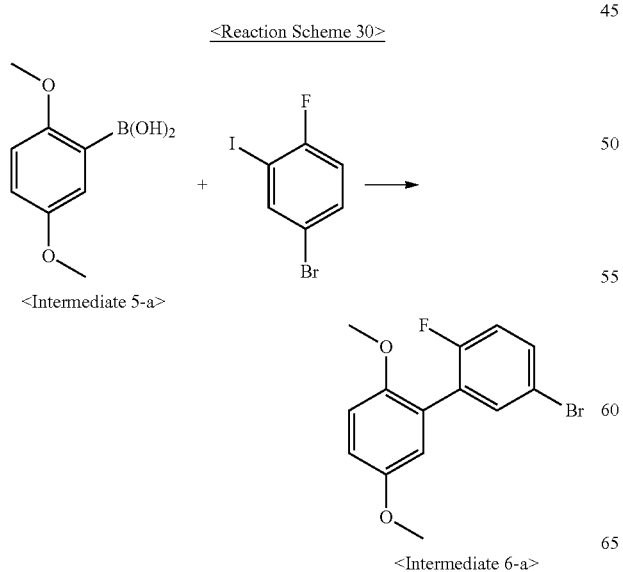

The same procedure as in Synthesis Example 1-(5) was performed, with the exception of using 4-bromo 1-fluoro 2-iodo benzene and Intermediate 5-a instead of Intermediate 1-d and phenyl boronic acid, respectively, to afford Intermediate 6-a. (21.3 g, 54%)

Synthesis Example 6-(2): Synthesis of Intermediate 6-b

Intermediate 6-b was synthesized as illustrated in the following Reaction Scheme 31:

<Reaction Scheme 31>

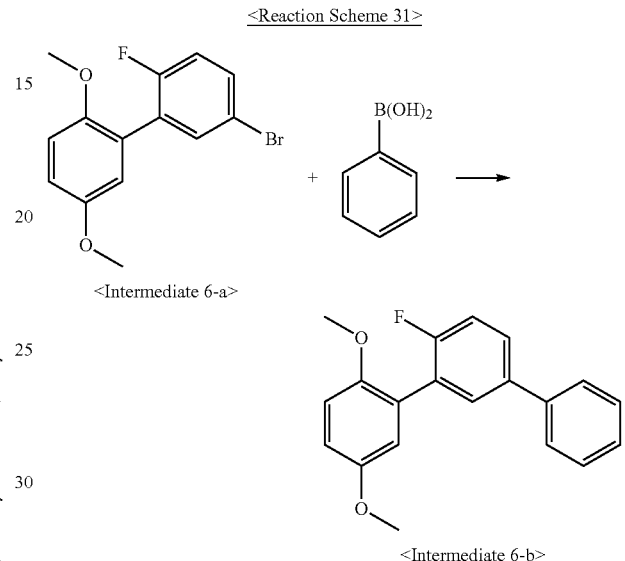

The same procedure as in Synthesis Example 1-(6) was performed, with the exception of using Intermediate 6-a and 10-phenyl(d5)-anthracene-9-boronic acid instead of Intermediate 1-e and phenyl boronic acid, respectively, to afford Intermediate 6-b. (15.8 g, 75%)

Synthesis Example 6-(3): Synthesis of Intermediate 6-c

Intermediate 6-c was synthesized as illustrated in the following Reaction Scheme 32:

<Reaction Scheme 32>

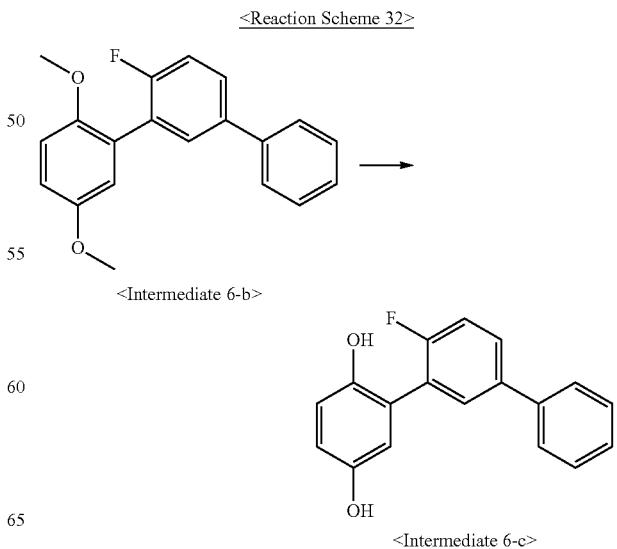

The same procedure as in Synthesis Example 5-(4) was performed, with the exception of using Intermediate 6-b instead of Intermediate 5-c, to afford Intermediate 6-c. (11 g, 77%)

Synthesis Example 6-(4): Synthesis of Intermediate 6-d

Intermediate 6-d was synthesized as illustrated in the following Reaction Scheme 33:

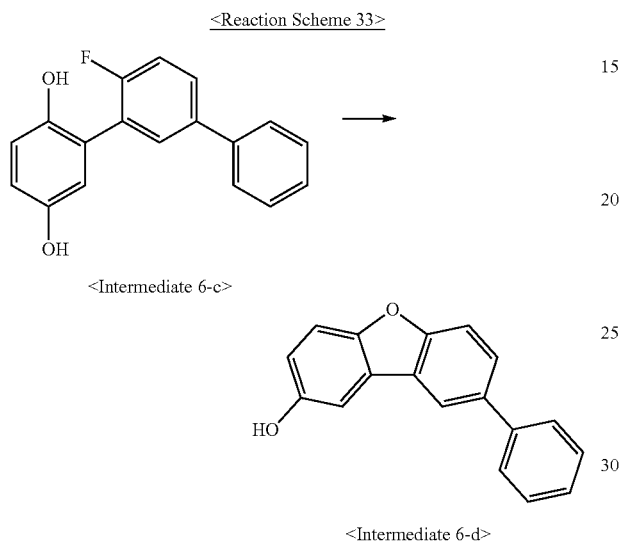

<Intermediate 6-c>

<Intermediate 6-d>

The same procedure as in Synthesis Example 5-(5) was performed, with the exception of using Intermediate 6-c instead of Intermediate 5-d, to afford Intermediate 6-d. (9.3 g, 91%)

Synthesis Example 6-(5): Synthesis of Intermediate 6-e

Intermediate 6-e was synthesized as illustrated in the following Reaction Scheme 34:

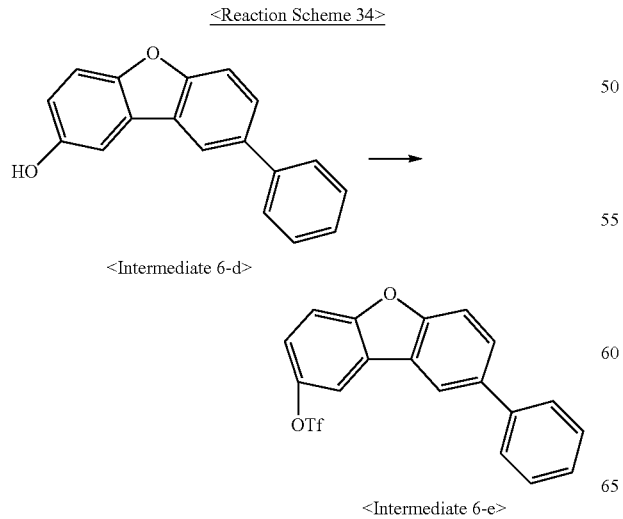

<Intermediate 6-d>

<Intermediate 6-e>

The same procedure as in Synthesis Example 5-(6) was performed, with the exception of using Intermediate 6-d instead of Intermediate 5-e, to afford Intermediate 6-e. (7.9 g, 56%)

Synthesis Example 6-(6): Synthesis of Compound 84

Compound 84 was synthesized as illustrated in the following Reaction Scheme 35:

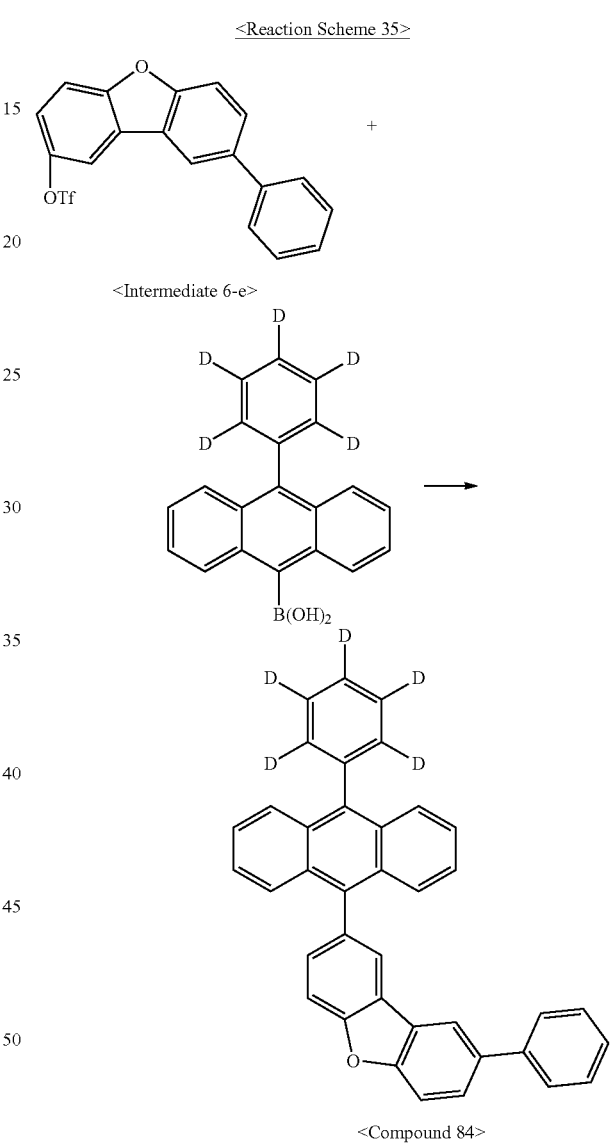

<Compound 84>

The same procedure as in Synthesis Example 5-(7) was performed, with the exception of using Intermediate 6-e instead of Intermediate 5-f, to afford Compound 84. (7.1 g, 70%)

MS: m/z 501.21 [M+]

Synthesis Example 7: Synthesis of Compound 85

Synthesis Example 7-(1): Synthesis of Compound 4-1

Compound 85 was synthesized as illustrated in the following Reaction Scheme 36:

<Reaction Scheme 36>

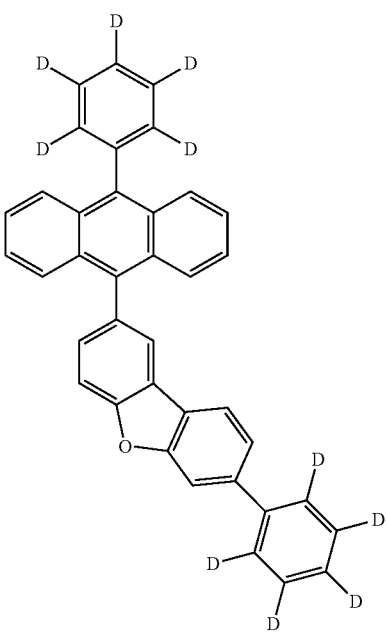

The same procedure as in Synthesis Example 5 was performed, with the exception of using d5-phenylboronic acid instead of phenylboronic acid, to afford Compound 85. (6.8 g, 67%)
MS: m/z 506.25 [M+]

Synthesis Example 8: Synthesis of Compound 86

Synthesis Example 8-(1): Synthesis of Compound 86

Compound 86 was synthesized as illustrated in the following Reaction Scheme 37:

<Reaction Scheme 37>

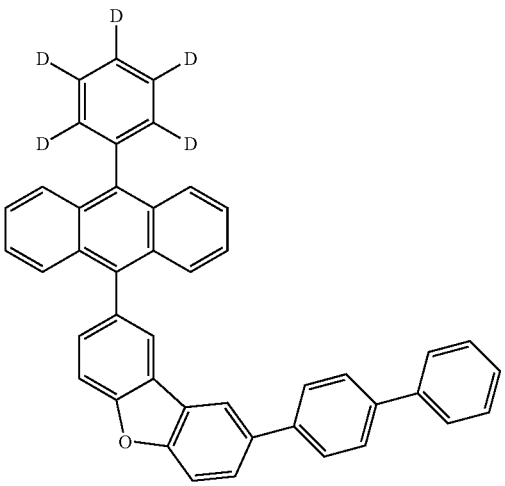

The same procedure as in Synthesis Example 6 was performed, with the exception of using 4-biphenyl boronic acid instead of phenyl boronic acid, to afford Compound 86. (7.3 g, 65%)
MS: m/z 577.25 [M+]

Synthesis Example 9: Synthesis of Compound 88

Synthesis Example 9-(1): Synthesis of Intermediate 7-a

Intermediate 7-a was synthesized as illustrated in the following Reaction Scheme 38:

<Reaction Scheme 38>

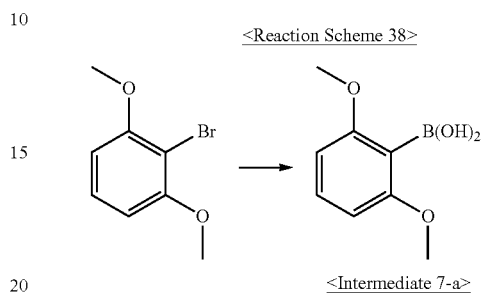

<Intermediate 7-a>

The same procedure as in Synthesis Example 5-(1) was performed, with the exception of using 2-bromo-1,3-dimethoxybenzene instead of 2-bromo-1,4-diethoxybenzene, to afford Intermediate 7-a. (23 g, 55%)

Synthesis Example 9-(2): Synthesis of Intermediate 7-b

Intermediate 7-b was synthesized as illustrated in the following Reaction Scheme 39:

<Reaction Scheme 39>

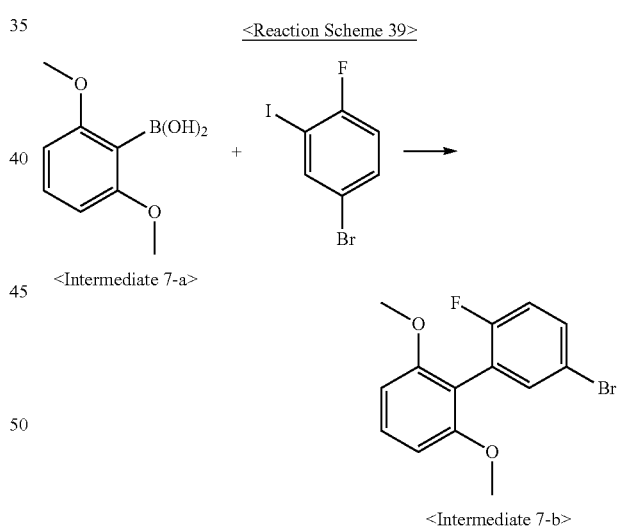

<Intermediate 7-b>

The same procedure as in Synthesis Example 1-(5) was performed, with the exception of using 4-bromo 1-fluoro 2-iodo benzene and Intermediate 7-a instead of Intermediate 1-d and phenyl boronic acid, respectively, to afford Intermediate 7-b. (21.3 g, 54%)

Synthesis Example 9-(3): Synthesis of Intermediate 7-c

Intermediate 7-c was synthesized as illustrated in the following Reaction Scheme 40:

\<Reaction Scheme 40\>

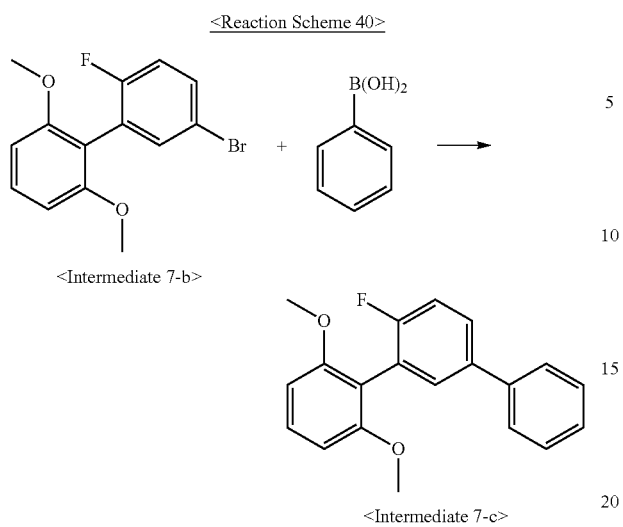

The same procedure as in Synthesis Example 1-(6) was performed, with the exception of using Intermediate 7-b and phenyl boronic acid instead of Intermediate 1-e and 10-phenyl(d5)-anthracene-9-boronic acid, respectively, to afford Intermediate 7-c. (15.8 g, 75%)

Synthesis Example 9-(4): Synthesis of Intermediate 7-d

Intermediate 7-d was synthesized as illustrated in the following Reaction Scheme 41:

\<Reaction Scheme 41\>

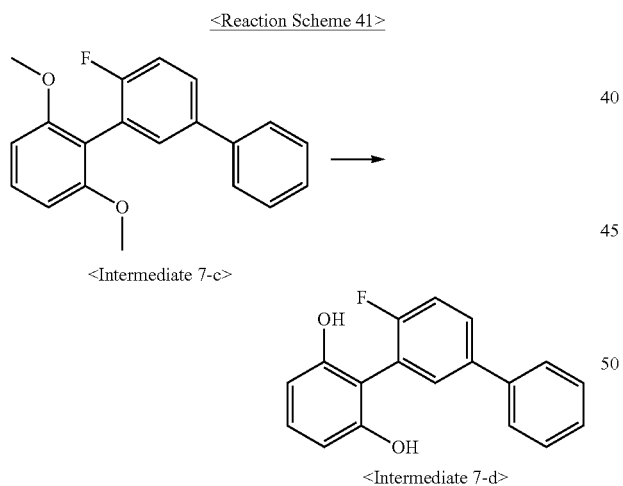

The same procedure as in Synthesis Example 5-(4) was performed, with the exception of using Intermediate 7-c instead of Intermediate 5-c, to afford Intermediate 7-d. (11 g, 77%)

Synthesis Example 9-(5): Synthesis of Intermediate 7-e

Intermediate 7-e was synthesized as illustrated in the following Reaction Scheme 42:

\<Reaction Scheme 42\>

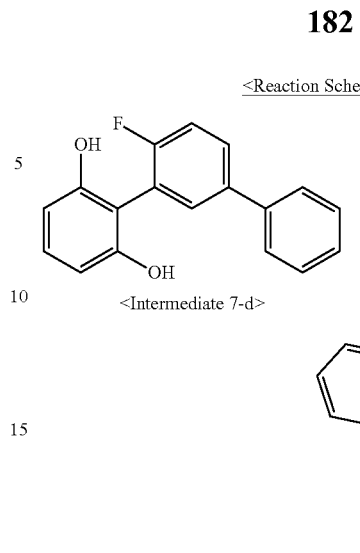

The same procedure as in Synthesis Example 5-(5) was performed, with the exception of using Intermediate 7-d instead of Intermediate 5-d, to afford Intermediate 7-e. (9.3 g, 91%)

Synthesis Example 9-(6): Synthesis of Intermediate 7-f

Intermediate 7-f was synthesized as illustrated in the following Reaction Scheme 43:

\<Reaction Scheme 43\>

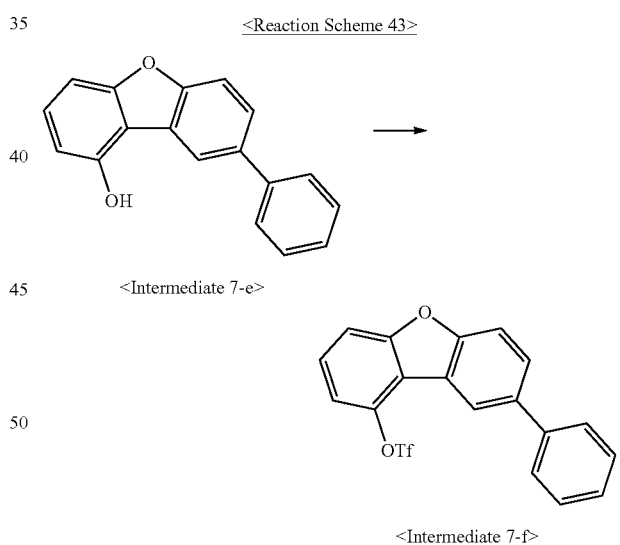

The same procedure as in Synthesis Example 5-(6) was performed, with the exception of using Intermediate 7-e instead of Intermediate 5-e, to afford Intermediate 7-f. (7.9 g, 56%)

Synthesis Example 9-(7): Synthesis of Compound 88

Compound 88 was synthesized as illustrated in the following Reaction Scheme 44:

<Reaction Scheme 44>

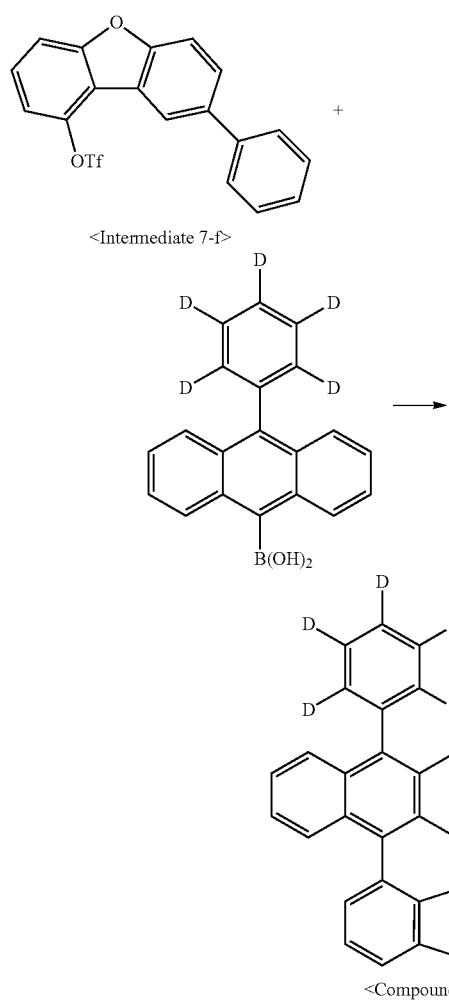

<Compound 88>

The same procedure as in Synthesis Example 5-(7) was performed, with the exception of using Intermediate 7-f instead of Intermediate 5-f, to afford Compound 88. (7.1 g, 70%)

MS: m/z 501.21 [M+]

Synthesis Example 10: Synthesis of Compound 89

Synthesis Example 10-(1): Synthesis of Intermediate 8-a

Intermediate 8-a was synthesized as illustrated in the following Reaction Scheme 45:

<Reaction Scheme 45>

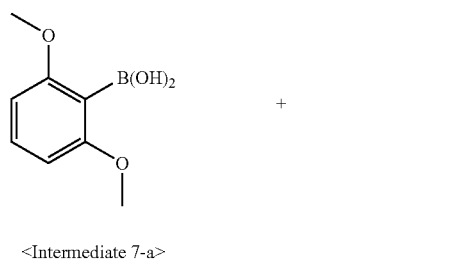

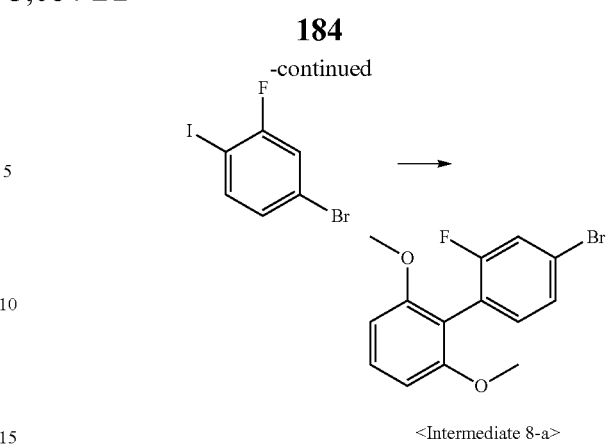

<Intermediate 8-a>

The same procedure as in Synthesis Example 1-(5) was performed, with the exception of using 1-bromo 3-fluoro 4-iodo benzene and Intermediate 7-a instead of Intermediate 1-d and phenyl boronic acid, respectively, to afford Intermediate 8-a. (38 g, 44%)

Synthesis Example 10-(2): Synthesis of Intermediate 8-b

Intermediate 8-b was synthesized as illustrated in the following Reaction Scheme 46:

<Reaction Scheme 46>

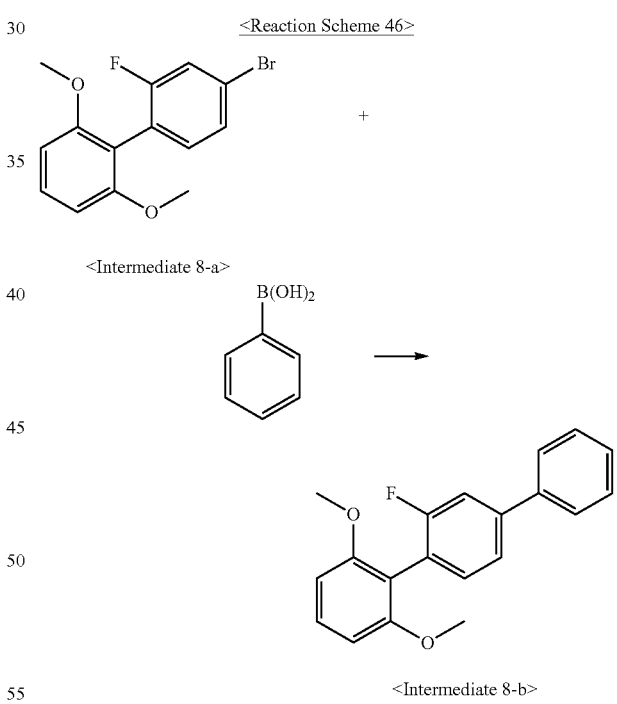

<Intermediate 8-b>

The same procedure as in Synthesis Example 1-(6) was performed, with the exception of using Intermediate 8-a and phenylboronic acid instead of Intermediate 1-e and 10-phenyl(d5)-anthracene-9-boronic acid, respectively, to afford Intermediate 8-b. (25.7 g, 68.2%)

Synthesis Example 10-(3): Synthesis of Intermediate 8-c

Intermediate 8-c was synthesized as illustrated in the following Reaction Scheme 47:

<Reaction Scheme 47>

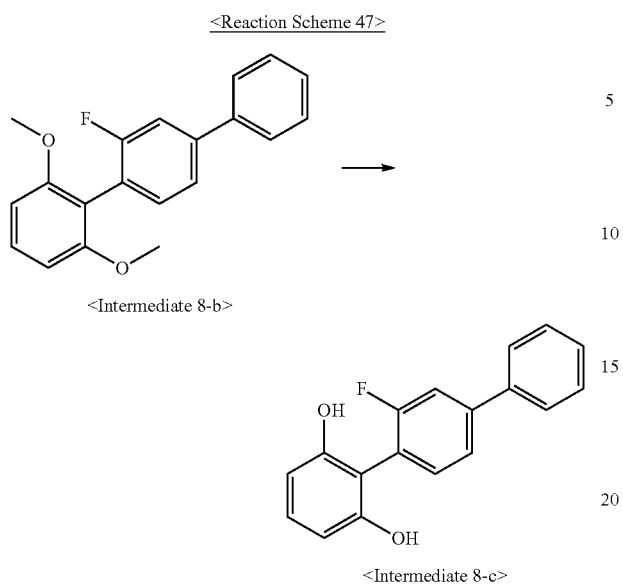

<Intermediate 8-b>

<Intermediate 8-c>

The same procedure as in Synthesis Example 5-(4) was performed, with the exception of using Intermediate 8-b instead of Intermediate 5-c, to afford Intermediate 8-c. (17.1 g, 73%)

Synthesis Example 10-(4): Synthesis of Intermediate 8-d

Intermediate 8-d was synthesized as illustrated in the following Reaction Scheme 48:

<Reaction Scheme 48>

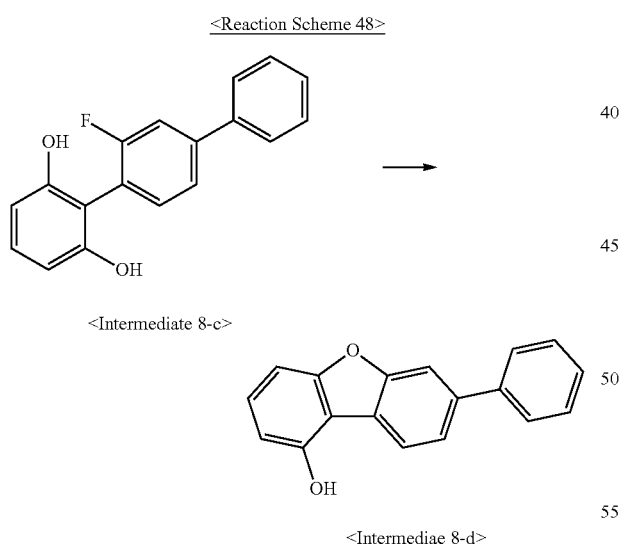

<Intermediate 8-c>

<Intermediae 8-d>

The same procedure as in Synthesis Example 5-(5) was performed, with the exception of using Intermediate 8-c instead of Intermediate 5-d, to afford Intermediate 8-d. (10.8 g, 68%)

Synthesis Example 10-(5): Synthesis of Intermediate 8-e

Intermediate 8-e was synthesized as illustrated in the following Reaction Scheme 49:

<Reaction Scheme 49>

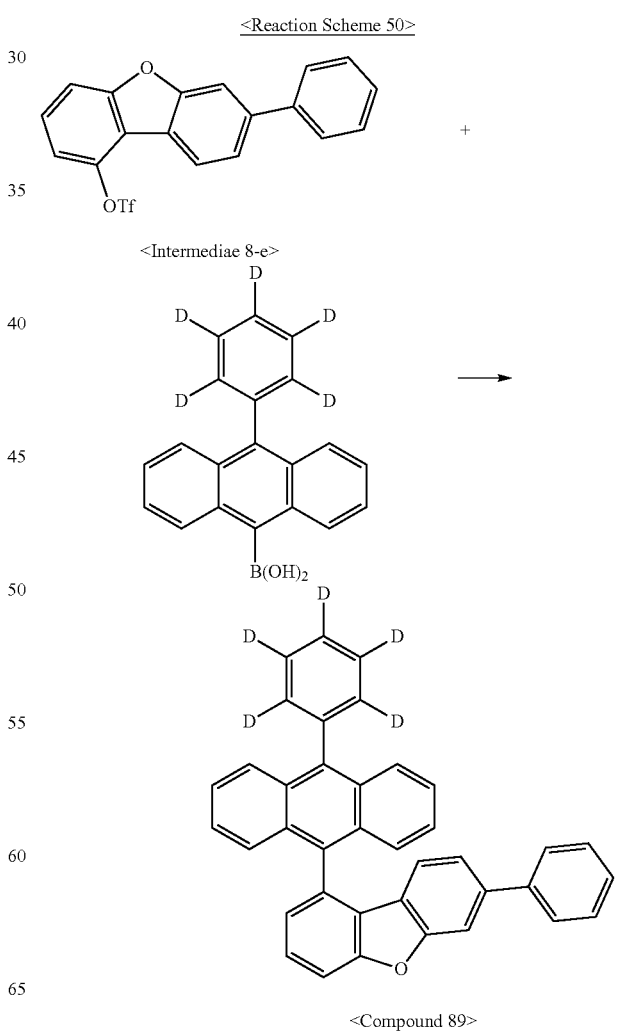

<Intermediae 8-d>

<Intermediae 8-e>

The same procedure as in Synthesis Example 5-(6) was performed, with the exception of using Intermediate 8-d instead of Intermediate 5-e, to afford Intermediate 8-e. (11.3 g, 69%)

Synthesis Example 10-(6): Synthesis of Compound 89

Compound 89 was synthesized as illustrated in the following Reaction Scheme 50:

<Reaction Scheme 50>

<Intermediae 8-e>

<Compound 89>

The same procedure as in Synthesis Example 5-(7) was performed, with the exception of using Intermediate 8-e instead of Intermediate 5-f, to afford Compound 89. (8.8 g, 61%)

MS: m/z 501.21 [M+]

Synthesis Example 11: Synthesis of Compound 90

Synthesis Example 11-(1): Synthesis of Compound 90

Compound 90 was synthesized as illustrated in the following Reaction Scheme 51:

<Reaction Scheme 51>

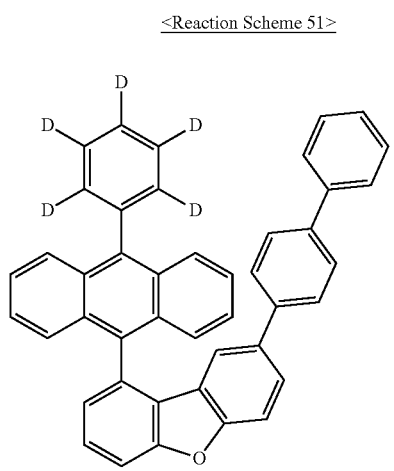

<Compound 90>

The same procedure as in Synthesis Example 9 was performed, with the exception of using 4-biphenyl boronic acid instead of phenyl boronic acid, to afford Compound 90. (4.7 g, 77%)

MS: m/z 577.25 [M+]

Synthesis Example 12: Synthesis of Compound 142

Synthesis Example 12-(1): Synthesis of Intermediate 9-a

Intermediate 9-a was synthesized as illustrated in the following Reaction Scheme 52:

<Reaction Scheme 52>

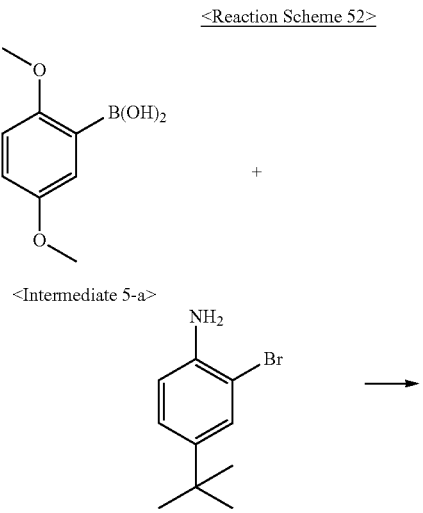

<Intermediate 5-a>

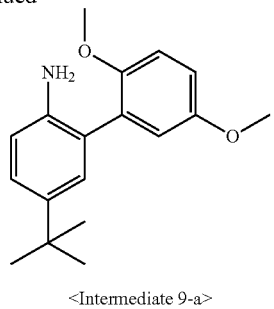

<Intermediate 9-a>

The same procedure as in Synthesis Example 1-(5) was performed, with the exception of using 2-bromo 4-tert-butyl aniline and Intermediate 5-a instead of Intermediate 1-d and phenylboronic acid, respectively, to afford Intermediate 9-a. (27.3 g, 44%)

Synthesis Example 12-(2): Synthesis of Intermediate 9-b

Intermediate 9-b was synthesized as illustrated in the following Reaction Scheme 53:

<Reaction Scheme 53>

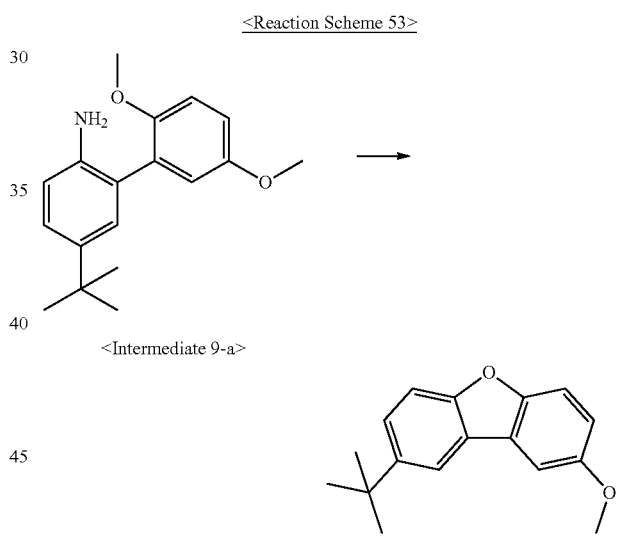

<Intermediate 9-a>

<Intermediate 9-b>

In a 1-L round-bottom flask reactor, a mixture of Intermediate 9-a (105 g, 368 mmol) and water (420 ml) was stirred. Drops of sulfuric acid were added little by little to the mixture which was then cooled to 0° C. An aqueous sodium nitrite solution (304.6 ml) was dropwise added and left for 3 hours at 0° C. before heating to room temperature. After completion of the reaction, water was evaporated to isolate the organic layer which was then purified by column chromatography to afford Intermediate 9-b. (20.1 g, 83%)

Synthesis Example 12-(3): Synthesis of Intermediate 9-c

Intermediate 9-c was synthesized as illustrated in the following Reaction Scheme 54:

<Reaction Scheme 54>

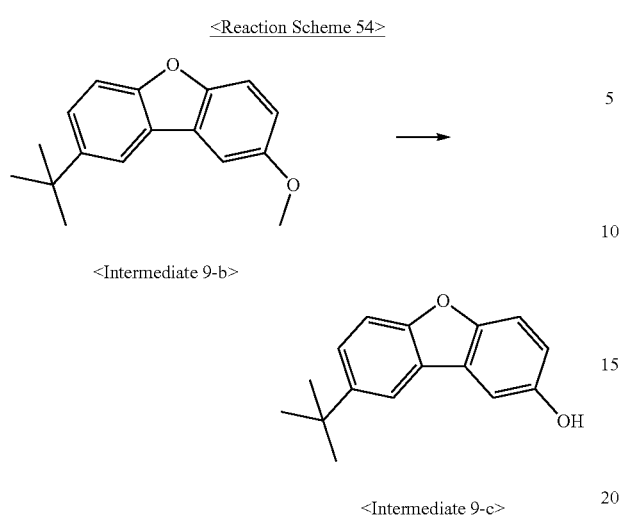

<Intermediate 9-b>

<Intermediate 9-c>

The same procedure as in Synthesis Example 5-(4) was performed, with the exception of using Intermediate 9-b instead of Intermediate 5-c, to afford Intermediate 9-c. (13.5 g, 71%)

Synthesis Example 12-(4): Synthesis of Intermediate 9-d

Intermediate 9-d was synthesized as illustrated in the following Reaction Scheme 55:

<Reaction Scheme 55>

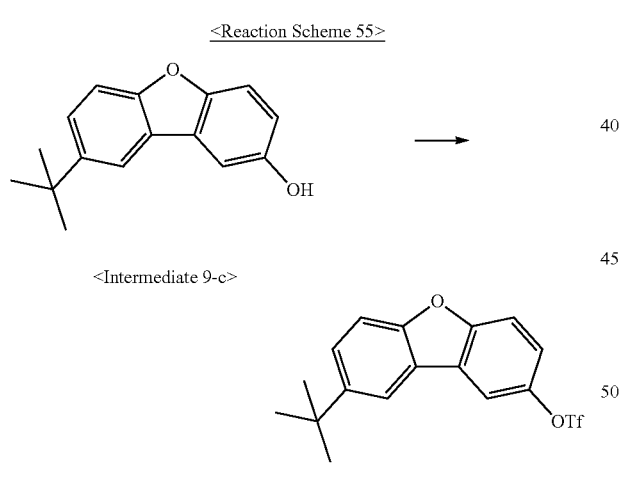

<Intermediate 9-c>

<Intermediate 9-d>

The same procedure as in Synthesis Example 5-(6) was performed, with the exception of Intermediate 9-c using instead of Intermediate 5-e, to afford Intermediate 9-d. (15 g, 72%)

Synthesis Example 12-(5): Synthesis of Compound 142

Compound 142 was synthesized as illustrated in the following Reaction Scheme 56:

<Reaction Scheme 56>

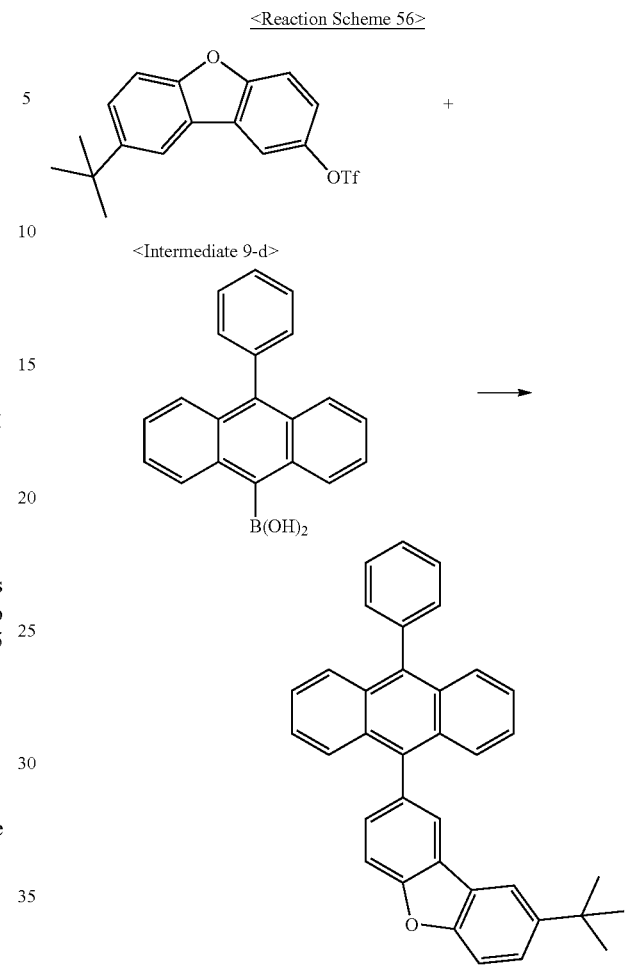

<Intermediate 9-d>

<Compound 142>

The same procedure as in Synthesis Example 5-(7) was performed, with the exception of using Intermediate 9-d and 9-phenylanthracen-10-yl-10-boronic acid instead of Intermediate 5-f and 10-phenyl(5d)-anthracene-9-boronic acid, respectively, to afford Compound 142. (14.4 g, 75%)
MS: m/z 476.21 [M$^+$]

Synthesis Example 13: Synthesis of Compound 150

Synthesis Example 13-(1): Synthesis of Intermediate 10-a

Intermediate 10-a was synthesized as illustrated in the following Reaction Scheme 57:

<Reaction Scheme 57>

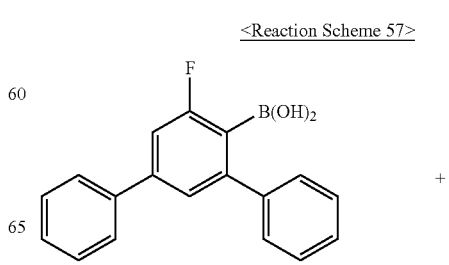

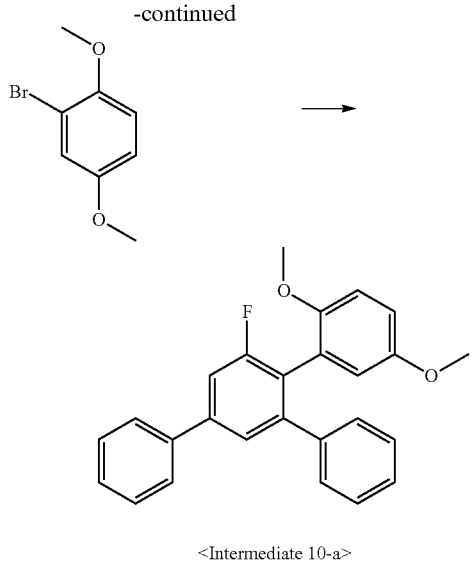

The same procedure as in Synthesis Example 1-(6) was performed, with the exception of using 2-bromo-1,4-dimethoxybenzene and 2-fluoro-4,6-diphenyl-phenyl-1-boronic acid instead of Intermediate 1-e and 10-phenyl(d5)-anthracene-9-boronic acid, respectively, to afford Intermediate 10-a. (22.6 g, 54%)

Synthesis Example 13-(2): Synthesis of Intermediate 10-b

Intermediate 10-b was synthesized as illustrated in the following Reaction Scheme 58

<Reaction Scheme 58>

The same procedure as in Synthesis Example 5-(4) was performed, with the exception of using Intermediate 10-a instead of Intermediate 5-c, to afford Intermediate 10-b. (15.7 g, 75%)

Synthesis Example 13-(3): Synthesis of Intermediate 10-c

Intermediate 10-c was synthesized as illustrated in the following Reaction Scheme 59:

<Reaction Scheme 59>

The same procedure as in Synthesis Example 5-(5) was performed, with the exception of using Intermediate 10-b instead of Intermediate 5-d, to afford Intermediate 10-c. (11.4 g, 77%)

Synthesis Example 13-(4): Synthesis of Intermediate 10-d

Intermediate 10-d was synthesized as illustrated in the following Reaction Scheme 60:

<Reaction Scheme 60>

The same procedure as in Synthesis Example 5-(6) was performed, with the exception of using Intermediate 10-c instead of Intermediate 5-e, to afford Intermediate 10-d. (9.9 g, 62%)

Synthesis Example 13-(5): Synthesis of Compound 150

Compound 150 was synthesized as illustrated in the following Reaction Scheme 61:

Examples 1 to 3: Fabrication of Organic Light-Emitting Device (Electron Density Control Layer Employed)

An ITO glass substrate was patterned to have a luminescent area of 2 mm×2 mm and cleansed. The ITO glass was mounted in a vacuum chamber, which was then set to have a base pressure of $1 \times 10^7$ torr. On the ITO glass substrate, films of DNTPD (700 Å) and α-NPD (300 Å) were formed in that order. A film (250 Å) was formed of a mixture of the compound of [BH] plus 3% of the compound of [BD]. Then, the compounds shown in Table 1 were deposited to form an electron density control layer (50 Å thick), on which [Chemical Formula E-2] for an electron transport layer (250 Å), [Chemical Formula E-1] for an electron injection layer (5 Å), and Al (1000 Å) were deposited in that order to fabricate an organic light-emitting device. The organic light-emitting device thus obtained was measured at 10 mA/cm² for luminescence properties.

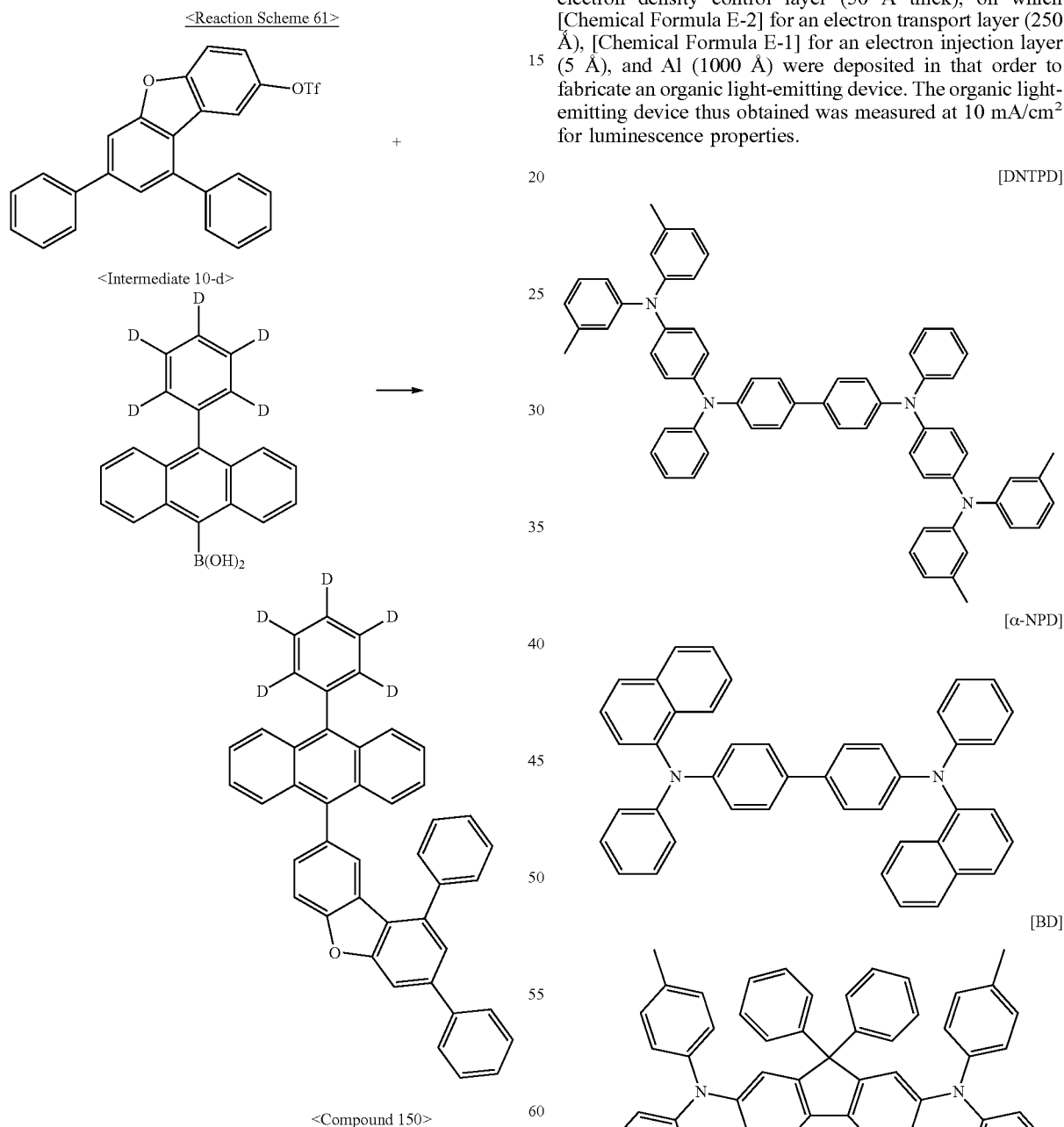

The same procedure as in Synthesis Example 5-(7) was performed, with the exception of using Intermediate 10-d instead of Intermediate 5-f, to afford Compound 150. (7.6 g, 62%)

MS: m/z 577.25 [M⁺]

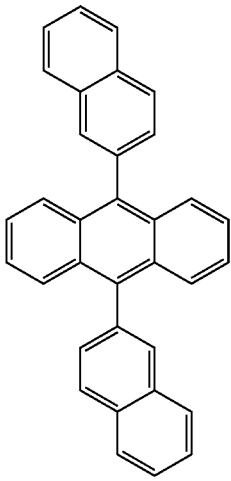

[BH]

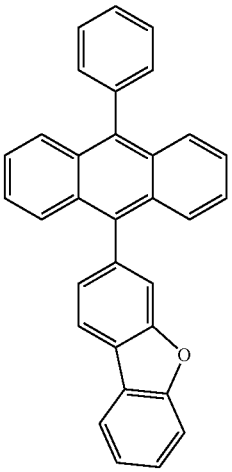

[E-4]

[E-1]

[E-2]

[E-3]

Comparative Example 1

An organic light-emitting device was fabricated in the same manner as in Examples 1 to 3, with the exception that an electron density control layer formed of the compounds, shown in Table 1, of the present invention, was not employed and that an electron transport layer (300 Å) was formed of the compound [E-2]. The organic light-emitting device was measured at 10 mA/cm² for luminescence properties.

Comparative Examples 2 and 3

Organic light-emitting devices were fabricated in the same manner as in Examples 1 to 3, with the exception that [E-2] and [E-4] were respectively used for an electron-density-controlling layer. The organic light-emitting devices were measured at 10 mA/cm² for luminescence properties.

The organic light-emitting devices fabricated according to Examples 1 to 3 and Comparative Examples 1 to 3 were measured for voltage, current efficiency, external quantum efficiency (EQE), and color coordinates and the results are summarized in Table 1, below and depicted in FIGS. 5 to 7. Measurement was conducted at 10 mA/cm2 for voltage, current efficiency, external quantum efficiency (EQE), and color coordinates.

Figure 7:
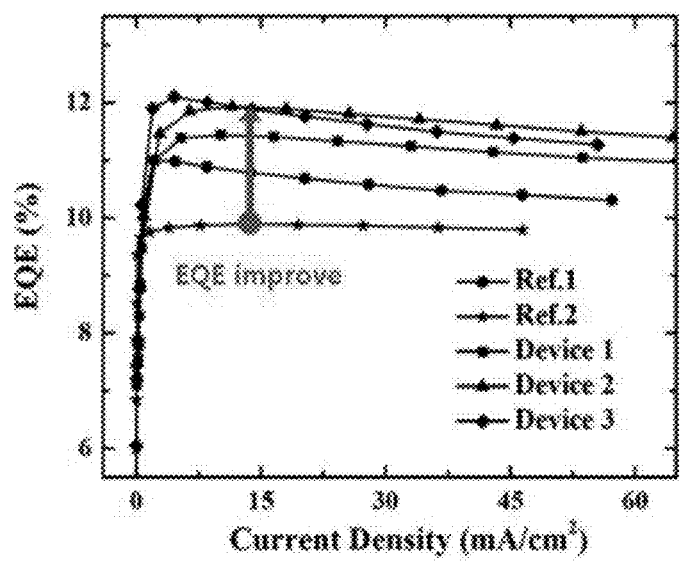
FIG. 7 shows changes in external quantum efficiency with current density in the organic light-emitting diodes of the Examples and the Comparative Examples.

In FIGS. 5 to 7, plots Devices 1 to 3 are depicted from the results of Examples 1 to 3, respectively while plots Refs. 1 and 2 are from the results of Comparative Examples 1 and 2, respectively.

TABLE 1

|  | Electron density control layer | Voltage (V) | Current Density (cd/A) | External Quantum Efficiency (EQE) | CIEx | CIEy |
|---|---|---|---|---|---|---|
| C. Ex. 1 | None | 3.86 | 8.77 | 10.86 | 0.1377 | 0.1078 |
| C. Ex. 2 | E-3 | 4.06 | 7.96 | 9.65 | 0.1379 | 0.1055 |
| C. Ex. 3 | E-4 | 4.04 | 7.88 | 9.57 | 0.1380 | 0.1051 |
| Ex. 1 | Compound 3 | 3.79 | 9.13 | 11.44 | 0.1378 | 0.1061 |
| Ex. 2 | Compound 9 | 3.74 | 9.37 | 11.67 | 0.1381 | 0.1042 |
| Ex. 3 | Compound 13 | 3.85 | 9.44 | 11.74 | 0.1381 | 0.1044 |

On the basis of the electric conductivity obtained using the following equation 1, as described above, the compounds used in the Examples were calculated for electron mobility, and the results are summarized in Table 2, below.

$$\sigma = \frac{1}{R} \times \frac{d}{A}, \quad R = \frac{V}{I} \quad \text{Equation (1)}$$

TABLE 2

|  | Compound 3 | Compound 9 | Compound 13 | Compound E-3 | BH1 | E-2 |
|---|---|---|---|---|---|---|
| Affinity | −3.147 | −3.192 | −3.224 | −3.112 | −3.067 | −3.265 |
| Electron Mobility | 1.766 | 1.676 | 1.556 | 1.362 |  | 1.479 |

As is understood from the data of Table 1, the device structure employing the compounds according to the present invention is far superior to that of Comparative Example 1 according to conventional art in terms of current efficiency and external quantum efficiency (EQE).

Results of Comparative Examples 2 and 3 indicate that a device structure in which a compound having a substituent at a position other than position 1 on the dibenzofuran moiety is used in an electron density control layer is inferior to that of Comparative Example in terms of electron transport capability, thus decreasing in density efficiency and external quantum efficiency (EQE) and increasing in driving voltage.

In the case of the substitution of anthracene at a position other than position 1, relatively low affinity is given, resulting in a large electron injection barrier to the electron injection layer (E-2) and a decrease in electron mobility, as shown in Table 2 and FIG. 6.

Therefore, the compounds in which an anthracene radical is substituted at position 1 on the dibenzofuran according to the present invention impart improved device properties to organic light-emitting devices, thus finding great applications in organic light-emitting devices.

Examples 4 to 12: Fabrication of Organic Light-Emitting Device (Host in Light-Emitting Layer)

An ITO glass substrate was patterned to have a luminescent area of 2 mm×2 mm and cleansed. The ITO glass was mounted in a vacuum chamber, which was then set to have a base pressure of 1×10⁻⁷ torr. On the ITO glass substrate, films of HATCN (50 Å) and α-NPD (600 Å) were formed in that order.

A film (200 Å) for a light-emitting layer was formed of a mixture of one of the anthracene derivatives (host) listed in Table 3 according to the present invention plus BD1 (5 wt %). Then, films were formed of a mixture of 1:1 of Chemical Formula E-1 and Chemical Formula E-2 at a thickness of 300 Å for an electron transport layer, Chemical Formula E-1 at a thickness of 10 Å for electron injection layer, and Al at a thickness of 1,000 Å in that order to fabricate an organic light-emitting device. The organic light-emitting device thus obtained was measured at 10 mA/cm² for luminescence properties. The results are summarized in Table 3, below.

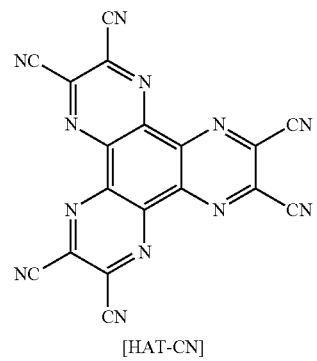

[HAT-CN]

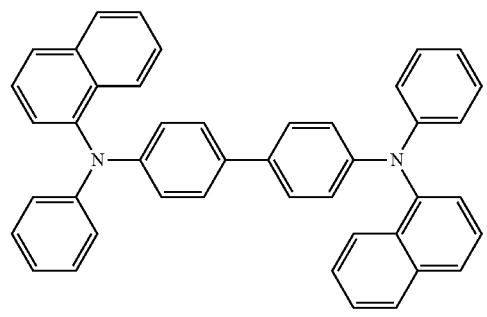

[α-NPD]

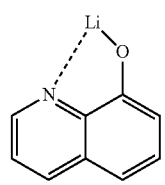

[Chemical Formula E-1]

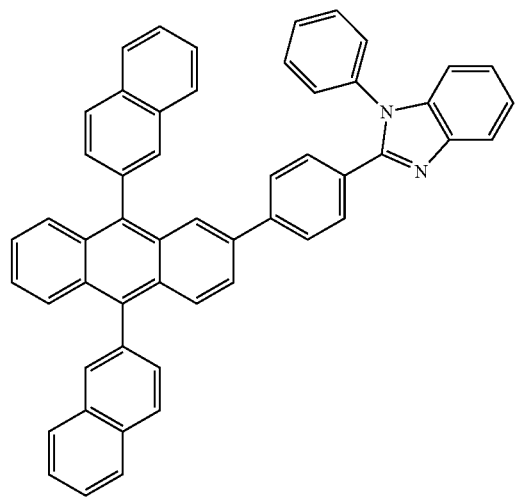

[Chemical Formula E-2]

[BD 1]

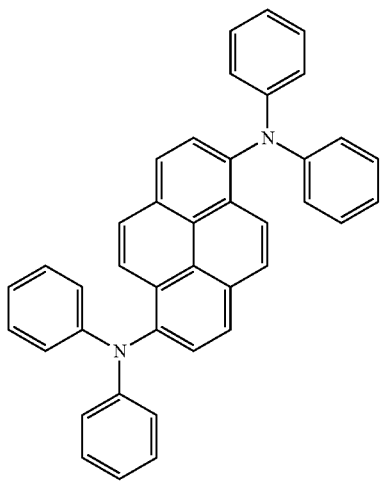

[BH 3]

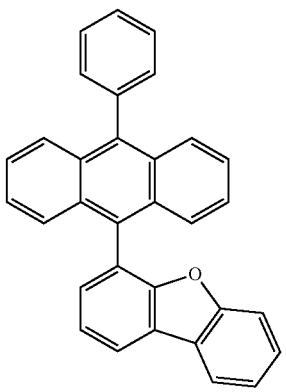

Comparative Examples 4 to 6

Organic light-emitting devices were fabricated in the same manner as in Examples 4 to 12, with the exception that BH1 to BH3 were respective employed, instead of the compounds used in Examples 4 to 12. Measurements of luminance properties are given in Table 3, below. Structures of BH1 to BH3 are as follows:

TABLE 3

| Host (BH) | | Driving Voltage (V) | CIEx | CIEy | Luminance Decrease Rate at low dynamic range (%) |
|---|---|---|---|---|---|
| Ex. 4 | Compound 83 | 3.45 | 0.137 | 0.112 | −4.05 |
| Ex. 5 | Compound 84 | 3.51 | 0.138 | 0.106 | −2.16 |
| Ex. 6 | Compound 85 | 3.44 | 0.138 | 0.108 | −4.64 |
| Ex. 7 | Compound 86 | 3.47 | 0.14 | 0.109 | −1.94 |
| Ex. 8 | Compound 142 | 3.52 | 0.138 | 0.104 | 3.25 |
| Ex. 9 | Compound 150 | 3.55 | 0.138 | 0.108 | −0.03 |
| Ex. 10 | Compound 88 | 3.31 | 0.137 | 0.112 | −1.67 |
| Ex. 11 | Compound 89 | 3.33 | 0.137 | 0.111 | −4.24 |
| Ex. 12 | Compound 90 | 3.27 | 0.137 | 0.112 | −1.00 |
| C. Ex. 4 | BH 1 | 3.71 | 0.137 | 0.109 | −9.46 |
| C. Ex. 5 | BH 2 | 3.81 | 0.136 | 0.118 | −35.17 |
| C. Ex. 6 | BH 3 | 4.06 | 0.136 | 0.116 | −37.08 |

[BH 1]

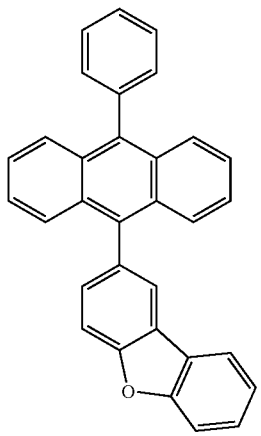

Comparative Examples 7 to 12

Organic light-emitting devices were fabricated in the same manner as in Examples 4 to 12, with the exception that BH4 to BH9 were respective employed, instead of the compounds used in Examples 4 to 12. Measurements of luminance properties are given in Table 4, below. Structures of BH4 to BH9 are as follows:

[BH 2]

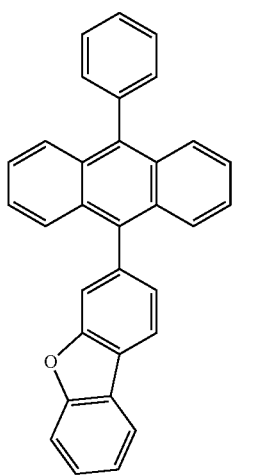

[BH 4]

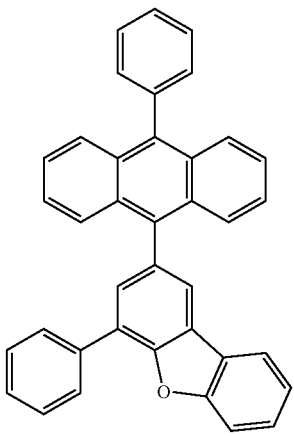

[BH 5]
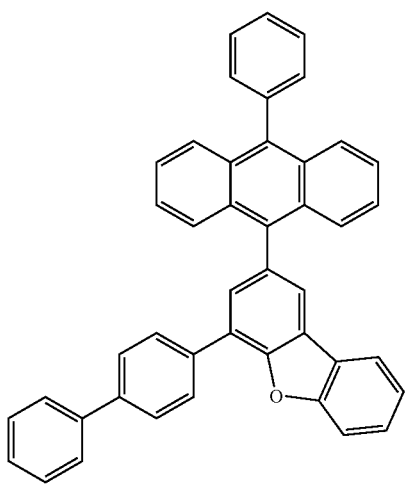

[BH 6]
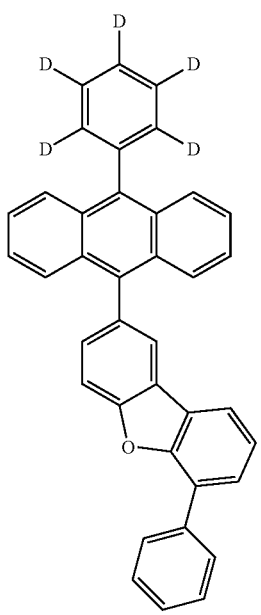

[BH 7]
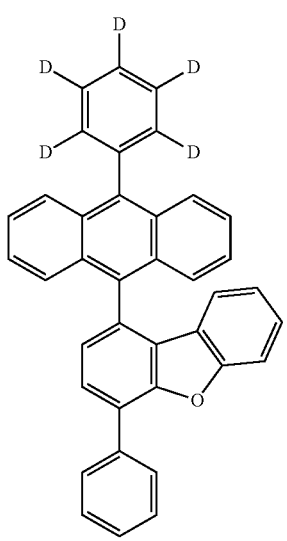

[BH 8]
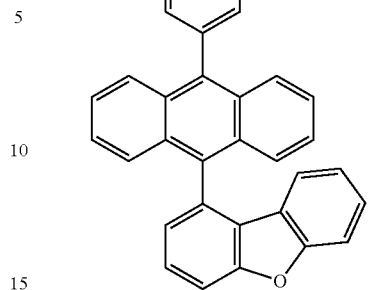

[BH 9]
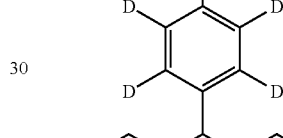

TABLE 4

| Host (BH) | Driving Voltage (V) | CIEx | CIEy | Luminance decrease rate at low dynamic range (%) |
|---|---|---|---|---|
| C. Ex. 7 | BH 4 | 3.88 | 0.137 | 0.114 | −54.8, −10.3 |
| C. Ex. 8 | BH 5 | 3.85 | 0.138 | 0.108 | −50.9, −17.4 |
| C. Ex. 9 | BH 6 | 3.74 | 0.137 | 0.120 | −39.8 |
| C. Ex. 10 | BH 7 | 3.54 | 0.137 | 0.116 | −21.7 |
| C. Ex. 11 | BH 8 | 3.40 | 0.138 | 0.115 | −20.5 |
| C. Ex. 12 | BH 9 | 3.47 | 0.137 | 0.113 | −13.3 |

Figure 8:
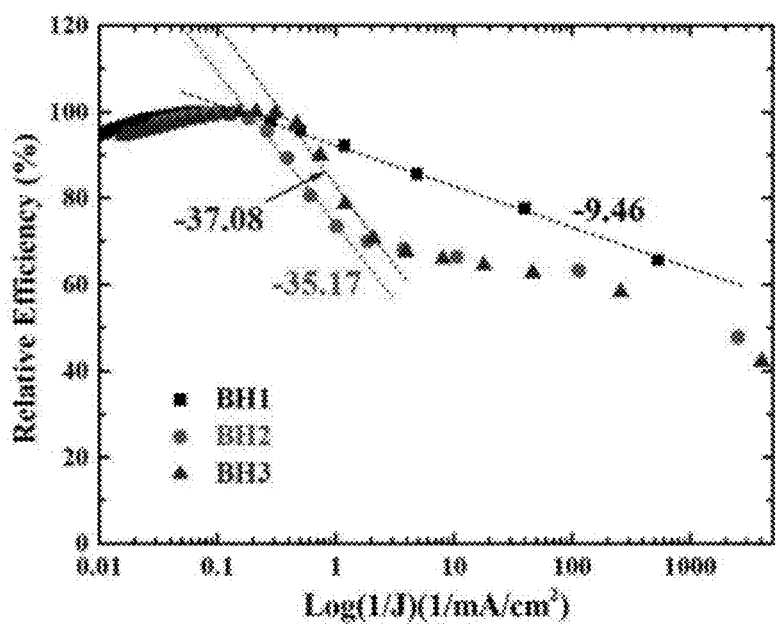
FIG. 8 is a diagram showing experiment results of low dynamic range properties in the devices of Comparative Examples 4 to 6.
Figure 9:
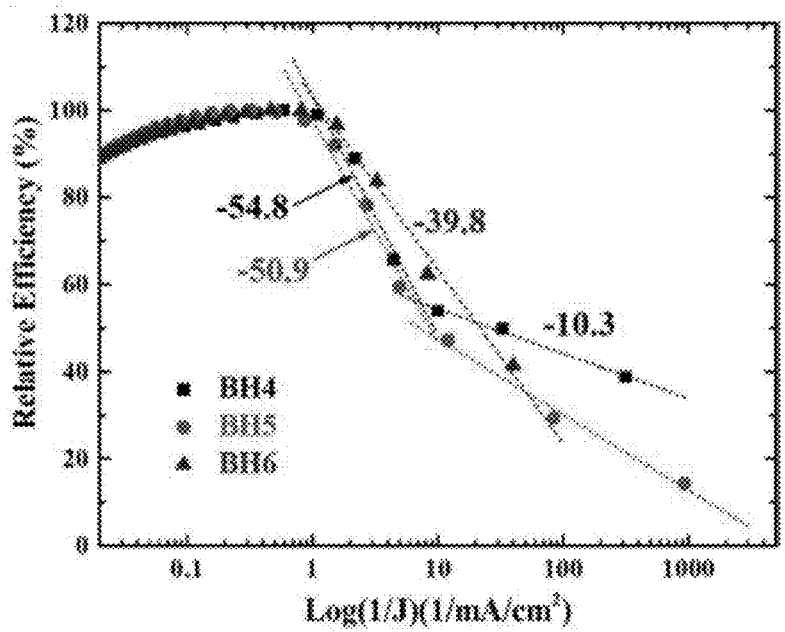
FIG. 9 is a diagram showing experiment results of low dynamic range properties in the devices of Comparative Examples 7 to 9.
Figure 10:
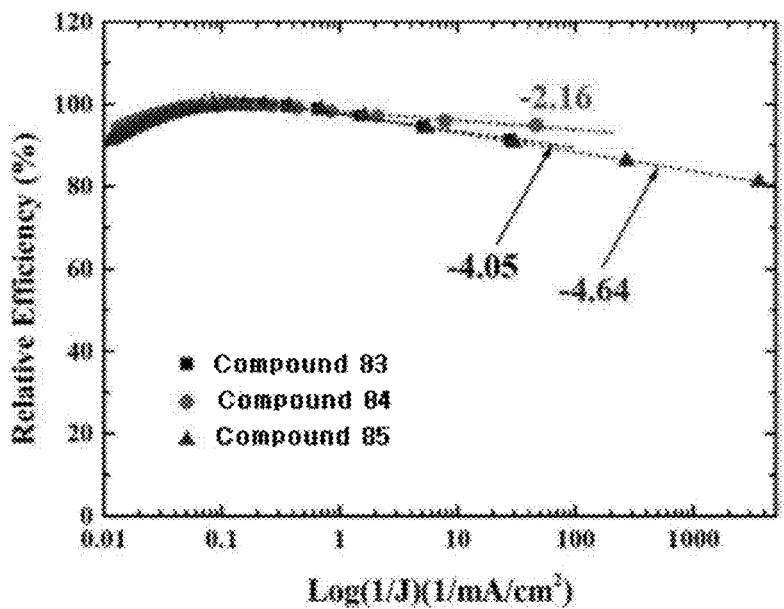
FIG. 10 is a diagram showing experiment results of low dynamic range properties in the devices of Examples 4 to 6.
Figure 11:
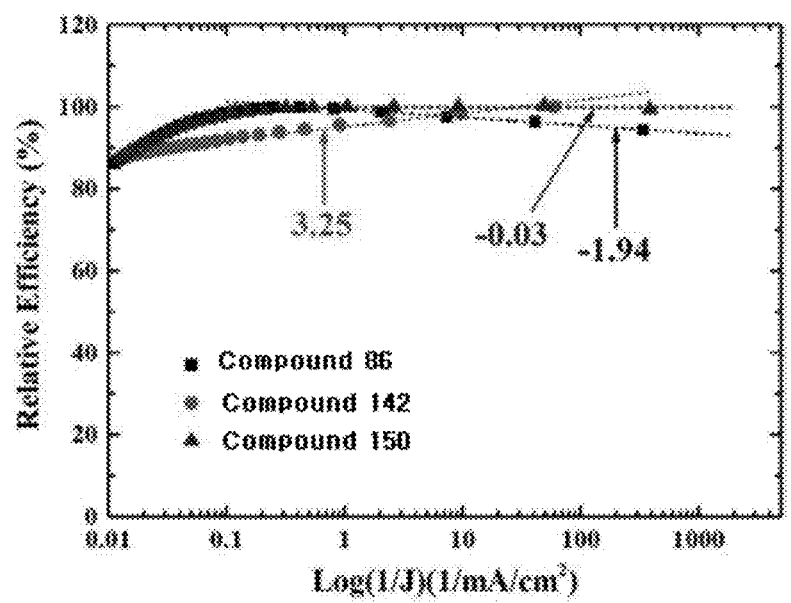
FIG. 11 is a diagram showing experiment results of low dynamic range properties in the devices of Comparative Examples 7 to 9.
Figure 12:
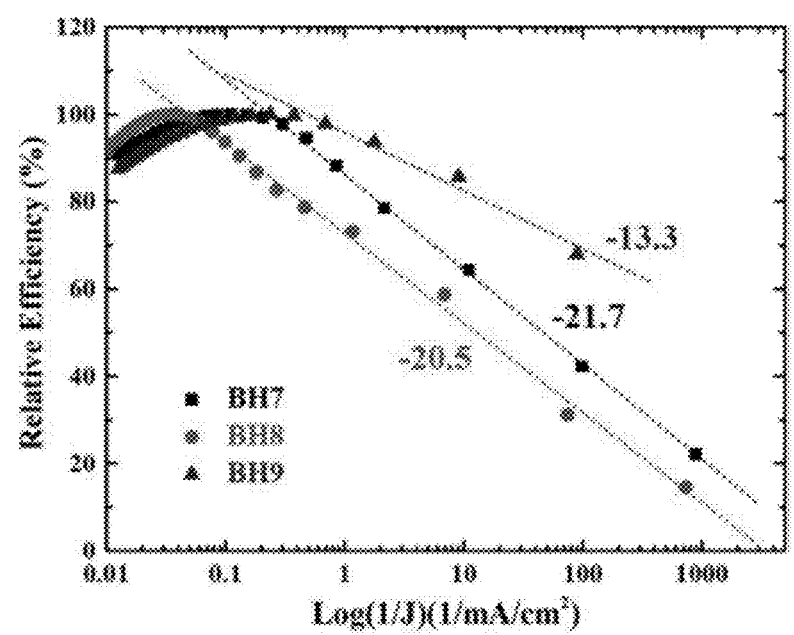
FIG. 12 is a diagram showing experiment results of low dynamic range properties in the devices of Comparative Examples 10 to 12.
Figure 13:
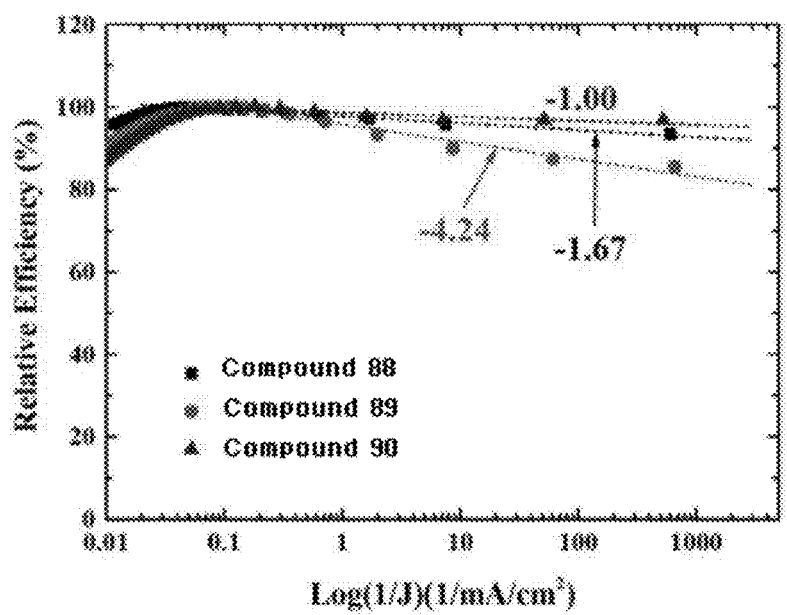
FIG. 13 is a diagram showing experiment results of low dynamic range properties in the devices of Examples 10 to 12.

In addition, experiment results of low dynamic range properties are depicted in FIG. 8 for Comparative Examples 4 to 6, in FIG. 9 for Comparative Examples 7 to 9, in FIG. 10 for Examples 4 to 6, in FIG. 11 for Examples 7 to 9, in FIG. 12 for Comparative Examples 10 to 12, and in FIG. 13 for Examples 10 to 12.

Taken together, the data of Tables 3 and 4 and FIGS. 8 to 13 demonstrate that the organic light-emitting devices structured to use the compounds of the Examples according to the present invention exhibit lower driving voltages and improved low dynamic range properties, compared to those according to the Comparative Examples.

INDUSTRIAL APPLICABILITY

Structured to have an electron density control layer for lowering a barrier to electron injection between a light-emitting layer and an electron transport layer, the organic light-emitting device of the present invention allows for the effective injection of electrons into the light-emitting layer so that the device can increase the electron density of the light-emitting layer and the density of excitons generated in the light-emitting layer, resulting in an improvement in external quantum efficiency (EQE).

In addition, the organic light-emitting device of the present disclosure has an advantage over conventional organic light-emitting diodes in that the use of the anthracene derivative according to the present invention as a host in a light-emitting layer enables the organic light-emitting device to operate at low voltages and to exhibit high luminance decrease rates at low dynamic range levels. Consequently, the anthracene derivatives of the present invention is industrially applicable.

The invention claimed is:

1. An anthracene derivative, selected from compounds represented by the following Chemical Formula A-1, A-2, B-1, and B-2:

[Chemical Formula A-1]

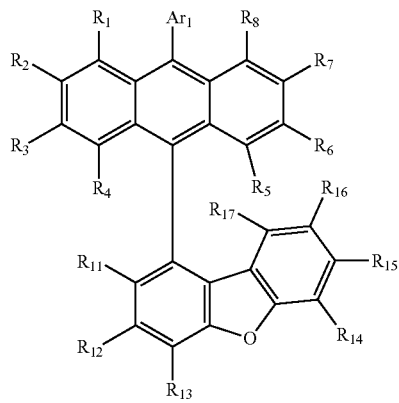

[Chemical Formula A-2]

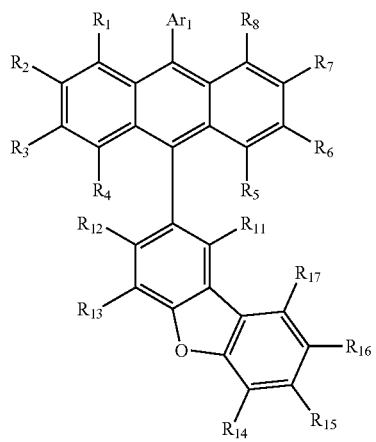

[Chemical Formula B-1]

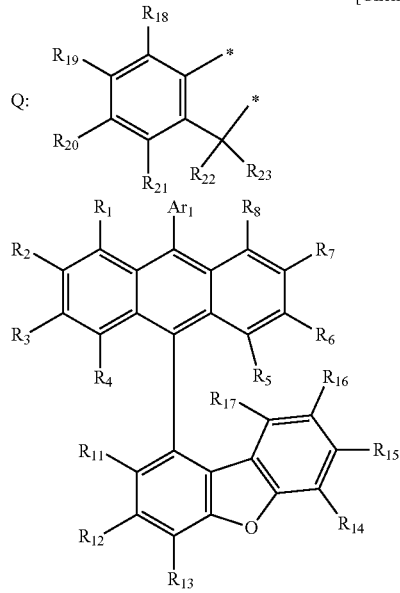

[Chemical Formula B-2]

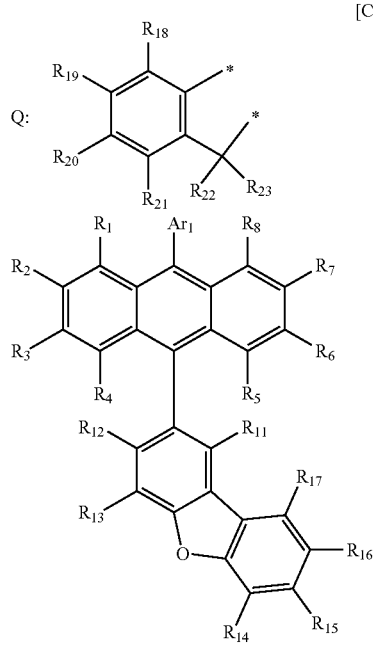

wherein,
in Chemical Formula A-1 and Chemical Formula B-1,
R1 to R8, and R11 to R13 are each hydrogen atom or deuterium,
R14 to R23, which are same or different, are each independently any one selected from among a hydrogen, a deuterium, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted aryl thioxy of 6 to 30 carbon atoms, a substituted or unsubstituted alkyl amine of 1 to 30 carbon atoms, a substituted or unsubstituted aryl amine of 6 to 30 carbon atoms, a substituted or unsubstituted aryl of 6 to 50 carbon atoms, heteroaryl of 2 to 50 carbon atoms bearing 0, N or S as a heteroatom, a cyano, a nitro, a halogen, a substituted or unsubstituted silyl of 1 to 30 carbon atoms, a substituted or unsubstituted germanium of 1 to 30 carbon atoms, a substituted or unsubstituted boron of 1 to 30 carbon atoms, a substituted or unsubstituted aluminum of 1 to 30 carbon atoms, a carbonyl, a phosphoryl, an amino, a thiol, a hydroxy, a selenium, a tellurium, an amide, an ether, and an ester, wherein, the anthracene derivative has the structure of -(L)m-(B)n for at least one of R15 to R17, L denotes a linker and is a single bond or a deuterium substituted or unsubstituted arylene of 6 to 60 carbon atoms, B is a deuterium substituted or unsubstituted aryl of 6 to 60 carbon atoms, m is an integer of 1 to 2, with a proviso that when m is 2, the corresponding L's may be same or different, and n is an integer of 1 to 5, with a proviso that when n is 2 or greater, the corresponding B's may be same or different, in Chemical Formula A-2 and Chemical Formula B-2, R1 to R8, and R12 to R13 are each hydrogen atom or deuterium, R11, R14 to R23, which are same or different, are each independently any one selected from among a hydrogen, a deuterium, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted aryl thioxy of 6 to 30 carbon atoms, a substituted or unsubstituted alkyl amine of 1 to 30 carbon atoms, a substituted or unsubstituted aryl amine of 6 to 30 carbon atoms, a substituted or unsubstituted aryl of 6 to 50 carbon atoms, heteroaryl of 2 to 50 carbon atoms bearing 0, N or S as a heteroatom, a cyano, a nitro, a halogen, a substituted or unsubstituted silyl of 1 to 30 carbon atoms, a substituted or unsubstituted germanium of 1 to 30 carbon atoms, a substituted or unsubstituted boron of 1 to 30 carbon atoms, a substituted or unsubstituted aluminum of 1 to 30 carbon atoms, a carbonyl, a phosphoryl, an amino, a thiol, a hydroxy, a selenium, a tellurium, an amide, an ether, and an ester, wherein, the anthracene derivative has the structure of -(L)m-(B)n for at least one of R11 and R15 to R17, L denotes a linker and is a single bond or a deuterium substituted or unsubstituted arylene of 6 to 60 carbon atoms, B is a deuterium substituted or unsubstituted aryl of 6 to 60 carbon atoms, m is an integer of 1 to 2, with a proviso that when m is 2, the corresponding L's may be same or different, and n is an integer of 1 to 5, with a proviso that when n is 2 or greater, the corresponding B's may be same or different, in Chemical Formula A-1, Chemical Formula A-2, Chemical Formula B-1, and Chemical Formula B-2, the substituent Ar1 is a substituted or unsubstituted aryl of 6 to 50 carbon atoms, or a substituted or unsubstituted heteroaryl of 2 to 50 carbon atoms;

two adjacent substituents of R11 to R13 in Chemical Formulas B-1 and B-2 are respective single bonds involved in forming a 5-membered ring as a fused ring with the carbon atom to which the substituents R22 and R23 in Structural Formula Q are both bonded; and R22 and R23 may be connected to each other to form a ring, wherein the term 'substituted' in the expression "substituted or unsubstituted" means having at least one substituent selected from the group consisting of a deuterium, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

2. The anthracene derivative of claim 1, wherein the substituents R22 and R23 are same or different and are each be independently a substituted or unsubstituted aryl of 6 to 24 carbon atoms.

3. The anthracene derivative of claim 1, wherein Ar1 is a substituted or unsubstituted aryl of 6 to 50 carbon atoms.

4. The anthracene derivative of claim 1, wherein Ar1 is a substituted or unsubstituted aryl of 6 to 18 carbon atoms, or a substituted or unsubstituted heteroaryl of 3 to 18 carbon atoms.

5. The anthracene derivative of claim 1, wherein Ar1 is a substituent represented by the following Structural Formula C:

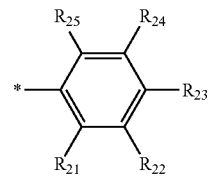

[Structural Formula C]

wherein the substituents R21 to R25, which are same or different, are each independently any one selected from among a hydrogen, a deuterium, a halogen, a cyano, a substituted or unsubstituted alkyl of 1 to 30 carbon atoms, a substituted or unsubstituted cycloalkyl of 3 to 30 carbon atoms, a substituted or unsubstituted alkoxy of 1 to 30 carbon atoms, a substituted or unsubstituted aryloxy of 6 to 30 carbon atoms, a substituted or unsubstituted aryl of 6 to 50 carbon atoms, and a substituted or unsubstituted silyl of 1 to 30 carbon atoms, and '*' refers to a bonding site to the anthracene moiety.

6. The anthracene derivative of claim 1, wherein the anthracene derivative has the structure of -(L)m-(B)n as only one of the substituents R15 to R17 in Chemical Formula A-1 or B-1 and as only one of the substituents R11 and R15 to R17 in Chemical Formula A-2 or B-2.

7. The anthracene derivative of claim 1, wherein B is any one selected from among a phenyl, a biphenyl, a naphthyl, and a phenanthrene.

8. The anthracene derivative of claim 1, wherein the linker L is a single bond or any one selected from among any one selected from among the following Structural Formulas 1 to 3:

[Structural Formula 1]

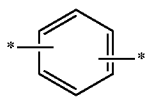

[Structural Formula 2]

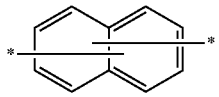

[Structural Formula 3]

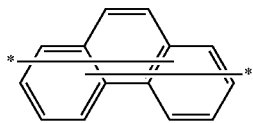

wherein each of the unsubstituted carbon atoms of the aromatic ring moiety is bound with a hydrogen atom or a deuterium atom.

9. The anthracene derivative of claim 5, wherein the substituents R21 to R25 are each hydrogen or deuterium.

10. The anthracene derivative of claim 1, wherein the anthracene derivative is any one selected from among the following Compounds 21, 39, 82 to 141, 144, 148 to 156:

<Compound 21>

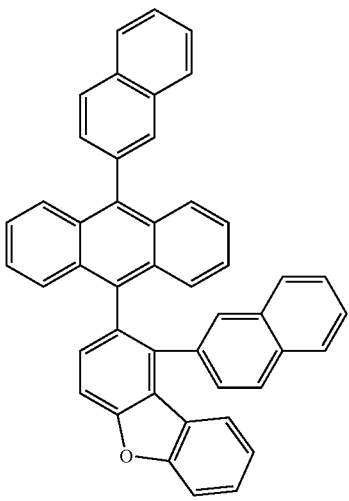

<Compound 39>

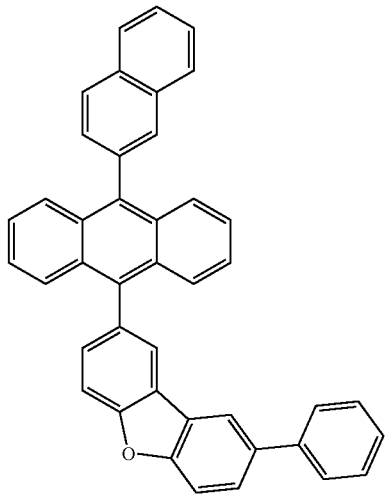

<Compound 82>

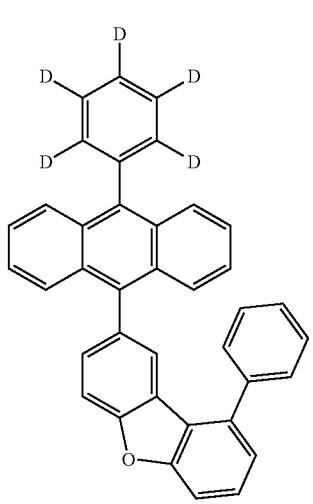

<Compound 83>

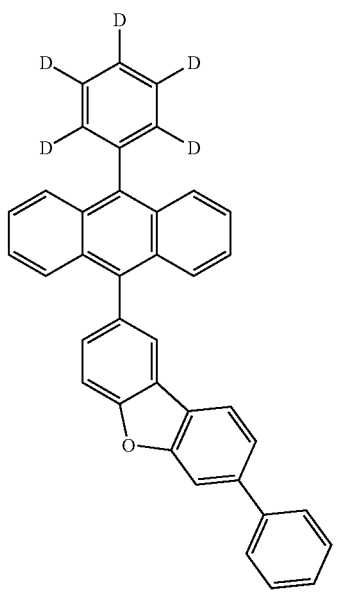

<Compound 84>
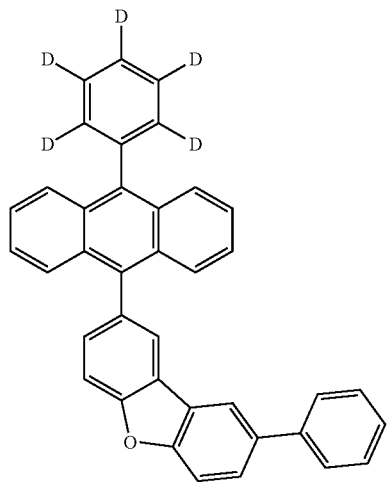
<Compound 85>
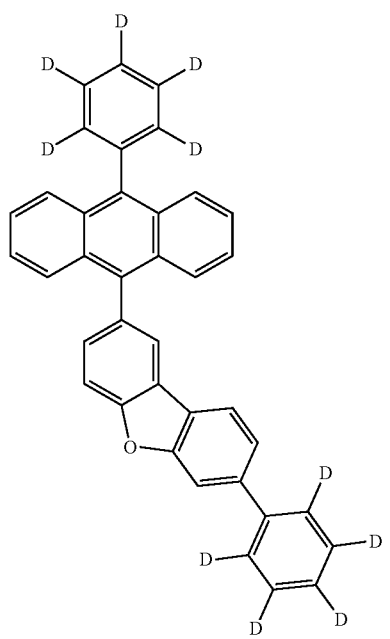
<Compound 86>
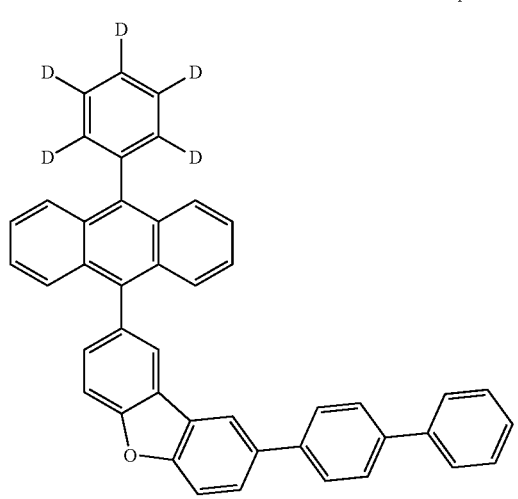
<Compound 87>
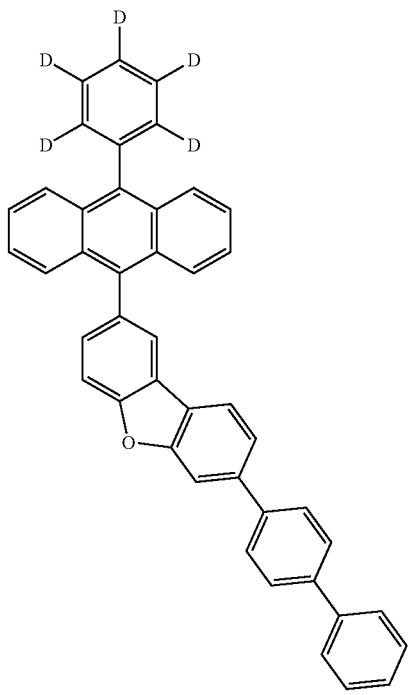
<Compound 88>
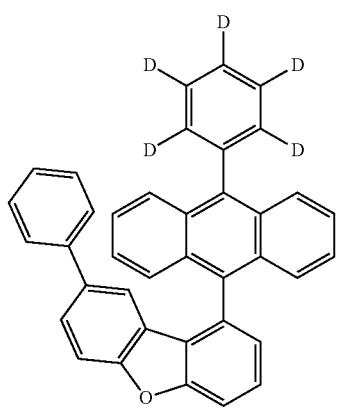
<Compound 89>
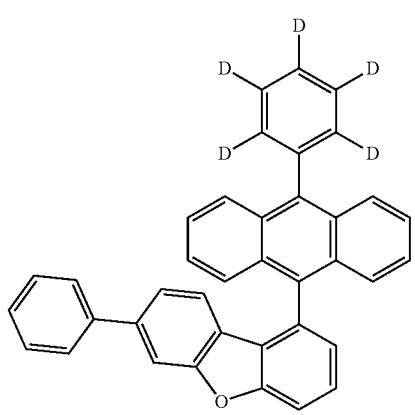

<Compound 90>
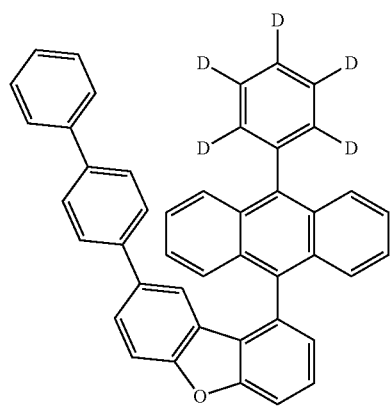
<Compound 91>
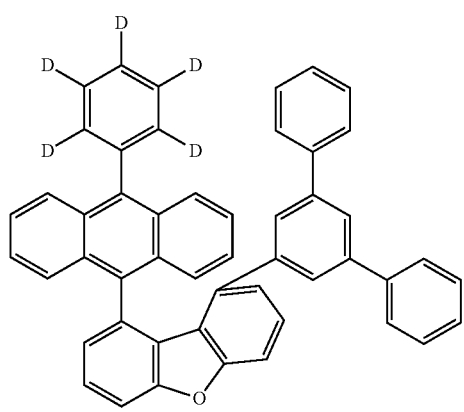
<Compound 92>
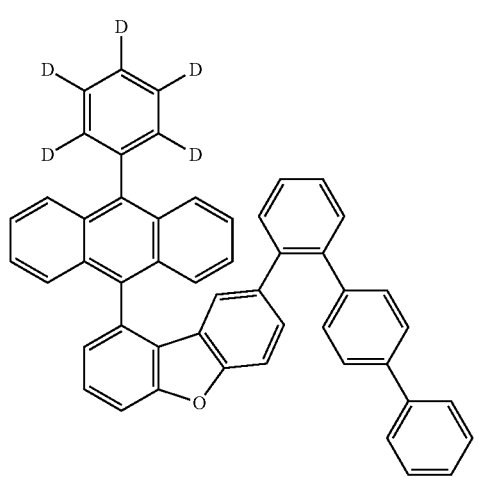
<Compound 93>
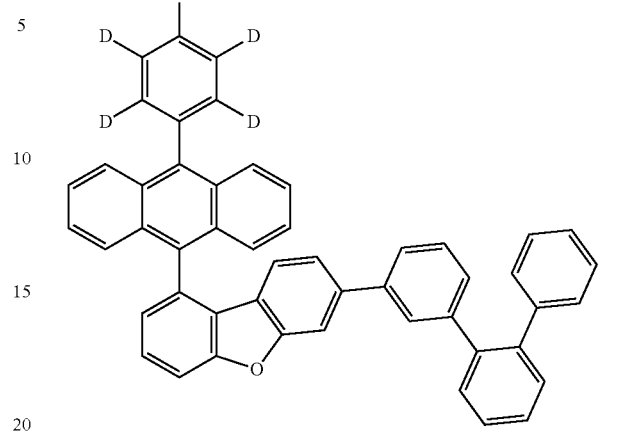
<Compound 94>
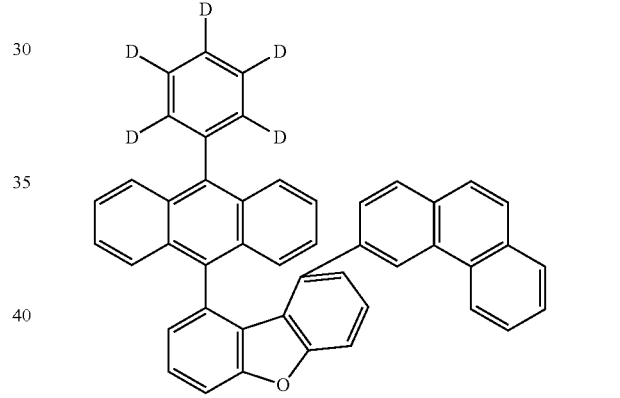
<Compound 95>
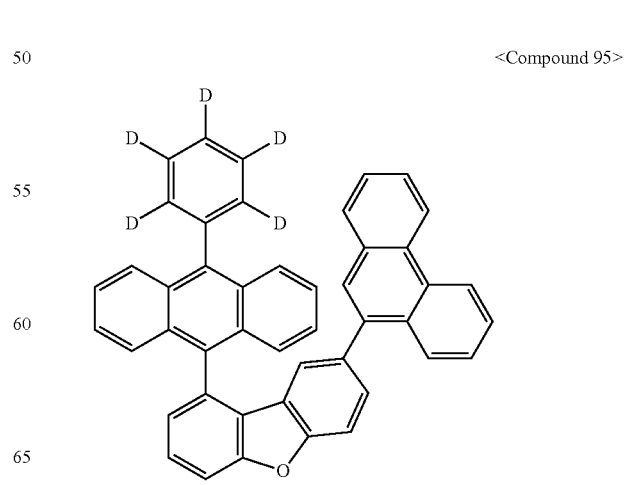

<Compound 96>
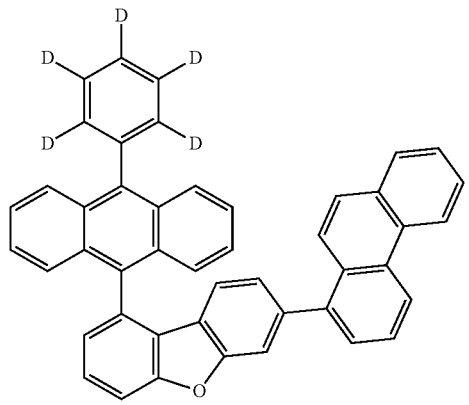
<Compound 97>
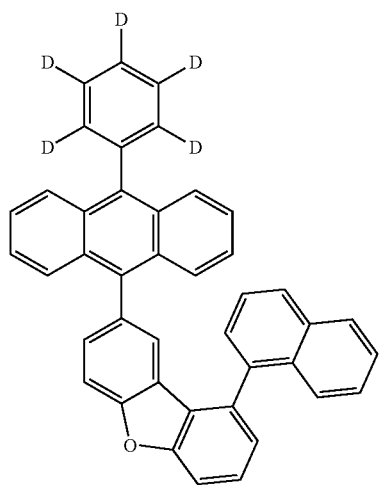
<Compound 98>
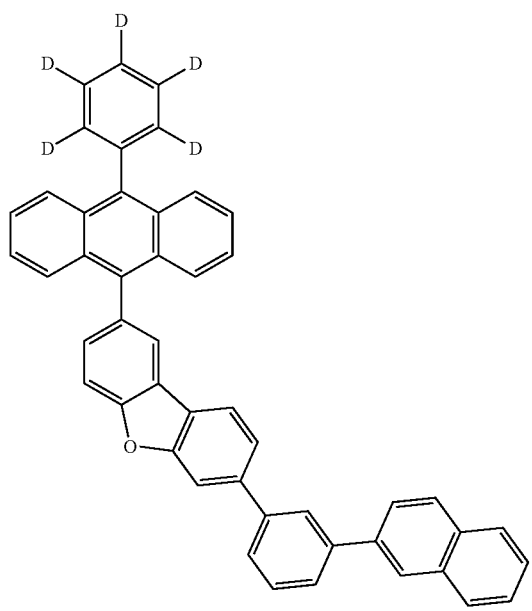
<Compound 99>
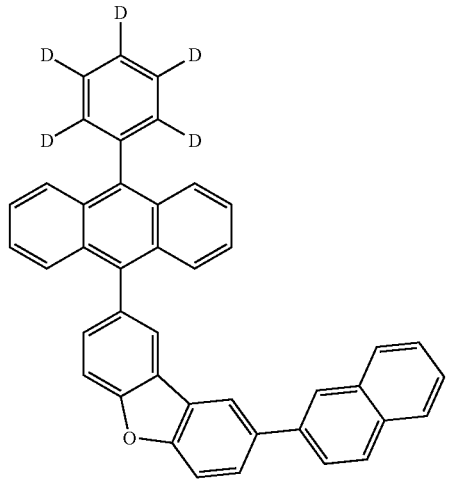
<Compound 100>
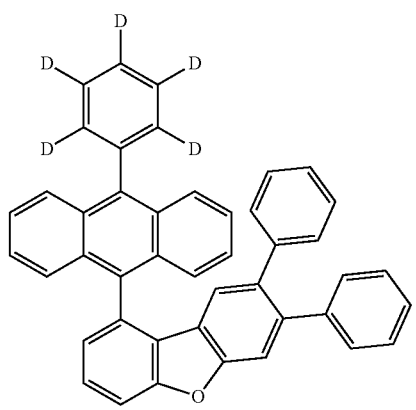
<Compound 101>
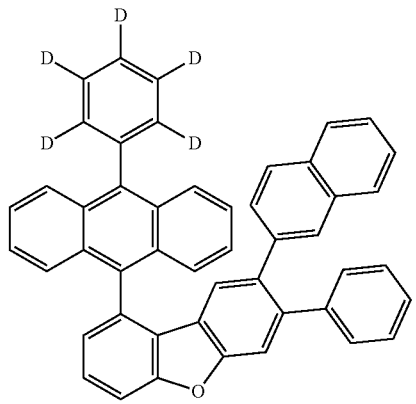

<Compound 102>
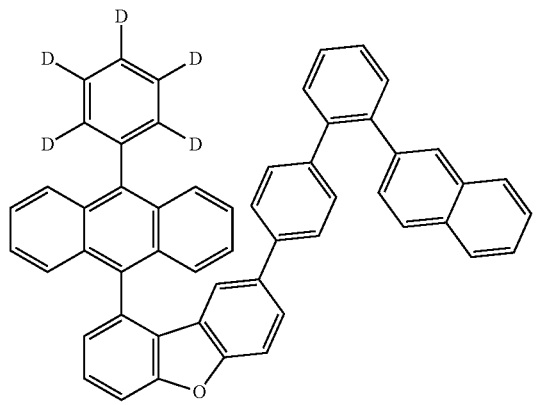
<Compound 103>
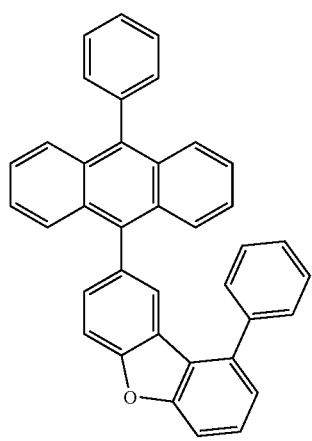
<Compound 104>
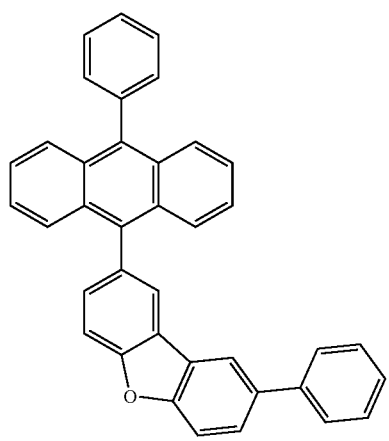
<Compound 105>
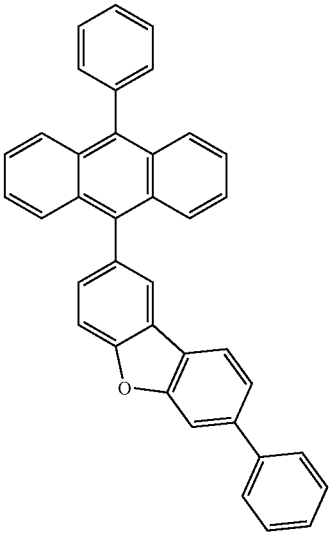
<Compound 106>
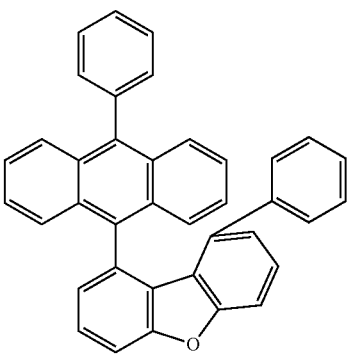
<Compound 107>
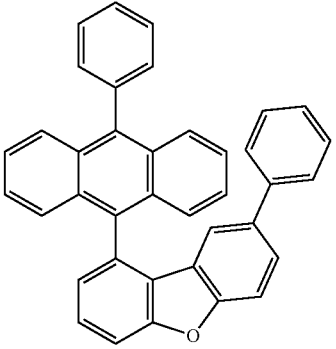
<Compound 108>
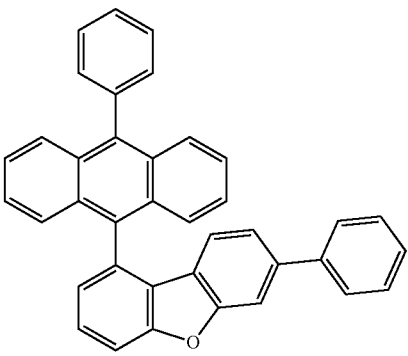

<Compound 109>
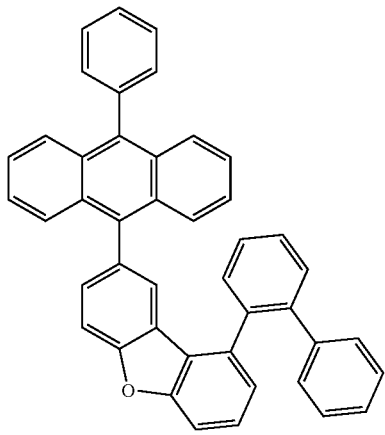
<Compound 110>
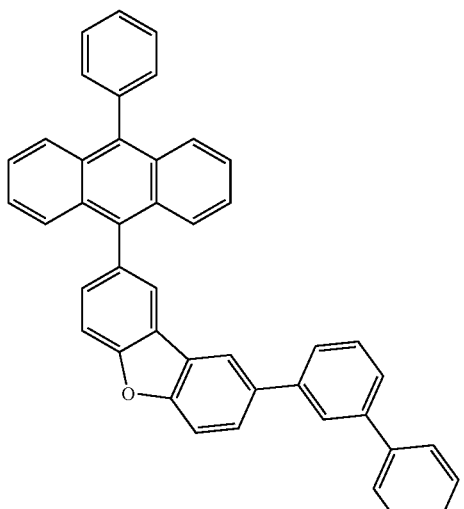
<Compound 111>
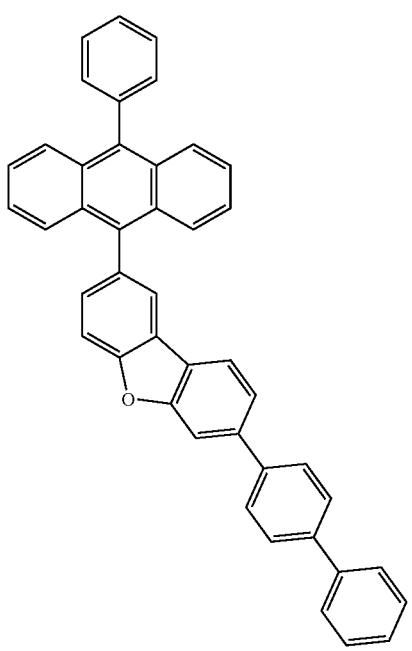
<Compound 112>
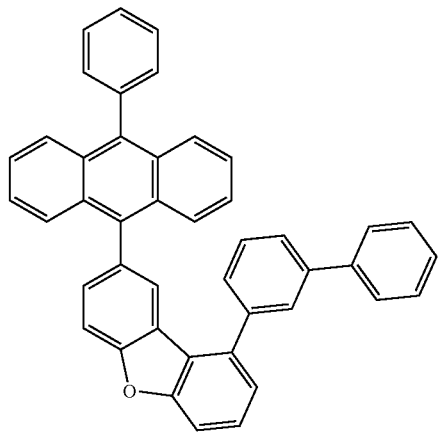
<Compound 113>
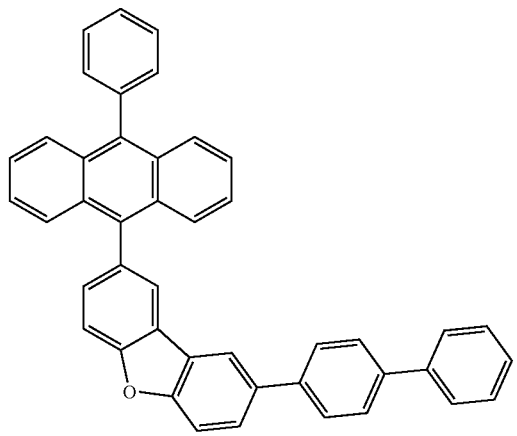
<Compound 114>
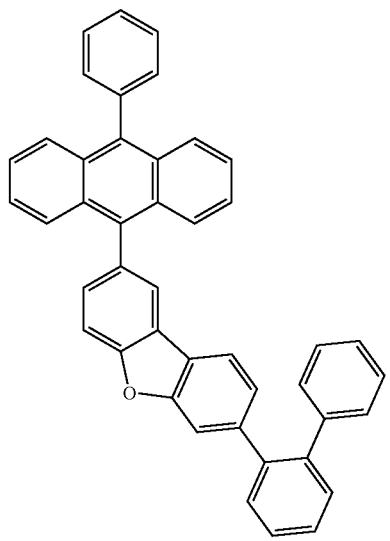

<Compound 115>
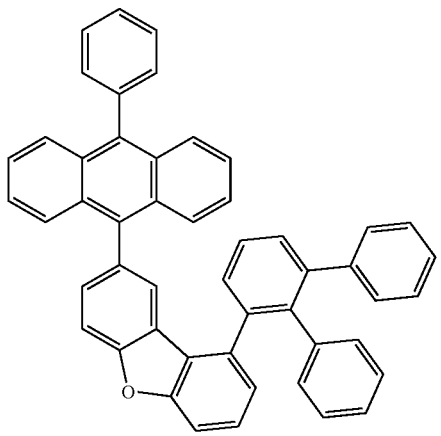
<Compound 116>
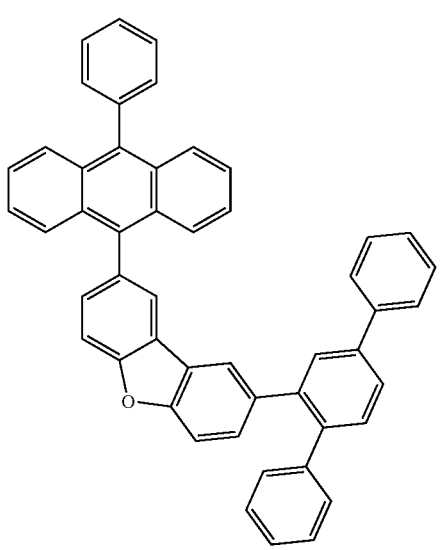
<Compound 117>
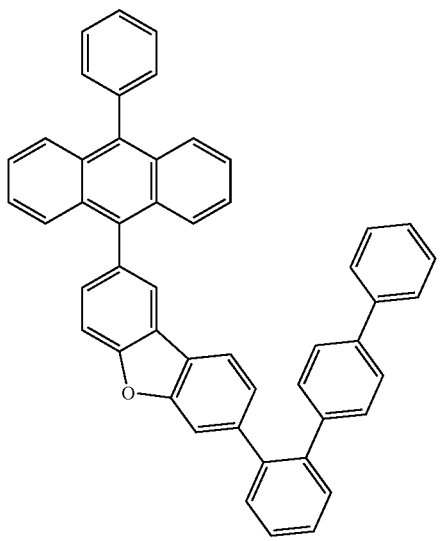
<Compound 118>
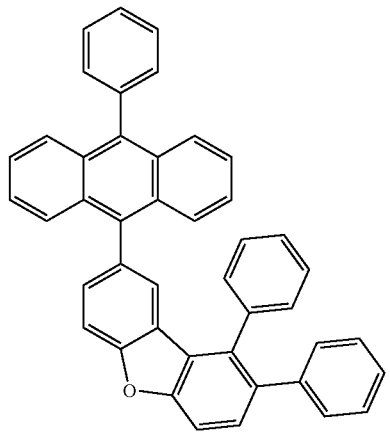
<Compound 119>
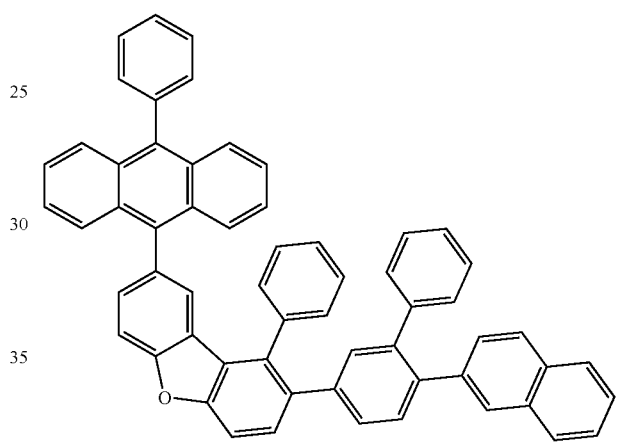
<Compound 120>
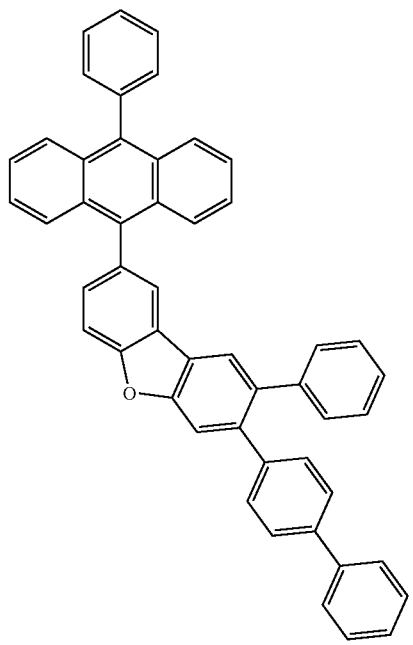

<Compound 121>
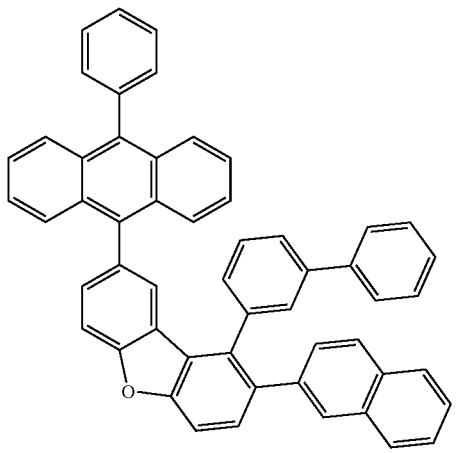
<Compound 122>
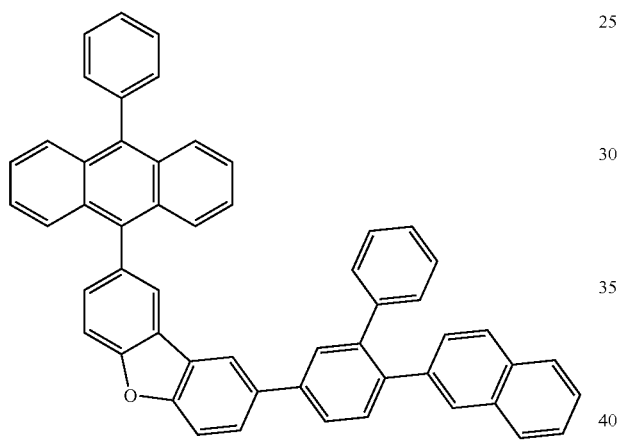
<Compound 123>
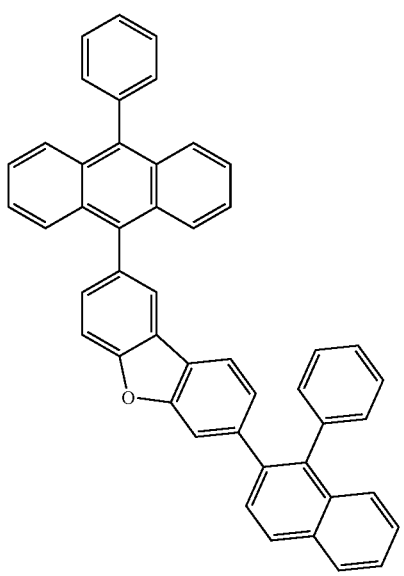
<Compound 124>
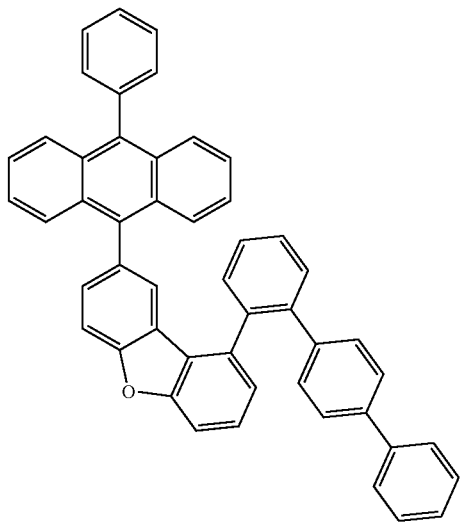
<Compound 125>
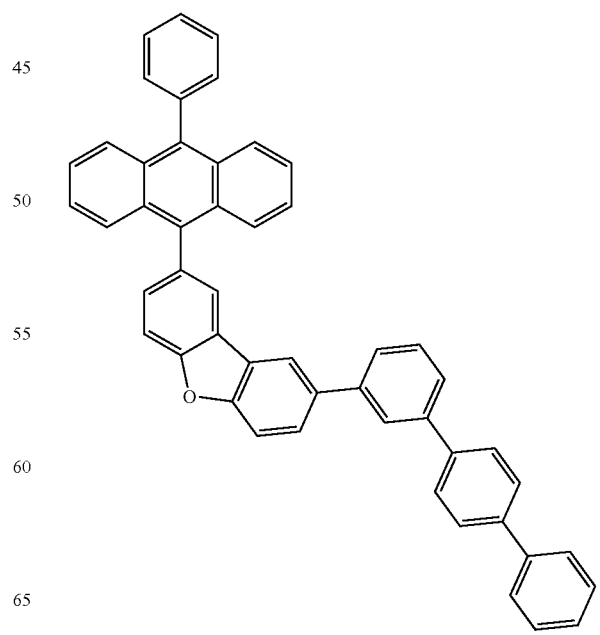

<Compound 126>
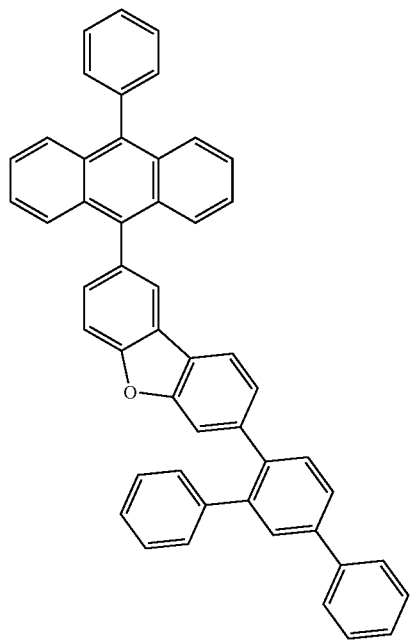
<Compound 127>
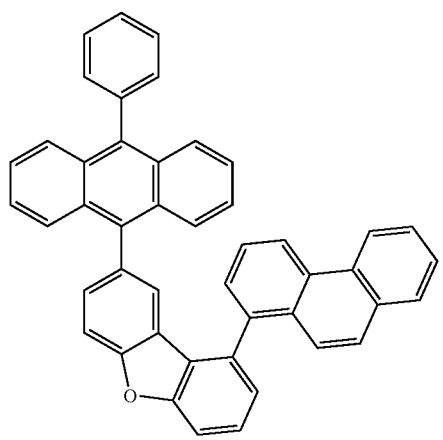
<Compound 128>
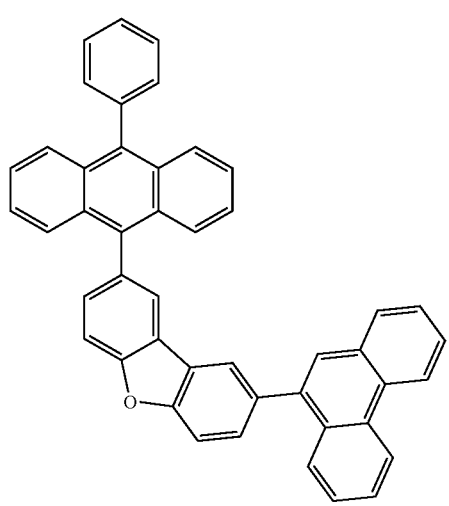
<Compound 129>
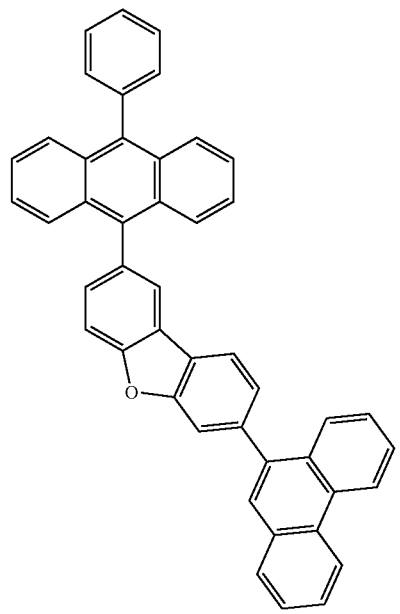
<Compound 130>
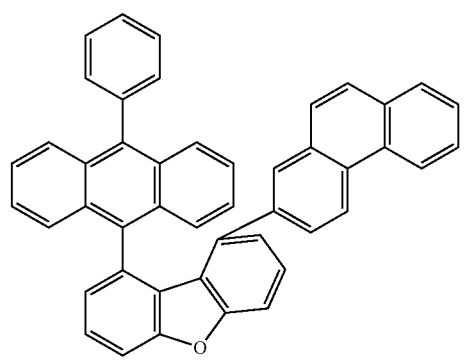
<Compound 131>
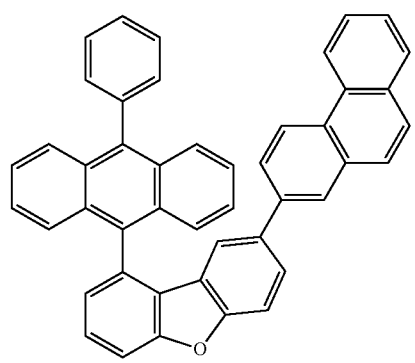

<Compound 132>
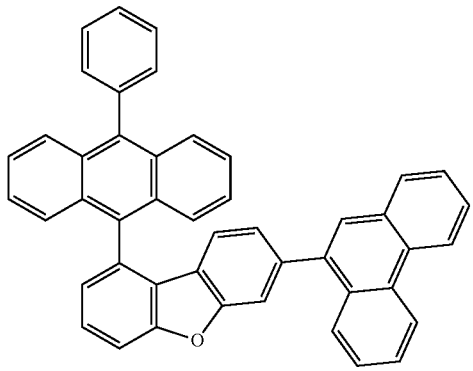
<Compound 133>
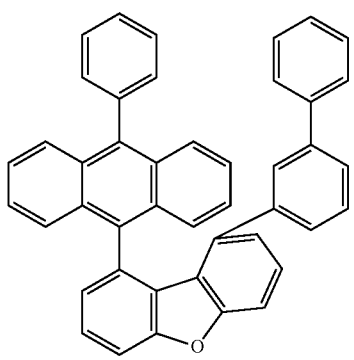
<Compound 134>
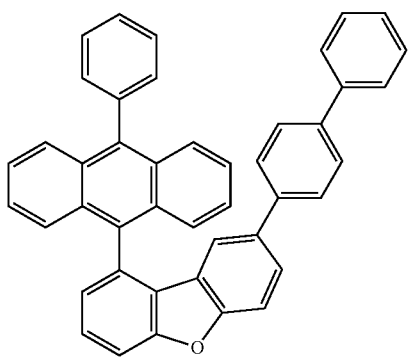
<Compound 135>
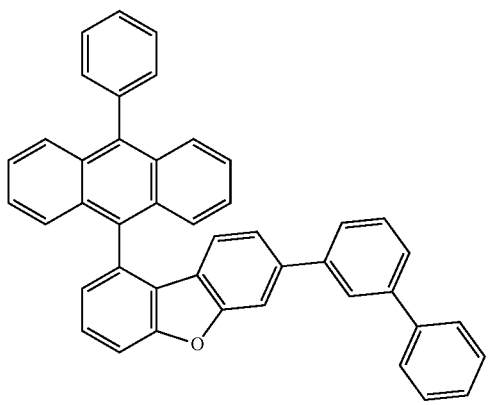
<Compound 136>
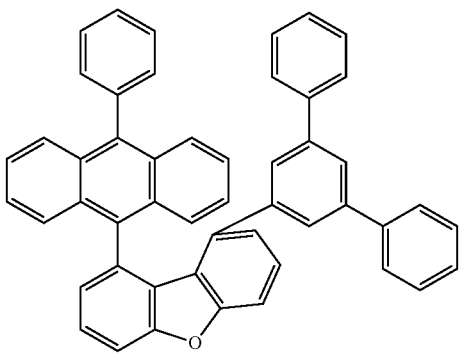
<Compound 137>
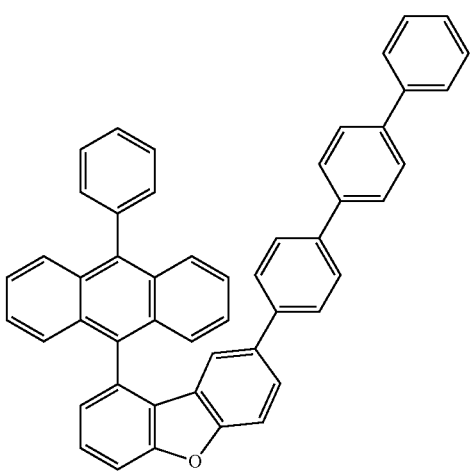
<Compound 138>
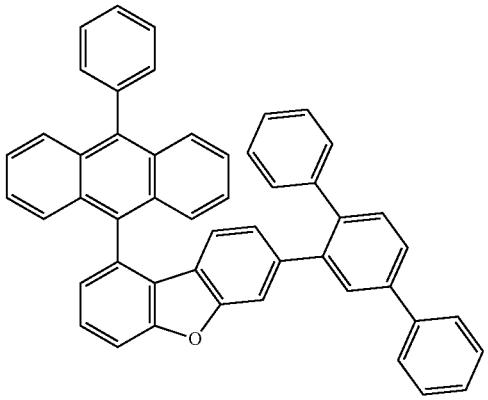
<Compound 139>
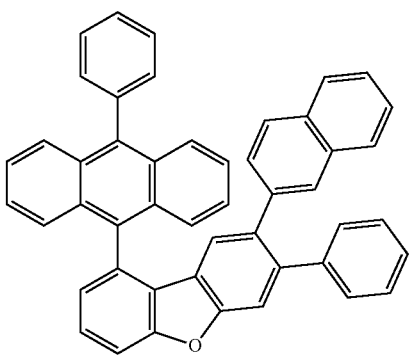

<Compound 140>
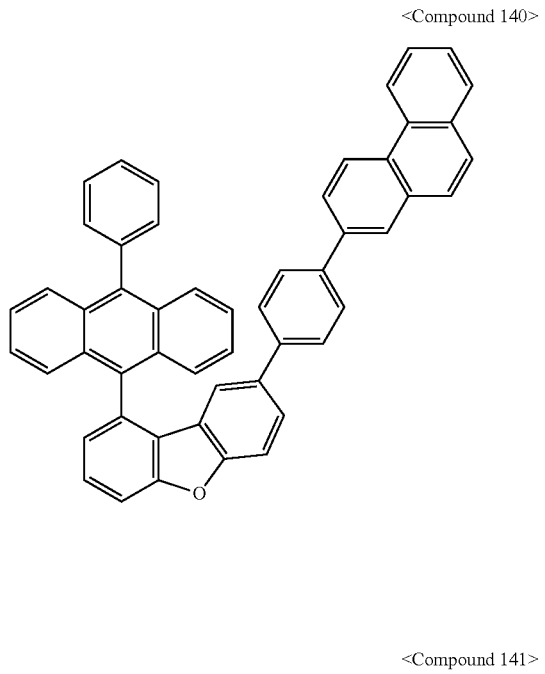
<Compound 141>
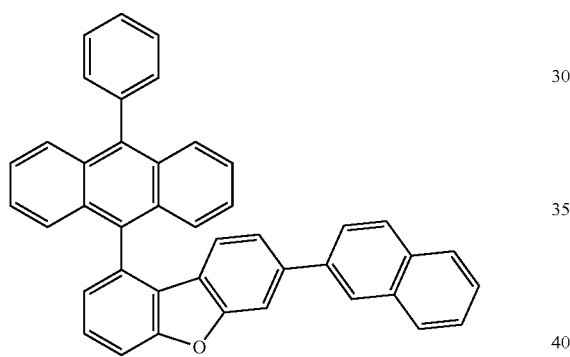
<Compound 144>
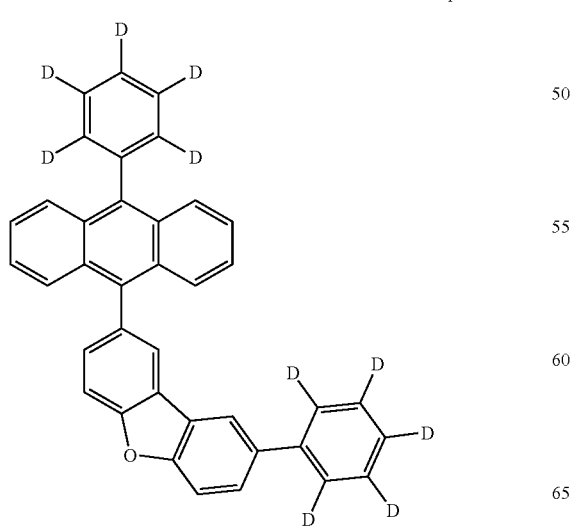
<Compound 148>
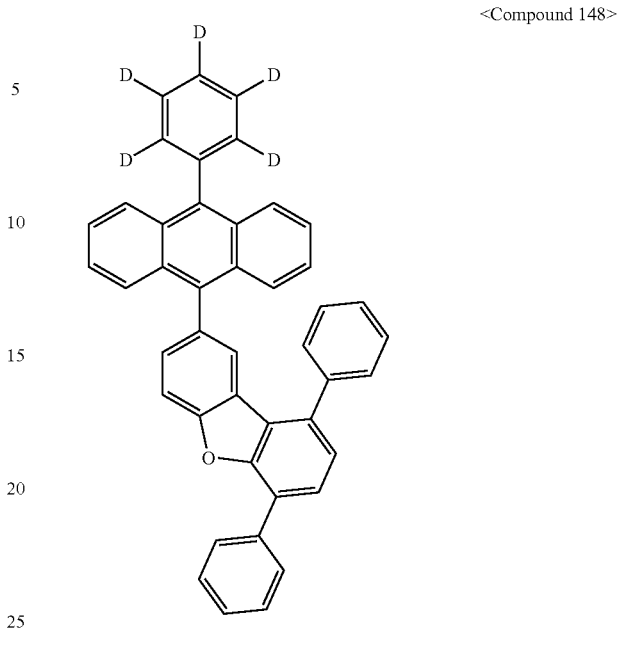
<Compound 149>

<Compound 150>
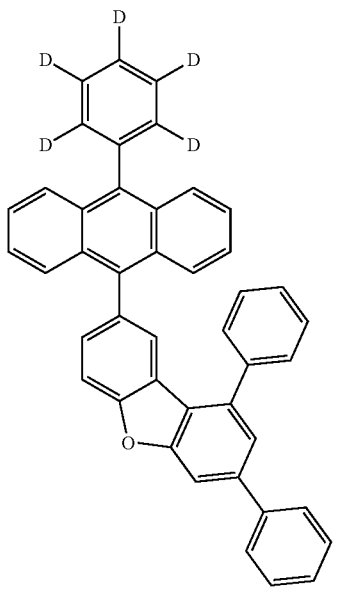
<Compound 151>
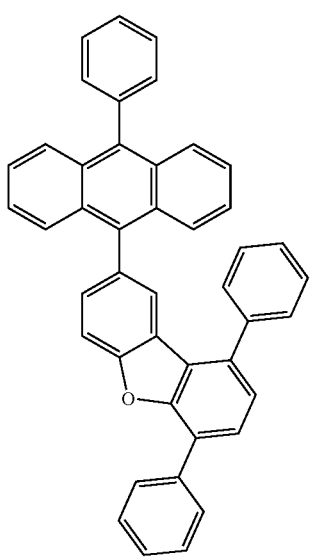
<Compound 152>
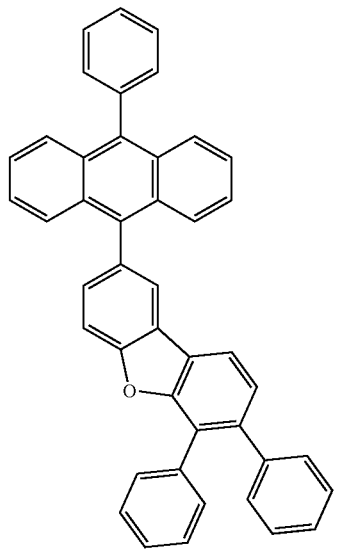
<Compound 153>
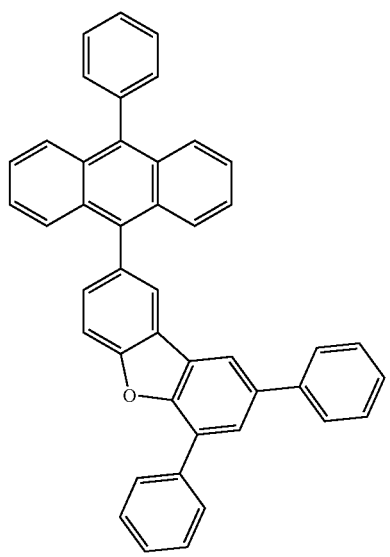

<Compound 154>

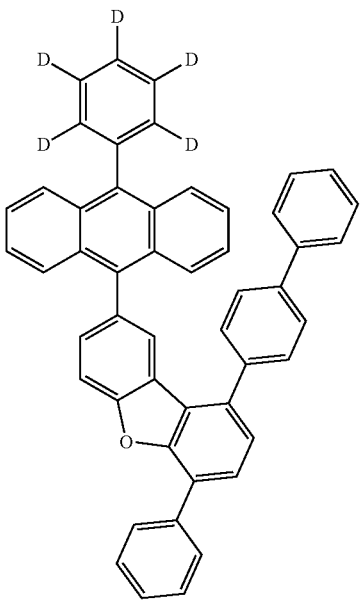

<Compound 155>

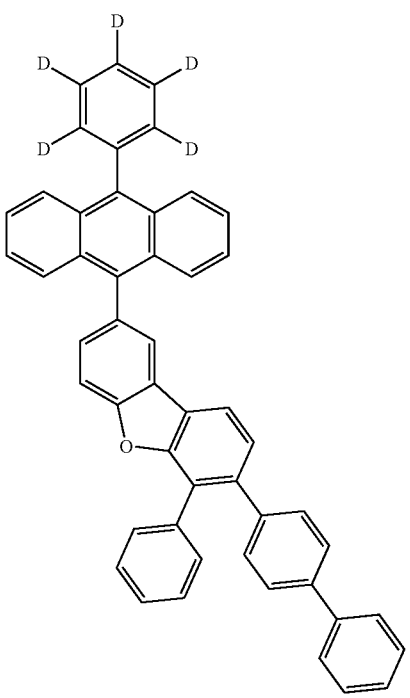

<Compound 156>

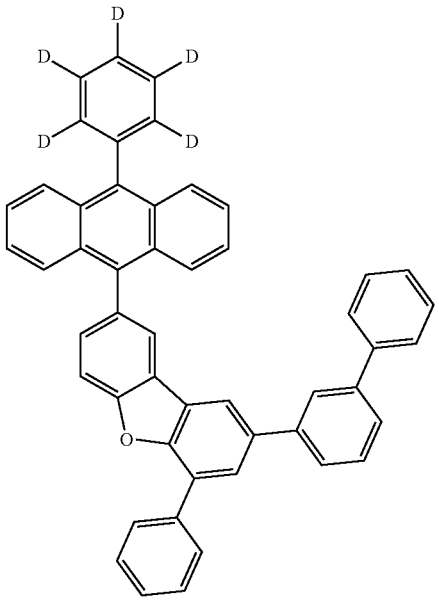

11. An organic light-emitting device, including:
a first electrode;
a second electrode facing the first electrode; and
an organic layer disposed between the first electrode and the second electrode, wherein the organic layer includes the anthracene derivative of claim 1.

12. The organic light-emitting device of claim 11, wherein the organic layer includes at least one of a hole injection layer, a hole transport layer, a functional layer capable of both hole injection and hole transport, an electron transport layer, and an electron injection layer.

13. The organic light-emitting device of claim 12, wherein the organic layer disposed between the first and the second electrode is a light-emitting layer composed of a host and a dopant, the anthracene derivative used in the light-emitting layer serving as a host.

14. The organic light-emitting device of claim 12, wherein at least one selected from the layers is formed using a single-molecule deposition process or a solution process.

15. The organic light-emitting device of claim 11, wherein the organic light-emitting device is used for a device selected from among a flat display device, a flexible display device, a monochrome or yellow to white flat illumination device, and a monochrome or yellow to white flexible illumination device.

16. An organic light-emitting device, including an anode, a hole transport layer, a light-emitting layer including both a host and a dopant, an electron density control layer containing at least one of the anthracene derivatives selected from compounds represented by the following Chemical Formula A-1, A-2, B-1, and B-2, an electron transport layer, and a cathode in that order,

[Chemical Formula A-1]

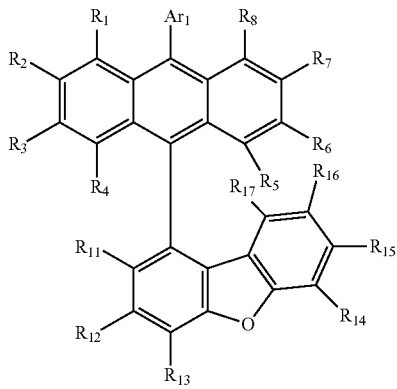

[Chemical Formula A-2]

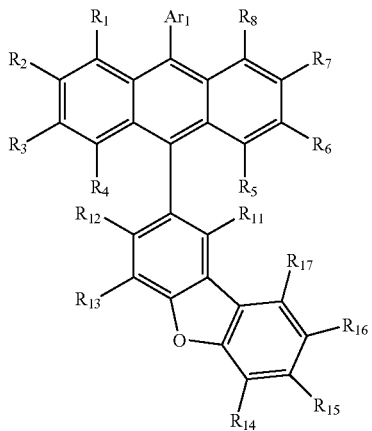

[Chemical Formula B-1]

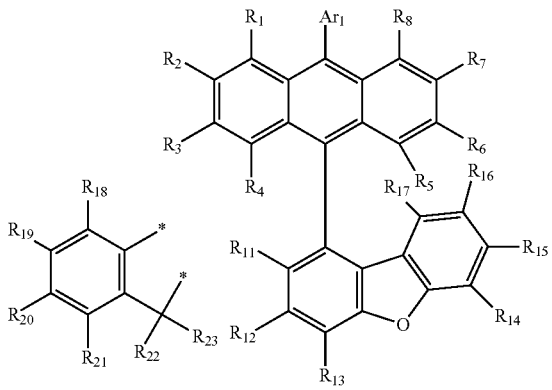

Q:

[Chemical Formula B-2]

wherein,

R1 to R8, and R11 to R23, which may be same or different, are each independently any one selected from among a hydrogen, a deuterium, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted aryl thioxy of 6 to 30 carbon atoms, a substituted or unsubstituted alkyl amine of 1 to 30 carbon atoms, a substituted or unsubstituted aryl amine of 6 to 30 carbon atoms, a substituted or unsubstituted aryl of 6 to 50 carbon atoms, heteroaryl of 2 to 50 carbon atoms bearing O, N or S as a heteroatom, a cyano, a nitro, a halogen, a substituted or unsubstituted silyl of 1 to 30 carbon atoms, a substituted or unsubstituted germanium of 1 to 30 carbon atoms, a substituted or unsubstituted boron of 1 to 30 carbon atoms, a substituted or unsubstituted aluminum of 1 to 30 carbon atoms, a carbonyl, a phosphoryl, an amino, a thiol, a hydroxy, a selenium, a tellurium, an amide, an ether, and an ester, the substituent Ar1 is a substituted or unsubstituted aryl of 6 to 50 carbon atoms, or a substituted or unsubstituted heteroaryl of 2 to 50 carbon atoms;

two adjacent substituents of R11 to R13 in Chemical Formulas B-1 and B-2 are respective single bonds involved in forming a 5-membered ring as a fused ring with the carbon atom to which the substituents R22 and R23 in Structural Formula Q are both bonded; and R22 and R23 may be connected to each other to form a ring, wherein the term 'substituted in the expression "substituted or unsubstituted" means having at least one substituent selected from the group consisting of a deuterium, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

17. The organic light-emitting device of claim 16, further including a hole injection layer between the anode and the hole transport layer, and an electron injection layer between the electron transport layer and the cathode.

18. The organic light-emitting device of claim 16, wherein the anthracene derivative in the electron density control layer is identical to or larger than a material in the electron transport layer in terms of electron mobility.

19. The organic light-emitting device of claim 16, wherein the affinity $A_{ed}$ (eV) of the electron density control layer falls between the affinity $A_h$ (eV) of the host in the light-emitting layer and the affinity $A_e$ (eV) of the electron transport layer ($A_h \geq A_{ed} \geq A_e$).

20. The organic light-emitting device of claim 16, further including a light-emitting layer, made of a blue light-emitting material, a green light-emitting material, or a red light-emitting material, all materials emitting light in a wavelength range of 380 nm to 800 nm, wherein the blue light-emitting material, the green light-emitting material, or the red light-emitting material is a fluorescent or phosphorescent material.

* * * * *